US012018066B1

(12) United States Patent
Lillo et al.

(10) Patent No.: US 12,018,066 B1
(45) Date of Patent: Jun. 25, 2024

(54) COMPOSITIONS FOR TARGETING SARS-COV-2 SPIKE PROTEIN RECEPTOR BINDING DOMAIN

(71) Applicant: Triad National Security, LLC, Los Alamos, NM (US)

(72) Inventors: Antonietta Maria Lillo, Los Alamos, NM (US); Nileena Velappan, Los Alamos, NM (US); Geoffrey S. Waldo, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 216 days.

(21) Appl. No.: 17/514,903

(22) Filed: Oct. 29, 2021

Related U.S. Application Data

(60) Provisional application No. 63/107,834, filed on Oct. 30, 2020.

(51) Int. Cl.
*C07K 16/00* (2006.01)
*C07K 16/10* (2006.01)

(52) U.S. Cl.
CPC .......... *C07K 16/10* (2013.01); *C07K 2317/33* (2013.01); *C07K 2317/622* (2013.01); *C07K 2317/92* (2013.01)

(58) Field of Classification Search
CPC ................ C07K 16/10; C07K 2317/33; C07K 2317/622; C07K 2317/92
See application file for complete search history.

(56) References Cited

U.S. PATENT DOCUMENTS

2017/0029812 A1 2/2017 Martinez et al.

OTHER PUBLICATIONS

"U. f. a. d. a. In Vitro Diagnostics EUAs—Antigen Diagnostic Tests for SARS-CoV-2," FDA, [Retrieved from the Internet 2020: <https://www.fda.gov/medical-devices/coronavirus-disease-2019-covid-19-emergency-use-authorizations-medical-devices/in-vitro-diagnostics-euas-antigen-diagnostic-tests-sars-cov-2>].

Allegrini, F. et al., "IUPAC-consistent approach to the limit of detection in partial least-squares calibration," Analytical Chemistry, 86:7858-7866, (2014).

Amin, M. et al., "Comparing the binding interactions in the receptor binding domains of SARS-CoV-2 and SARS-CoV," The Journal of Physical Chemistry Letters, 11:4897-4900, (2020).

Arbeitman, C. R. et al., "Structural and functional comparison of SARS-CoV-2-spike receptor binding domain produced in Pichia pastoris and mammalian cells," Scientific Reports, 10, (2020).

Bailly, M. et al., "Predicting Antibody Developability Profiles Through Early Stage Discovery Screening," MABS 12:1743053-1743053, (2020).

Baum, A. et al., "Antibody cocktail to SARS-CoV-2 spike protein prevents rapid mutational escape seen with individual antibodies," Science, 369:1014-1018, (2020).

Beckett, D. et al., "A minimal peptide substrate in biotin holoenzyme synthetase-catalyzed biotinylation," Protein Science, 8:921-929, (1999).

Bell, B. N. et al., "Neutralizing antibodies targeting the SARS-CoV-2 receptor binding domain isolated from a naïve human antibody library," The Protein Society, 30:716-727, (2021).

Berghman, L.R., et al., "Antibodies: an alternative for antibiotics?," Poultry Science, 84:660- 666, (2005).

Bertoglio, F. et al., "SARS-CoV-2 neutralizing human recombinant antibodies selected from pre-pandemic healthy donors binding at RBD-ACE2 interface," Nature Communications, 12:1-15, (2021).

Boder, E. T. et al., "Yeast surface display for directed evolution of protein expression, affinity, and stability," Methods in Enzymology, 328:430-444, (2000).

Bradbury, A. et al., "Reproducibility: Standardize antibodies used in research," Nature News, 518:27-29, (2015).

Bradfute, S. B. et al., "Severe Acute Respiratory Syndrome Coronavirus 2 Neutralizing Antibody Titers in Convalescent Plasma and Recipients in New Mexico: An Open Treatment Study in Patients With Coronavirus Disease 2019," The Journal of Infectious Diseases, 222:1620-1628, (2020).

Chakraborty, S., "Evolutionary and structural analysis elucidates mutations on SARS-CoV2 spike protein with altered human ACE2 binding affinity," Biochemical and Biophysical Research Communications, 538:97-103, (2021).

Chen, H. et al., "Point of care testing for infectious diseases," Clinica Chimica Acta, 493:138- 147, (2019).

Chi, X. et al., "Humanized single domain antibodies neutralize SARS-CoV-2 by targeting the spike receptor binding domain," Nature communications, 11:1-7, (2020).

Close, D. W. et al., "Using phage display selected antibodies to dissect microbiomes for complete de novo genome sequencing of low abundance microbes," BMC microbiology 13:1-14, (2013).

Datta, M. et al., "Molecular Diagnostic Tools for the Detection of SARS-CoV-2," International Reviews of Immunology, 40(1-21):143-156, (2021).

Di Marzo Veronese, F. et al., Loss of a neutralizing epitope by a spontaneous point mutation in the V3 loop of HIV-1 isolated from an infected laboratory worker, Journal of Biological Chemistry, 268:25894-25901 (1993).

Dimitrov, D. S. et al., Therapeutic Antibodies: Current State and Future Trends—Is a Paradigm Change Coming Soon? Methods in Molecular Biology, Methods and Protocols, vol. 525, chapter 1, (2009).

Erasmus, M. F. et al., "A single donor is sufficient to produce a highly functional in vitro antibody library," Communications Biology, 4:1-16, (2021).

Felding-Habermann, B. et al., "Combinatorial antibody libraries from cancer patients yield ligand-mimetic Arg-Gly-Asp-containing immunoglobulins that inhibit breast cancer metastasis," Proceedings of the National Academy of Sciences, 101:17210-17215, (2004).

Ferrara, F. et al., "A pandemic-enabled comparison of discovery platforms demonstrates a naïve antibody library can match the best immune-sourced antibodies," Nature Communications, 13:1-12, (2022).

(Continued)

*Primary Examiner* — Lei Yao

(74) *Attorney, Agent, or Firm* — Alston & Bird LLP

(57) ABSTRACT

The invention provides antibodies that specifically bind the SARS-CoV-2 receptor binding domain. The antibodies are useful in treating SARS-CoV-2 virus infection and in diagnostic methods, agents, and kits thereof.

8 Claims, 40 Drawing Sheets
(11 of 40 Drawing Sheet(s) Filed in Color)

Specification includes a Sequence Listing.

(56) References Cited

OTHER PUBLICATIONS

Gervais, L. et al., "Toward one-step point-of-care immunodiagnostics using capillary-driven microfluidics and PDMS substrates," Lab on a Chip, 9:3330-3337, (2009).
Gottlieb, R. L. et al., "Effect of bamlanivimab as monotherapy or in combination with etesevimab on viral load in patients with mild to moderate COVID-19: a randomized clinical trial," JAMA, 325:632-644, (2021).
Grifoni, A. et al. "A sequence homology and bioinformatic approach can predict candidate targets for immune responses to SARS-CoV-2," Cell Host & Microbe, 27:671-680, e61-2, (2020).
Gubala, V. et al., "Immunodiagnostics and immunosensor design (IUPAC Technical Report)," Pure and Applied Chemistry, 86:1539-1571, (2014).
Hansen, J. et al., "Studies in humanized mice and convalescent humans yield a SARS-CoV- 2 antibody cocktail," Science, 369:1010-1014, (2020).
Hastie, K. M. et al., "Defining variant-resistant epitopes targeted by SARS-CoV-2 antibodies: A global consortium study," Science, 374:472-478, (2021).
Hirotsu, Y. et al., "Comparison of automated SARS-CoV-2 antigen test for COVID-19 infection with quantitative RT-PCR using 313 nasopharyngeal swabs, including from seven serially followed patients," International Journal of Infectious Diseases, 99:397-402, (2020).
Jiang, S. et al., "A distinct name is needed for the new coronavirus," Lancet, 395:949 (2020).
Kehoe, J. W. et al., "Using phage display to select antibodies recognizing post-translational modifications independently of sequence context," Molecular & Cellular Proteomics, 5:2350-2363, (2006).
Kieke, M. C. et al., "Isolation of anti-T cell receptor scFv mutants by yeast surface display," Protein Engineering, 10:1303-1310, (1997).
Kieke, M. C. et al., "Selection of functional T cell receptor mutants from a yeast surface-display library," Proceedings of the National Academy of Sciences, 96:5651-5656, (1999).
Kim, Y. et al., "Targeting heat shock protein 90 Overrides the Resistance of Lung Cancer Cells by Blocking Radiation-Induced Stabilization of Hypoxia-Inducible Factor-1α," Cancer Res, 69(4):1624-1632, (2009).
Koh, C.-Y. et al., "Centrifugal microfluidic platform for ultrasensitive detection of botulinum toxin," Analytical Chemistry, 87:922-928, (2015).
Korber, B. et al., "Tracking changes in SARS-CoV-2 Spike: evidence that D614G increases infectivity of the COVID-19 virus," Cell, 182:812-827, e819, (2020).
Kozel, T. R. et al., "Point-of-care testing for infectious diseases: past, present, and future," Journal of Clinical Microbiology, 55:2313-2320, (2017).
Lan, J. et al., "Structure of SARS-CoV-2 spike receptor-binding domain bound to the ACE2 receptor," Nature, 581:215-220, (2020).
Li, B. et al., "In vitro affinity maturation of a natural human antibody overcomes a barrier to in vivo affinity maturation," MABS, 437-445, (2014).
Lillo A. M. et al., "Development of Anti-Yersinia pestis Human Antibodies with Features Required for Diagnostic and Therapeutic Applications Immuno Targets and Therapy," 9:299, (2020).
Lillo A. M. et al., "Development of phage-based single chain Fv antibody reagents for detection of Yersinia pestis" PloS one 6, e27756, (2011).
Lillo, A. M. et al., "A human single-chain antibody specific for integrin a3β1 capable of cell internalization and delivery of anti-tumor agents," Chemistry & Biology 11:897-906, (2004).
Lillo, A. M. et al., Phage-displayed antibody libraries, Cell Biology, 491-496 (Elsevier, 2006).
Litvinov, J. et al., "Centrifugal sedimentation immunoassays for multiplexed detection of enteric bacteria in ground water," Biomicrofluidics, 10:014103, (2016).
Lorenzo-Redondo, R. et al., "A unique clade of SARS-CoV-2 viruses is associated with lower viral loads in patient upper airways," MedRxiv (2020).
Lu, R. et al., "Genomic characterisation and epidemiology of 2019 novel coronavirus: implications for virus origins and receptor binding," The Lancet, 395:565-574, (2020).
Mahmuda, A. et al., "Monoclonal antibodies in immunodiagnostic assays: a review of recent applications," Sokoto Journal of Veterinary Sciences, 15:1-10, (2017).
McConnell, M. J., "Where are we with monoclonal antibodies for multidrug-resistant infections?," Drug Discovery Today, 24:1132-1138, (2019).
Mehalko, J. et al., "Improved production of SARS-CoV-2 spike receptor-binding domain (RBD) for serology assays," Protein Expression and Purification, 179:105802, (2021).
Moon, S. A. et al., "Antibodies against non-immunizing antigens derived from a large immune scFv library," Molecules and Cells, 31:509-513, (2011).
Pan, Y. et al., "Viral load of SARS-CoV-2 in clinical samples," The Lancet Infectious Diseases, 20:411-412, (2020).
Phaneuf, C. R. et al., "Integrated LAMP and immunoassay platform for diarrheal disease detection," Biosensors and Bioelectronics, 120:93-101, (2018).
Phaneuf, C. R. et al., "Rapid, portable, multiplexed detection of bacterial pathogens directly from clinical sample matrices," Biosensors, 6:49, (2016).
Phipps, M. L. et al., "Beyond Helper Phage: Using"Helper Cells" to Select Peptide Affinity Ligands," PloS one 11, e0160940 (2016).
Rattanapisit, K. et al., "Rapid production of SARS-CoV-2 receptor binding domain (RBD) and spike specific monoclonal antibody CR3022 in Nicotiana benthamiana," Scientific Reports, 10:1-11, (2020).
Sachdeva, S. et al., "Microfluidic Point-of-Care Testing: Commercial Landscape and Future Directions," Frontiers in Bioengineering and Biotechnology, 8:1537, (2021).
Sblattero, D. et al., "Exploiting recombination in single bacteria to make large phage antibody libraries," Nature Biotechnology, 18:75-80, (2000).
Shi, R. et al., "A human neutralizing antibody targets the receptor-binding site of SARS-CoV-2," Nature 584:120-124, (2020).
Shusta, E. V. et al. "Yeast polypeptide fusion surface display levels predict thermal stability and soluble secretion efficiency," Journal of Molecular Biology, 292:949-956, (1999).
Smith, G. P. et al. "Phage display," Chemical reviews 97:391-410, (1997).
Spellberg, B. et al., "The epidemic of antibiotic-resistant infections: a call to action for the medical community from the Infectious Diseases Society of America," Clinical Infectious Diseases, 46:155-164, (2008).
Stefan, M.A. et al., "Development of potent and effective synthetic SARS-CoV-2 neutralizing nanobodies," MABS, 13(1):1958663, (2021).
Tan, T. J. C. et al., "Sequence signatures of two public antibody clonotypes that bind SARS-CoV-2 receptor binding domain," Nat. Commun., 12:3815, (2021).
Ter Meulen, J. et al., "Human monoclonal antibody combination against SARS coronavirus: synergy and coverage of escape mutants," PLoS Med, 3(7):1071-1079, (2006).
Valldorf, B. et al., "Antibody display technologies: selecting the cream of the crop," Biological Chemistry,403(5-6):455-477, (2022).
Vanhercke, T. et al., Rescue and in Situe Selection and Evaluation (RISE): A Method for High-Throughput Panning of Phage Display LibrariesJ. Biomolecular screening 10(2):108-117, (2005).
Velappan, N. et al., "Fluorescence linked immunosorbant assays using microtiter plates," Journal of Immunological Methods 336:135-141, (2008).
Velappan, N. et al., "Selection and characterization of FcεRI phospho-ITAM specific antibodies," MABS 11:1206-1218, (2019).
Velappan, N. et al., "Selection and characterization of scFv antibodies against the Sin Nombre hantavirus nucleocapsid protein," Journal of Immunological Methods, 321:60-69, (2007).

(56) References Cited

OTHER PUBLICATIONS

Velappan, N. et al., Selection and verification of antibodies against the cytoplasmic domain of M2 of influenza, a transmembrane protein, MABS, 12(1):e1843754-1-10, (2020).
Walsh, III, D. I. et al., "A centrifugal fluidic immunoassay for ocular diagnostics with an enzymatically hydrolyzed fluorogenic substrate," Lab on a Chip, 14:2673-2680, (2014).
Wang, P. et al., "Antibody resistance of SARS-CoV-2 variants B. 1.351 and B. 1.1. 7.," Nature 1-6, (2021).
Wentz, A. E. et al., "A novel high-throughput screen reveals yeast genes that increase secretion of heterologous proteins" Applied and Environmental Microbiology, 73:1189-1198, (2007).
Wrapp, D. et al., "Cryo-EM structure of the 2019-nCOV spike in the prefusion confirmation," Science 367:1260-1263, (2020).
Wu, F. et al., "A new coronavirus associated with human respiratory disease in China," Nature, 579:265-269, (2020).
Wu, Y. et al., "Identification of human single-domain antibodies against SARS-CoV-2," Cell host & microbe, 27:891-898. e895, (2020).
Xia, S. et al., "Fusion mechanism of 2019-nCOV and fusion inhibitors targeting HR1 domain in spike protein," Cellular & Molecular Immunology, 17:765-767, (2020).
Xu, J. L. et al., "Diversity in the CDR3 region of VH is sufficient for most antibody specificities" Immunity, 13:37-45, (2000).
Yang, J. et al., "Molecular interaction and inhibition of SARS-CoV-2 binding to the ACE2 receptor," Nature Communications, 11:1-10, (2020).
Ye, J. et al., "IgBLAST: an immunoglobulin variable domain sequence analysis tool," Nucleic Acids Research, 41:W34-W40, (2013).
Yuan, M. et al., "A highly conserved cryptic epitope in the receptor binding domains of SARS-CoV-2 and SARS-CoV," Science, 368:630-633, (2020).
Zeng, X. et al., "Isolation of a human monoclonal antibody specific for the receptor binding domain of SARS-CoV-2 using a competitive phage biopanning strategy," Antibody Therapeutics, 3:95-100, (2020).
Zhang, S. et al., "Development of resistance to passive therapy with a potently neutralizing humanized monoclonal antibody against West Nile virus," The Journal of Infectious Diseases, 200:202-205, (2009).
Zhou, P. et al., "A pneumonia outbreak associated with a new coronavirus of probable bat origin," Nature, 579:270-273, (2020).

| | D07 | H01 | E01 | R26 | D11 | D12 |
|---|---|---|---|---|---|---|
| D07 | | 96.9% | 67.6% | 66.2% | 69.8% | 67.1% |
| H01 | 96.9% | | 66.0% | 66.2% | 69.8% | 66.7% |
| E01 | 67.6% | 66.0% | | 64.4% | 66.3% | 65.1% |
| R26 | 66.2% | 66.2% | 64.4% | | 80.2% | 79.4% |
| D11 | 69.8% | 69.8% | 66.3% | 80.2% | | 82.0% |
| D12 | 67.1% | 66.7% | 65.1% | 79.4% | 82.0% | |
| H03 | 68.6% | 68.6% | 67.4% | 81.3% | 83.9% | 88.6% |
| R09 | 55.4% | 57.0% | 59.4% | 62.3% | 66.1% | 62.5% |
| H05 | 62.1% | 62.1% | 64.8% | 69.0% | 69.0% | 68.2% |
| D04 | 61.4% | 61.0% | 64.2% | 68.8% | 69.5% | 69.4% |
| E08 | 63.5% | 63.1% | 66.3% | 70.0% | 71.2% | 71.1% |
| B04 | 63.2% | 62.8% | 66.3% | 70.0% | 71.0% | 70.2% |
| F07 | 66.3% | 66.7% | 67.0% | 71.2% | 74.9% | 72.2% |
| D10 | 51.7% | 52.9% | 54.4% | 56.4% | 60.1% | 58.7% |
| G07 | 49.4% | 51.3% | 52.1% | 55.6% | 57.0% | 56.7% |
| B10 | 55.9% | 56.7% | 59.8% | 55.0% | 59.2% | 57.8% |
| H02 | 53.6% | 54.0% | 59.0% | 55.3% | 56.9% | 56.6% |
| R04 | 46.7% | 47.5% | 50.8% | 47.7% | 48.8% | 47.7% |
| S01 | 45.8% | 46.5% | 48.3% | 62.9% | 62.3% | 58.9% |

| | H03 | R09 | H05 | D04 | E08 | B04 |
|---|---|---|---|---|---|---|
| D07 | 68.6% | 55.4% | 62.1% | 61.4% | 63.5% | 63.2% |
| H01 | 68.6% | 57.0% | 62.1% | 61.0% | 63.1% | 62.8% |
| E01 | 67.4% | 59.4% | 64.8% | 64.2% | 66.3% | 66.3% |
| R26 | 81.3% | 62.3% | 69.0% | 68.8% | 70.0% | 70.0% |
| D11 | 83.9% | 66.1% | 69.0% | 69.5% | 71.2% | 71.0% |
| D12 | 88.6% | 62.5% | 68.2% | 69.4% | 71.1% | 70.2% |
| H03 | | 63.4% | 69.4% | 69.8% | 71.9% | 72.8% |
| R09 | 63.4% | | 73.3% | 75.1% | 76.0% | 77.6% |
| H05 | 69.4% | 73.3% | | 90.3% | 91.5% | 82.2% |
| D04 | 69.8% | 75.1% | 90.3% | | 97.6% | 83.0% |
| E08 | 71.9% | 76.0% | 91.5% | 97.6% | | 84.3% |
| B04 | 72.8% | 77.6% | 82.2% | 83.0% | 84.3% | |
| F07 | 75.6% | 76.0% | 81.4% | 81.8% | 83.5% | 90.0% |
| D10 | 57.6% | 64.7% | 62.7% | 63.9% | 63.3% | 64.4% |
| G07 | 57.2% | 61.4% | 58.8% | 61.2% | 60.9% | 61.3% |
| B10 | 57.9% | 52.6% | 51.0% | 53.1% | 52.9% | 53.7% |
| H02 | 57.1% | 53.5% | 53.6% | 55.4% | 55.6% | 54.1% |
| R04 | 49.0% | 44.0% | 45.2% | 45.3% | 45.9% | 44.3% |
| S01 | 60.2% | 51.8% | 49.6% | 49.8% | 50.4% | 53.6% |

| | F07 | D10 | G07 | B10 | H02 | R04 | S01 |
|---|---|---|---|---|---|---|---|
| D07 | 66.3% | 51.7% | 49.4% | 55.9% | 53.6% | 46.7% | 45.8% |
| H01 | 66.7% | 52.9% | 51.3% | 56.7% | 54.0% | 47.5% | 46.5% |
| E01 | 67.0% | 54.4% | 52.1% | 59.8% | 59.0% | 50.8% | 48.3% |
| R26 | 71.2% | 56.4% | 55.6% | 55.0% | 55.3% | 47.7% | 62.9% |
| D11 | 74.9% | 60.1% | 57.0% | 59.2% | 56.9% | 48.8% | 62.3% |
| D12 | 72.2% | 58.7% | 56.7% | 57.8% | 56.6% | 47.7% | 58.9% |
| H03 | 75.6% | 57.6% | 57.2% | 57.9% | 57.1% | 49.0% | 60.2% |
| R09 | 76.0% | 64.7% | 61.4% | 52.6% | 53.5% | 44.0% | 51.8% |
| H05 | 81.4% | 62.7% | 58.8% | 51.0% | 53.6% | 45.2% | 49.6% |
| D04 | 81.8% | 63.9% | 61.2% | 53.1% | 55.4% | 45.3% | 49.8% |
| E08 | 83.5% | 63.3% | 60.9% | 52.9% | 55.6% | 45.9% | 50.4% |
| B04 | 90.0% | 64.4% | 61.3% | 53.7% | 54.1% | 44.3% | 53.6% |
| F07 | | 64.8% | 62.1% | 56.1% | 53.3% | 45.1% | 52.4% |
| D10 | 64.8% | | 86.1% | 66.7% | 62.7% | 46.3% | 54.8% |
| G07 | 62.1% | 86.1% | | 63.9% | 60.4% | 46.5% | 53.0% |
| B10 | 56.1% | 66.7% | 63.9% | | 85.8% | 66.5% | 53.5% |
| H02 | 53.3% | 62.7% | 60.4% | 85.8% | | 69.0% | 53.7% |
| R04 | 45.1% | 46.3% | 46.5% | 66.5% | 69.0% | | 69.6% |
| S01 | 52.4% | 54.8% | 53.0% | 53.5% | 53.7% | 69.6% | |

FIG. 3A-3

| | D07 | H01 | E01 | R26 | D11 | D12 | H03 | R09 |
|---|---|---|---|---|---|---|---|---|
| D07 | | 99.2% | 82.8% | 85.0% | 86.4% | 84.9% | 86.0% | 77.9% |
| H01 | 99.2% | | 82.1% | 84.2% | 85.7% | 84.1% | 85.3% | 78.7% |
| E01 | 82.8% | 82.1% | | 82.0% | 83.5% | 81.6% | 82.4% | 76.2% |
| R26 | 85.0% | 84.2% | 82.0% | | 91.1% | 90.3% | 90.3% | 82.5% |
| D11 | 86.4% | 85.7% | 83.5% | 91.1% | | 90.6% | 92.9% | 86.2% |
| D12 | 84.9% | 84.1% | 81.6% | 90.3% | 90.6% | | 94.1% | 84.5% |
| H03 | 86.0% | 85.3% | 82.4% | 90.3% | 92.9% | 94.1% | | 83.9% |
| R09 | 77.9% | 78.7% | 76.2% | 82.5% | 86.2% | 84.2% | 83.9% | |
| H05 | 79.7% | 79.3% | 79.3% | 84.1% | 84.9% | 84.5% | 84.9% | 84.5% |
| D04 | 80.3% | 79.9% | 80.8% | 84.4% | 85.9% | 85.5% | 84.7% | 86.2% |
| E08 | 80.4% | 80.0% | 81.2% | 84.4% | 86.4% | 86.3% | 85.5% | 86.6% |
| B04 | 80.6% | 80.2% | 79.3% | 85.6% | 87.8% | 88.5% | 88.6% | 88.0% |
| F07 | 82.6% | 82.2% | 80.8% | 86.4% | 89.0% | 88.1% | 90.2% | 87.2% |
| D10 | 75.9% | 76.2% | 75.7% | 80.3% | 82.6% | 83.9% | 81.3% | 84.5% |
| G07 | 74.3% | 74.3% | 73.4% | 78.4% | 79.5% | 80.3% | 79.8% | 81.7% |
| B10 | 78.9% | 79.3% | 75.9% | 76.0% | 79.2% | 80.9% | 79.2% | 75.9% |
| H02 | 78.5% | 78.2% | 75.9% | 75.6% | 78.5% | 81.3% | 78.4% | 77.2% |
| R04 | 72.0% | 71.6% | 69.5% | 70.2% | 71.9% | 73.4% | 71.8% | 69.0% |
| S01 | 71.9% | 71.5% | 71.5% | 77.2% | 79.8% | 77.5% | 76.6% | 77.5% |

FIG. 3B-1

| | H05 | D04 | E08 | B04 | F07 | D10 | G07 | B10 |
|---|---|---|---|---|---|---|---|---|
| D07 | 79.7% | 80.3% | 80.4% | 80.6% | 82.6% | 75.9% | 74.3% | 78.9% |
| H01 | 79.3% | 79.9% | 80.0% | 80.2% | 82.2% | 76.2% | 74.3% | 79.3% |
| E01 | 79.3% | 80.8% | 81.2% | 79.3% | 80.8% | 75.7% | 73.4% | 75.9% |
| R26 | 84.1% | 84.4% | 84.4% | 85.6% | 86.4% | 80.3% | 78.4% | 76.0% |
| D11 | 84.9% | 85.9% | 86.4% | 87.8% | 89.0% | 82.6% | 79.5% | 79.2% |
| D12 | 84.5% | 85.5% | 86.3% | 88.5% | 88.1% | 83.9% | 80.3% | 80.9% |
| H03 | 84.9% | 84.7% | 85.5% | 88.6% | 90.2% | 81.3% | 79.8% | 79.2% |
| R09 | 84.5% | 86.2% | 86.6% | 88.0% | 87.2% | 84.5% | 81.7% | 75.9% |
| H05 | | 94.2% | 94.2% | 88.4% | 88.0% | 82.7% | 80.0% | 73.4% |
| D04 | 94.2% | | 99.2% | 89.7% | 89.3% | 84.7% | 82.7% | 75.2% |
| E08 | 94.2% | 99.2% | | 89.8% | 89.4% | 85.2% | 82.8% | 75.7% |
| B04 | 88.4% | 89.7% | 89.8% | | 95.2% | 84.6% | 81.4% | 76.9% |
| F07 | 88.0% | 89.3% | 89.4% | 95.2% | | 85.4% | 82.6% | 78.4% |
| D10 | 82.7% | 84.7% | 85.2% | 84.6% | 85.4% | | 93.7% | 82.4% |
| G07 | 80.0% | 82.7% | 82.8% | 81.4% | 82.6% | 93.7% | | 82.5% |
| B10 | 73.4% | 75.2% | 75.7% | 76.9% | 78.4% | 82.4% | 82.5% | |
| H02 | 74.9% | 77.1% | 77.2% | 77.3% | 76.9% | 82.4% | 80.0% | 94.1% |
| R04 | 66.2% | 67.4% | 68.3% | 68.6% | 71.4% | 70.6% | 71.3% | 82.7% |
| S01 | 73.5% | 75.3% | 76.2% | 77.8% | 78.6% | 78.2% | 77.7% | 76.0% |

FIG. 3B-2

| | H02 | R04 | S01 |
|---|---|---|---|
| D07 | 78.5% | 72.0% | 71.9% |
| H01 | 78.2% | 71.6% | 71.5% |
| E01 | 75.9% | 69.5% | 71.5% |
| R26 | 75.6% | 70.2% | 77.2% |
| D11 | 78.5% | 71.9% | 79.8% |
| D12 | 81.3% | 73.4% | 77.5% |
| H03 | 78.4% | 71.8% | 76.6% |
| R09 | 77.2% | 69.0% | 77.5% |
| H05 | 74.9% | 66.2% | 73.5% |
| D04 | 77.1% | 67.4% | 75.3% |
| E08 | 77.2% | 68.3% | 76.2% |
| B04 | 77.3% | 68.6% | 77.8% |
| F07 | 76.9% | 71.4% | 78.6% |
| D10 | 82.4% | 70.6% | 78.2% |
| G07 | 80.0% | 71.3% | 77.7% |
| B10 | 94.1% | 82.7% | 76.0% |
| H02 | | 83.9% | 76.9% |
| R04 | 83.9% | | 84.8% |
| S01 | 76.9% | 84.8% | |

FIG. 3B-3

B04 (SEQ ID NO:41)
SYVLTQPPSVSVAPGKTARITCGGNNIGIRSVHWYQQKPGQAPVLVIYYDSDRPSGIPERFSGSKSGNTATLTISRVEAGDEADYYCQV
WDSSSDHPVFGGGTKLTVL*SGGSTITSYNVYYTKLSSSGT*QVQLVESGAEVKKPGASVKVSCKASGYTFTRYYMHWVRQAPGQGLEWMG
IINPSGGTTSYAQKFQGRVTMTRDTSTSTVYMELSSLRSEDTAVYYCARSFGELTSFDYWGQGTLVTVSS

B10 (SEQ ID NO:42)
QSVVTQPPSVSGAPGQRVTISCTGSSSNIGSRTVNWYQQLPGTAPKLLIYANNQRPSGVPDRFSGSKSGTSASLAISGLQSEDEADYYC
AAWDDSLNGYVFGTGTKLTVL*SGGSTITSYNVYYTKLSSSGT*QVQLQQSGPGLVKPSQTLSLTCAISGDSVSSNSATWNWIRQSPSRGL
EWLGRTYYGSKWHSDYAVSVKSRITINPDTSKNQISLHLNPVTPEDTAVYYCARGRSYAFDIWDQGTMVTVSS

D04 (SEQ ID NO:43)
SYVLTQPPSVSVAPGKTARITCGGNNIGWKSVHWYQQKPGQAPVLVVYNDNDRPSGVPERFSGSNSGNTATLTISRVVAGDEADYYCQV
WDSSSDHVLFGGGTKLTVL*SGGSTITSYNVYYTKLSSSGT*QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCARASGRWLQFWHYYGMDVWGQGTTVTVS

D07 (SEQ ID NO:44)
SYELTQPPSVSVAPGETARMTCGGNNIGTKGVHWYQQKPGQAPVLVVYDDSDRPSGIPERFSGSNAGNTATLTISRVEAGDEADYYCQV
WDSRSDQYVFGTRTKLTVL*SGGSTITSYNVYYTKLSSSGA*QVTLKESGPVLVKPTETLTLTCTVSGFSLSNARMGVSWIRQPPGKALEW
LAHIFSNGEKSYSTSLKSRLTISKDTSKSQVVLTMTNMDPVDTATYYCARTLDYYDSSGYLVGGAFDIWGQGTMVTVSS

D10 (SEQ ID NO:45)
QSVVTQPPSASGSPGQTVTISCSGNSANIGGNPVNWYQQLPGTAPKLLIYSNNQRPSGVPDRFSGSKSGISASLAISGLQSEDEADYYC
AAWDDSLNGVIFGGGTKLTVL*SGGSTITSYNVYYTKLSSSGT*QVQLVQSGAEVKKPGESLKISCKGSGYSFTSYWIGWVRQMPGKGLEW
MGIIYPGDSDTRYSPSFQGQVTISADKSISTAYLQWSSLKASDTAMYYCARRHSGSYSGAFDIWGQGTMVTVSS

D11 (SEQ ID NO:46)
SYELTQPPSVSVAPGQTARITCGGNNIGSKSVHWYQQKPGQAPVLVVYDDSDRPSGIPERFSGSNSGNTATLTISGTQAMDEADYYCQA
WDSSTAYVFGSGTKLTVL*SGGSTITSYNVYYTKLSSSGT*QVQLEESGGGLVQPGGSLRLSCAASGFTFSNYAMSWVRQAPGKGLEWVSA
ISGSGGATFHADSVKGRFTISRDNSKNTLYLQMNSLRAEDTAVYYCARRVGYDSSGYYWSDAFDIWGQGTMVTVSS

D12 (SEQ ID NO:66)
SYELTQPPSVSVAPGQTARITCGGNNIGSKPVHWYQQMPGQAPVLVVYDNNNRPSGIPERFSGSNSGNTATLTISRVEAGDEADYFCQV
WDSSSDLWVFGGRTKLTVL*SGGSTITSYNVYYTKLSSSGT*QVQLVESGGGLVQPGRSLRLSCAASGFTFDDYAMHWVRQAPGKGLEWVS
GTSWNSGSIGYADSVKGRFTISRDNAKNSLYLQMNSLRAEDTALYYCAKDKGYYDSSAGFDIWGQGTMVTVSS

FIG. 4A

E01 (SEQ ID NO:47)

SYELTQPPSVSVAPGETARITCGGDNIGRRHVHWYQQKPGQAPVLVIYDDSDRPSGIPDRFSGSNSGNTATLTIGRVEAGDEADYYCQV
WGSSNDPEVFGTGTKLTVL*SGGSTITSNNVYYTKLSSSGT*QVQLQQWGAGLLKPSETLSLKCAVYGGSFSGYYWGWIRQSTGKGLEWIG
EINRSGSTNYNPSLKSRVTISVDTSKNQFSLKLSSVTAADTAVYYCARGGARYYYGSGSYRSTPRPYYFDYWGQGTLVTVSS

E08 (SEQ ID NO:48)

SYVLTQPPSVSVAPGKTARITCGGNNIGWKSVHWYQQKPGQAPVLVVYDDSDRPSGIPERFSGSNSGNTATLTISRVEAGDEADYYCQV
WDSSSDLVVFGGGTKLTVL*SGGSTITSYNVYYTKLSSSG*TQVQLVQSGAEVKKPGSSVKVSCKASGGTFSSYAISWVRQAPGQGLEWMG
GIIPIFGTANYAQKFQGRVTITADESTSTAYMELSSLRSEDTAVYYCARASGRWLQFWEYYGMDVWGQGTTVTVSS

F07 (SEQ ID NO:49)

SYVLTQPPSVSVAPGQTARITCGGNNIGSKSVHWYQQKPGQAPVLVVYDDSDRPSGIPERFSGSNSGNTATLIISRVEAGDEADYYCQV
WDSSSVHYVFGTGTKLTVL*SGGSTITSYNVYYTKLSSSG*TQVQLVQSGAEVKKPGSSVRVSCKVSGYTFTGYYMHWVRQAPGQGLEWMG
IINPSGGSTSYAQKFQGRVTMTRDTSTSTVYMELSSLRSEDTAVYYCARVRVGASDAFDIWGQGTMVTVSS

G07 (SEQ ID NO:50)

QSVLIQPPSASGTPGQRVTISCSGSNSNFGSNSVSWYQQRPGTAPKLLIEGNNQRPSGVPERFSGSKSGTSASLAISGLQSEDEAEYSC
ASWDDSLNAFVFGPGTKLTVL*SGGSAITSYNVYYTKLSSSGT*QVQLVQSGAEVKKPGESLKISCKGSGYSFTSYWIGWVRQMPGKGLEW
MGIIYPGDSDIRYSPSFQGQVTISADKSFSSAYLQWSSLKASDTAMYYCARLGATGAFDIWGQGTTVTVSS

H01 (SEQ ID NO:51)

QPGLTQPPSVSLAPGQTARITCGGNNIGSKSVHWYQQKPGQAPVLVVYDDSDRPSGIPERFSGSNAGNTATLTISRVEAGDEADYYCQV
WDSRSDQYVFGTRTKLTVL*SGGSTITSYNVYYTKLSSSGA*QVTLKESGPVLVKPTETLTLTCTVSGFSLSNARMGVSWIRQPPGKALEW
LAHIFSNGEKSYSTSLKSRLTISKDTSKSQVVLTMTNMDPVDTATYYCARTLDYYDSSGYLVGGAFDIWGQGTMVTVSS

H02 (SEQ ID NO:52)

QSVVTQPPSVSAAPGQKVTISCSGSSSNIGNNYVSWYQQLPGTAPKLLIYRDTQRPSGVPDRFSGSKSGTSASLAISGLRSEDEADYYC
ATWDKSLSGPVFGGGTKVTVL*SGGSTITSYNVYYTKLSSSGT*QVQLQQSGPGLVKPSQTLSLTCAISGDSVSSNSAAWNWIRQSPSRGL
EWLGRTYYRSKWYNDYAVSVKSRIIINPDTSKNQFSLQLNSVTPEDTAVYYCARQDNNPYYGLDVWGQGTTVTVSS

FIG. 4B

H03 (SEQ ID NO:53)

SYELTQPPSVSVAPGQTARITCGGNNIGSKSVHWYQQKPGQAPVLVIYYDSDRPSGIPERFSGSNSGNTATLTISRVEAGDEADYYCQV WDSSSALYVFGTRTKVTVL*SGGSTITSYNVYYTKLSSSGT*QVQLVESGGGLVQPGRSLRLSCAASGFTFDDYAMHWVRQAPGKGLEWVS GISWNSGSIGYADSVKGRFTISRDNAKNSLYLQVNSLRAEDTAVYYCARELIVGTTSPQTDAFDIWGQGTMVTVSS

H05 (SEQ ID NO:54)

SYVLTQPPSVSVAPGQTARITCGANNIGRISVHWYQQKPGQAPVLVVYDDSDRPSGIPERFSGSNFGNTATLTISRVEAGDEADYYCQV WDSYSDEVIFGGGTKLTVL*SGGSTITSYNVYYTKLSSSGT*QVQLVQSGAEVKKPGSSVKVSCKASGGTFSSYAISWVRQAPGQGLEWMG GIIPIFGTANYAQKFQGRVTITADESTSTAYMELSSLRSEDTAVYYCARSIFGVVIISHADGYYYGMDVWGQGTTVTVSS

R04 (SEQ ID NO:55)

EIVMTQSPSSLSASVGDRVTITCQASQDISNYLNWCQQKPGKAPKLLIYDASNLETGVPSRFSGSGSGTGFTFTISSLQPEDFATYYCQ QSYSTPYTFGQGTKVEIK*SGGSTITSYNVNYTKLSSSGA*QVQLQQSGPGLVKSSQTLSLTCAISGDSVSSNGAAWHWIRQSPSRGLEWL GRTYYRSGWYNDYAVSVKSRITINQDTSKNQFSLQLNSVTPEDTAVYFCAREGGGGRMDVWSQGTTVTVSS

R09 (SEQ ID NO:56)

QPGLTQPPSVSVSPGQTASITCSGDKLGYKYVSWYQQKPGQSPVLVIYEDTKRPSGIPKRFSGSNSGNTATLTICGTQAVDEADYYCQA WDSSVVFGGGTKLTVL*SGGSTITSYNVYDTKLSSSGT*QVQLVQSGAEVKKPGASVKVSCKASGYTFTSYGISWVRQAPGQGLEWMGWIS AYNGNTNYAQKFQGRVTMTTDTSTSTAYMELRSLRSDDTAVYYCARDMELRPPFDYWGQGTLVTVSS

R26 (SEQ ID NO:57)

SYELTQPPSVSVAPGQTATITCGGKNIESKSVHWYQQKPGQAPVLVVSDDTDRASGIPERFSGSNSGGAATLTISRVEAGDEADYYCQV WDSPSDEYVFGPGTKLTVL*SGGSTITSYNVYYTKLSSSGT*QVQLVESGGGVVQPGRSLRLSCAASGFTFSSYAMHWVRQAPGKGLEWVA VISYDGSNKYYADSVKGRFTISRDKAKNTLYLQMNSLRGEDTAVYYCARELSYYDSSGYLRGDWYFDLWGRGTLVTVSS

S01 (SEQ ID NO:58)

EIVMTQSPSSLSASVGDSVTITCQASQDISNYLNWYQQKPGKAPKLLIYDASNLETGVPSRFSGGGSGTDFTLTITSLQPEDIATYYCQ QYDNFPPTFGPGTKVDIK*SGGSTITSYNVYYTKLSSSDT*QVQLVESGGGLVKPGGSLRLSCAASGFTVGSNYMSWVRQAPGKGLEWVSV IYSGGSTYYADSVKGRFTISRDNSKNTLYLQMNSLRAEDTAVYYCARGSSGAWYFDLWGRGTLVTVSS

FIG. 4C

| $y = AB_{max}*x/(K_D+x)$ | | |
|---|---|---|
| | Value | Error |
| $AB_{max}$ | 31019 | 1111.7 |
| $K_D$ | 13.907 | 1.5145 |
| Chisq | 4.6997e+6 | NA |
| R | 0.9967 | NA |

| $y = AB_{max}*x/(K_D+x)$ | | |
|---|---|---|
| | Value | Error |
| $AB_{max}$ | 50489 | 1258.8 |
| $K_D$ | 32.994 | 2.9878 |
| Chisq | 1.2137e+7 | NA |
| R | 0.99688 | NA |

| $y = AB_{max}*x/(K_D+x)$ | | |
|---|---|---|
| | Value | Error |
| $AB_{max}$ | 67323 | 4237.2 |
| $K_D$ | 112.78 | 18.864 |
| Chisq | 3.7009e+7 | NA |
| R | 0.99294 | NA |

| $y = AB_{max}*x/(K_D+x)$ | | |
|---|---|---|
| | Value | Error |
| $AB_{max}$ | 1.544e+5 | 4991.2 |
| $K_D$ | 137.55 | 11.138 |
| Chisq | 3.8181e+7 | NA |
| R | 0.99854 | NA |

B04 D04 D07 high D07 low

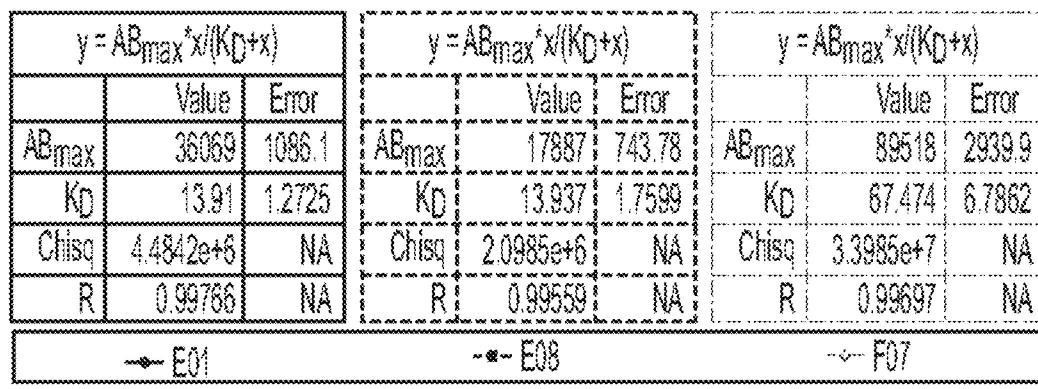
| $y = AB_{max}*x/(K_D+x)$ | | |
|---|---|---|
| | Value | Error |
| $AB_{max}$ | 36069 | 1086.1 |
| $K_D$ | 13.91 | 1.2725 |
| Chisq | 4.4842e+6 | NA |
| R | 0.99766 | NA |
| $y = AB_{max}*x/(K_D+x)$ | | |
|---|---|---|
| | Value | Error |
| $AB_{max}$ | 17887 | 743.78 |
| $K_D$ | 13.937 | 1.7599 |
| Chisq | 2.0985e+6 | NA |
| R | 0.99559 | NA |
| $y = AB_{max}*x/(K_D+x)$ | | |
|---|---|---|
| | Value | Error |
| $AB_{max}$ | 89518 | 2939.9 |
| $K_D$ | 67.474 | 6.7862 |
| Chisq | 3.3985e+7 | NA |
| R | 0.99697 | NA |
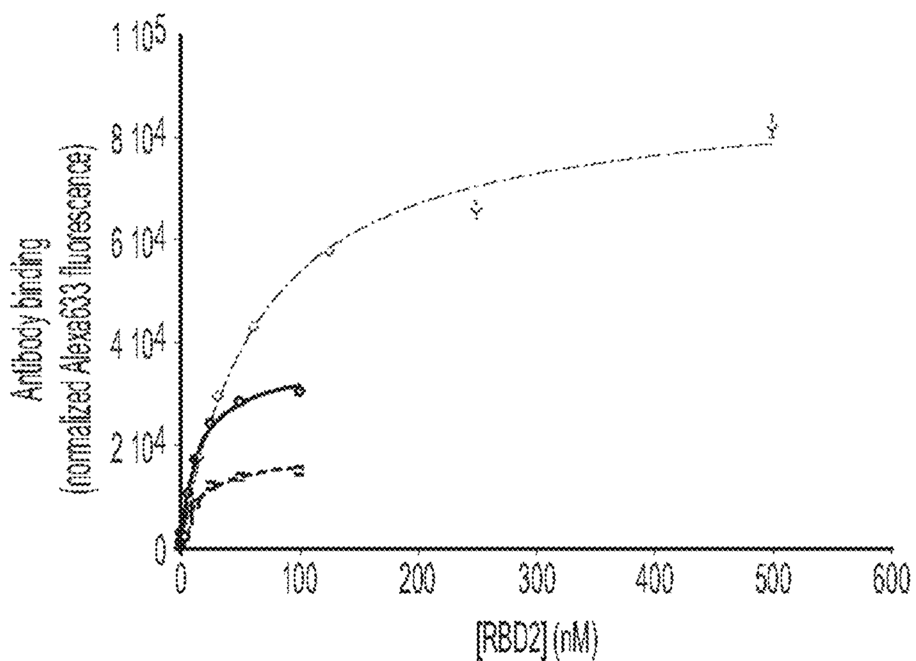
FIG. 8B

| $y = AB_{max}*x/(K_D+x)$ | Value | Error |
|---|---|---|
| $AB_{max}$ | 30053 | 1496.8 |
| $K_D$ | 175.12 | 20.271 |
| Chisq | 2.3014e+6 | NA |
| R | 0.99736 | NA |

| $y = AB_{max}*x/(K_D+x)$ | Value | Error |
|---|---|---|
| $AB_{max}$ | 34719 | 1442.2 |
| $K_D$ | 293.31 | 23.983 |
| Chisq | 7.7378e+5 | NA |
| R | 0.99907 | NA |

| $y = AB_{max}*x/(K_D+x)$ | Value | Error |
|---|---|---|
| $AB_{max}$ | 84320 | 1083.4 |
| $K_D$ | 65.349 | 2.5927 |
| Chisq | 4.7803e+6 | NA |
| R | 0.99953 | NA |

| $y = AB_{max}*x/(K_D+x)$ | Value | Error |
|---|---|---|
| $AB_{max}$ | 36604 | 959.88 |
| $K_D$ | 44.842 | 2.5254 |
| Chisq | 5.9854e+5 | NA |
| R | 0.99949 | NA |

R04 RBD1 R04 RBD2 R26 S01 Z3

FIG. 11B

| | Bins | | | | | | | | | | | |
|---|---|---|---|---|---|---|---|---|---|---|---|---|
| Bins | ID | E08 | CR3022 | H05 | H01 | S01 | E01 | B04 | G07 | F07 | NN54 | ACE2-F |
| | Anti-His | 1.81 | 1.45 | 1.35 | 1.75 | 1.00 | 2.00 | 1.68 | 0.92 | 1.48 | 1.25 | 1.54 |
| | E08 | -0.09 | -0.10 | -0.12 | -0.03 | 1.79 | 2.33 | 2.24 | 1.86 | 1.78 | N/D | 0.67 |
| | CR3022 | -0.08 | -0.14 | -0.15 | -0.05 | 1.39 | 2.39 | 2.22 | 1.56 | 0.90 | N/D | 0.61 |
| | H05 | -0.11 | -0.14 | -0.17 | -0.05 | 1.20 | 2.18 | 1.87 | 1.03 | 1.39 | N/D | 0.08 |
| | H01 | 0.13 | -0.01 | -0.10 | -0.03 | -0.03 | 2.35 | 0.71 | 0.94 | 0.10 | N/D | -0.24 |
| | S01 | 1.85 | 1.83 | 1.73 | -0.11 | -0.03 | 0.03 | -0.59 | 0.43 | 1.28 | 0.95 | -0.08 |
| | E01 | 2.15 | 1.63 | 1.81 | 0.41 | -0.13 | -0.07 | -0.15 | 1.57 | 1.90 | 1.62 | 0.07 |
| | B04 | 2.12 | 1.64 | 1.75 | 0.77 | 0.06 | -0.09 | -0.11 | -0.03 | -0.05 | 1.29 | 1.06 |
| | G07 | 2.62 | 1.35 | 0.90 | 1.28 | 0.11 | 2.43 | -0.07 | -0.05 | 0.14 | 1.85 | 0.73 |
| | F07 | 1.32 | 0.23 | 0.90 | 0.03 | 0.48 | 0.62 | 0.05 | 0.08 | 0.07 | 1.63 | 0.24 |
| | NN54 | N/D | N/D | N/D | N/D | 1.64 | 2.78 | 2.50 | 1.73 | 2.34 | 0.01 | 0.01 |

| ID | ACE2-Fc |
| --- | --- |
| B04 | 1.06 |
| E01 | 0.07 |
| F07 | 0.24 |
| G07 | 0.73 |
| S01 | 0.08 |
| CR3022 | 0.61 |
| NN54 | -0.10 |

SEQUENCE LISTING

```
<160> NUMBER OF SEQ ID NOS: 192

<210> SEQ ID NO 1
<211> LENGTH: 108
<212> TYPE: PRT
<213> ORGANISM: Artificial sequence
<220> FEATURE:
<223> OTHER INFORMATION: Synthesized

<400> SEQUENCE: 1

Ser Tyr Val Leu Thr Gln Pro Pro Ser Val Ser Val Ala Pro Gly Lys
1               5                   10                  15
```

Thr Ala Arg Ile Thr Cys Gly Gly Asn Asn Ile Gly Ile Arg Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Glu Arg Phe Ser Gly Ser
50 55 60

Lys Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Pro Val Phe Gly Gly Gly Thr Lys Leu Thr Val Leu
100 105

<210> SEQ ID NO 2
<211> LENGTH: 110
<212> TYPE: PRT
<213> ORGANISM: Artificial sequence
<220> FEATURE:
<223> OTHER INFORMATION: Synthesized

<400> SEQUENCE: 2

Gln Ser Val Val Thr Gln Pro Pro Ser Val Ser Gly Ala Pro Gly Gln
1 5 10 15

Arg Val Thr Ile Ser Cys Thr Gly Ser Ser Ser Asn Ile Gly Ser Arg
20 25 30

Thr Val Asn Trp Tyr Gln Gln Leu Pro Gly Thr Ala Pro Lys Leu Leu
35 40 45

Ile Tyr Ala Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Tyr Val Phe Gly Thr Gly Thr Lys Leu Thr Val Leu
100 105 110

<210> SEQ ID NO 3
<211> LENGTH: 108
<212> TYPE: PRT
<213> ORGANISM: Artificial sequence
<220> FEATURE:
<223> OTHER INFORMATION: Synthesized

<400> SEQUENCE: 3

Ser Tyr Glu Leu Thr Gln Pro Pro Ser Val Ser Val Ala Pro Gly Glu
1 5 10 15

Thr Ala Arg Met Thr Cys Gly Gly Asn Asn Ile Gly Thr Lys Gly Val
20 25 30

His Trp Tyr Gln Gln Lys Pro Gly Gln Ala Pro Val Leu Val Val Tyr
35 40 45

Asp Asp Ser Asp Arg Pro Ser Gly Ile Pro Glu Arg Phe Ser Gly Ser
50 55 60

Asn Ala Gly Asn Thr Ala Thr Leu Thr Ile Ser Arg Val Glu Ala Gly
65 70 75 80

Asp Glu Ala Asp Tyr Tyr Cys Gln Val Trp Asp Ser Arg Ser Asp Gln
85 90 95

Tyr Val Phe Gly Thr Arg Thr Lys Leu Thr Val Leu

```
            100                 105


<210> SEQ ID NO 4
<211> LENGTH: 110
<212> TYPE: PRT
<213> ORGANISM: Artificial sequence
<220> FEATURE:
<223> OTHER INFORMATION: Synthesized

<400> SEQUENCE: 4

Gln Ser Val Val Thr Gln Pro Pro Ser Ala Ser Gly Ser Pro Gly Gln
1               5                   10                  15

Thr Val Thr Ile Ser Cys Ser Gly Asn Ser Ala Asn Ile Gly Gly Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Ile Phe Gly Gly Gly Thr Lys Leu Thr Val Leu
            100                 105                 110


<210> SEQ ID NO 5
<211> LENGTH: 107
<212> TYPE: PRT
<213> ORGANISM: Artificial sequence
<220> FEATURE:
<223> OTHER INFORMATION: Synthesized

<400> SEQUENCE: 5

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Tyr
                85                  90                  95

Val Phe Gly Ser Gly Thr Lys Leu Thr Val Leu
            100                 105


<210> SEQ ID NO 6
<211> LENGTH: 108
<212> TYPE: PRT
<213> ORGANISM: Artificial sequence
<220> FEATURE:
<223> OTHER INFORMATION: Synthesized

<400> SEQUENCE: 6

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Pro Val
            20                  25                  30
```

```
His Trp Tyr Gln Gln Met Pro Gly Gln Ala Pro Val Leu Val Val Tyr
        35                  40                  45

Asp Asn Asn Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp Leu
                85                  90                  95

Trp Val Phe Gly Gly Arg Thr Lys Leu Thr Val Leu
            100                 105


<210> SEQ ID NO 7
<211> LENGTH: 108
<212> TYPE: PRT
<213> ORGANISM: Artificial sequence
<220> FEATURE:
<223> OTHER INFORMATION: Synthesized

<400> SEQUENCE: 7

Ser Tyr Glu Leu Thr Gln Pro Pro Ser Val Ser Val Ala Pro Gly Glu
1               5                   10                  15

Thr Ala Arg Ile Thr Cys Gly Gly Asp Asn Ile Gly Arg Arg His Val
            20                  25                  30

His Trp Tyr Gln Gln Lys Pro Gly Gln Ala Pro Val Leu Val Ile Tyr
        35                  40                  45

Asp Asp Ser Asp Arg Pro Ser Gly Ile Pro Asp Arg Phe Ser Gly Ser
    50                  55                  60

Asn Ser Gly Asn Thr Ala Thr Leu Thr Ile Gly Arg Val Glu Ala Gly
65                  70                  75                  80

Asp Glu Ala Asp Tyr Tyr Cys Gln Val Trp Gly Ser Ser Asn Asp Pro
                85                  90                  95

His Val Phe Gly Thr Gly Thr Lys Leu Thr Val Leu
            100                 105


<210> SEQ ID NO 8
<211> LENGTH: 108
<212> TYPE: PRT
<213> ORGANISM: Artificial sequence
<220> FEATURE:
<223> OTHER INFORMATION: Synthesized

<400> SEQUENCE: 8

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Val His
                85                  90                  95

Tyr Val Phe Gly Thr Gly Thr Lys Leu Thr Val Leu
            100                 105
```

```
<210> SEQ ID NO 9
<211> LENGTH: 108
<212> TYPE: PRT
<213> ORGANISM: Artificial sequence
<220> FEATURE:
<223> OTHER INFORMATION: Synthesized

<400> SEQUENCE: 9

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Trp Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Val Val Phe Gly Gly Gly Thr Lys Leu Thr Val Leu
            100                 105


<210> SEQ ID NO 10
<211> LENGTH: 108
<212> TYPE: PRT
<213> ORGANISM: Artificial sequence
<220> FEATURE:
<223> OTHER INFORMATION: Synthesized

<400> SEQUENCE: 10

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Val His
                85                  90                  95

Tyr Val Phe Gly Thr Gly Thr Lys Leu Thr Val Leu
            100                 105


<210> SEQ ID NO 11
<211> LENGTH: 110
<212> TYPE: PRT
<213> ORGANISM: Artificial sequence
<220> FEATURE:
<223> OTHER INFORMATION: Synthesized

<400> SEQUENCE: 11

Gln Ser Val Leu Ile Gln Pro Pro Ser Ala Ser Gly Thr Pro Gly Gln
1               5                   10                  15

Arg Val Thr Ile Ser Cys Ser Gly Ser Asn Ser Asn Phe Gly Ser Asn
            20                  25                  30

Ser Val Ser Trp Tyr Gln Gln Arg Pro Gly Thr Ala Pro Lys Leu Leu
        35                  40                  45
```

```
Ile Glu Gly Asn Asn Gln Arg Pro Ser Gly Val Pro Glu Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Ser Cys Ala Ser Trp Asp Asp Ser Leu
                85                  90                  95

Asn Ala Phe Val Phe Gly Pro Gly Thr Lys Leu Thr Val Leu
            100                 105                 110


<210> SEQ ID NO 12
<211> LENGTH: 108
<212> TYPE: PRT
<213> ORGANISM: Artificial sequence
<220> FEATURE:
<223> OTHER INFORMATION: Synthesized

<400> SEQUENCE: 12

Gln Pro Gly Leu Thr Gln Pro Pro Ser Val Ser Leu Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ala Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp Gln
                85                  90                  95

Tyr Val Phe Gly Thr Arg Thr Lys Leu Thr Val Leu
            100                 105


<210> SEQ ID NO 13
<211> LENGTH: 110
<212> TYPE: PRT
<213> ORGANISM: Artificial sequence
<220> FEATURE:
<223> OTHER INFORMATION: Synthesized

<400> SEQUENCE: 13

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Arg Asp Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Lys Ser Leu
                85                  90                  95

Ser Gly Pro Val Phe Gly Gly Gly Thr Lys Val Thr Val Leu
            100                 105                 110


<210> SEQ ID NO 14
<211> LENGTH: 108
<212> TYPE: PRT
```

<213> ORGANISM: Artificial sequence
<220> FEATURE:
<223> OTHER INFORMATION: Synthesized

<400> SEQUENCE: 14

```
Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Ala Leu
                85                  90                  95

Tyr Val Phe Gly Thr Arg Thr Lys Val Thr Val Leu
            100                 105
```

<210> SEQ ID NO 15
<211> LENGTH: 108
<212> TYPE: PRT
<213> ORGANISM: Artificial sequence
<220> FEATURE:
<223> OTHER INFORMATION: Synthesized

<400> SEQUENCE: 15

```
Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Arg Ile Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Phe Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Tyr Ser Asp His
                85                  90                  95

Val Ile Phe Gly Gly Gly Thr Lys Leu Thr Val Leu
            100                 105
```

<210> SEQ ID NO 16
<211> LENGTH: 107
<212> TYPE: PRT
<213> ORGANISM: Artificial sequence
<220> FEATURE:
<223> OTHER INFORMATION: Synthesized

<400> SEQUENCE: 16

```
Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Cys Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Gly Ser Gly Thr Gly Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105


<210> SEQ ID NO 17
<211> LENGTH: 105
<212> TYPE: PRT
<213> ORGANISM: Artificial sequence
<220> FEATURE:
<223> OTHER INFORMATION: Synthesized

<400> SEQUENCE: 17

Gln Pro Gly Leu Thr Gln Pro Pro Ser Val Ser Val Ser Pro Gly Gln
1               5                   10                  15

Thr Ala Ser Ile Thr Cys Ser Gly Asp Lys Leu Gly Tyr Lys Tyr Val
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Gly Ile Pro Lys Arg Phe Ser Gly Ser
    50                  55                  60

Asn Ser Gly Asn Thr Ala Thr Leu Thr Ile Cys Gly Thr Gln Ala Val
65                  70                  75                  80

Asp Glu Ala Asp Tyr Tyr Cys Gln Ala Trp Asp Ser Ser Val Val Phe
                85                  90                  95

Gly Gly Gly Thr Lys Leu Thr Val Leu
            100                 105


<210> SEQ ID NO 18
<211> LENGTH: 108
<212> TYPE: PRT
<213> ORGANISM: Artificial sequence
<220> FEATURE:
<223> OTHER INFORMATION: Synthesized

<400> SEQUENCE: 18

Ser Tyr Glu Leu Thr Gln Pro Pro Ser Val Ser Val Ala Pro Gly Gln
1               5                   10                  15

Thr Ala Thr Ile Thr Cys Gly Gly Lys Asn Ile Glu Ser Lys Ser Val
            20                  25                  30

His Trp Tyr Gln Gln Lys Pro Gly Gln Ala Pro Val Leu Val Val Ser
        35                  40                  45

Asp Asp Thr Asp Arg Ala Ser Gly Ile Pro Glu Arg Phe Ser Gly Ser
    50                  55                  60

Asn Ser Gly Gly Ala Ala Thr Leu Thr Ile Ser Arg Val Glu Ala Gly
65                  70                  75                  80

Asp Glu Ala Asp Tyr Tyr Cys Gln Val Trp Asp Ser Pro Ser Asp His
                85                  90                  95

Tyr Val Phe Gly Pro Gly Thr Lys Leu Thr Val Leu
            100                 105


<210> SEQ ID NO 19
<211> LENGTH: 107
<212> TYPE: PRT
<213> ORGANISM: Artificial sequence
<220> FEATURE:
<223> OTHER INFORMATION: Synthesized
```

<400> SEQUENCE: 19

```
Glu Ile Val Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Gly Gly Ser Gly Thr Asp Phe Thr Leu Thr Ile Thr Ser Leu Gln Pro
65                  70                  75                  80

Glu Asp Ile Ala Thr Tyr Tyr Cys Gln Gln Tyr Asp Asn Phe Pro Pro
                85                  90                  95

Thr Phe Gly Pro Gly Thr Lys Val Asp Ile Lys
            100                 105
```

<210> SEQ ID NO 20
<211> LENGTH: 119
<212> TYPE: PRT
<213> ORGANISM: Artificial sequence
<220> FEATURE:
<223> OTHER INFORMATION: Synthesized

<400> SEQUENCE: 20

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Thr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Gly Glu Leu Thr Ser Phe Asp Tyr Trp Gly Gln Gly
            100                 105                 110

Thr Leu Val Thr Val Ser Ser
        115
```

<210> SEQ ID NO 21
<211> LENGTH: 120
<212> TYPE: PRT
<213> ORGANISM: Artificial sequence
<220> FEATURE:
<223> OTHER INFORMATION: Synthesized

<400> SEQUENCE: 21

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Gly Ser Lys Trp His Ser Asp Tyr Ala
    50                  55                  60
```

```
Val Ser Val Lys Ser Arg Ile Thr Ile Asn Pro Asp Thr Ser Lys Asn
65                  70                  75                  80

Gln Ile Ser Leu His Leu Asn Pro Val Thr Pro Glu Asp Thr Ala Val
                85                  90                  95

Tyr Tyr Cys Ala Arg Gly Arg Ser Tyr Ala Phe Asp Ile Trp Asp Gln
            100                 105                 110

Gly Thr Met Val Thr Val Ser Ser
        115                 120


<210> SEQ ID NO 22
<211> LENGTH: 128
<212> TYPE: PRT
<213> ORGANISM: Artificial sequence
<220> FEATURE:
<223> OTHER INFORMATION: Synthesized

<400> SEQUENCE: 22

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Gly Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Thr Leu Asp Tyr Tyr Asp Ser Ser Gly Tyr Leu Val Gly
            100                 105                 110

Gly Ala Phe Asp Ile Trp Gly Gln Gly Thr Met Val Thr Val Ser Ser
        115                 120                 125


<210> SEQ ID NO 23
<211> LENGTH: 121
<212> TYPE: PRT
<213> ORGANISM: Artificial sequence
<220> FEATURE:
<223> OTHER INFORMATION: Synthesized

<400> SEQUENCE: 23

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg His Ser Gly Ser Tyr Ser Gly Ala Phe Asp Ile Trp Gly
            100                 105                 110

Gln Gly Thr Met Val Thr Val Ser Ser
```

```
        115                 120


<210> SEQ ID NO 24
<211> LENGTH: 126
<212> TYPE: PRT
<213> ORGANISM: Artificial sequence
<220> FEATURE:
<223> OTHER INFORMATION: Synthesized

<400> SEQUENCE: 24

Gln Val Gln Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ala Thr Phe His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Gly Tyr Asp Ser Ser Gly Tyr Tyr Trp Ser Asp Ala
            100                 105                 110

Phe Asp Ile Trp Gly Gln Gly Thr Met Val Thr Val Ser Ser
        115                 120                 125


<210> SEQ ID NO 25
<211> LENGTH: 122
<212> TYPE: PRT
<213> ORGANISM: Artificial sequence
<220> FEATURE:
<223> OTHER INFORMATION: Synthesized

<400> SEQUENCE: 25

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Thr Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Gly Tyr Tyr Asp Ser Ser Ala Gly Phe Asp Ile Trp
            100                 105                 110

Gly Gln Gly Thr Met Val Thr Val Ser Ser
        115                 120


<210> SEQ ID NO 26
<211> LENGTH: 131
<212> TYPE: PRT
<213> ORGANISM: Artificial sequence
<220> FEATURE:
<223> OTHER INFORMATION: Synthesized

<400> SEQUENCE: 26
```

```
Gln Val Gln Leu Gln Gln Trp Gly Ala Gly Leu Leu Lys Pro Ser Glu
1               5                   10                  15

Thr Leu Ser Leu Lys Cys Ala Val Tyr Gly Gly Ser Phe Ser Gly Tyr
            20                  25                  30

Tyr Trp Gly Trp Ile Arg Gln Ser Thr Gly Lys Gly Leu Glu Trp Ile
        35                  40                  45

Gly Glu Ile Asn Arg Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ala Arg Tyr Tyr Tyr Gly Ser Gly Ser Tyr Arg Ser Thr
            100                 105                 110

Pro Arg Pro Tyr Tyr Phe Asp Tyr Trp Gly Gln Gly Thr Leu Val Thr
        115                 120                 125

Val Ser Ser
    130


<210> SEQ ID NO 27
<211> LENGTH: 120
<212> TYPE: PRT
<213> ORGANISM: Artificial sequence
<220> FEATURE:
<223> OTHER INFORMATION: Synthesized

<400> SEQUENCE: 27

Gln Val Gln Leu Val Gln Ser Gly Ala Glu Val Lys Lys Pro Gly Ser
1               5                   10                  15

Ser Val Arg Val Ser Cys Lys Val Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Arg Val Gly Ala Ser Asp Ala Phe Asp Ile Trp Gly Gln
            100                 105                 110

Gly Thr Met Val Thr Val Ser Ser
        115                 120


<210> SEQ ID NO 28
<211> LENGTH: 125
<212> TYPE: PRT
<213> ORGANISM: Artificial sequence
<220> FEATURE:
<223> OTHER INFORMATION: Synthesized

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Gly Arg Trp Leu Gln Phe Trp His Tyr Tyr Gly Met
            100                 105                 110

Asp Val Trp Gly Gln Gly Thr Thr Val Thr Val Ser Ser
        115                 120                 125


<210> SEQ ID NO 29
<211> LENGTH: 120
<212> TYPE: PRT
<213> ORGANISM: Artificial sequence
<220> FEATURE:
<223> OTHER INFORMATION: Synthesized

<400> SEQUENCE: 29

Gln Val Gln Leu Val Gln Ser Gly Ala Glu Val Lys Lys Pro Gly Ser
1               5                   10                  15

Ser Val Arg Val Ser Cys Lys Val Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Arg Val Gly Ala Ser Asp Ala Phe Asp Ile Trp Gly Gln
            100                 105                 110

Gly Thr Met Val Thr Val Ser Ser
        115                 120


<210> SEQ ID NO 30
<211> LENGTH: 118
<212> TYPE: PRT
<213> ORGANISM: Artificial sequence
<220> FEATURE:
<223> OTHER INFORMATION: Synthesized

<400> SEQUENCE: 30

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Phe Ser Ser Ala Tyr
65                  70                  75                  80

Leu Gln Trp Ser Ser Leu Lys Ala Ser Asp Thr Ala Met Tyr Tyr Cys
                85                  90                  95
```

```
Ala Arg Leu Gly Ala Thr Gly Ala Phe Asp Ile Trp Gly Gln Gly Thr
            100                 105                 110

Thr Val Thr Val Ser Ser
        115


<210> SEQ ID NO 31
<211> LENGTH: 128
<212> TYPE: PRT
<213> ORGANISM: Artificial sequence
<220> FEATURE:
<223> OTHER INFORMATION: Synthesized

<400> SEQUENCE: 31

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Gly Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Thr Leu Asp Tyr Tyr Asp Ser Ser Gly Tyr Leu Val Gly
            100                 105                 110

Gly Ala Phe Asp Ile Trp Gly Gln Gly Thr Met Val Thr Val Ser Ser
        115                 120                 125


<210> SEQ ID NO 32
<211> LENGTH: 123
<212> TYPE: PRT
<213> ORGANISM: Artificial sequence
<220> FEATURE:
<223> OTHER INFORMATION: Synthesized

<400> SEQUENCE: 32

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Asp Asn Asn Pro Tyr Tyr Gly Leu Asp Val
            100                 105                 110

Trp Gly Gln Gly Thr Thr Val Thr Val Ser Ser
        115                 120


<210> SEQ ID NO 33
<211> LENGTH: 125
<212> TYPE: PRT
<213> ORGANISM: Artificial sequence
```

<220> FEATURE:
<223> OTHER INFORMATION: Synthesized

<400> SEQUENCE: 33

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Val Asn Ser Leu Arg Ala Glu Asp Thr Ala Val Tyr Tyr Cys
                85                  90                  95

Ala Arg Glu Leu Ile Val Gly Thr Thr Ser Pro Gln Thr Asp Ala Phe
            100                 105                 110

Asp Ile Trp Gly Gln Gly Thr Met Val Thr Val Ser Ser
        115                 120                 125
```

<210> SEQ ID NO 34
<211> LENGTH: 129
<212> TYPE: PRT
<213> ORGANISM: Artificial sequence
<220> FEATURE:
<223> OTHER INFORMATION: Synthesized

<400> SEQUENCE: 34

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Phe Gly Val Val Ile Ile Ser His Ala Asp Gly Tyr
            100                 105                 110

Tyr Tyr Gly Met Asp Val Trp Gly Gln Gly Thr Thr Val Thr Val Ser
        115                 120                 125

Ser
```

<210> SEQ ID NO 35
<211> LENGTH: 121
<212> TYPE: PRT
<213> ORGANISM: Artificial sequence
<220> FEATURE:
<223> OTHER INFORMATION: Synthesized

<400> SEQUENCE: 35

```
Gln Val Gln Leu Gln Gln Ser Gly Pro Gly Leu Val Lys Ser Ser Gln
1               5                   10                  15

Thr Leu Ser Leu Thr Cys Ala Ile Ser Gly Asp Ser Val Ser Ser Asn
```

```
            20                  25                  30

Gly Ala Ala Trp His Trp Ile Arg Gln Ser Pro Ser Arg Gly Leu Glu
        35                  40                  45

Trp Leu Gly Arg Thr Tyr Tyr Arg Ser Gly Trp Tyr Asn Asp Tyr Ala
    50                  55                  60

Val Ser Val Lys Ser Arg Ile Thr Ile Asn Gln Asp Thr Ser Lys Asn
65                  70                  75                  80

Gln Phe Ser Leu Gln Leu Asn Ser Val Thr Pro Glu Asp Thr Ala Val
                85                  90                  95

Tyr Phe Cys Ala Arg Glu Gly Gly Gly Gly Arg Met Asp Val Trp Ser
            100                 105                 110

Gln Gly Thr Thr Val Thr Val Ser Ser
        115                 120


<210> SEQ ID NO 36
<211> LENGTH: 119
<212> TYPE: PRT
<213> ORGANISM: Artificial sequence
<220> FEATURE:
<223> OTHER INFORMATION: Synthesized

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Met Glu Leu Arg Pro Pro Phe Asp Tyr Trp Gly Gln Gly
            100                 105                 110

Thr Leu Val Thr Val Ser Ser
        115


<210> SEQ ID NO 37
<211> LENGTH: 128
<212> TYPE: PRT
<213> ORGANISM: Artificial sequence
<220> FEATURE:
<223> OTHER INFORMATION: Synthesized

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Lys Ala Lys Asn Thr Leu Tyr
65                  70                  75                  80
```

```
Leu Gln Met Asn Ser Leu Arg Gly Glu Asp Thr Ala Val Tyr Tyr Cys
                85                  90                  95

Ala Arg Glu Leu Ser Tyr Tyr Asp Ser Ser Gly Tyr Leu Arg Gly Asp
            100                 105                 110

Trp Tyr Phe Asp Leu Trp Gly Arg Gly Thr Leu Val Thr Val Ser Ser
        115                 120                 125
```

<210> SEQ ID NO 38
<211> LENGTH: 118
<212> TYPE: PRT
<213> ORGANISM: Artificial sequence
<220> FEATURE:
<223> OTHER INFORMATION: Synthesized

<400> SEQUENCE: 38

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Val Gly Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ser Gly Ala Trp Tyr Phe Asp Leu Trp Gly Arg Gly Thr
            100                 105                 110

Leu Val Thr Val Ser Ser
        115
```

<210> SEQ ID NO 39
<211> LENGTH: 21
<212> TYPE: PRT
<213> ORGANISM: Artificial sequence
<220> FEATURE:
<223> OTHER INFORMATION: Synthesized

<400> SEQUENCE: 39

```
Ser Gly Gly Ser Thr Ile Thr Ser Asn Asn Val Tyr Tyr Thr Lys Leu
1               5                   10                  15

Ser Ser Ser Gly Thr
            20
```

<210> SEQ ID NO 40
<211> LENGTH: 21
<212> TYPE: PRT
<213> ORGANISM: Artificial sequence
<220> FEATURE:
<223> OTHER INFORMATION: Synthesized

<400> SEQUENCE: 40

```
Ser Gly Gly Ser Ala Ile Thr Ser Tyr Asn Val Tyr Tyr Thr Lys Leu
1               5                   10                  15

Ser Ser Ser Gly Thr
            20
```

<210> SEQ ID NO 41
<211> LENGTH: 248
<212> TYPE: PRT

<213> ORGANISM: Artificial sequence
<220> FEATURE:
<223> OTHER INFORMATION: Synthesized

<400> SEQUENCE: 41

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ile Arg Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Val Phe Gly Gly Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Glu Ser Gly Ala Glu Val Lys Lys Pro Gly
    130                 135                 140

Ala Ser Val Lys Val Ser Cys Lys Ala Ser Gly Tyr Thr Phe Thr Arg
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Thr Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Ser Phe Gly Glu Leu Thr Ser Phe Asp Tyr Trp Gly Gln
225                 230                 235                 240

Gly Thr Leu Val Thr Val Ser Ser
                245
```

<210> SEQ ID NO 42
<211> LENGTH: 251
<212> TYPE: PRT
<213> ORGANISM: Artificial sequence
<220> FEATURE:
<223> OTHER INFORMATION: Synthesized

<400> SEQUENCE: 42

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Arg
            20                  25                  30

Thr Val Asn Trp Tyr Gln Gln Leu Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu Ser Gly
            100                 105                 110

Gly Ser Thr Ile Thr Ser Tyr Asn Val Tyr Tyr Thr Lys Leu Ser Ser
        115                 120                 125

Ser Gly Thr Gln Val Gln Leu Gln Gln Ser Gly Pro Gly Leu Val Lys
    130                 135                 140

Pro Ser Gln Thr Leu Ser Leu Thr Cys Ala Ile Ser Gly Asp Ser Val
145                 150                 155                 160

Ser Ser Asn Ser Ala Thr Trp Asn Trp Ile Arg Gln Ser Pro Ser Arg
                165                 170                 175

Gly Leu Glu Trp Leu Gly Arg Thr Tyr Tyr Gly Ser Lys Trp His Ser
            180                 185                 190

Asp Tyr Ala Val Ser Val Lys Ser Arg Ile Thr Ile Asn Pro Asp Thr
        195                 200                 205

Ser Lys Asn Gln Ile Ser Leu His Leu Asn Pro Val Thr Pro Glu Asp
    210                 215                 220

Thr Ala Val Tyr Tyr Cys Ala Arg Gly Arg Ser Tyr Ala Phe Asp Ile
225                 230                 235                 240

Trp Asp Gln Gly Thr Met Val Thr Val Ser Ser
                245                 250
```

<210> SEQ ID NO 43
<211> LENGTH: 253
<212> TYPE: PRT
<213> ORGANISM: Artificial sequence
<220> FEATURE:
<223> OTHER INFORMATION: Synthesized

<400> SEQUENCE: 43

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Trp Lys Ser Val
            20                  25                  30

His Trp Tyr Gln Gln Lys Pro Gly Gln Ala Pro Val Leu Val Val Tyr
        35                  40                  45

Asn Asp Asn Asp Arg Pro Ser Gly Val Pro Glu Arg Phe Ser Gly Ser
    50                  55                  60

Asn Ser Gly Asn Thr Ala Thr Leu Thr Ile Ser Arg Val Val Ala Gly
65                  70                  75                  80

Asp Glu Ala Asp Tyr Tyr Cys Gln Val Trp Asp Ser Ser Ser Asp His
                85                  90                  95

Val Leu Phe Gly Gly Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Gln Ser Gly Ala Glu Val Lys Lys Pro Gly
    130                 135                 140

Ser Ser Val Lys Val Ser Cys Lys Ala Ser Gly Gly Thr Phe Ser Ser
145                 150                 155                 160

Tyr Ala Ile Ser Trp Val Arg Gln Ala Pro Gly Gln Gly Leu Glu Trp
                165                 170                 175

Met Gly Gly Ile Ile Pro Ile Phe Gly Thr Ala Asn Tyr Ala Gln Lys
            180                 185                 190
```

```
Phe Gln Gly Arg Val Thr Ile Thr Ala Asp Glu Ser Thr Ser Thr Ala
        195                 200                 205

Tyr Met Glu Leu Ser Ser Leu Arg Ser Glu Asp Thr Ala Val Tyr Tyr
    210                 215                 220

Cys Ala Arg Ala Ser Gly Arg Trp Leu Gln Phe Trp His Tyr Tyr Gly
225                 230                 235                 240

Met Asp Val Trp Gly Gln Gly Thr Thr Val Thr Val Ser
                245                 250


<210> SEQ ID NO 44
<211> LENGTH: 257
<212> TYPE: PRT
<213> ORGANISM: Artificial sequence
<220> FEATURE:
<223> OTHER INFORMATION: Synthesized

<400> SEQUENCE: 44

Ser Tyr Glu Leu Thr Gln Pro Pro Ser Val Ser Val Ala Pro Gly Glu
1               5                   10                  15

Thr Ala Arg Met Thr Cys Gly Gly Asn Asn Ile Gly Thr Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ala Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp Gln
                85                  90                  95

Tyr Val Phe Gly Thr Arg Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Ala Gln Val Thr Leu Lys Glu Ser Gly Pro Val Leu Val Lys Pro Thr
    130                 135                 140

Glu Thr Leu Thr Leu Thr Cys Thr Val Ser Gly Phe Ser Leu Ser Asn
145                 150                 155                 160

Ala Arg Met Gly Val Ser Trp Ile Arg Gln Pro Pro Gly Lys Ala Leu
                165                 170                 175

Glu Trp Leu Ala His Ile Phe Ser Asn Gly Glu Lys Ser Tyr Ser Thr
            180                 185                 190

Ser Leu Lys Ser Arg Leu Thr Ile Ser Lys Asp Thr Ser Lys Ser Gln
        195                 200                 205

Val Val Leu Thr Met Thr Asn Met Asp Pro Val Asp Thr Ala Thr Tyr
    210                 215                 220

Tyr Cys Ala Arg Thr Leu Asp Tyr Tyr Asp Ser Ser Gly Tyr Leu Val
225                 230                 235                 240

Gly Gly Ala Phe Asp Ile Trp Gly Gln Gly Thr Met Val Thr Val Ser
                245                 250                 255

Ser


<210> SEQ ID NO 45
<211> LENGTH: 252
<212> TYPE: PRT
<213> ORGANISM: Artificial sequence
<220> FEATURE:
<223> OTHER INFORMATION: Synthesized
```

<400> SEQUENCE: 45

```
Gln Ser Val Val Thr Gln Pro Pro Ser Ala Ser Gly Ser Pro Gly Gln
1               5                   10                  15

Thr Val Thr Ile Ser Cys Ser Gly Asn Ser Ala Asn Ile Gly Gly Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Ile Phe Gly Gly Gly Thr Lys Leu Thr Val Leu Ser Gly
            100                 105                 110

Gly Ser Thr Ile Thr Ser Tyr Asn Val Tyr Tyr Thr Lys Leu Ser Ser
        115                 120                 125

Ser Gly Thr Gln Val Gln Leu Val Gln Ser Gly Ala Glu Val Lys Lys
    130                 135                 140

Pro Gly Glu Ser Leu Lys Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

Glu Trp Met Gly Ile Ile Tyr Pro Gly Asp Ser Asp Thr Arg Tyr Ser
            180                 185                 190

Pro Ser Phe Gln Gly Gln Val Thr Ile Ser Ala Asp Lys Ser Ile Ser
        195                 200                 205

Thr Ala Tyr Leu Gln Trp Ser Ser Leu Lys Ala Ser Asp Thr Ala Met
    210                 215                 220

Tyr Tyr Cys Ala Arg Arg His Ser Gly Ser Tyr Ser Gly Ala Phe Asp
225                 230                 235                 240

Ile Trp Gly Gln Gly Thr Met Val Thr Val Ser Ser
                245                 250
```

<210> SEQ ID NO 46
<211> LENGTH: 254
<212> TYPE: PRT
<213> ORGANISM: Artificial sequence
<220> FEATURE:
<223> OTHER INFORMATION: Synthesized

<400> SEQUENCE: 46

```
Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Tyr
                85                  90                  95
```

```
Val Phe Gly Ser Gly Thr Lys Leu Thr Val Leu Ser Gly Gly Ser Thr
            100                 105                 110

Ile Thr Ser Tyr Asn Val Tyr Tyr Thr Lys Leu Ser Ser Ser Gly Thr
        115                 120                 125

Gln Val Gln Leu Glu Glu Ser Gly Gly Gly Leu Val Gln Pro Gly Gly
    130                 135                 140

Ser Leu Arg Leu Ser Cys Ala Ala Ser Gly Phe Thr Phe Ser Asn Tyr
145                 150                 155                 160

Ala Met Ser Trp Val Arg Gln Ala Pro Gly Lys Gly Leu Glu Trp Val
                165                 170                 175

Ser Ala Ile Ser Gly Ser Gly Gly Ala Thr Phe His Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Arg Val Gly Tyr Asp Ser Ser Gly Tyr Tyr Trp Ser Asp Ala
225                 230                 235                 240

Phe Asp Ile Trp Gly Gln Gly Thr Met Val Thr Val Ser Ser
                245                 250


<210> SEQ ID NO 47
<211> LENGTH: 260
<212> TYPE: PRT
<213> ORGANISM: Artificial sequence
<220> FEATURE:
<223> OTHER INFORMATION: Synthesized

<400> SEQUENCE: 47

Ser Tyr Glu Leu Thr Gln Pro Pro Ser Val Ser Val Ala Pro Gly Glu
1               5                   10                  15

Thr Ala Arg Ile Thr Cys Gly Gly Asp Asn Ile Gly Arg Arg His Val
            20                  25                  30

His Trp Tyr Gln Gln Lys Pro Gly Gln Ala Pro Val Leu Val Ile Tyr
        35                  40                  45

Asp Asp Ser Asp Arg Pro Ser Gly Ile Pro Asp Arg Phe Ser Gly Ser
    50                  55                  60

Asn Ser Gly Asn Thr Ala Thr Leu Thr Ile Gly Arg Val Glu Ala Gly
65                  70                  75                  80

Asp Glu Ala Asp Tyr Tyr Cys Gln Val Trp Gly Ser Ser Asn Asp Pro
                85                  90                  95

His Val Phe Gly Thr Gly Thr Lys Leu Thr Val Leu Ser Gly Gly Ser
            100                 105                 110

Thr Ile Thr Ser Asn Asn Val Tyr Tyr Thr Lys Leu Ser Ser Ser Gly
        115                 120                 125

Thr Gln Val Gln Leu Gln Gln Trp Gly Ala Gly Leu Leu Lys Pro Ser
    130                 135                 140

Glu Thr Leu Ser Leu Lys Cys Ala Val Tyr Gly Gly Ser Phe Ser Gly
145                 150                 155                 160

Tyr Tyr Trp Gly Trp Ile Arg Gln Ser Thr Gly Lys Gly Leu Glu Trp
                165                 170                 175

Ile Gly Glu Ile Asn Arg Ser Gly Ser Thr Asn Tyr Asn Pro Ser Leu
            180                 185                 190

Lys Ser Arg Val Thr Ile Ser Val Asp Thr Ser Lys Asn Gln Phe Ser
        195                 200                 205
```

```
Leu Lys Leu Ser Ser Val Thr Ala Ala Asp Thr Ala Val Tyr Tyr Cys
    210                 215                 220

Ala Arg Gly Gly Ala Arg Tyr Tyr Tyr Gly Ser Gly Ser Tyr Arg Ser
225                 230                 235                 240

Thr Pro Arg Pro Tyr Tyr Phe Asp Tyr Trp Gly Gln Gly Thr Leu Val
                245                 250                 255

Thr Val Ser Ser
            260


<210> SEQ ID NO 48
<211> LENGTH: 254
<212> TYPE: PRT
<213> ORGANISM: Artificial sequence
<220> FEATURE:
<223> OTHER INFORMATION: Synthesized

<400> SEQUENCE: 48

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Trp Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Val Val Phe Gly Gly Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Gln Ser Gly Ala Glu Val Lys Lys Pro Gly
    130                 135                 140

Ser Ser Val Lys Val Ser Cys Lys Ala Ser Gly Gly Thr Phe Ser Ser
145                 150                 155                 160

Tyr Ala Ile Ser Trp Val Arg Gln Ala Pro Gly Gln Gly Leu Glu Trp
                165                 170                 175

Met Gly Gly Ile Ile Pro Ile Phe Gly Thr Ala Asn Tyr Ala Gln Lys
            180                 185                 190

Phe Gln Gly Arg Val Thr Ile Thr Ala Asp Glu Ser Thr Ser Thr Ala
        195                 200                 205

Tyr Met Glu Leu Ser Ser Leu Arg Ser Glu Asp Thr Ala Val Tyr Tyr
    210                 215                 220

Cys Ala Arg Ala Ser Gly Arg Trp Leu Gln Phe Trp His Tyr Tyr Gly
225                 230                 235                 240

Met Asp Val Trp Gly Gln Gly Thr Thr Val Thr Val Ser Ser
                245                 250


<210> SEQ ID NO 49
<211> LENGTH: 249
<212> TYPE: PRT
<213> ORGANISM: Artificial sequence
<220> FEATURE:
<223> OTHER INFORMATION: Synthesized

<400> SEQUENCE: 49
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Val His
                85                  90                  95

Tyr Val Phe Gly Thr Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Gln Ser Gly Ala Glu Val Lys Lys Pro Gly
    130                 135                 140

Ser Ser Val Arg Val Ser Cys Lys Val Ser Gly Tyr Thr Phe Thr Gly
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Val Arg Val Gly Ala Ser Asp Ala Phe Asp Ile Trp Gly
225                 230                 235                 240

Gln Gly Thr Met Val Thr Val Ser Ser
                245
```

<210> SEQ ID NO 50
<211> LENGTH: 249
<212> TYPE: PRT
<213> ORGANISM: Artificial sequence
<220> FEATURE:
<223> OTHER INFORMATION: Synthesized

<400> SEQUENCE: 50

```
Gln Ser Val Leu Ile Gln Pro Pro Ser Ala Ser Gly Thr Pro Gly Gln
1               5                   10                  15

Arg Val Thr Ile Ser Cys Ser Gly Ser Asn Ser Asn Phe Gly Ser Asn
            20                  25                  30

Ser Val Ser Trp Tyr Gln Gln Arg Pro Gly Thr Ala Pro Lys Leu Leu
        35                  40                  45

Ile Glu Gly Asn Asn Gln Arg Pro Ser Gly Val Pro Glu Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Ser Cys Ala Ser Trp Asp Asp Ser Leu
                85                  90                  95

Asn Ala Phe Val Phe Gly Pro Gly Thr Lys Leu Thr Val Leu Ser Gly
            100                 105                 110
```

```
Gly Ser Ala Ile Thr Ser Tyr Asn Val Tyr Tyr Thr Lys Leu Ser Ser
        115                 120                 125

Ser Gly Thr Gln Val Gln Leu Val Gln Ser Gly Ala Glu Val Lys Lys
    130                 135                 140

Pro Gly Glu Ser Leu Lys Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

Glu Trp Met Gly Ile Ile Tyr Pro Gly Asp Ser Asp Ile Arg Tyr Ser
            180                 185                 190

Pro Ser Phe Gln Gly Gln Val Thr Ile Ser Ala Asp Lys Ser Phe Ser
        195                 200                 205

Ser Ala Tyr Leu Gln Trp Ser Ser Leu Lys Ala Ser Asp Thr Ala Met
    210                 215                 220

Tyr Tyr Cys Ala Arg Leu Gly Ala Thr Gly Ala Phe Asp Ile Trp Gly
225                 230                 235                 240

Gln Gly Thr Thr Val Thr Val Ser Ser
                245
```

<210> SEQ ID NO 51
<211> LENGTH: 257
<212> TYPE: PRT
<213> ORGANISM: Artificial sequence
<220> FEATURE:
<223> OTHER INFORMATION: Synthesized

<400> SEQUENCE: 51

```
Gln Pro Gly Leu Thr Gln Pro Pro Ser Val Ser Leu Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ala Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp Gln
                85                  90                  95

Tyr Val Phe Gly Thr Arg Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Ala Gln Val Thr Leu Lys Glu Ser Gly Pro Val Leu Val Lys Pro Thr
    130                 135                 140

Glu Thr Leu Thr Leu Thr Cys Thr Val Ser Gly Phe Ser Leu Ser Asn
145                 150                 155                 160

Ala Arg Met Gly Val Ser Trp Ile Arg Gln Pro Pro Gly Lys Ala Leu
                165                 170                 175

Glu Trp Leu Ala His Ile Phe Ser Asn Gly Glu Lys Ser Tyr Ser Thr
            180                 185                 190

Ser Leu Lys Ser Arg Leu Thr Ile Ser Lys Asp Thr Ser Lys Ser Gln
        195                 200                 205

Val Val Leu Thr Met Thr Asn Met Asp Pro Val Asp Thr Ala Thr Tyr
    210                 215                 220
```

```
Tyr Cys Ala Arg Thr Leu Asp Tyr Tyr Asp Ser Ser Gly Tyr Leu Val
225                 230                 235                 240

Gly Gly Ala Phe Asp Ile Trp Gly Gln Gly Thr Met Val Thr Val Ser
                245                 250                 255

Ser


<210> SEQ ID NO 52
<211> LENGTH: 254
<212> TYPE: PRT
<213> ORGANISM: Artificial sequence
<220> FEATURE:
<223> OTHER INFORMATION: Synthesized

<400> SEQUENCE: 52

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Arg Asp Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Lys Ser Leu
                85                  90                  95

Ser Gly Pro Val Phe Gly Gly Gly Thr Lys Val Thr Val Leu Ser Gly
            100                 105                 110

Gly Ser Thr Ile Thr Ser Tyr Asn Val Tyr Tyr Thr Lys Leu Ser Ser
        115                 120                 125

Ser Gly Thr Gln Val Gln Leu Gln Gln Ser Gly Pro Gly Leu Val Lys
    130                 135                 140

Pro Ser Gln Thr Leu Ser Leu Thr Cys Ala Ile Ser Gly Asp Ser Val
145                 150                 155                 160

Ser Ser Asn Ser Ala Ala Trp Asn Trp Ile Arg Gln Ser Pro Ser Arg
                165                 170                 175

Gly Leu Glu Trp Leu Gly Arg Thr Tyr Tyr Arg Ser Lys Trp Tyr Asn
            180                 185                 190

Asp Tyr Ala Val Ser Val Lys Ser Arg Ile Ile Ile Asn Pro Asp Thr
        195                 200                 205

Ser Lys Asn Gln Phe Ser Leu Gln Leu Asn Ser Val Thr Pro Glu Asp
    210                 215                 220

Thr Ala Val Tyr Tyr Cys Ala Arg Gln Asp Asn Asn Pro Tyr Tyr Gly
225                 230                 235                 240

Leu Asp Val Trp Gly Gln Gly Thr Thr Val Thr Val Ser Ser
                245                 250


<210> SEQ ID NO 53
<211> LENGTH: 254
<212> TYPE: PRT
<213> ORGANISM: Artificial sequence
<220> FEATURE:
<223> OTHER INFORMATION: Synthesized

<400> SEQUENCE: 53

Ser Tyr Glu Leu Thr Gln Pro Pro Ser Val Ser Val Ala Pro Gly Gln
1               5                   10                  15
```

```
Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Ala Leu
                85                  90                  95

Tyr Val Phe Gly Thr Arg Thr Lys Val Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Glu Ser Gly Gly Gly Leu Val Gln Pro Gly
    130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Ile Ser Trp Asn Ser Gly Ser Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Val Asn Ser Leu Arg Ala Glu Asp Thr Ala Val Tyr Tyr
    210                 215                 220

Cys Ala Arg Glu Leu Ile Val Gly Thr Thr Ser Pro Gln Thr Asp Ala
225                 230                 235                 240

Phe Asp Ile Trp Gly Gln Gly Thr Met Val Thr Val Ser Ser
                245                 250
```

```
<210> SEQ ID NO 54
<211> LENGTH: 258
<212> TYPE: PRT
<213> ORGANISM: Artificial sequence
<220> FEATURE:
<223> OTHER INFORMATION: Synthesized

<400> SEQUENCE: 54

Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Arg Ile Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Phe Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Tyr Ser Asp His
                85                  90                  95

Val Ile Phe Gly Gly Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125
```

```
Thr Gln Val Gln Leu Val Gln Ser Gly Ala Glu Val Lys Lys Pro Gly
    130                 135                 140

Ser Ser Val Lys Val Ser Cys Lys Ala Ser Gly Gly Thr Phe Ser Ser
145                 150                 155                 160

Tyr Ala Ile Ser Trp Val Arg Gln Ala Pro Gly Gln Gly Leu Glu Trp
                165                 170                 175

Met Gly Gly Ile Ile Pro Ile Phe Gly Thr Ala Asn Tyr Ala Gln Lys
            180                 185                 190

Phe Gln Gly Arg Val Thr Ile Thr Ala Asp Glu Ser Thr Ser Thr Ala
        195                 200                 205

Tyr Met Glu Leu Ser Ser Leu Arg Ser Glu Asp Thr Ala Val Tyr Tyr
    210                 215                 220

Cys Ala Arg Ser Ile Phe Gly Val Val Ile Ile Ser His Ala Asp Gly
225                 230                 235                 240

Tyr Tyr Tyr Gly Met Asp Val Trp Gly Gln Gly Thr Thr Val Thr Val
                245                 250                 255

Ser Ser


<210> SEQ ID NO 55
<211> LENGTH: 249
<212> TYPE: PRT
<213> ORGANISM: Artificial sequence
<220> FEATURE:
<223> OTHER INFORMATION: Synthesized

<400> SEQUENCE: 55

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Cys Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Gly Phe Thr Phe Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Ser Gly Gly Ser Thr
            100                 105                 110

Ile Thr Ser Tyr Asn Val Asn Tyr Thr Lys Leu Ser Ser Ser Gly Ala
        115                 120                 125

Gln Val Gln Leu Gln Gln Ser Gly Pro Gly Leu Val Lys Ser Ser Gln
    130                 135                 140

Thr Leu Ser Leu Thr Cys Ala Ile Ser Gly Asp Ser Val Ser Ser Asn
145                 150                 155                 160

Gly Ala Ala Trp His Trp Ile Arg Gln Ser Pro Ser Arg Gly Leu Glu
                165                 170                 175

Trp Leu Gly Arg Thr Tyr Tyr Arg Ser Gly Trp Tyr Asn Asp Tyr Ala
            180                 185                 190

Val Ser Val Lys Ser Arg Ile Thr Ile Asn Gln Asp Thr Ser Lys Asn
        195                 200                 205

Gln Phe Ser Leu Gln Leu Asn Ser Val Thr Pro Glu Asp Thr Ala Val
    210                 215                 220
```

```
Tyr Phe Cys Ala Arg Glu Gly Gly Gly Gly Arg Met Asp Val Trp Ser
225                 230                 235                 240

Gln Gly Thr Thr Val Thr Val Ser Ser
                245


<210> SEQ ID NO 56
<211> LENGTH: 245
<212> TYPE: PRT
<213> ORGANISM: Artificial sequence
<220> FEATURE:
<223> OTHER INFORMATION: Synthesized

<400> SEQUENCE: 56

Gln Pro Gly Leu Thr Gln Pro Pro Ser Val Ser Val Ser Pro Gly Gln
1               5                   10                  15

Thr Ala Ser Ile Thr Cys Ser Gly Asp Lys Leu Gly Tyr Lys Tyr Val
            20                  25                  30

Ser Trp Tyr Gln Gln Lys Pro Gly Gln Ser Pro Val Leu Val Ile Tyr
        35                  40                  45

Glu Asp Thr Lys Arg Pro Ser Gly Ile Pro Lys Arg Phe Ser Gly Ser
    50                  55                  60

Asn Ser Gly Asn Thr Ala Thr Leu Thr Ile Cys Gly Thr Gln Ala Val
65                  70                  75                  80

Asp Glu Ala Asp Tyr Tyr Cys Gln Ala Trp Asp Ser Ser Val Val Phe
                85                  90                  95

Gly Gly Gly Thr Lys Leu Thr Val Leu Ser Gly Gly Ser Thr Ile Thr
            100                 105                 110

Ser Tyr Asn Val Tyr Asp Thr Lys Leu Ser Ser Ser Gly Thr Gln Val
        115                 120                 125

Gln Leu Val Gln Ser Gly Ala Glu Val Lys Lys Pro Gly Ala Ser Val
    130                 135                 140

Lys Val Ser Cys Lys Ala Ser Gly Tyr Thr Phe Thr Ser Tyr Gly Ile
145                 150                 155                 160

Ser Trp Val Arg Gln Ala Pro Gly Gln Gly Leu Glu Trp Met Gly Trp
                165                 170                 175

Ile Ser Ala Tyr Asn Gly Asn Thr Asn Tyr Ala Gln Lys Phe Gln Gly
            180                 185                 190

Arg Val Thr Met Thr Thr Asp Thr Ser Thr Ser Thr Ala Tyr Met Glu
        195                 200                 205

Leu Arg Ser Leu Arg Ser Asp Asp Thr Ala Val Tyr Tyr Cys Ala Arg
    210                 215                 220

Asp Met Glu Leu Arg Pro Pro Phe Asp Tyr Trp Gly Gln Gly Thr Leu
225                 230                 235                 240

Val Thr Val Ser Ser
                245


<210> SEQ ID NO 57
<211> LENGTH: 257
<212> TYPE: PRT
<213> ORGANISM: Artificial sequence
<220> FEATURE:
<223> OTHER INFORMATION: Synthesized

<400> SEQUENCE: 57

Ser Tyr Glu Leu Thr Gln Pro Pro Ser Val Ser Val Ala Pro Gly Gln
1               5                   10                  15

Thr Ala Thr Ile Thr Cys Gly Gly Lys Asn Ile Glu Ser Lys Ser Val
            20                  25                  30
```

```
His Trp Tyr Gln Gln Lys Pro Gly Gln Ala Pro Val Leu Val Val Ser
        35                  40                  45

Asp Asp Thr Asp Arg Ala Ser Gly Ile Pro Glu Arg Phe Ser Gly Ser
    50                  55                  60

Asn Ser Gly Gly Ala Ala Thr Leu Thr Ile Ser Arg Val Glu Ala Gly
65                  70                  75                  80

Asp Glu Ala Asp Tyr Tyr Cys Gln Val Trp Asp Ser Pro Ser Asp His
                85                  90                  95

Tyr Val Phe Gly Pro Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Glu Ser Gly Gly Gly Val Val Gln Pro Gly
    130                 135                 140

Arg Ser Leu Arg Leu Ser Cys Ala Ala Ser Gly Phe Thr Phe Ser Ser
145                 150                 155                 160

Tyr Ala Met His Trp Val Arg Gln Ala Pro Gly Lys Gly Leu Glu Trp
                165                 170                 175

Val Ala Val Ile Ser Tyr Asp Gly Ser Asn Lys Tyr Tyr Ala Asp Ser
            180                 185                 190

Val Lys Gly Arg Phe Thr Ile Ser Arg Asp Lys Ala Lys Asn Thr Leu
        195                 200                 205

Tyr Leu Gln Met Asn Ser Leu Arg Gly Glu Asp Thr Ala Val Tyr Tyr
    210                 215                 220

Cys Ala Arg Glu Leu Ser Tyr Tyr Asp Ser Ser Gly Tyr Leu Arg Gly
225                 230                 235                 240

Asp Trp Tyr Phe Asp Leu Trp Gly Arg Gly Thr Leu Val Thr Val Ser
                245                 250                 255

Ser


<210> SEQ ID NO 58
<211> LENGTH: 246
<212> TYPE: PRT
<213> ORGANISM: Artificial sequence
<220> FEATURE:
<223> OTHER INFORMATION: Synthesized

<400> SEQUENCE: 58

Glu Ile Val Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Gly Gly Ser Gly Thr Asp Phe Thr Leu Thr Ile Thr Ser Leu Gln Pro
65                  70                  75                  80

Glu Asp Ile Ala Thr Tyr Tyr Cys Gln Gln Tyr Asp Asn Phe Pro Pro
                85                  90                  95

Thr Phe Gly Pro Gly Thr Lys Val Asp Ile Lys Ser Gly Gly Ser Thr
            100                 105                 110

Ile Thr Ser Tyr Asn Val Tyr Tyr Thr Lys Leu Ser Ser Ser Asp Thr
        115                 120                 125
```

```
Gln Val Gln Leu Val Glu Ser Gly Gly Gly Leu Val Lys Pro Gly Gly
    130                 135                 140

Ser Leu Arg Leu Ser Cys Ala Ala Ser Gly Phe Thr Val Gly Ser Asn
145                 150                 155                 160

Tyr Met Ser Trp Val Arg Gln Ala Pro Gly Lys Gly Leu Glu Trp Val
                165                 170                 175

Ser Val Ile Tyr Ser Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Arg Gly Ser Ser Gly Ala Trp Tyr Phe Asp Leu Trp Gly Arg Gly Thr
225                 230                 235                 240

Leu Val Thr Val Ser Ser
                245


<210> SEQ ID NO 59
<211> LENGTH: 21
<212> TYPE: PRT
<213> ORGANISM: Artificial sequence
<220> FEATURE:
<223> OTHER INFORMATION: Synthesized

<400> SEQUENCE: 59

Ser Gly Gly Ser Thr Ile Thr Ser Tyr Asn Val Tyr Tyr Thr Lys Leu
1               5                   10                  15

Ser Ser Ser Gly Ala
            20


<210> SEQ ID NO 60
<211> LENGTH: 21
<212> TYPE: PRT
<213> ORGANISM: Artificial sequence
<220> FEATURE:
<223> OTHER INFORMATION: Synthesized

<400> SEQUENCE: 60

Ser Gly Gly Ser Thr Ile Thr Ser Tyr Asn Val Asn Tyr Thr Lys Leu
1               5                   10                  15

Ser Ser Ser Gly Ala
            20


<210> SEQ ID NO 61
<211> LENGTH: 21
<212> TYPE: PRT
<213> ORGANISM: Artificial sequence
<220> FEATURE:
<223> OTHER INFORMATION: Synthesized

<400> SEQUENCE: 61

Ser Gly Gly Ser Thr Ile Thr Ser Tyr Asn Val Tyr Asp Thr Lys Leu
1               5                   10                  15

Ser Ser Ser Gly Thr
            20


<210> SEQ ID NO 62
<211> LENGTH: 21
<212> TYPE: PRT
<213> ORGANISM: Artificial sequence
<220> FEATURE:
<223> OTHER INFORMATION: Synthesized
```

<400> SEQUENCE: 62

Ser Gly Gly Ser Thr Ile Thr Ser Tyr Asn Val Tyr Tyr Thr Lys Leu
1 5 10 15

Ser Ser Ser Gly Thr
20

<210> SEQ ID NO 63
<211> LENGTH: 21
<212> TYPE: PRT
<213> ORGANISM: Artificial sequence
<220> FEATURE:
<223> OTHER INFORMATION: Synthesized

<400> SEQUENCE: 63

Ser Gly Gly Ser Thr Ile Thr Ser Tyr Asn Val Tyr Tyr Thr Lys Leu
1 5 10 15

Ser Ser Ser Asp Thr
20

<210> SEQ ID NO 64
<211> LENGTH: 108
<212> TYPE: PRT
<213> ORGANISM: Artificial sequence
<220> FEATURE:
<223> OTHER INFORMATION: Synthesized

<400> SEQUENCE: 64

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Trp Lys Ser Val
20 25 30

His Trp Tyr Gln Gln Lys Pro Gly Gln Ala Pro Val Leu Val Val Tyr
35 40 45

Asn Asp Asn Asp Arg Pro Ser Gly Val Pro Glu Arg Phe Ser Gly Ser
50 55 60

Asn Ser Gly Asn Thr Ala Thr Leu Thr Ile Ser Arg Val Val Ala Gly
65 70 75 80

Asp Glu Ala Asp Tyr Tyr Cys Gln Val Trp Asp Ser Ser Ser Asp His
85 90 95

Val Leu Phe Gly Gly Gly Thr Lys Leu Thr Val Leu
100 105

<210> SEQ ID NO 65
<211> LENGTH: 124
<212> TYPE: PRT
<213> ORGANISM: Artificial sequence
<220> FEATURE:
<223> OTHER INFORMATION: Synthesized

<400> SEQUENCE: 65

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr

```
65                  70                  75                  80

Met Glu Leu Ser Ser Leu Arg Ser Glu Asp Thr Ala Val Tyr Tyr Cys
                85                  90                  95

Ala Arg Ala Ser Gly Arg Trp Leu Gln Phe Trp His Tyr Tyr Gly Met
            100                 105                 110

Asp Val Trp Gly Gln Gly Thr Thr Val Thr Val Ser
        115                 120


<210> SEQ ID NO 66
<211> LENGTH: 251
<212> TYPE: PRT
<213> ORGANISM: Artificial sequence
<220> FEATURE:
<223> OTHER INFORMATION: Synthesized

<400> SEQUENCE: 66

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Pro Val
            20                  25                  30

His Trp Tyr Gln Gln Met Pro Gly Gln Ala Pro Val Leu Val Val Tyr
        35                  40                  45

Asp Asn Asn Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Ser Ser Asp Leu
                85                  90                  95

Trp Val Phe Gly Gly Arg Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Glu Ser Gly Gly Gly Leu Val Gln Pro Gly
    130                 135                 140

Arg Ser Leu Arg Leu Ser Cys Ala Ala Ser Gly Phe Thr Phe Asp Asp
145                 150                 155                 160

Tyr Ala Met His Trp Val Arg Gln Ala Pro Gly Lys Gly Leu Glu Trp
                165                 170                 175

Val Ser Gly Thr Ser Trp Asn Ser Gly Ser Ile Gly Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Leu Tyr Tyr
    210                 215                 220

Cys Ala Lys Asp Lys Gly Tyr Tyr Asp Ser Ser Ala Gly Phe Asp Ile
225                 230                 235                 240

Trp Gly Gln Gly Thr Met Val Thr Val Ser Ser
                245                 250


<210> SEQ ID NO 67
<211> LENGTH: 249
<212> TYPE: PRT
<213> ORGANISM: Artificial sequence
<220> FEATURE:
<223> OTHER INFORMATION: Synthesized

<400> SEQUENCE: 67
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Ile Ile Ser Arg Val Glu Ala Gly
65                  70                  75                  80

Asp Glu Ala Asp Tyr Tyr Cys Gln Val Trp Asp Ser Ser Ser Val His
                85                  90                  95

Tyr Val Phe Gly Thr Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Val Gln Ser Gly Ala Glu Val Lys Lys Pro Gly
    130                 135                 140

Ser Ser Val Arg Val Ser Cys Lys Val Ser Gly Tyr Thr Phe Thr Gly
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Ser Thr Ser Tyr Ala Gln Lys
            180                 185                 190

Phe Gln Gly Arg Val Thr Met Thr Arg Asp Thr Ser Thr Ser Thr Val
        195                 200                 205

Tyr Met Glu Leu Ser Ser Leu Arg Ser Glu Asp Thr Ala Val Tyr Tyr
    210                 215                 220

Cys Ala Arg Val Arg Val Gly Ala Ser Asp Ala Phe Asp Ile Trp Gly
225                 230                 235                 240

Gln Gly Thr Met Val Thr Val Ser Ser
                245
```

```
<210> SEQ ID NO 68
<211> LENGTH: 250
<212> TYPE: PRT
<213> ORGANISM: Artificial sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Glx = Gln or Glu
<220> FEATURE:
<221> NAME/KEY: MISC_FEATURE
<222> LOCATION: (187)..(187)
<223> OTHER INFORMATION: Xaa = any amino acid
<220> FEATURE:
<221> NAME/KEY: MISC_FEATURE
<222> LOCATION: (194)..(194)
<223> OTHER INFORMATION: Xaa = any amino acid
<220> FEATURE:
<221> NAME/KEY: MISC_FEATURE
<222> LOCATION: (214)..(214)
<223> OTHER INFORMATION: Xaa = any amino acid
<220> FEATURE:
<221> NAME/KEY: MISC_FEATURE
<222> LOCATION: (229)..(229)
<223> OTHER INFORMATION: Xaa = any amino acid
<220> FEATURE:
<221> NAME/KEY: MISC_FEATURE
<222> LOCATION: (233)..(234)
<223> OTHER INFORMATION: Xaa = any amino acid
```

<400> SEQUENCE: 68

```
Glx Ser Tyr Val Leu Thr Gln Pro Pro Ser Val Ser Val Ala Pro Gly
1               5                   10                  15

Gln Thr Ala Arg Ile Thr Cys Gly Gly Asn Asn Ile Gly Ser Lys Ser
            20                  25                  30

Val His Trp Tyr Gln Gln Lys Pro Gly Gln Ala Pro Val Leu Val Ile
        35                  40                  45

Tyr Asp Asp Ser Asp Arg Pro Ser Gly Ile Pro Glu Arg Phe Ser Gly
    50                  55                  60

Ser Asn Ser Gly Asn Thr Ala Thr Leu Thr Ile Ser Arg Val Glu Ala
65                  70                  75                  80

Gly Asp Glu Ala Asp Tyr Tyr Cys Gln Val Trp Asp Ser Ser Ser Asp
                85                  90                  95

His Tyr Val Phe Gly Gly Gly Thr Lys Leu Thr Val Leu Ser Gly Gly
            100                 105                 110

Ser Thr Ile Thr Ser Tyr Asn Val Tyr Tyr Thr Lys Leu Ser Ser Ser
        115                 120                 125

Gly Thr Gln Val Gln Leu Val Gln Ser Gly Ala Gly Leu Val Lys Pro
    130                 135                 140

Gly Glu Ser Leu Lys Leu Ser Cys Ala Ala Ser Gly Phe Thr Phe Ser
145                 150                 155                 160

Ser Tyr Ala Met Ser Trp Val Arg Gln Ala Pro Gly Lys Gly Leu Glu
                165                 170                 175

Trp Met Gly Gly Ile Tyr Pro Gly Ser Gly Xaa Thr Asn Tyr Ala Gln
            180                 185                 190

Ser Xaa Lys Gly Arg Val Thr Ile Ser Arg Asp Thr Ser Lys Ser Thr
        195                 200                 205

Ala Tyr Leu Gln Leu Xaa Ser Leu Arg Ala Glu Asp Thr Ala Val Tyr
    210                 215                 220

Tyr Cys Ala Arg Xaa Leu Gly Gly Xaa Xaa Tyr Ala Phe Asp Ile Trp
225                 230                 235                 240

Gly Gln Gly Thr Met Val Thr Val Ser Ser
                245                 250
```

<210> SEQ ID NO 69
<211> LENGTH: 33
<212> TYPE: DNA
<213> ORGANISM: Artificial sequence
<220> FEATURE:
<223> OTHER INFORMATION: Synthesized

<400> SEQUENCE: 69

```
gttctggtgg tggtggttct gctagaggcg cgc                                   33
```

<210> SEQ ID NO 70
<211> LENGTH: 25
<212> TYPE: DNA
<213> ORGANISM: Artificial sequence
<220> FEATURE:
<223> OTHER INFORMATION: Synthesized

<400> SEQUENCE: 70

```
gcagtgggtt tgggattggt ttgcc                                            25
```

<210> SEQ ID NO 71
<211> LENGTH: 21
<212> TYPE: DNA

<213> ORGANISM: Artificial sequence
<220> FEATURE:
<223> OTHER INFORMATION: Synthesized

<400> SEQUENCE: 71
cactgtactt ttagctcgta c 21

<210> SEQ ID NO 72
<211> LENGTH: 20
<212> TYPE: DNA
<213> ORGANISM: Artificial sequence
<220> FEATURE:
<223> OTHER INFORMATION: Synthesized

<400> SEQUENCE: 72
tagataccca tacgacgttc 20

<210> SEQ ID NO 73
<211> LENGTH: 11
<212> TYPE: PRT
<213> ORGANISM: Artificial sequence
<220> FEATURE:
<223> OTHER INFORMATION: Synthesized

<400> SEQUENCE: 73

Gly Gly Asn Asn Ile Gly Ile Arg Ser Val His
1 5 10

<210> SEQ ID NO 74
<211> LENGTH: 8
<212> TYPE: PRT
<213> ORGANISM: Artificial sequence
<220> FEATURE:
<223> OTHER INFORMATION: Synthesized

<400> SEQUENCE: 74

Tyr Tyr Asp Ser Asp Arg Pro Ser
1 5

<210> SEQ ID NO 75
<211> LENGTH: 11
<212> TYPE: PRT
<213> ORGANISM: Artificial sequence
<220> FEATURE:
<223> OTHER INFORMATION: Synthesized

<400> SEQUENCE: 75

Gln Val Trp Asp Ser Ser Ser Asp His Pro Val
1 5 10

<210> SEQ ID NO 76
<211> LENGTH: 10
<212> TYPE: PRT
<213> ORGANISM: Artificial sequence
<220> FEATURE:
<223> OTHER INFORMATION: Synthesized

<400> SEQUENCE: 76

Gly Tyr Thr Phe Thr Arg Tyr Tyr Met His
1 5 10

<210> SEQ ID NO 77
<211> LENGTH: 17
<212> TYPE: PRT
<213> ORGANISM: Artificial sequence
<220> FEATURE:
<223> OTHER INFORMATION: Synthesized

```
<400> SEQUENCE: 77

Ile Ile Asn Pro Ser Gly Gly Thr Thr Ser Tyr Ala Gln Lys Phe Gln
1               5                   10                  15

Gly


<210> SEQ ID NO 78
<211> LENGTH: 10
<212> TYPE: PRT
<213> ORGANISM: Artificial sequence
<220> FEATURE:
<223> OTHER INFORMATION: Synthesized

<400> SEQUENCE: 78

Ser Phe Gly Glu Leu Thr Ser Phe Asp Tyr
1               5                   10


<210> SEQ ID NO 79
<211> LENGTH: 13
<212> TYPE: PRT
<213> ORGANISM: Artificial sequence
<220> FEATURE:
<223> OTHER INFORMATION: Synthesized

<400> SEQUENCE: 79

Thr Gly Ser Ser Ser Asn Ile Gly Ser Arg Thr Val Asn
1               5                   10


<210> SEQ ID NO 80
<211> LENGTH: 8
<212> TYPE: PRT
<213> ORGANISM: Artificial sequence
<220> FEATURE:
<223> OTHER INFORMATION: Synthesized

<400> SEQUENCE: 80

Tyr Ala Asn Asn Gln Arg Pro Ser
1               5


<210> SEQ ID NO 81
<211> LENGTH: 11
<212> TYPE: PRT
<213> ORGANISM: Artificial sequence
<220> FEATURE:
<223> OTHER INFORMATION: Synthesized

<400> SEQUENCE: 81

Ala Ala Trp Asp Asp Ser Leu Asn Gly Tyr Val
1               5                   10


<210> SEQ ID NO 82
<211> LENGTH: 10
<212> TYPE: PRT
<213> ORGANISM: Artificial sequence
<220> FEATURE:
<223> OTHER INFORMATION: Synthesized

<400> SEQUENCE: 82

Gly Asp Ser Val Ser Ser Asn Ser Ala Thr
1               5                   10


<210> SEQ ID NO 83
<211> LENGTH: 18
<212> TYPE: PRT
<213> ORGANISM: Artificial sequence
<220> FEATURE:
```

<223> OTHER INFORMATION: Synthesized

<400> SEQUENCE: 83

```
Arg Thr Tyr Tyr Gly Ser Lys Trp His Ser Asp Tyr Ala Val Ser Val
1               5                   10                  15

Lys Ser
```

<210> SEQ ID NO 84
<211> LENGTH: 8
<212> TYPE: PRT
<213> ORGANISM: Artificial sequence
<220> FEATURE:
<223> OTHER INFORMATION: Synthesized

<400> SEQUENCE: 84

```
Gly Arg Ser Tyr Ala Phe Asp Ile
1               5
```

<210> SEQ ID NO 85
<211> LENGTH: 11
<212> TYPE: PRT
<213> ORGANISM: Artificial sequence
<220> FEATURE:
<223> OTHER INFORMATION: Synthesized

<400> SEQUENCE: 85

```
Gly Gly Asn Asn Ile Gly Trp Lys Ser Val His
1               5                   10
```

<210> SEQ ID NO 86
<211> LENGTH: 8
<212> TYPE: PRT
<213> ORGANISM: Artificial sequence
<220> FEATURE:
<223> OTHER INFORMATION: Synthesized

<400> SEQUENCE: 86

```
Tyr Asn Asp Asn Asp Arg Pro Ser
1               5
```

<210> SEQ ID NO 87
<211> LENGTH: 11
<212> TYPE: PRT
<213> ORGANISM: Artificial sequence
<220> FEATURE:
<223> OTHER INFORMATION: Synthesized

<400> SEQUENCE: 87

```
Gln Val Trp Asp Ser Ser Ser Asp His Val Leu
1               5                   10
```

<210> SEQ ID NO 88
<211> LENGTH: 10
<212> TYPE: PRT
<213> ORGANISM: Artificial sequence
<220> FEATURE:
<223> OTHER INFORMATION: Synthesized

<400> SEQUENCE: 88

```
Gly Gly Thr Phe Ser Ser Tyr Ala Ile Ser
1               5                   10
```

<210> SEQ ID NO 89
<211> LENGTH: 17
<212> TYPE: PRT
<213> ORGANISM: Artificial sequence
<220> FEATURE:
<223> OTHER INFORMATION: Synthesized

<400> SEQUENCE: 89

Gly Ile Ile Pro Ile Phe Gly Thr Ala Asn Tyr Ala Gln Lys Phe Gln
1 5 10 15

Gly

<210> SEQ ID NO 90
<211> LENGTH: 8
<212> TYPE: PRT
<213> ORGANISM: Artificial sequence
<220> FEATURE:
<223> OTHER INFORMATION: Synthesized

<400> SEQUENCE: 90

Ala Ser Gly Arg Trp Leu Gln Phe
1 5

<210> SEQ ID NO 91
<211> LENGTH: 11
<212> TYPE: PRT
<213> ORGANISM: Artificial sequence
<220> FEATURE:
<223> OTHER INFORMATION: Synthesized

<400> SEQUENCE: 91

Gly Gly Asn Asn Ile Gly Thr Lys Gly Val His
1 5 10

<210> SEQ ID NO 92
<211> LENGTH: 8
<212> TYPE: PRT
<213> ORGANISM: Artificial sequence
<220> FEATURE:
<223> OTHER INFORMATION: Synthesized

<400> SEQUENCE: 92

Tyr Asp Asp Ser Asp Arg Pro Ser
1 5

<210> SEQ ID NO 93
<211> LENGTH: 11
<212> TYPE: PRT
<213> ORGANISM: Artificial sequence
<220> FEATURE:
<223> OTHER INFORMATION: Synthesized

<400> SEQUENCE: 93

Gln Val Trp Asp Ser Arg Ser Asp Gln Tyr Val
1 5 10

<210> SEQ ID NO 94
<211> LENGTH: 12
<212> TYPE: PRT
<213> ORGANISM: Artificial sequence
<220> FEATURE:
<223> OTHER INFORMATION: Synthesized

<400> SEQUENCE: 94

Gly Phe Ser Leu Ser Asn Ala Arg Met Gly Val Ser
1 5 10

<210> SEQ ID NO 95
<211> LENGTH: 16
<212> TYPE: PRT

<213> ORGANISM: Artificial sequence
<220> FEATURE:
<223> OTHER INFORMATION: Synthesized

<400> SEQUENCE: 95

His Ile Phe Ser Asn Gly Glu Lys Ser Tyr Ser Thr Ser Leu Lys Ser
1               5                   10                  15

<210> SEQ ID NO 96
<211> LENGTH: 18
<212> TYPE: PRT
<213> ORGANISM: Artificial sequence
<220> FEATURE:
<223> OTHER INFORMATION: Synthesized

<400> SEQUENCE: 96

Thr Leu Asp Tyr Tyr Asp Ser Ser Gly Tyr Leu Val Gly Gly Ala Phe
1               5                   10                  15

Asp Ile

<210> SEQ ID NO 97
<211> LENGTH: 13
<212> TYPE: PRT
<213> ORGANISM: Artificial sequence
<220> FEATURE:
<223> OTHER INFORMATION: Synthesized

<400> SEQUENCE: 97

Ser Gly Asn Ser Ala Asn Ile Gly Gly Asn Pro Val Asn
1               5                   10

<210> SEQ ID NO 98
<211> LENGTH: 8
<212> TYPE: PRT
<213> ORGANISM: Artificial sequence
<220> FEATURE:
<223> OTHER INFORMATION: Synthesized

<400> SEQUENCE: 98

Tyr Ser Asn Asn Gln Arg Pro Ser
1               5

<210> SEQ ID NO 99
<211> LENGTH: 11
<212> TYPE: PRT
<213> ORGANISM: Artificial sequence
<220> FEATURE:
<223> OTHER INFORMATION: Synthesized

<400> SEQUENCE: 99

Ala Ala Trp Asp Asp Ser Leu Asn Gly Val Ile
1               5                   10

<210> SEQ ID NO 100
<211> LENGTH: 10
<212> TYPE: PRT
<213> ORGANISM: Artificial sequence
<220> FEATURE:
<223> OTHER INFORMATION: Synthesized

<400> SEQUENCE: 100

Gly Tyr Ser Phe Thr Ser Tyr Trp Ile Gly
1               5                   10

<210> SEQ ID NO 101
<211> LENGTH: 17

<212> TYPE: PRT
<213> ORGANISM: Artificial sequence
<220> FEATURE:
<223> OTHER INFORMATION: Synthesized

<400> SEQUENCE: 101

Ile Ile Tyr Pro Gly Asp Ser Asp Thr Arg Tyr Ser Pro Ser Phe Gln
1 5 10 15

Gly

<210> SEQ ID NO 102
<211> LENGTH: 12
<212> TYPE: PRT
<213> ORGANISM: Artificial sequence
<220> FEATURE:
<223> OTHER INFORMATION: Synthesized

<400> SEQUENCE: 102

Arg His Ser Gly Ser Tyr Ser Gly Ala Phe Asp Ile
1 5 10

<210> SEQ ID NO 103
<211> LENGTH: 11
<212> TYPE: PRT
<213> ORGANISM: Artificial sequence
<220> FEATURE:
<223> OTHER INFORMATION: Synthesized

<400> SEQUENCE: 103

Gly Gly Asn Asn Ile Gly Ser Lys Ser Val His
1 5 10

<210> SEQ ID NO 104
<211> LENGTH: 8
<212> TYPE: PRT
<213> ORGANISM: Artificial sequence
<220> FEATURE:
<223> OTHER INFORMATION: Synthesized

<400> SEQUENCE: 104

Tyr Asp Asp Ser Asp Arg Pro Ser
1 5

<210> SEQ ID NO 105
<211> LENGTH: 10
<212> TYPE: PRT
<213> ORGANISM: Artificial sequence
<220> FEATURE:
<223> OTHER INFORMATION: Synthesized

<400> SEQUENCE: 105

Gln Ala Trp Asp Ser Ser Thr Ala Tyr Val
1 5 10

<210> SEQ ID NO 106
<211> LENGTH: 10
<212> TYPE: PRT
<213> ORGANISM: Artificial sequence
<220> FEATURE:
<223> OTHER INFORMATION: Synthesized

<400> SEQUENCE: 106

Gly Phe Thr Phe Ser Asn Tyr Ala Met Ser
1 5 10

<210> SEQ ID NO 107

<211> LENGTH: 17
<212> TYPE: PRT
<213> ORGANISM: Artificial sequence
<220> FEATURE:
<223> OTHER INFORMATION: Synthesized

<400> SEQUENCE: 107

Ala Ile Ser Gly Ser Gly Gly Ala Thr Phe His Ala Asp Ser Val Lys
1               5                   10                  15

Gly

<210> SEQ ID NO 108
<211> LENGTH: 17
<212> TYPE: PRT
<213> ORGANISM: Artificial sequence
<220> FEATURE:
<223> OTHER INFORMATION: Synthesized

<400> SEQUENCE: 108

Arg Val Gly Tyr Asp Ser Ser Gly Tyr Tyr Trp Ser Asp Ala Phe Asp
1               5                   10                  15

Ile

<210> SEQ ID NO 109
<211> LENGTH: 11
<212> TYPE: PRT
<213> ORGANISM: Artificial sequence
<220> FEATURE:
<223> OTHER INFORMATION: Synthesized

<400> SEQUENCE: 109

Gly Gly Asn Asn Ile Gly Ser Lys Pro Val His
1               5                   10

<210> SEQ ID NO 110
<211> LENGTH: 8
<212> TYPE: PRT
<213> ORGANISM: Artificial sequence
<220> FEATURE:
<223> OTHER INFORMATION: Synthesized

<400> SEQUENCE: 110

Tyr Asp Asn Asn Asn Arg Pro Ser
1               5

<210> SEQ ID NO 111
<211> LENGTH: 11
<212> TYPE: PRT
<213> ORGANISM: Artificial sequence
<220> FEATURE:
<223> OTHER INFORMATION: Synthesized

<400> SEQUENCE: 111

Gln Val Trp Asp Ser Ser Ser Asp Leu Trp Val
1               5                   10

<210> SEQ ID NO 112
<211> LENGTH: 10
<212> TYPE: PRT
<213> ORGANISM: Artificial sequence
<220> FEATURE:
<223> OTHER INFORMATION: Synthesized

<400> SEQUENCE: 112

Gly Phe Thr Phe Asp Asp Tyr Ala Met His
1               5                   10

<210> SEQ ID NO 113
<211> LENGTH: 17
<212> TYPE: PRT
<213> ORGANISM: Artificial sequence
<220> FEATURE:
<223> OTHER INFORMATION: Synthesized

<400> SEQUENCE: 113

Gly Thr Ser Trp Asn Ser Gly Ser Ile Gly Tyr Ala Asp Ser Val Lys
1 5 10 15

Gly

<210> SEQ ID NO 114
<211> LENGTH: 13
<212> TYPE: PRT
<213> ORGANISM: Artificial sequence
<220> FEATURE:
<223> OTHER INFORMATION: Synthesized

<400> SEQUENCE: 114

Asp Lys Gly Tyr Tyr Asp Ser Ser Ala Gly Phe Asp Ile
1 5 10

<210> SEQ ID NO 115
<211> LENGTH: 11
<212> TYPE: PRT
<213> ORGANISM: Artificial sequence
<220> FEATURE:
<223> OTHER INFORMATION: Synthesized

<400> SEQUENCE: 115

Gly Gly Asp Asn Ile Gly Arg Arg His Val His
1 5 10

<210> SEQ ID NO 116
<211> LENGTH: 7
<212> TYPE: PRT
<213> ORGANISM: Artificial sequence
<220> FEATURE:
<223> OTHER INFORMATION: Synthesized

<400> SEQUENCE: 116

Asp Asp Ser Asp Arg Pro Ser
1 5

<210> SEQ ID NO 117
<211> LENGTH: 11
<212> TYPE: PRT
<213> ORGANISM: Artificial sequence
<220> FEATURE:
<223> OTHER INFORMATION: Synthesized

<400> SEQUENCE: 117

Gln Val Trp Gly Ser Ser Asn Asp Pro His Val
1 5 10

<210> SEQ ID NO 118
<211> LENGTH: 10
<212> TYPE: PRT
<213> ORGANISM: Artificial sequence
<220> FEATURE:
<223> OTHER INFORMATION: Synthesized

<400> SEQUENCE: 118

Gly Gly Ser Phe Ser Gly Tyr Tyr Trp Gly 1 5 10

<210> SEQ ID NO 119
<211> LENGTH: 16
<212> TYPE: PRT
<213> ORGANISM: Artificial sequence
<220> FEATURE:
<223> OTHER INFORMATION: Synthesized

<400> SEQUENCE: 119

Glu Ile Asn Arg Ser Gly Ser Thr Asn Tyr Asn Pro Ser Leu Lys Ser
1 5 10 15

<210> SEQ ID NO 120
<211> LENGTH: 22
<212> TYPE: PRT
<213> ORGANISM: Artificial sequence
<220> FEATURE:
<223> OTHER INFORMATION: Synthesized

<400> SEQUENCE: 120

Gly Gly Ala Arg Tyr Tyr Tyr Gly Ser Gly Ser Tyr Arg Ser Thr Pro
1 5 10 15

Arg Pro Tyr Tyr Phe Asp
20

<210> SEQ ID NO 121
<211> LENGTH: 11
<212> TYPE: PRT
<213> ORGANISM: Artificial sequence
<220> FEATURE:
<223> OTHER INFORMATION: Synthesized

<400> SEQUENCE: 121

Gly Gly Asn Asn Ile Gly Ser Lys Ser Val His
1 5 10

<210> SEQ ID NO 122
<211> LENGTH: 7
<212> TYPE: PRT
<213> ORGANISM: Artificial sequence
<220> FEATURE:
<223> OTHER INFORMATION: Synthesized

<400> SEQUENCE: 122

Asp Asp Ser Asp Arg Pro Ser
1 5

<210> SEQ ID NO 123
<211> LENGTH: 11
<212> TYPE: PRT
<213> ORGANISM: Artificial sequence
<220> FEATURE:
<223> OTHER INFORMATION: Synthesized

<400> SEQUENCE: 123

Gln Val Trp Asp Ser Ser Ser Val His Tyr Val
1 5 10

<210> SEQ ID NO 124
<211> LENGTH: 10
<212> TYPE: PRT
<213> ORGANISM: Artificial sequence
<220> FEATURE:
<223> OTHER INFORMATION: Synthesized

<400> SEQUENCE: 124

Gly Tyr Thr Phe Thr Gly Tyr Tyr Met His
1               5                   10

<210> SEQ ID NO 125
<211> LENGTH: 17
<212> TYPE: PRT
<213> ORGANISM: Artificial sequence
<220> FEATURE:
<223> OTHER INFORMATION: Synthesized

<400> SEQUENCE: 125

Ile Ile Asn Pro Ser Gly Gly Ser Thr Ser Tyr Ala Gln Lys Phe Gln
1               5                   10                  15

Gly

<210> SEQ ID NO 126
<211> LENGTH: 11
<212> TYPE: PRT
<213> ORGANISM: Artificial sequence
<220> FEATURE:
<223> OTHER INFORMATION: Synthesized

<400> SEQUENCE: 126

Val Arg Val Gly Ala Ser Asp Ala Phe Asp Ile
1               5                   10

<210> SEQ ID NO 127
<211> LENGTH: 11
<212> TYPE: PRT
<213> ORGANISM: Artificial sequence
<220> FEATURE:
<223> OTHER INFORMATION: Synthesized

<400> SEQUENCE: 127

Gly Gly Asn Asn Ile Gly Trp Lys Ser Val His
1               5                   10

<210> SEQ ID NO 128
<211> LENGTH: 7
<212> TYPE: PRT
<213> ORGANISM: Artificial sequence
<220> FEATURE:
<223> OTHER INFORMATION: Synthesized

<400> SEQUENCE: 128

Asp Asp Ser Asp Arg Pro Ser
1               5

<210> SEQ ID NO 129
<211> LENGTH: 11
<212> TYPE: PRT
<213> ORGANISM: Artificial sequence
<220> FEATURE:
<223> OTHER INFORMATION: Synthesized

<400> SEQUENCE: 129

Gln Val Trp Asp Ser Ser Ser Asp Leu Val Val
1               5                   10

<210> SEQ ID NO 130
<211> LENGTH: 10
<212> TYPE: PRT
<213> ORGANISM: Artificial sequence
<220> FEATURE:
<223> OTHER INFORMATION: Synthesized

<400> SEQUENCE: 130

Gly Gly Thr Phe Ser Ser Tyr Ala Ile Ser
1 5 10

<210> SEQ ID NO 131
<211> LENGTH: 17
<212> TYPE: PRT
<213> ORGANISM: Artificial sequence
<220> FEATURE:
<223> OTHER INFORMATION: Synthesized

<400> SEQUENCE: 131

Gly Ile Ile Pro Ile Phe Gly Thr Ala Asn Tyr Ala Gln Lys Phe Gln
1 5 10 15

Gly

<210> SEQ ID NO 132
<211> LENGTH: 16
<212> TYPE: PRT
<213> ORGANISM: Artificial sequence
<220> FEATURE:
<223> OTHER INFORMATION: Synthesized

<400> SEQUENCE: 132

Ala Ser Gly Arg Trp Leu Gln Phe Trp His Tyr Tyr Gly Met Asp Val
1 5 10 15

<210> SEQ ID NO 133
<211> LENGTH: 11
<212> TYPE: PRT
<213> ORGANISM: Artificial sequence
<220> FEATURE:
<223> OTHER INFORMATION: Synthesized

<400> SEQUENCE: 133

Gly Gly Asn Asn Ile Gly Ser Lys Ser Val His
1 5 10

<210> SEQ ID NO 134
<211> LENGTH: 7
<212> TYPE: PRT
<213> ORGANISM: Artificial sequence
<220> FEATURE:
<223> OTHER INFORMATION: Synthesized

<400> SEQUENCE: 134

Asp Asp Ser Asp Arg Pro Ser
1 5

<210> SEQ ID NO 135
<211> LENGTH: 11
<212> TYPE: PRT
<213> ORGANISM: Artificial sequence
<220> FEATURE:
<223> OTHER INFORMATION: Synthesized

<400> SEQUENCE: 135

Gln Val Trp Asp Ser Ser Ser Val His Tyr Val
1 5 10

<210> SEQ ID NO 136
<211> LENGTH: 10
<212> TYPE: PRT
<213> ORGANISM: Artificial sequence
<220> FEATURE:
<223> OTHER INFORMATION: Synthesized

<400> SEQUENCE: 136

Gly Tyr Thr Phe Thr Gly Tyr Tyr Met His
1 5 10

<210> SEQ ID NO 137
<211> LENGTH: 17
<212> TYPE: PRT
<213> ORGANISM: Artificial sequence
<220> FEATURE:
<223> OTHER INFORMATION: Synthesized

<400> SEQUENCE: 137

Ile Ile Asn Pro Ser Gly Gly Ser Thr Ser Tyr Ala Gln Lys Phe Gln
1 5 10 15

Gly

<210> SEQ ID NO 138
<211> LENGTH: 11
<212> TYPE: PRT
<213> ORGANISM: Artificial sequence
<220> FEATURE:
<223> OTHER INFORMATION: Synthesized

<400> SEQUENCE: 138

Val Arg Val Gly Ala Ser Asp Ala Phe Asp Ile
1 5 10

<210> SEQ ID NO 139
<211> LENGTH: 13
<212> TYPE: PRT
<213> ORGANISM: Artificial sequence
<220> FEATURE:
<223> OTHER INFORMATION: Synthesized

<400> SEQUENCE: 139

Ser Gly Ser Asn Ser Asn Phe Gly Ser Asn Ser Val Ser
1 5 10

<210> SEQ ID NO 140
<211> LENGTH: 7
<212> TYPE: PRT
<213> ORGANISM: Artificial sequence
<220> FEATURE:
<223> OTHER INFORMATION: Synthesized

<400> SEQUENCE: 140

Gly Asn Asn Gln Arg Pro Ser
1 5

<210> SEQ ID NO 141
<211> LENGTH: 11
<212> TYPE: PRT
<213> ORGANISM: Artificial sequence
<220> FEATURE:
<223> OTHER INFORMATION: Synthesized

<400> SEQUENCE: 141

Ala Ser Trp Asp Asp Ser Leu Asn Ala Phe Val
1 5 10

<210> SEQ ID NO 142
<211> LENGTH: 10
<212> TYPE: PRT
<213> ORGANISM: Artificial sequence
<220> FEATURE:

<223> OTHER INFORMATION: Synthesized

<400> SEQUENCE: 142

```
Gly Tyr Ser Phe Thr Ser Tyr Trp Ile Gly
1               5                   10
```

<210> SEQ ID NO 143
<211> LENGTH: 17
<212> TYPE: PRT
<213> ORGANISM: Artificial sequence
<220> FEATURE:
<223> OTHER INFORMATION: Synthesized

<400> SEQUENCE: 143

```
Ile Ile Tyr Pro Gly Asp Ser Asp Ile Arg Tyr Ser Pro Ser Phe Gln
1               5                   10                  15

Gly
```

<210> SEQ ID NO 144
<211> LENGTH: 9
<212> TYPE: PRT
<213> ORGANISM: Artificial sequence
<220> FEATURE:
<223> OTHER INFORMATION: Synthesized

<400> SEQUENCE: 144

```
Leu Gly Ala Thr Gly Ala Phe Asp Ile
1               5
```

<210> SEQ ID NO 145
<211> LENGTH: 11
<212> TYPE: PRT
<213> ORGANISM: Artificial sequence
<220> FEATURE:
<223> OTHER INFORMATION: Synthesized

<400> SEQUENCE: 145

```
Gly Gly Asn Asn Ile Gly Ser Lys Ser Val His
1               5                   10
```

<210> SEQ ID NO 146
<211> LENGTH: 7
<212> TYPE: PRT
<213> ORGANISM: Artificial sequence
<220> FEATURE:
<223> OTHER INFORMATION: Synthesized

<400> SEQUENCE: 146

```
Asp Asp Ser Asp Arg Pro Ser
1               5
```

<210> SEQ ID NO 147
<211> LENGTH: 11
<212> TYPE: PRT
<213> ORGANISM: Artificial sequence
<220> FEATURE:
<223> OTHER INFORMATION: Synthesized

<400> SEQUENCE: 147

```
Gln Val Trp Asp Ser Arg Ser Asp Gln Tyr Val
1               5                   10
```

<210> SEQ ID NO 148
<211> LENGTH: 12
<212> TYPE: PRT
<213> ORGANISM: Artificial sequence
<220> FEATURE:
<223> OTHER INFORMATION: Synthesized

<400> SEQUENCE: 148

Gly Phe Ser Leu Ser Asn Ala Arg Met Gly Val Ser
1 5 10

<210> SEQ ID NO 149
<211> LENGTH: 16
<212> TYPE: PRT
<213> ORGANISM: Artificial sequence
<220> FEATURE:
<223> OTHER INFORMATION: Synthesized

<400> SEQUENCE: 149

His Ile Phe Ser Asn Gly Glu Lys Ser Tyr Ser Thr Ser Leu Lys Ser
1 5 10 15

<210> SEQ ID NO 150
<211> LENGTH: 18
<212> TYPE: PRT
<213> ORGANISM: Artificial sequence
<220> FEATURE:
<223> OTHER INFORMATION: Synthesized

<400> SEQUENCE: 150

Thr Leu Asp Tyr Tyr Asp Ser Ser Gly Tyr Leu Val Gly Gly Ala Phe
1 5 10 15

Asp Ile

<210> SEQ ID NO 151
<211> LENGTH: 13
<212> TYPE: PRT
<213> ORGANISM: Artificial sequence
<220> FEATURE:
<223> OTHER INFORMATION: Synthesized

<400> SEQUENCE: 151

Ser Gly Ser Ser Ser Asn Ile Gly Asn Asn Tyr Val Ser
1 5 10

<210> SEQ ID NO 152
<211> LENGTH: 7
<212> TYPE: PRT
<213> ORGANISM: Artificial sequence
<220> FEATURE:
<223> OTHER INFORMATION: Synthesized

<400> SEQUENCE: 152

Arg Asp Thr Gln Arg Pro Ser
1 5

<210> SEQ ID NO 153
<211> LENGTH: 11
<212> TYPE: PRT
<213> ORGANISM: Artificial sequence
<220> FEATURE:
<223> OTHER INFORMATION: Synthesized

<400> SEQUENCE: 153

Ala Thr Trp Asp Lys Ser Leu Ser Gly Pro Val
1 5 10

<210> SEQ ID NO 154
<211> LENGTH: 10
<212> TYPE: PRT

<213> ORGANISM: Artificial sequence
<220> FEATURE:
<223> OTHER INFORMATION: Synthesized

<400> SEQUENCE: 154

Gly Asp Ser Val Ser Ser Asn Ser Ala Ala
1               5                   10

<210> SEQ ID NO 155
<211> LENGTH: 18
<212> TYPE: PRT
<213> ORGANISM: Artificial sequence
<220> FEATURE:
<223> OTHER INFORMATION: Synthesized

<400> SEQUENCE: 155

Arg Thr Tyr Tyr Arg Ser Lys Trp Tyr Asn Asp Tyr Ala Val Ser Val
1               5                   10                  15

Lys Ser

<210> SEQ ID NO 156
<211> LENGTH: 11
<212> TYPE: PRT
<213> ORGANISM: Artificial sequence
<220> FEATURE:
<223> OTHER INFORMATION: Synthesized

<400> SEQUENCE: 156

Gln Asp Asn Asn Pro Tyr Tyr Gly Leu Asp Val
1               5                   10

<210> SEQ ID NO 157
<211> LENGTH: 11
<212> TYPE: PRT
<213> ORGANISM: Artificial sequence
<220> FEATURE:
<223> OTHER INFORMATION: Synthesized

<400> SEQUENCE: 157

Gly Gly Asn Asn Ile Gly Ser Lys Ser Val His
1               5                   10

<210> SEQ ID NO 158
<211> LENGTH: 7
<212> TYPE: PRT
<213> ORGANISM: Artificial sequence
<220> FEATURE:
<223> OTHER INFORMATION: Synthesized

<400> SEQUENCE: 158

Tyr Asp Ser Asp Arg Pro Ser
1               5

<210> SEQ ID NO 159
<211> LENGTH: 11
<212> TYPE: PRT
<213> ORGANISM: Artificial sequence
<220> FEATURE:
<223> OTHER INFORMATION: Synthesized

<400> SEQUENCE: 159

Gln Val Trp Asp Ser Ser Ser Ala Leu Tyr Val
1               5                   10

<210> SEQ ID NO 160
<211> LENGTH: 10

<212> TYPE: PRT
<213> ORGANISM: Artificial sequence
<220> FEATURE:
<223> OTHER INFORMATION: Synthesized

<400> SEQUENCE: 160

Gly Phe Thr Phe Asp Asp Tyr Ala Met His
1               5                   10

<210> SEQ ID NO 161
<211> LENGTH: 17
<212> TYPE: PRT
<213> ORGANISM: Artificial sequence
<220> FEATURE:
<223> OTHER INFORMATION: Synthesized

<400> SEQUENCE: 161

Gly Ile Ser Trp Asn Ser Gly Ser Ile Gly Tyr Ala Asp Ser Val Lys
1               5                   10                  15

Gly

<210> SEQ ID NO 162
<211> LENGTH: 16
<212> TYPE: PRT
<213> ORGANISM: Artificial sequence
<220> FEATURE:
<223> OTHER INFORMATION: Synthesized

<400> SEQUENCE: 162

Glu Leu Ile Val Gly Thr Thr Ser Pro Gln Thr Asp Ala Phe Asp Ile
1               5                   10                  15

<210> SEQ ID NO 163
<211> LENGTH: 11
<212> TYPE: PRT
<213> ORGANISM: Artificial sequence
<220> FEATURE:
<223> OTHER INFORMATION: Synthesized

<400> SEQUENCE: 163

Gly Ala Asn Asn Ile Gly Arg Ile Ser Val His
1               5                   10

<210> SEQ ID NO 164
<211> LENGTH: 7
<212> TYPE: PRT
<213> ORGANISM: Artificial sequence
<220> FEATURE:
<223> OTHER INFORMATION: Synthesized

<400> SEQUENCE: 164

Asp Asp Ser Asp Arg Pro Ser
1               5

<210> SEQ ID NO 165
<211> LENGTH: 11
<212> TYPE: PRT
<213> ORGANISM: Artificial sequence
<220> FEATURE:
<223> OTHER INFORMATION: Synthesized

<400> SEQUENCE: 165

Gln Val Trp Asp Ser Tyr Ser Asp His Val Ile
1               5                   10

<210> SEQ ID NO 166

<211> LENGTH: 10
<212> TYPE: PRT
<213> ORGANISM: Artificial sequence
<220> FEATURE:
<223> OTHER INFORMATION: Synthesized

<400> SEQUENCE: 166

Gly Gly Thr Phe Ser Ser Tyr Ala Ile Ser
1               5                   10

<210> SEQ ID NO 167
<211> LENGTH: 17
<212> TYPE: PRT
<213> ORGANISM: Artificial sequence
<220> FEATURE:
<223> OTHER INFORMATION: Synthesized

<400> SEQUENCE: 167

Gly Ile Ile Pro Ile Phe Gly Thr Ala Asn Tyr Ala Gln Lys Phe Gln
1               5                   10                  15

Gly

<210> SEQ ID NO 168
<211> LENGTH: 20
<212> TYPE: PRT
<213> ORGANISM: Artificial sequence
<220> FEATURE:
<223> OTHER INFORMATION: Synthesized

<400> SEQUENCE: 168

Ser Ile Phe Gly Val Val Ile Ile Ser His Ala Asp Gly Tyr Tyr Tyr
1               5                   10                  15

Gly Met Asp Val
            20

<210> SEQ ID NO 169
<211> LENGTH: 11
<212> TYPE: PRT
<213> ORGANISM: Artificial sequence
<220> FEATURE:
<223> OTHER INFORMATION: Synthesized

<400> SEQUENCE: 169

Gln Ala Ser Gln Asp Ile Ser Asn Tyr Leu Asn
1               5                   10

<210> SEQ ID NO 170
<211> LENGTH: 7
<212> TYPE: PRT
<213> ORGANISM: Artificial sequence
<220> FEATURE:
<223> OTHER INFORMATION: Synthesized

<400> SEQUENCE: 170

Asp Ala Ser Asn Leu Glu Thr
1               5

<210> SEQ ID NO 171
<211> LENGTH: 9
<212> TYPE: PRT
<213> ORGANISM: Artificial sequence
<220> FEATURE:
<223> OTHER INFORMATION: Synthesized

<400> SEQUENCE: 171

Gln Gln Ser Tyr Ser Thr Pro Tyr Thr 1 5

<210> SEQ ID NO 172
<211> LENGTH: 10
<212> TYPE: PRT
<213> ORGANISM: Artificial sequence
<220> FEATURE:
<223> OTHER INFORMATION: Synthesized

<400> SEQUENCE: 172

Gly Asp Ser Val Ser Ser Asn Gly Ala Ala
1 5 10

<210> SEQ ID NO 173
<211> LENGTH: 18
<212> TYPE: PRT
<213> ORGANISM: Artificial sequence
<220> FEATURE:
<223> OTHER INFORMATION: Synthesized

<400> SEQUENCE: 173

Arg Thr Tyr Tyr Arg Ser Gly Trp Tyr Asn Asp Tyr Ala Val Ser Val
1 5 10 15

Lys Ser

<210> SEQ ID NO 174
<211> LENGTH: 9
<212> TYPE: PRT
<213> ORGANISM: Artificial sequence
<220> FEATURE:
<223> OTHER INFORMATION: Synthesized

<400> SEQUENCE: 174

Glu Gly Gly Gly Gly Arg Met Asp Val
1 5

<210> SEQ ID NO 175
<211> LENGTH: 11
<212> TYPE: PRT
<213> ORGANISM: Artificial sequence
<220> FEATURE:
<223> OTHER INFORMATION: Synthesized

<400> SEQUENCE: 175

Ser Gly Asp Lys Leu Gly Tyr Lys Tyr Val Ser
1 5 10

<210> SEQ ID NO 176
<211> LENGTH: 7
<212> TYPE: PRT
<213> ORGANISM: Artificial sequence
<220> FEATURE:
<223> OTHER INFORMATION: Synthesized

<400> SEQUENCE: 176

Glu Asp Thr Lys Arg Pro Ser
1 5

<210> SEQ ID NO 177
<211> LENGTH: 8
<212> TYPE: PRT
<213> ORGANISM: Artificial sequence
<220> FEATURE:
<223> OTHER INFORMATION: Synthesized

<400> SEQUENCE: 177

```
Gln Ala Trp Asp Ser Ser Val Val
1               5


<210> SEQ ID NO 178
<211> LENGTH: 10
<212> TYPE: PRT
<213> ORGANISM: Artificial sequence
<220> FEATURE:
<223> OTHER INFORMATION: Synthesized

<400> SEQUENCE: 178

Gly Tyr Thr Phe Thr Ser Tyr Gly Ile Ser
1               5                   10


<210> SEQ ID NO 179
<211> LENGTH: 17
<212> TYPE: PRT
<213> ORGANISM: Artificial sequence
<220> FEATURE:
<223> OTHER INFORMATION: Synthesized

<400> SEQUENCE: 179

Trp Ile Ser Ala Tyr Asn Gly Asn Thr Asn Tyr Ala Gln Lys Phe Gln
1               5                   10                  15

Gly


<210> SEQ ID NO 180
<211> LENGTH: 9
<212> TYPE: PRT
<213> ORGANISM: Artificial sequence
<220> FEATURE:
<223> OTHER INFORMATION: Synthesized

<400> SEQUENCE: 180

Met Glu Leu Arg Pro Pro Phe Asp Tyr
1               5


<210> SEQ ID NO 181
<211> LENGTH: 11
<212> TYPE: PRT
<213> ORGANISM: Artificial sequence
<220> FEATURE:
<223> OTHER INFORMATION: Synthesized

<400> SEQUENCE: 181

Gly Gly Lys Asn Ile Glu Ser Lys Ser Val His
1               5                   10


<210> SEQ ID NO 182
<211> LENGTH: 7
<212> TYPE: PRT
<213> ORGANISM: Artificial sequence
<220> FEATURE:
<223> OTHER INFORMATION: Synthesized

<400> SEQUENCE: 182

Asp Asp Thr Asp Arg Ala Ser
1               5


<210> SEQ ID NO 183
<211> LENGTH: 11
<212> TYPE: PRT
<213> ORGANISM: Artificial sequence
<220> FEATURE:
<223> OTHER INFORMATION: Synthesized

<400> SEQUENCE: 183
```

```
Gln Val Trp Asp Ser Pro Ser Asp His Tyr Val
1               5                   10


<210> SEQ ID NO 184
<211> LENGTH: 10
<212> TYPE: PRT
<213> ORGANISM: Artificial sequence
<220> FEATURE:
<223> OTHER INFORMATION: Synthesized

<400> SEQUENCE: 184

Gly Phe Thr Phe Ser Ser Tyr Ala Met His
1               5                   10


<210> SEQ ID NO 185
<211> LENGTH: 17
<212> TYPE: PRT
<213> ORGANISM: Artificial sequence
<220> FEATURE:
<223> OTHER INFORMATION: Synthesized

<400> SEQUENCE: 185

Val Ile Ser Tyr Asp Gly Ser Asn Lys Tyr Tyr Ala Asp Ser Val Lys
1               5                   10                  15

Gly


<210> SEQ ID NO 186
<211> LENGTH: 19
<212> TYPE: PRT
<213> ORGANISM: Artificial sequence
<220> FEATURE:
<223> OTHER INFORMATION: Synthesized

<400> SEQUENCE: 186

Glu Leu Ser Tyr Tyr Asp Ser Ser Gly Tyr Leu Arg Gly Asp Trp Tyr
1               5                   10                  15

Phe Asp Leu


<210> SEQ ID NO 187
<211> LENGTH: 11
<212> TYPE: PRT
<213> ORGANISM: Artificial sequence
<220> FEATURE:
<223> OTHER INFORMATION: Synthesized

<400> SEQUENCE: 187

Gln Ala Ser Gln Asp Ile Ser Asn Tyr Leu Asn
1               5                   10


<210> SEQ ID NO 188
<211> LENGTH: 7
<212> TYPE: PRT
<213> ORGANISM: Artificial sequence
<220> FEATURE:
<223> OTHER INFORMATION: Synthesized

<400> SEQUENCE: 188

Asp Ala Ser Asn Leu Glu Thr
1               5


<210> SEQ ID NO 189
<211> LENGTH: 9
<212> TYPE: PRT
<213> ORGANISM: Artificial sequence
<220> FEATURE:
```

-continued

<223> OTHER INFORMATION: Synthesized

<400> SEQUENCE: 189

Gln Gln Tyr Asp Asn Phe Pro Pro Thr
1 5

<210> SEQ ID NO 190
<211> LENGTH: 10
<212> TYPE: PRT
<213> ORGANISM: Artificial sequence
<220> FEATURE:
<223> OTHER INFORMATION: Synthesized

<400> SEQUENCE: 190

Gly Phe Thr Val Gly Ser Asn Tyr Met Ser
1 5 10

<210> SEQ ID NO 191
<211> LENGTH: 16
<212> TYPE: PRT
<213> ORGANISM: Artificial sequence
<220> FEATURE:
<223> OTHER INFORMATION: Synthesized

<400> SEQUENCE: 191

Val Ile Tyr Ser Gly Gly Ser Thr Tyr Tyr Ala Asp Ser Val Lys Gly
1 5 10 15

<210> SEQ ID NO 192
<211> LENGTH: 10
<212> TYPE: PRT
<213> ORGANISM: Artificial sequence
<220> FEATURE:
<223> OTHER INFORMATION: Synthesized

<400> SEQUENCE: 192

Gly Ser Ser Gly Ala Trp Tyr Phe Asp Leu
1 5 10

COMPOSITIONS FOR TARGETING SARS-COV-2 SPIKE PROTEIN RECEPTOR BINDING DOMAIN

CROSS REFERENCE TO RELATED APPLICATION

This application claims the benefit of U.S. 63/107,834 filed Oct. 30, 2020, which is incorporated by reference in its entirety for all purposes.

STATEMENT OF GOVERNMENT SUPPORT

This invention was made with government support under Contract No. 89233218CNA000001 between the United States Department of Energy and TRIAD National Security, LLC for the operation of Los Alamos National Laboratory and under the Coronavirus CARES Act through the National Virtual Biotechnology Laboratory (Department of Energy Office of Science). The government has certain rights in this invention.

REFERENCE TO A SEQUENCE LISTING

The Sequence Listing written in file 559418SEQLIST.txt is 119,852 bytes, was created on Oct. 26, 2021, and is hereby incorporated by reference.

BACKGROUND

The World Health Organization has determined the SARS-CoV-2 outbreak to be a global pandemic. To combat the rapid spread of the virus, governments across the world, including the United States, have taken steps to limit spread, including travel restrictions and quarantines.

In severe cases, the infection by the novel coronavirus SARS-CoV-2 causes respiratory failure and death. SARS-CoV-2 gains access to airway cells through binding to the angiotensin converting enzyme 2 (ACE2).

There remains an immediate need for more effective diagnostics to manage the outbreak and therapeutics to treat and prevent SARS-CoV-2 infection.

BRIEF SUMMARY

In one aspect, the invention provides an antibody that competes for binding to the receptor binding domain of SARS-CoV-2 virus with antibody B04, B10, D04, D07, D10, D11, D12, E01, E07, E08, F07, G07, H01, H02, H03, H05, R04, R09, R26, or 501. Some antibodies bind to the same epitope on the receptor binding domain of SARS-CoV-2 virus as antibody B04, B10, D04, D07, D10, D11, D12, E01, E07, E08, F07, G07, H01, H02, H03, H05, R04, R09, R26, or S01.

In another aspect, the invention provides an antibody selected from the group consisting of an antibody characterized by: a light chain variable region comprising three light chain CDRs of SEQ ID NO:1 and a heavy chain variable region comprising three heavy chain CDRs of SEQ ID NO:20; a light chain variable region comprising three light chain CDRs of SEQ ID NO:2 and a heavy chain variable region comprising three heavy chain CDRs of SEQ ID NO:21; a light chain variable region comprising three light chain CDRs of SEQ ID NO:64 and a heavy chain variable region comprising three heavy chain CDRs of SEQ ID NO:65; a light chain variable region comprising three light chain CDRs of SEQ ID NO:3 and a heavy chain variable region comprising three heavy chain CDRs of SEQ ID NO:22; a light chain variable region comprising three light chain CDRs of SEQ ID NO:4 and a heavy chain variable region comprising three heavy chain CDRs of SEQ ID NO:23; a light chain variable region comprising three light chain CDRs of SEQ ID NO:5 and a heavy chain variable region comprising three heavy chain CDRs of SEQ ID NO:24; a light chain variable region comprising three light chain CDRs of SEQ ID NO:6 and a heavy chain variable region comprising three heavy chain CDRs of SEQ ID NO:25; a light chain variable region comprising three light chain CDRs of SEQ ID NO:7 and a heavy chain variable region comprising three heavy chain CDRs of SEQ ID NO:26; a light chain variable region comprising three light chain CDRs of SEQ ID NO:8 and a heavy chain variable region comprising three heavy chain CDRs of SEQ ID NO:27; a light chain variable region comprising three light chain CDRs of SEQ ID NO:9 and a heavy chain variable region comprising three heavy chain CDRs of SEQ ID NO:28; a light chain variable region comprising three light chain CDRs of SEQ ID NO:10 and a heavy chain variable region comprising three heavy chain CDRs of SEQ ID NO:29; a light chain variable region comprising three light chain CDRs of SEQ ID NO:11 and a heavy chain variable region comprising three heavy chain CDRs of SEQ ID NO:30; a light chain variable region comprising three light chain CDRs of SEQ ID NO:12 and a heavy chain variable region comprising three heavy chain CDRs of SEQ ID NO:31; a light chain variable region comprising three light chain CDRs of SEQ ID NO:13 and a heavy chain variable region comprising three heavy chain CDRs of SEQ ID NO:32; a light chain variable region comprising three light chain CDRs of SEQ ID NO:14 and a heavy chain variable region comprising three heavy chain CDRs of SEQ ID NO:33; a light chain variable region comprising three light chain CDRs of SEQ ID NO:15 and a heavy chain variable region comprising three heavy chain CDRs of SEQ ID NO:34; a light chain variable region comprising three light chain CDRs of SEQ ID NO:16 and a heavy chain variable region comprising three heavy chain CDRs of SEQ ID NO:35; a light chain variable region comprising three light chain CDRs of SEQ ID NO:17 and a heavy chain variable region comprising three heavy chain CDRs of SEQ ID NO:36; a light chain variable region comprising three light chain CDRs of SEQ ID NO:18 and a heavy chain variable region comprising three heavy chain CDRs of SEQ ID NO:37; and a light chain variable region comprising three light chain CDRs of SEQ ID NO:19 and a heavy chain variable region comprising three heavy chain CDRs of SEQ ID NO:38.

In another aspect, the antibody is selected from the group consisting of an antibody characterized by: a light chain variable region comprising three Kabat-Chothia Composite light chain CDRs SEQ ID NO:73, SEQ ID NO:74, and SEQ ID NO:75 and a heavy chain variable region comprising three Kabat-Chothia Composite heavy chain CDRs SEQ ID NO:76, SEQ ID NO:77, and SEQ ID NO:78; a light chain variable region comprising three Kabat-Chothia Composite light chain CDRs SEQ ID NO:79, SEQ ID NO:80, and SEQ ID NO:81 and a heavy chain variable region comprising three Kabat-Chothia Composite heavy chain CDRs SEQ ID NO:82, SEQ ID NO:83, and SEQ ID NO:84; a light chain variable region comprising three Kabat-Chothia Composite light chain CDRs SEQ ID NO:85, SEQ ID NO:86 and SEQ ID NO:87 and a heavy chain variable region comprising three Kabat-Chothia Composite heavy chain CDRs SEQ ID NO:88, SEQ ID NO:89, and SEQ ID NO:90; a light chain variable region comprising three Kabat-Chothia Composite light chain CDRs SEQ ID NO:91, SEQ ID NO:92, and SEQ ID NO:93 and a heavy chain variable region comprising three Kabat-Chothia Composite heavy chain CDRs SEQ ID NO:94, SEQ ID NO:95, and SEQ ID NO:96; a light chain variable region comprising three Kabat-Chothia Composite light chain CDRs SEQ ID NO:97, SEQ ID NO:98, and SEQ ID NO:99 and a heavy chain variable region comprising three Kabat-Chothia Composite heavy chain CDRs SEQ ID NO:100, SEQ ID NO:101, and SEQ ID NO:102; a light chain variable region comprising three Kabat-Chothia Composite light chain CDRs SEQ ID NO:103, SEQ ID NO:104, and SEQ ID NO:105 and a heavy chain variable region comprising three Kabat-Chothia Composite heavy chain CDRs SEQ ID NO:106, SEQ ID NO:107, and SEQ ID NO:108; a light chain variable region comprising three Kabat-Chothia Composite light chain CDRs SEQ ID NO:109, SEQ ID NO:110, and SEQ ID NO:111 and a heavy chain variable region comprising three Kabat-Chothia Composite heavy chain CDRs SEQ ID NO:112, SEQ ID NO:113, and SEQ ID NO:114; a light chain variable region comprising three Kabat-Chothia Composite light chain CDRs SEQ ID NO: 115, SEQ ID NO: 116, and SEQ ID NO: 117 and a heavy chain variable region comprising three Kabat-Chothia Composite heavy chain CDRs SEQ ID NO: 118, SEQ ID NO: 119, and SEQ ID NO:120; a light chain variable region comprising three Kabat-Chothia Composite light chain CDRs SEQ ID NO:121, SEQ ID NO:122, and SEQ ID NO:123 and a heavy chain variable region comprising three Kabat-Chothia Composite heavy chain CDRs SEQ ID NO:124, SEQ ID NO:125, and SEQ ID NO:126; a light chain variable region comprising three Kabat-Chothia Composite light chain CDRs SEQ ID NO:127, SEQ ID NO:128, and SEQ ID NO:129 and a heavy chain variable region comprising three Kabat-Chothia Composite heavy chain CDRs SEQ ID NO:130, SEQ ID NO:131, and SEQ ID NO:132; a light chain variable region comprising three Kabat-Chothia Composite light chain CDRs SEQ ID NO:133, SEQ ID NO:134, and SEQ ID NO:135 and a heavy chain variable region comprising three Kabat-Chothia Composite heavy chain CDRs SEQ ID NO:136, SEQ ID NO:137, and SEQ ID NO:138; a light chain variable region comprising three Kabat-Chothia Composite light chain CDRs SEQ ID NO:139, SEQ ID NO:140, and SEQ ID NO:141 and a heavy chain variable region comprising three Kabat-Chothia Composite heavy chain CDRs SEQ ID NO:142, SEQ ID NO:143, and SEQ ID NO:144; a light chain variable region comprising three Kabat-Chothia Composite light chain CDRs SEQ ID NO:145, SEQ ID NO:146, and SEQ ID NO:147 and a heavy chain variable region comprising three Kabat-Chothia Composite heavy chain CDRs SEQ ID NO:148, SEQ ID NO:149, and SEQ ID NO:150; a light chain variable region comprising three Kabat-Chothia Composite light chain CDRs SEQ ID NO:151, SEQ ID NO:152, and SEQ ID NO:153 and a heavy chain variable region comprising three Kabat-Chothia Composite heavy chain CDRs SEQ ID NO:154, SEQ ID NO:155, and SEQ ID NO:156; a light chain variable region comprising three Kabat-Chothia Composite light chain CDRs SEQ ID NO:157, SEQ ID NO:158, and SEQ ID NO:159 and a heavy chain variable region comprising three Kabat-Chothia Composite heavy chain CDRs SEQ ID NO:160, SEQ ID NO:161, and SEQ ID NO:162; a light chain variable region comprising three Kabat-Chothia Composite light chain CDRs SEQ ID NO:163, SEQ ID NO:164, and SEQ ID NO:165 and a heavy chain variable region comprising three Kabat-Chothia Composite heavy chain CDRs SEQ ID NO:166, SEQ ID NO:167, and SEQ ID NO:168; a light chain variable region comprising three Kabat-Chothia Composite light chain CDRs SEQ ID NO:169, SEQ ID NO:170, and SEQ ID NO:171 and a heavy chain variable region comprising three Kabat-Chothia Composite heavy chain CDRs SEQ ID NO:172, SEQ ID NO:173, and SEQ ID NO:174; a light chain variable region comprising three Kabat-Chothia Composite light chain CDRs SEQ ID NO:175, SEQ ID NO:176, and SEQ ID NO:177 and a heavy chain variable region comprising three Kabat-Chothia Composite heavy chain CDRs SEQ ID NO:178, SEQ ID NO:179, and SEQ ID NO:180; a light chain variable region comprising three Kabat-Chothia Composite light chain CDRs SEQ ID NO:181, SEQ ID NO:182, and SEQ ID NO:183 and a heavy chain variable region comprising three Kabat-Chothia Composite heavy chain CDRs SEQ ID NO:184, SEQ ID NO:185, and SEQ ID NO:186; and a light chain variable region comprising three Kabat-Chothia Composite light chain CDRs SEQ ID NO:187, SEQ ID NO:188, and SEQ ID NO:189 and a heavy chain variable region comprising three Kabat-Chothia Composite heavy chain CDRs SEQ ID NO:190, SEQ ID NO:191, and SEQ ID NO:192.

In some antibodies, the variable light chain region comprises SEQ ID NO: 1 and the variable heavy chain region comprises SEQ ID NO: 20; the variable light chain region comprises SEQ ID NO: 2 and the variable heavy chain region comprises SEQ ID NO: 21; the variable light chain region comprises SEQ ID NO: 64 and the variable heavy chain region comprises SEQ ID NO: 65; the variable light chain region comprises SEQ ID NO: 3 and the variable heavy chain region comprises SEQ ID NO: 22; the variable light chain region comprises SEQ ID NO: 4 and the variable heavy chain region comprises SEQ ID NO: 23; the variable light chain region comprises SEQ ID NO: 5 and the variable heavy chain region comprises SEQ ID NO: 24; the variable light chain region comprises SEQ ID NO: 6 and the variable heavy chain region comprises SEQ ID NO: 25; the variable light chain region comprises SEQ ID NO: 7 and the variable heavy chain region comprises SEQ ID NO: 26; the variable light chain region comprises SEQ ID NO: 8 and the variable heavy chain region comprises SEQ ID NO: 27; the variable light chain region comprises SEQ ID NO: 9 and the variable heavy chain region comprises SEQ ID NO: 28; the variable light chain region comprises SEQ ID NO: 10 and the variable heavy chain region comprises SEQ ID NO: 29; the variable light chain region comprises SEQ ID NO: 11 and the variable heavy chain region comprises SEQ ID NO: 30; the variable light chain region comprises SEQ ID NO: 12 and the variable heavy chain region comprises SEQ ID NO: 31; the variable light chain region comprises SEQ ID NO: 13 and the variable heavy chain region comprises SEQ ID NO: 32; the variable light chain region comprises SEQ ID NO: 14 and the variable heavy chain region comprises SEQ ID NO: 33; the variable light chain region comprises SEQ ID NO: 15 and the variable heavy chain region comprises SEQ ID NO:34; the variable light chain region comprises SEQ ID NO: 16 and the variable heavy chain region comprises SEQ ID NO: 35; the variable light chain region comprises SEQ ID NO: 17 and the variable heavy chain region comprises SEQ ID NO: 36; the variable light chain region comprises SEQ ID NO: 18 and the variable heavy chain region comprises SEQ ID NO: 37; or the variable light chain region comprises SEQ ID NO: 19 and the variable heavy chain region comprises SEQ ID NO: 38.

In some antibodies, the variable light chain region comprises SEQ ID NO: 1 and the variable heavy chain region comprises SEQ ID NO: 20. In some antibodies, the variable light chain region comprises SEQ ID NO: 7 and the variable heavy chain region comprises SEQ ID NO: 26. In some antibodies, the variable light chain region comprises SEQ ID NO: 9 and the variable heavy chain region comprises SEQ ID NO: 28. In some antibodies, the variable light chain region comprises SEQ ID NO: 10 and the variable heavy chain region comprises SEQ ID NO: 29. In some antibodies, the variable light chain region comprises SEQ ID NO: 11 and the variable heavy chain region comprises SEQ ID NO: 30.

In some antibodies, the variable light chain region comprises SEQ ID NO: 12 and the variable heavy chain region comprises SEQ ID NO: 31. In some antibodies, the variable light chain region comprises SEQ ID NO: 15 and the variable heavy chain region comprises SEQ ID NO:34. In some antibodies, the variable light chain region comprises SEQ ID NO: 16 and the variable heavy chain region comprises SEQ ID NO:35. In some antibodies, the variable light chain region comprises SEQ ID NO: 19 and the variable heavy chain region comprises SEQ ID NO: 38. Some antibodies comprise an amino acid sequence selected from the group consisting of SEQ ID NOs:41-58 and 66-67.

The antibody can be an intact antibody or a binding fragment. In some such antibodies, the binding fragment is a single-chain antibody, Fab fragment, F(ab')2 fragment, scFv, or minibody. In another aspect the invention provides a composition comprising any of the antibodies disclosed herein and a pharmaceutically acceptable excipient.

In another aspect, the invention provides a composition comprising at least two antibodies selected from the group consisting of an antibody characterized by: a light chain variable region comprising three light chain CDRs of SEQ ID NO:1 and a heavy chain variable region comprising three heavy chain CDRs of SEQ ID NO:20; a light chain variable region comprising three light chain CDRs of SEQ ID NO:7 and a heavy chain variable region comprising three heavy chain CDRs of SEQ ID NO:26; a light chain variable region comprising three light chain CDRs of SEQ ID NO:9 and a heavy chain variable region comprising three heavy chain CDRs of SEQ ID NO:28; a light chain variable region comprising three light chain CDRs of SEQ ID NO:10 and a heavy chain variable region comprising three heavy chain CDRs of SEQ ID NO:29; a light chain variable region comprising three light chain CDRs of SEQ ID NO:11 and a heavy chain variable region comprising three heavy chain CDRs of SEQ ID NO:30; a light chain variable region comprising three light chain CDRs of SEQ ID NO:12 and a heavy chain variable region comprising three heavy chain CDRs of SEQ ID NO:31; a light chain variable region comprising three light chain CDRs of SEQ ID NO:15 and a heavy chain variable region comprising three heavy chain CDRs of SEQ ID NO:34; and a light chain variable region comprising three light chain CDRs of SEQ ID NO:19 and a heavy chain variable region comprising three heavy chain CDRs of SEQ ID NO:38; and a pharmaceutically acceptable excipient.

Some compositions comprise at least two antibodies selected from the group consisting of B04, B10, D04, D07, D10, D11, D12, E01, E07, E08, F07, G07, H01, H02, H03, H05, R04, R09, R26, and S0. Some compositions comprise 501 and F07. Some compositions comprise S01 and G07. Some compositions comprise G07 and F07. Some compositions comprise E01 and F07. Some compositions comprise E01 and G07.

In another aspect, the invention provides a method of treating SARS-CoV-2 virus infection in a subject, the method comprising administering an effective amount of any of the antibodies or compositions disclosed herein to a subject.

In yet another aspect, the invention provides a kit for treating or diagnosing SARS-CoV-2 virus infection, the kit comprising an effective amount of any of the antibodies or compositions disclosed herein and directions for use thereof.

In another aspect, the invention provides a method of detecting SARS-CoV-2 virus infection in a subject, the method comprising assaying a sample from the subject for binding with any of the antibodies disclosed herein, wherein binding by the antibody is indicative of the subject being infected with SARS-CoV-2 virus. In some methods, the assay is a lateral flow assay.

In another aspect, the invention provides a diagnostic agent comprising (1) any of the antibodies disclosed herein that binds RBD2 of SARS-CoV-2 virus attached to (2) a label that produces a detectable signal, directly or indirectly. In some diagnostic agents, the label is a radioisotope, a fluorescent compound, a chemiluminescent compound, an enzyme, an imaging agent, or a metal ion.

In yet another aspect, the invention provides a kit comprising any of the diagnostic agents disclosed herein and instructions for use thereof.

BRIEF DESCRIPTION OF THE DRAWINGS

The patent application file contains at least one drawing executed in color. Copies of this patent application with color drawing(s) will be provided by the Office upon request and payment of the necessary fee.

Having thus described the invention in general terms, reference will now be made to the accompanying drawings, which are not necessarily drawn to scale.

Figure 1:
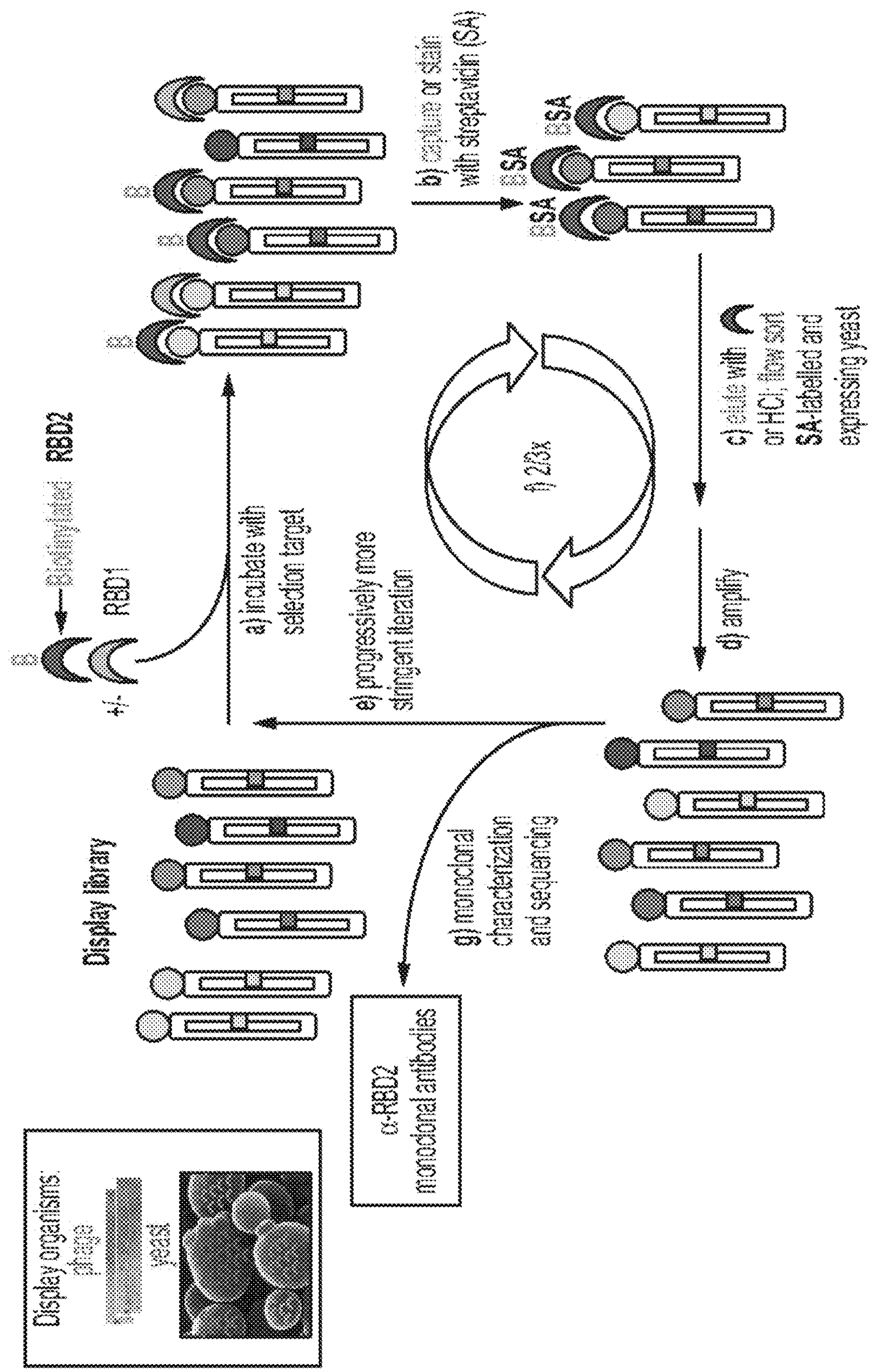

FIG. 1 illustrates the selection of monoclonal antibodies by in vitro selection of display libraries in accordance with certain embodiments of the invention.

Figure 2A:
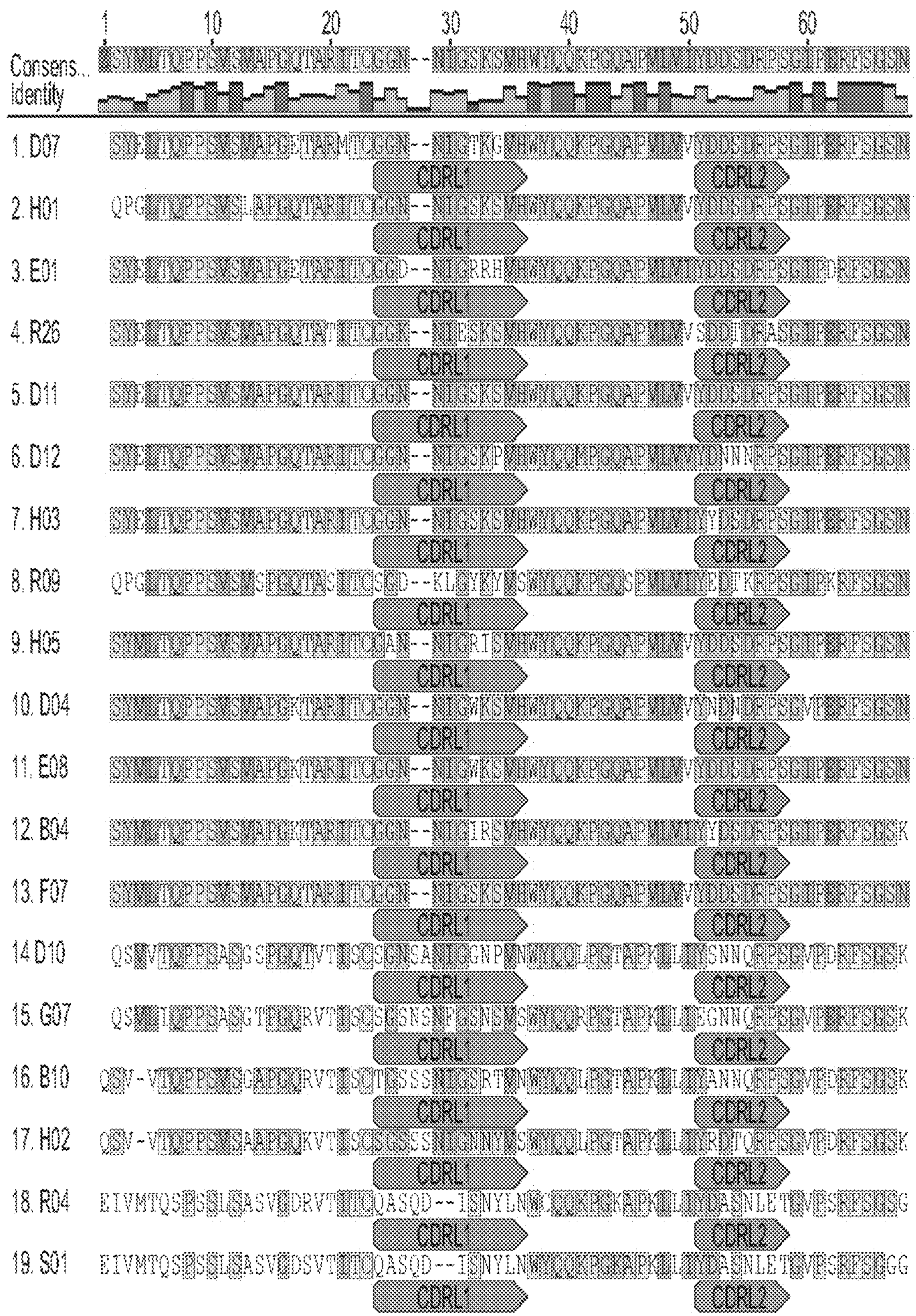
Figure 2B:
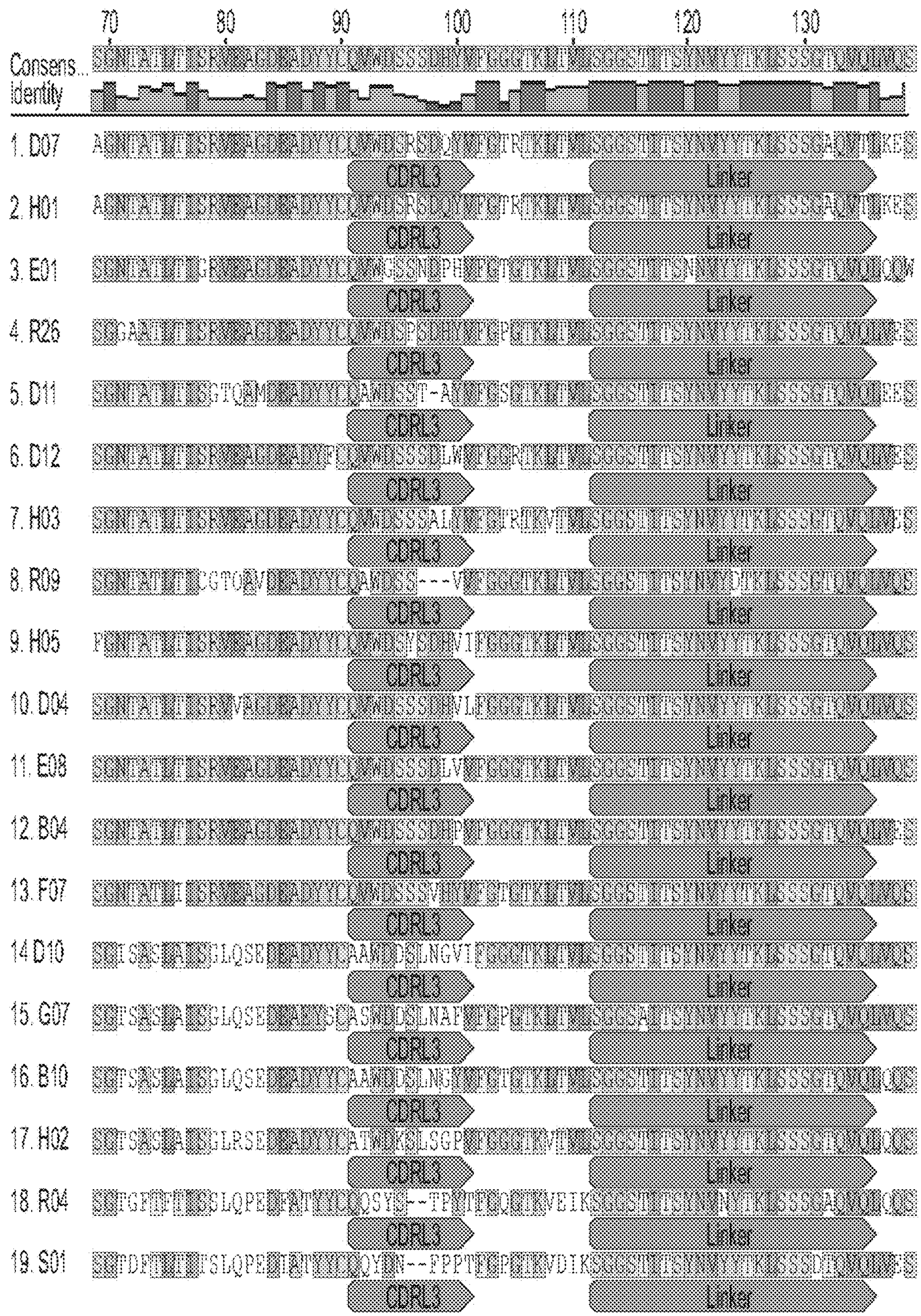
Figure 2C:
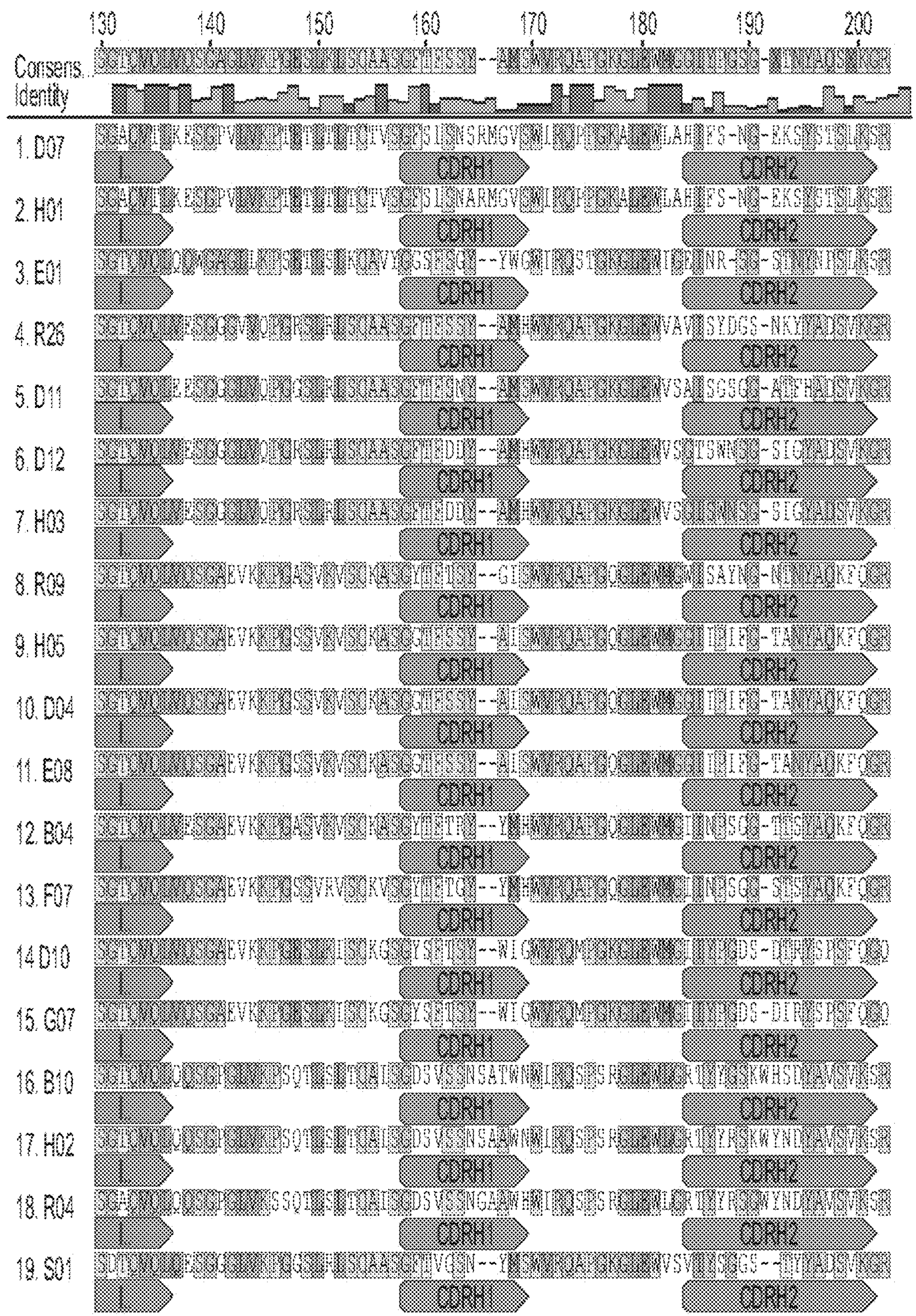
Figure 2D:
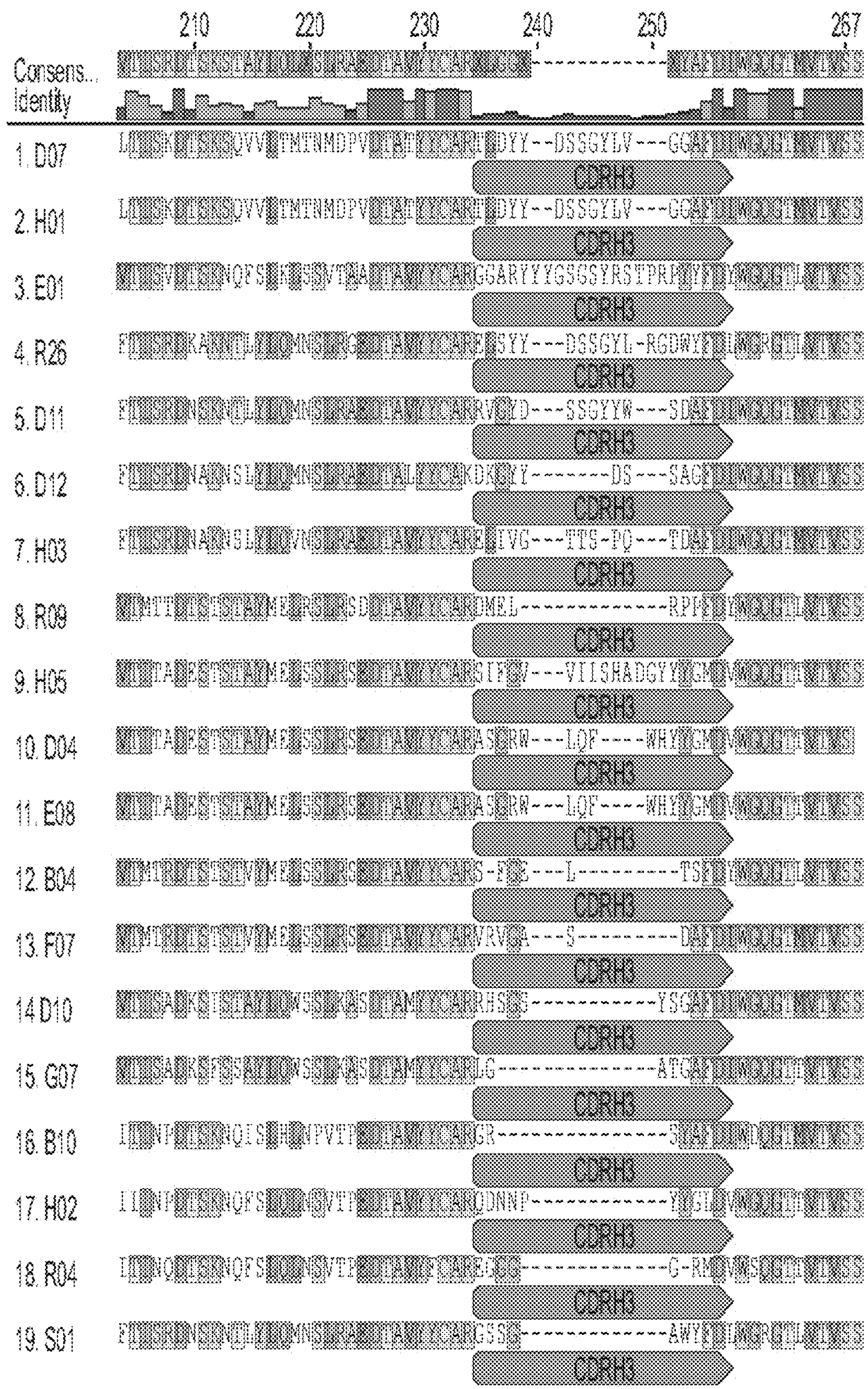
Figures 1, 3A:
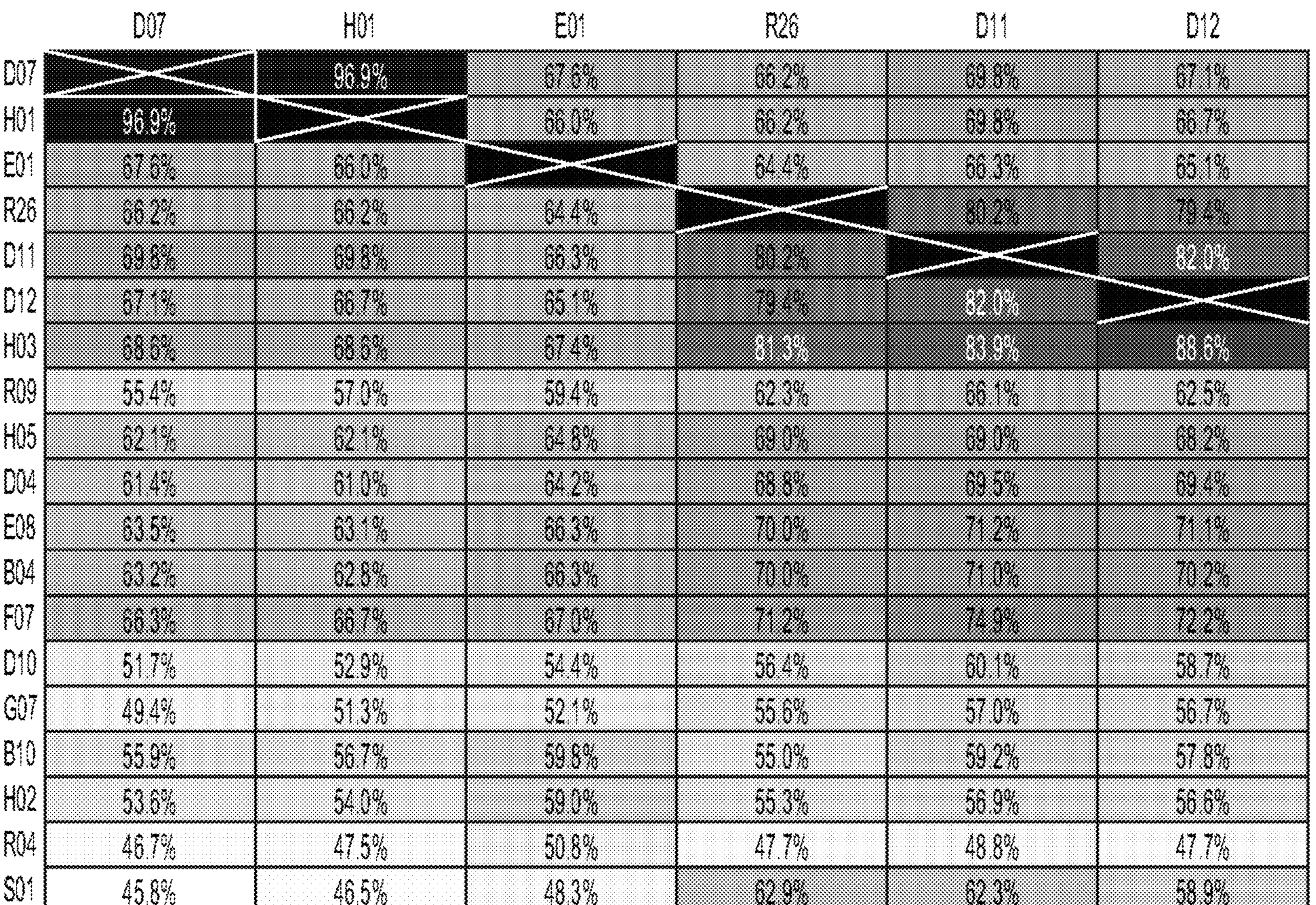
Figures 2, 3A:
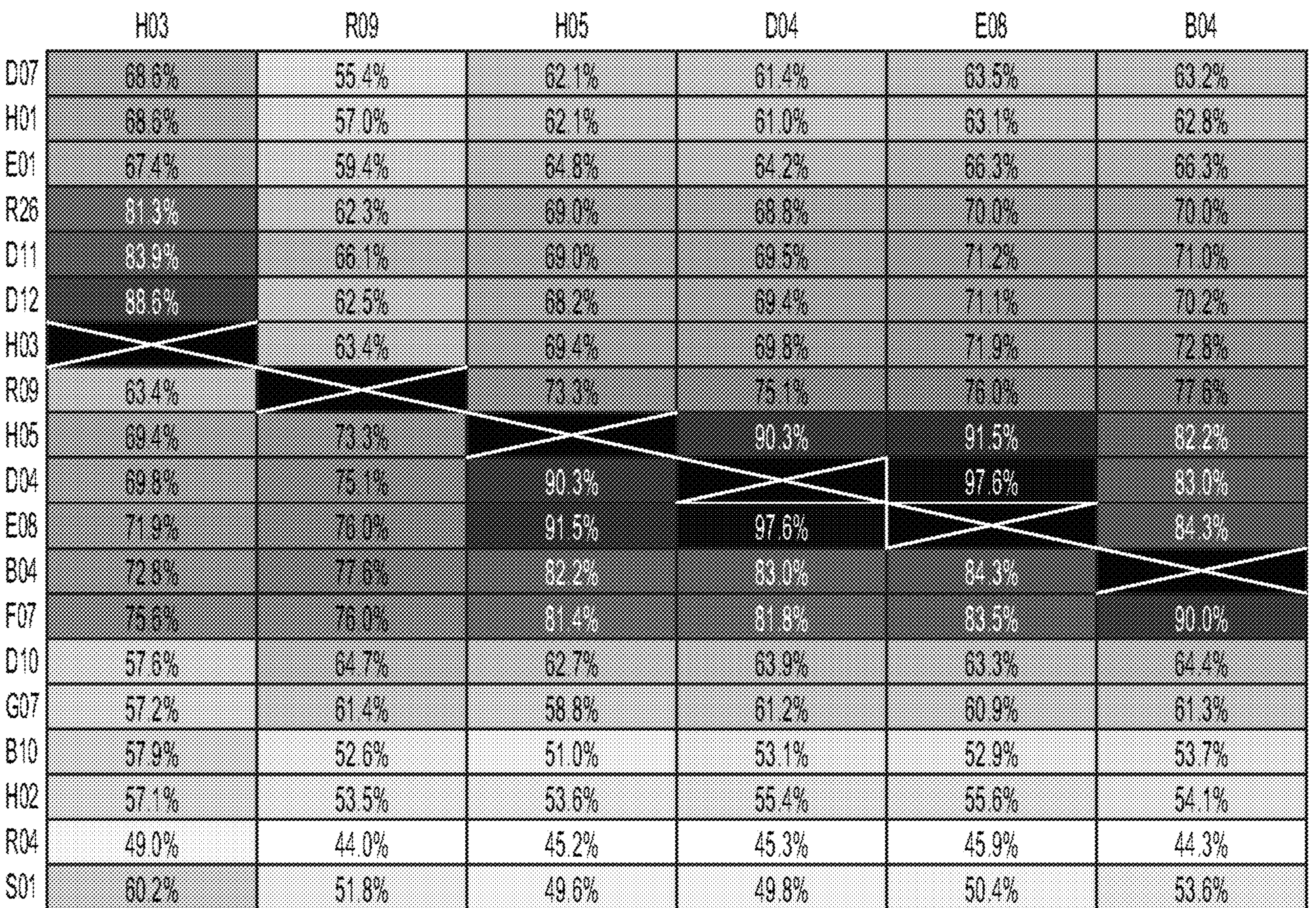
Figure 5:
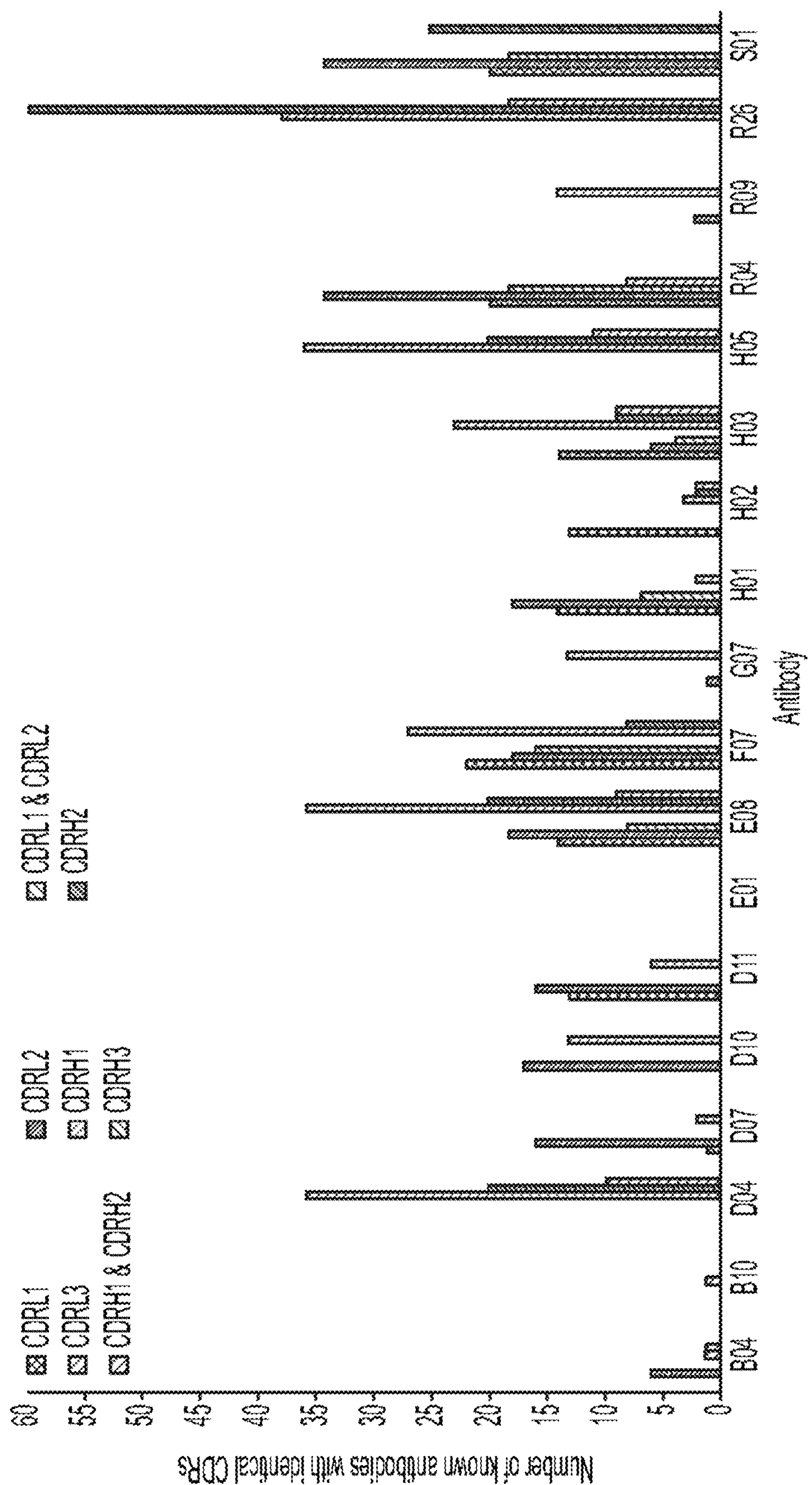

FIGS. 2A and 2B illustrate variable light region sequences of unique scFvs selected in accordance with certain embodiments of the invention;

FIGS. 2C and 2D illustrate variable heavy region sequences of unique scFvs selected in accordance with certain embodiments of the invention;

FIGS. 3A-1, 3A-2, and 3A-3 illustrate identity of selected scFvs in accordance with certain embodiments of the invention;

FIGS. 3B-1, 3B-2, and 3B-3 illustrate similarity of selected scFvs in accordance with certain embodiments of the invention;

FIGS. 4A, 4B, and 4C illustrate the scFv sequences described herein and in FIG. 2A, 2B, 2C, and 2D in accordance with certain embodiments of the invention;

FIG. 5 illustrates a comparison of CDR sequences of selected antibodies of the invention with CDR sequences of antibodies from CoV-AbDab database (World Wide Web-opig.stats.ox.ac.uk/webapps/covabdab Oct. 16, 2020).

Figure 6:
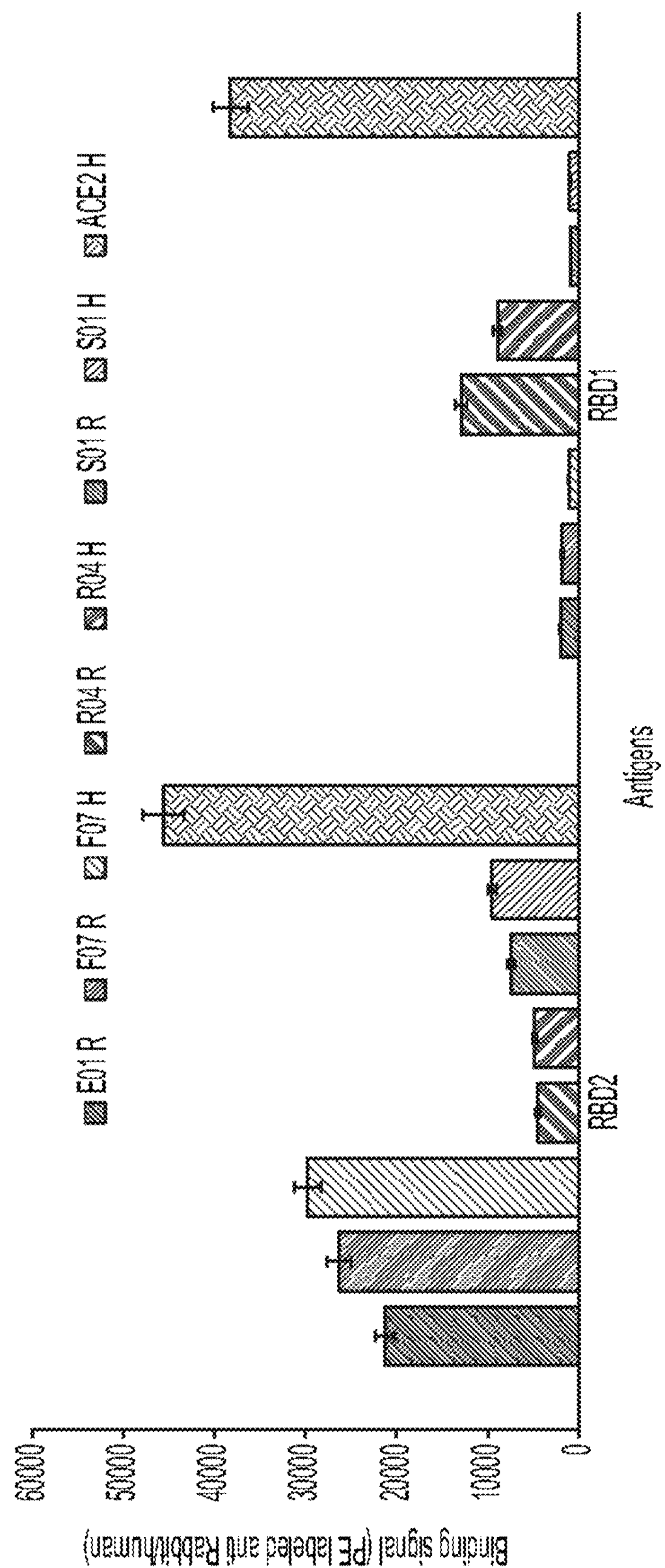
Figure 7A:
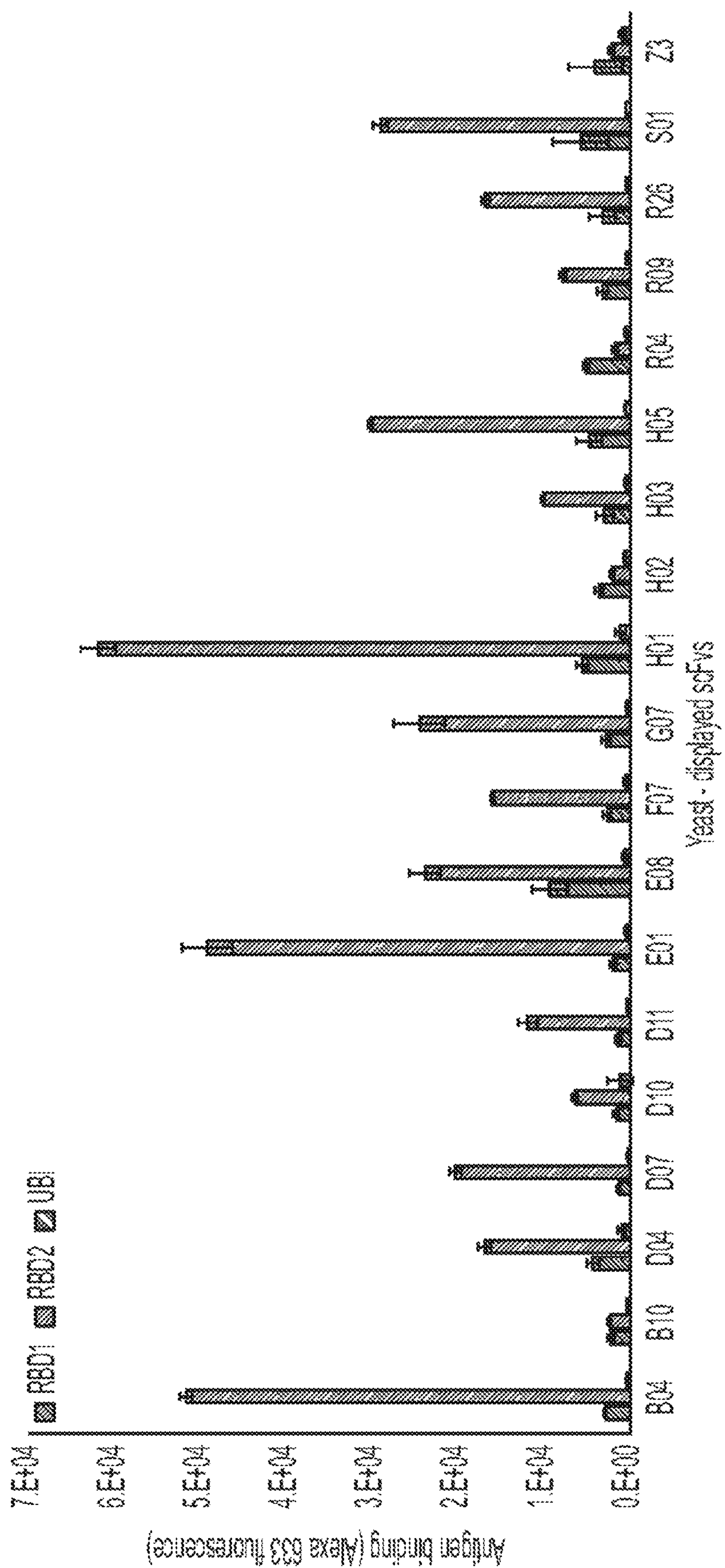
Figure 7B:
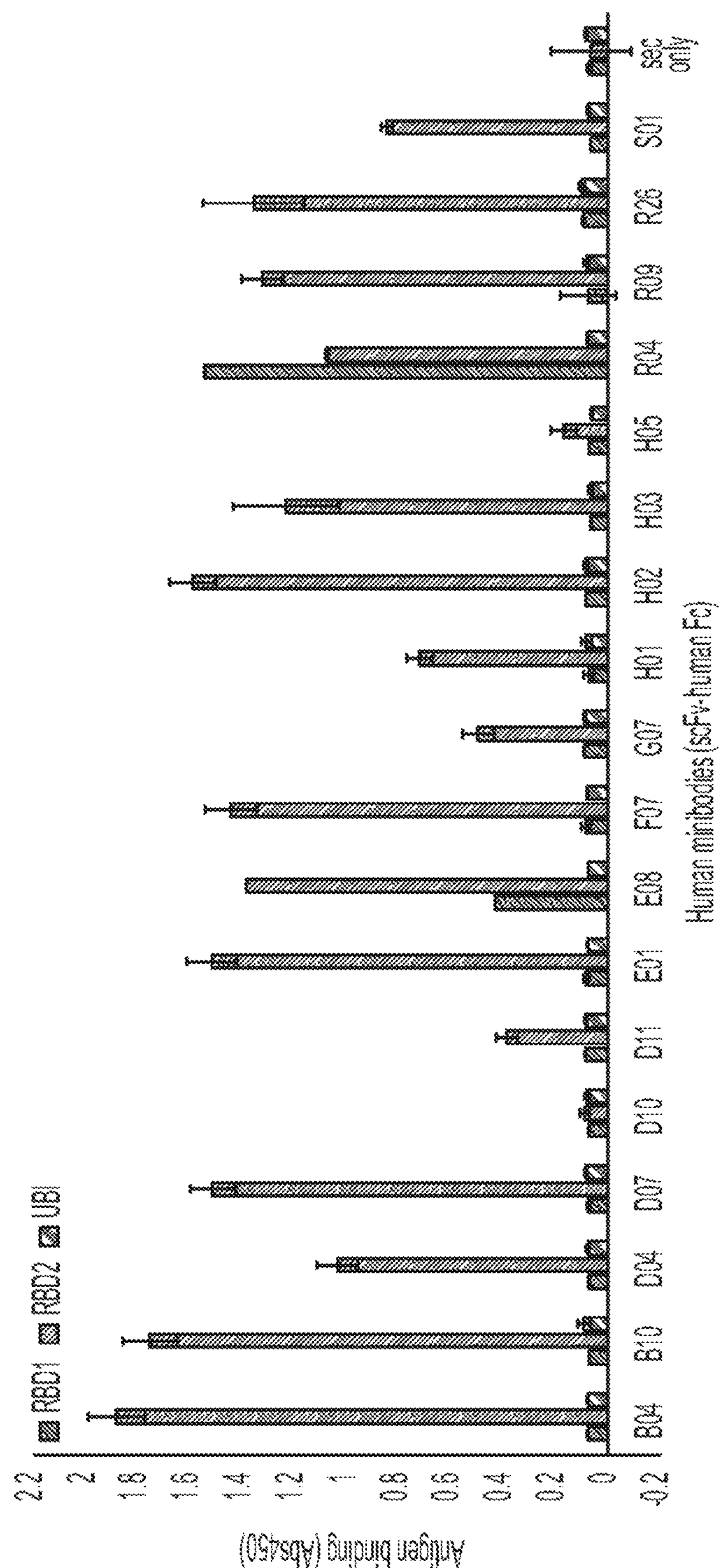
Figure 7C:
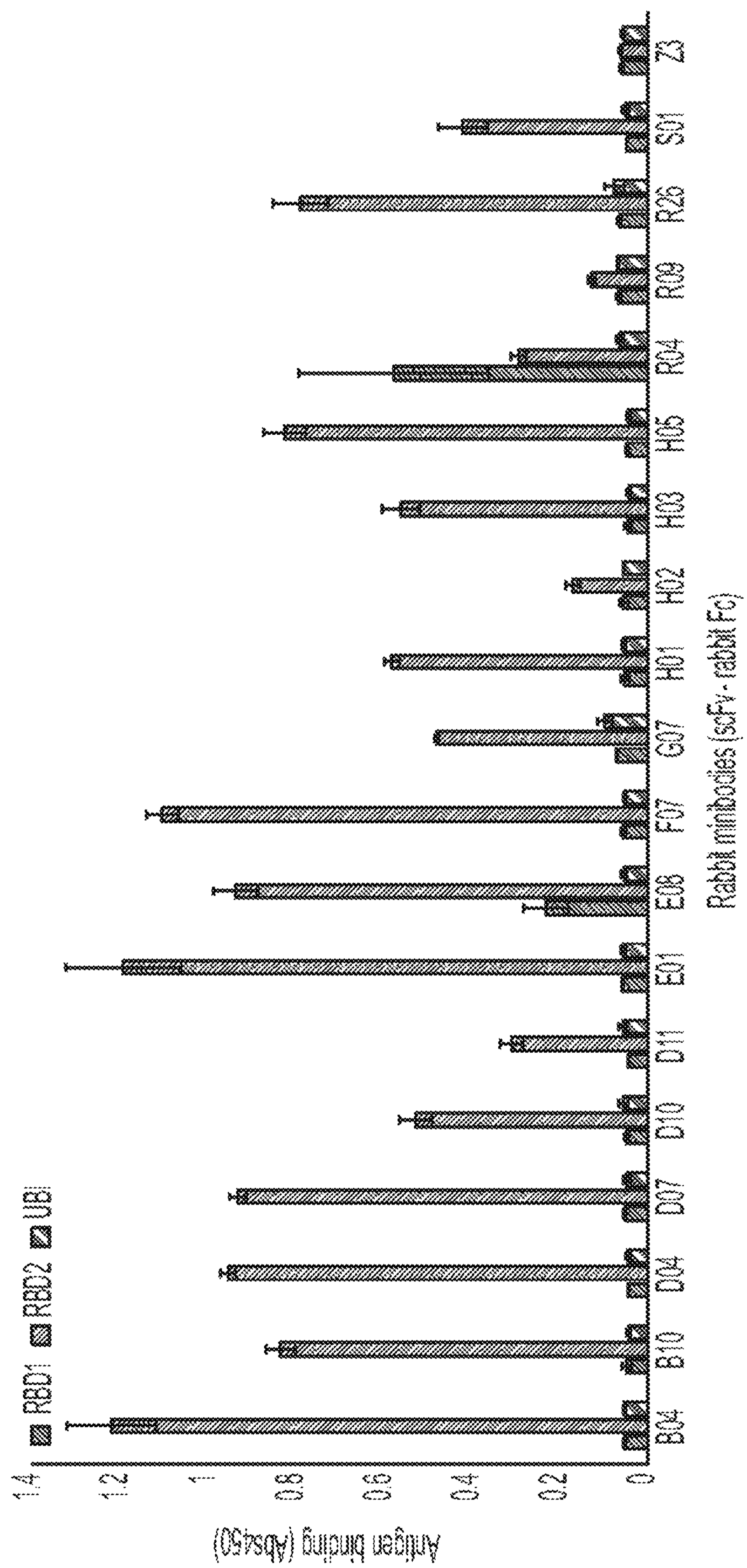
Figure 8A:
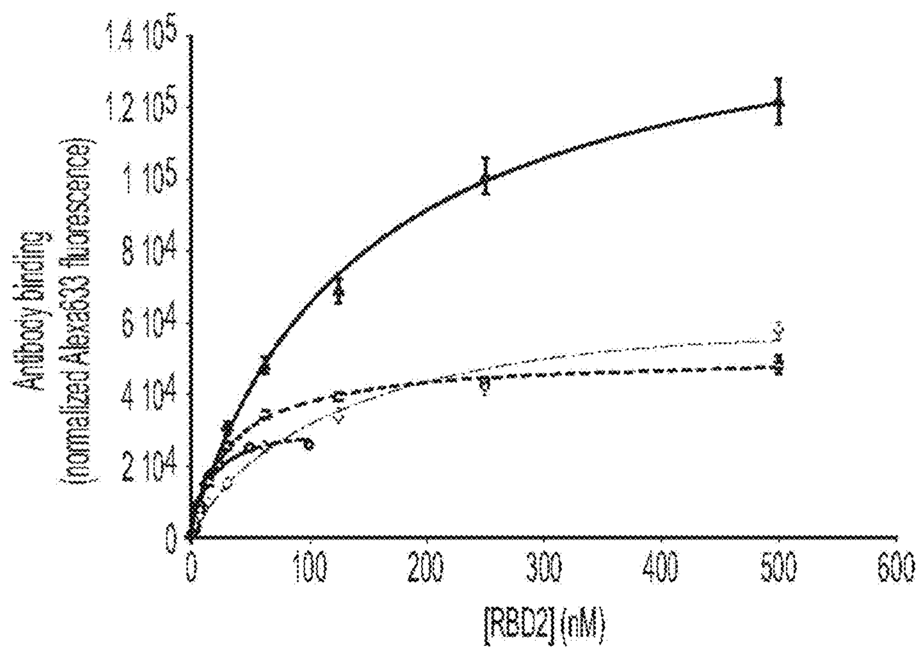
Figure 8C:
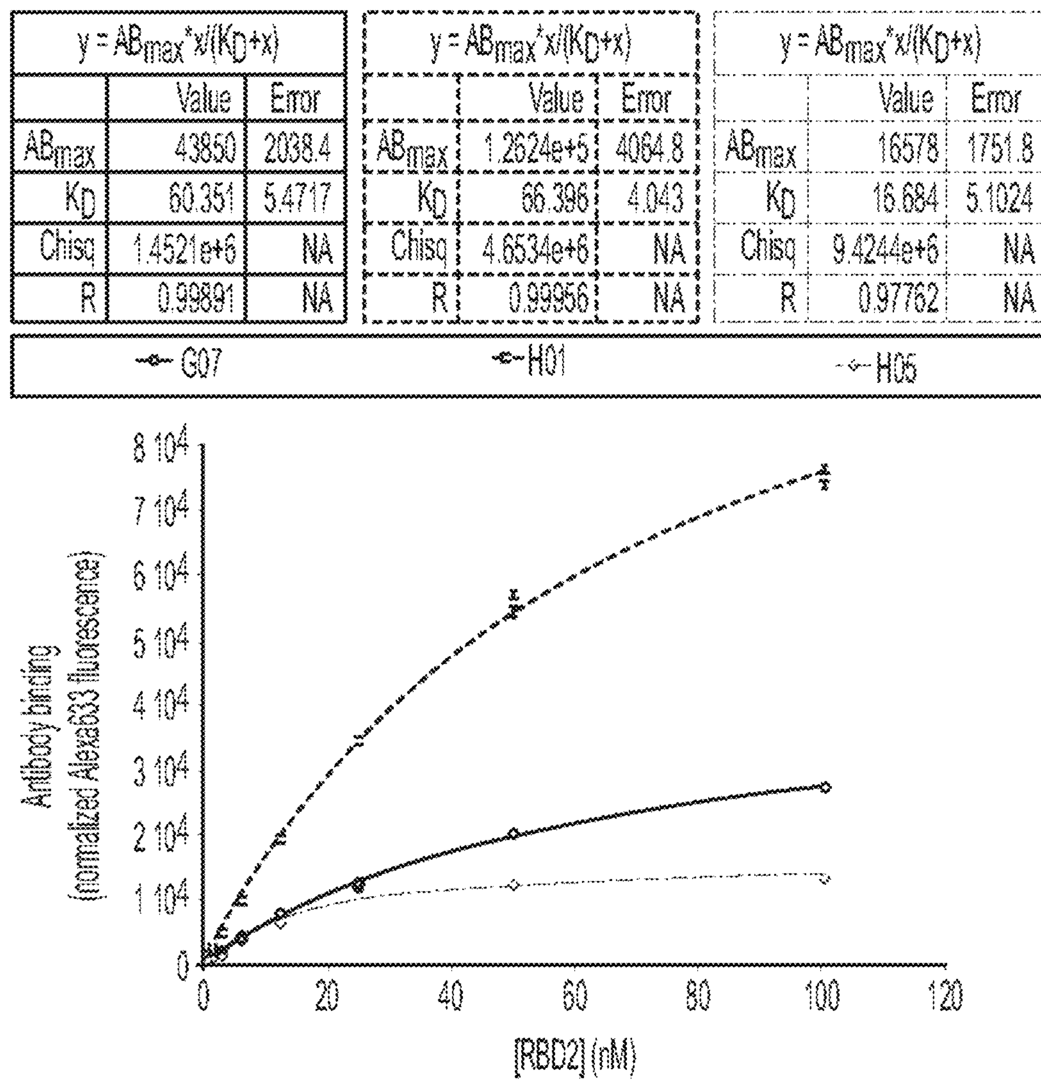

FIG. 6 illustrates antigen specificity of soluble antibodies in accordance with certain embodiments of the invention, FIG. 7A illustrates relative binding affinity and specificity of selected monoclonal yeast-displayed scFvs measured at antigen concentration below saturation in accordance with certain embodiments of the invention;

FIG. 7B illustrates relative binding affinity and specificity of selected human minibodies, i.e. scFv-Fc chimeras with human Fc measured at antigen concentration below saturation in accordance with certain embodiments of the invention;

FIG. 7C illustrates relative binding affinity and specificity of selected rabbit minibodies, i.e. scFv-Fc chimeras with rabbit Fc measured at antigen concentration below saturation in accordance with certain embodiments of the invention;

FIGS. 8A. 8B, 8C, and 8D illustrate kinetic data from flow cytometry-based kinetic measurements of yeast-displayed single chain antibodies (scFv).

Figure 8D:
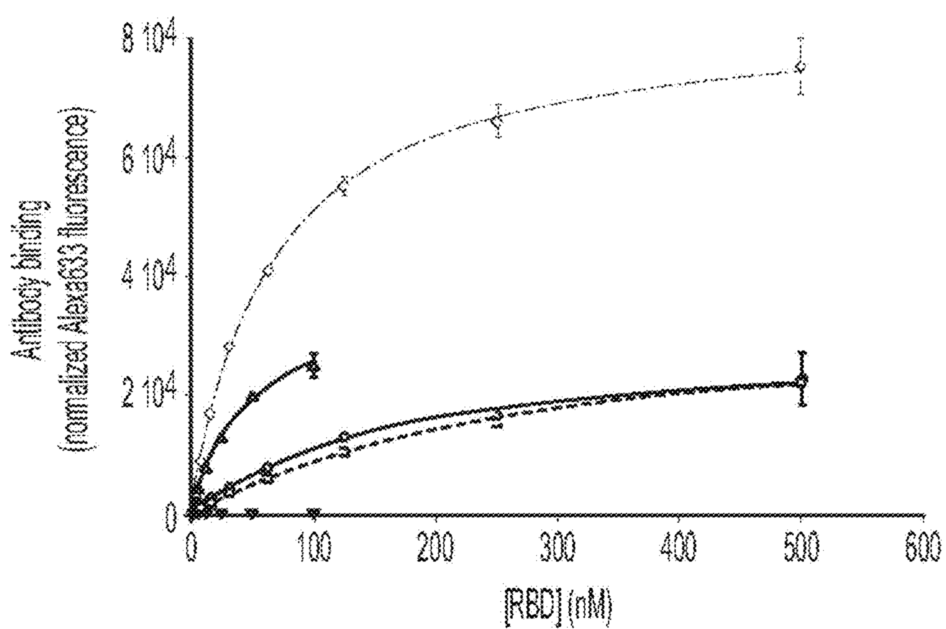
Figure 8E:
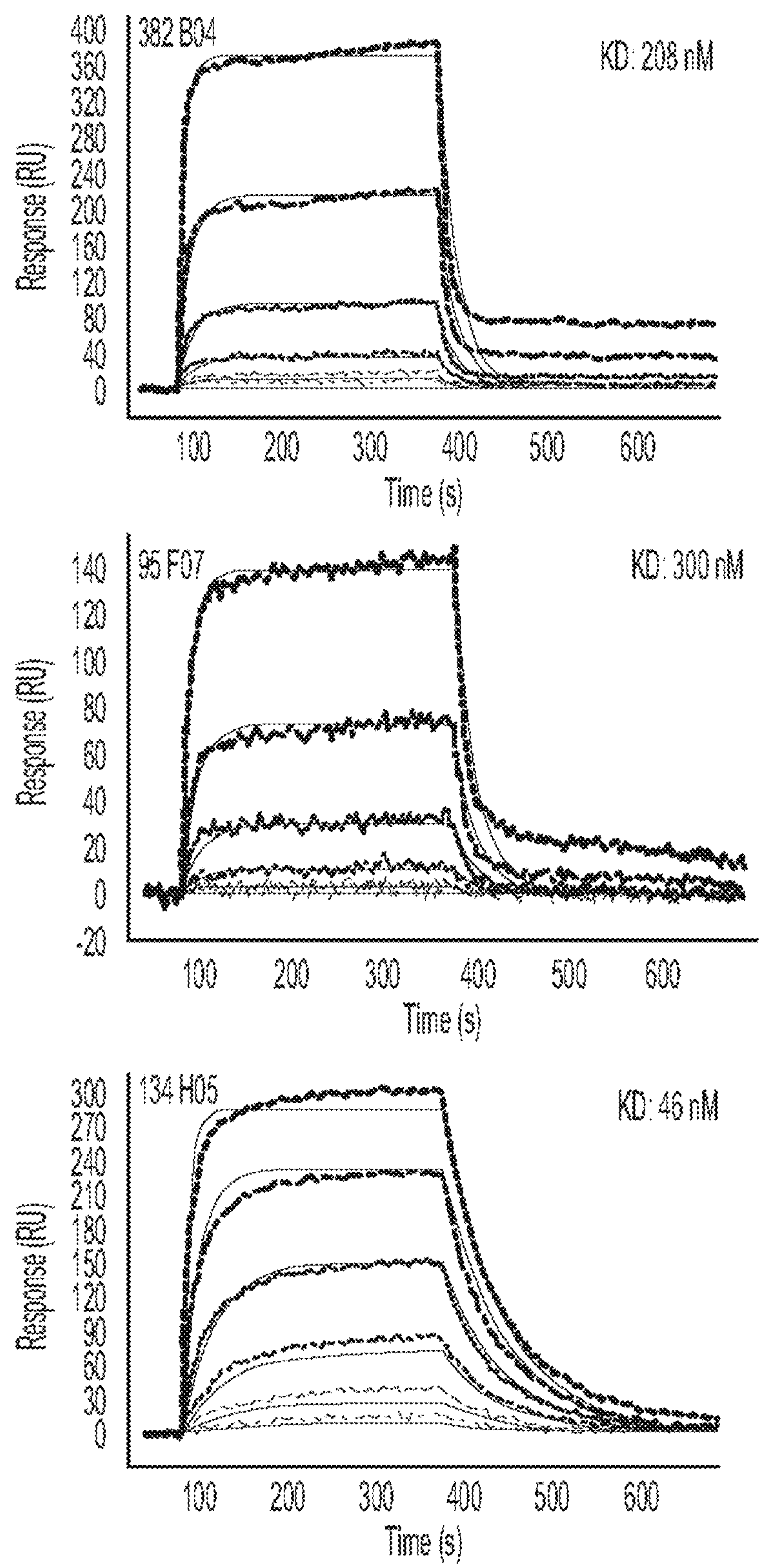
Figure 8F:
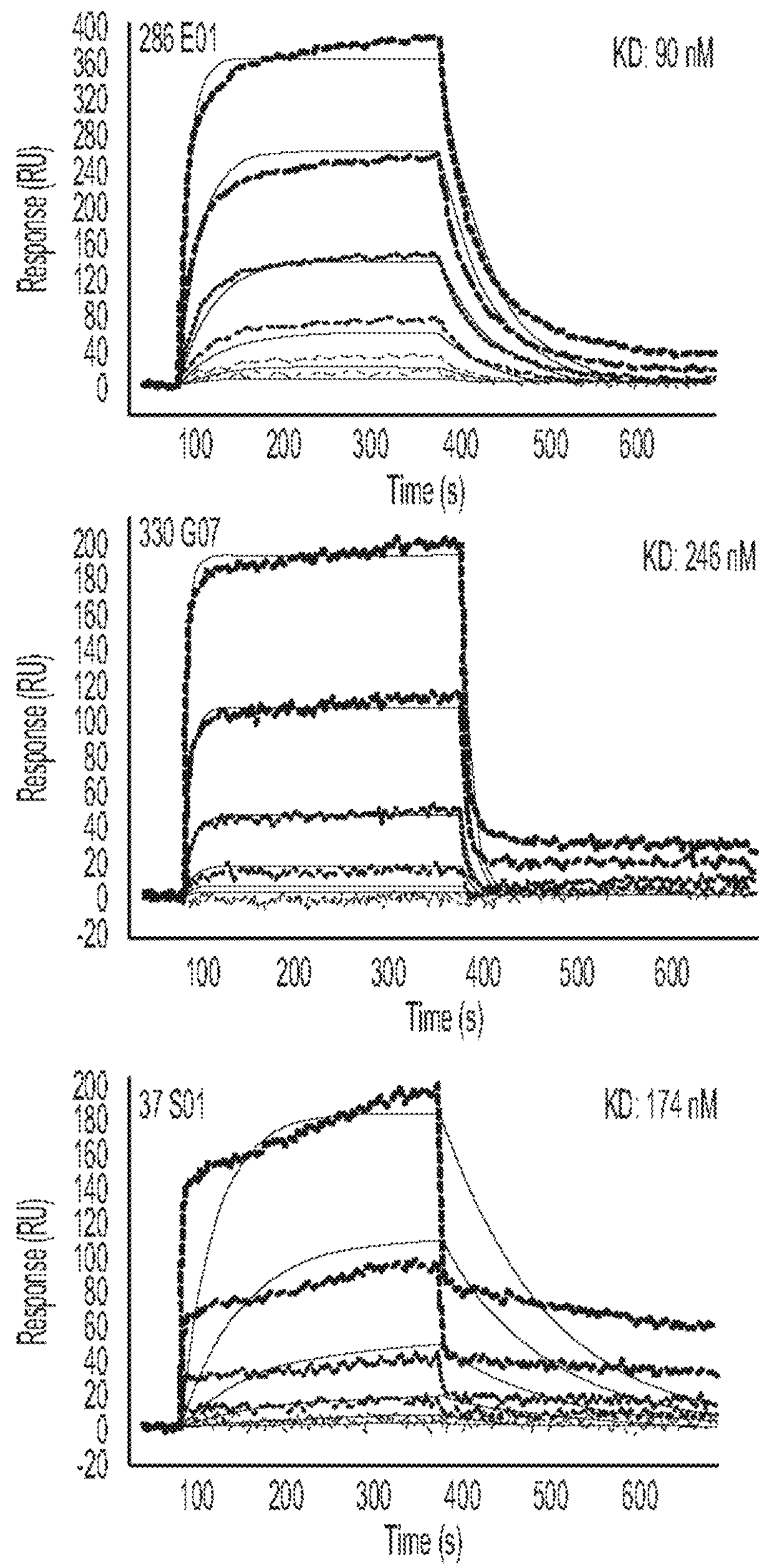
Figure 8G:
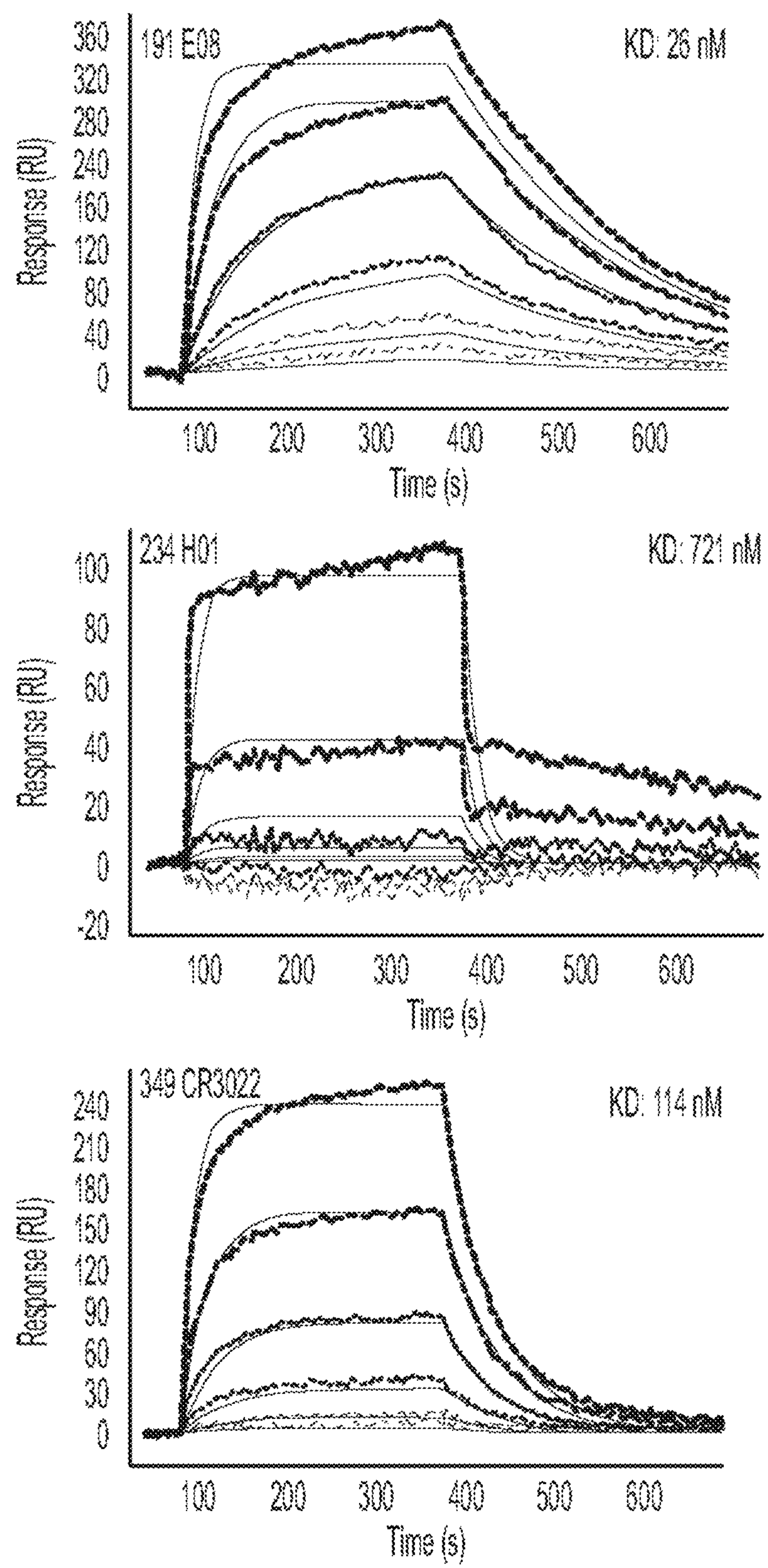

FIGS. 8E, 8F, and 8G illustrate representative sensorgrams from surface plasmon resonance (SPR)-based kinetic measurements reported in Tables 6 and 9.

Figure 9B:
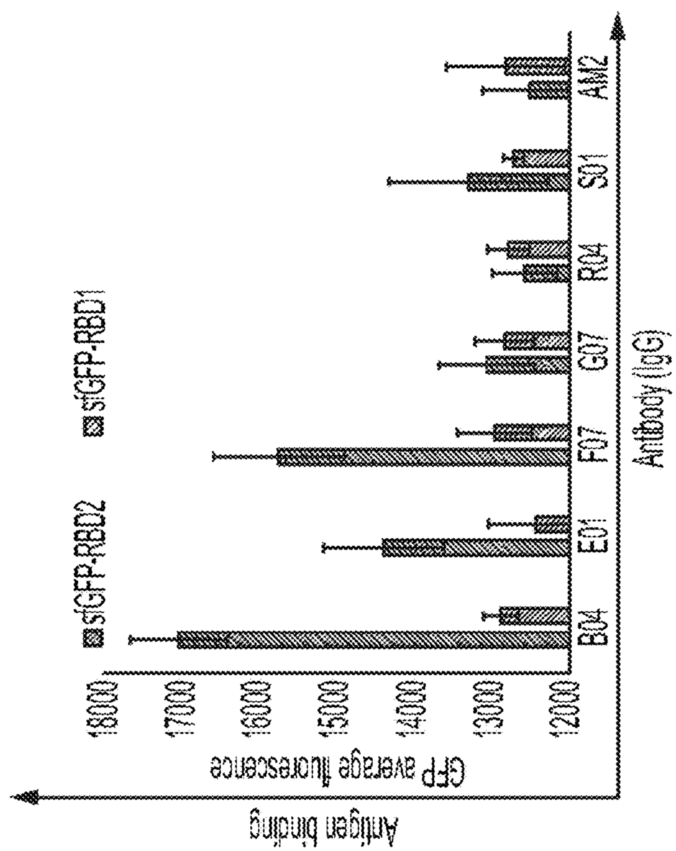
Figure 9A:
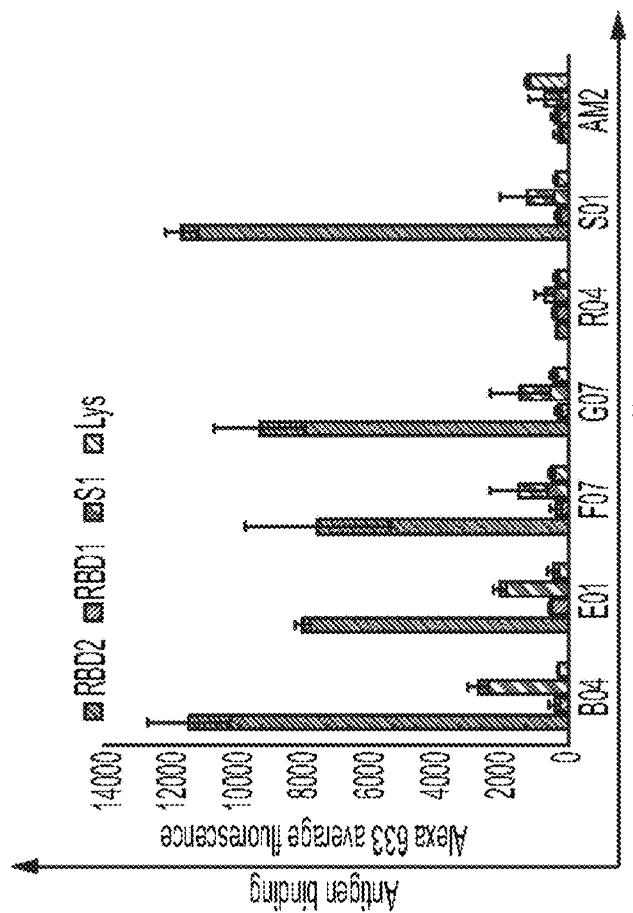
Figure 10:
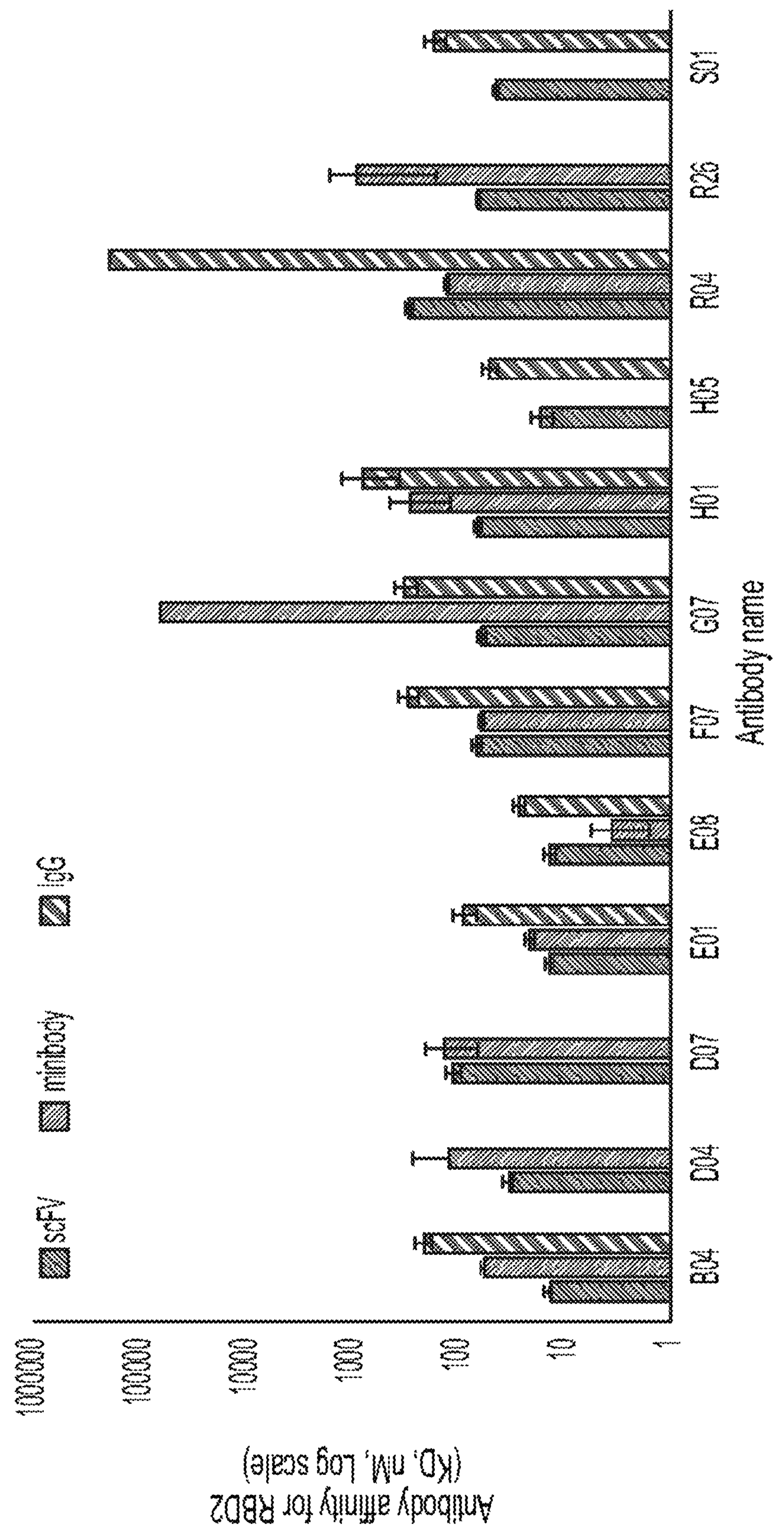
Figure 11A:
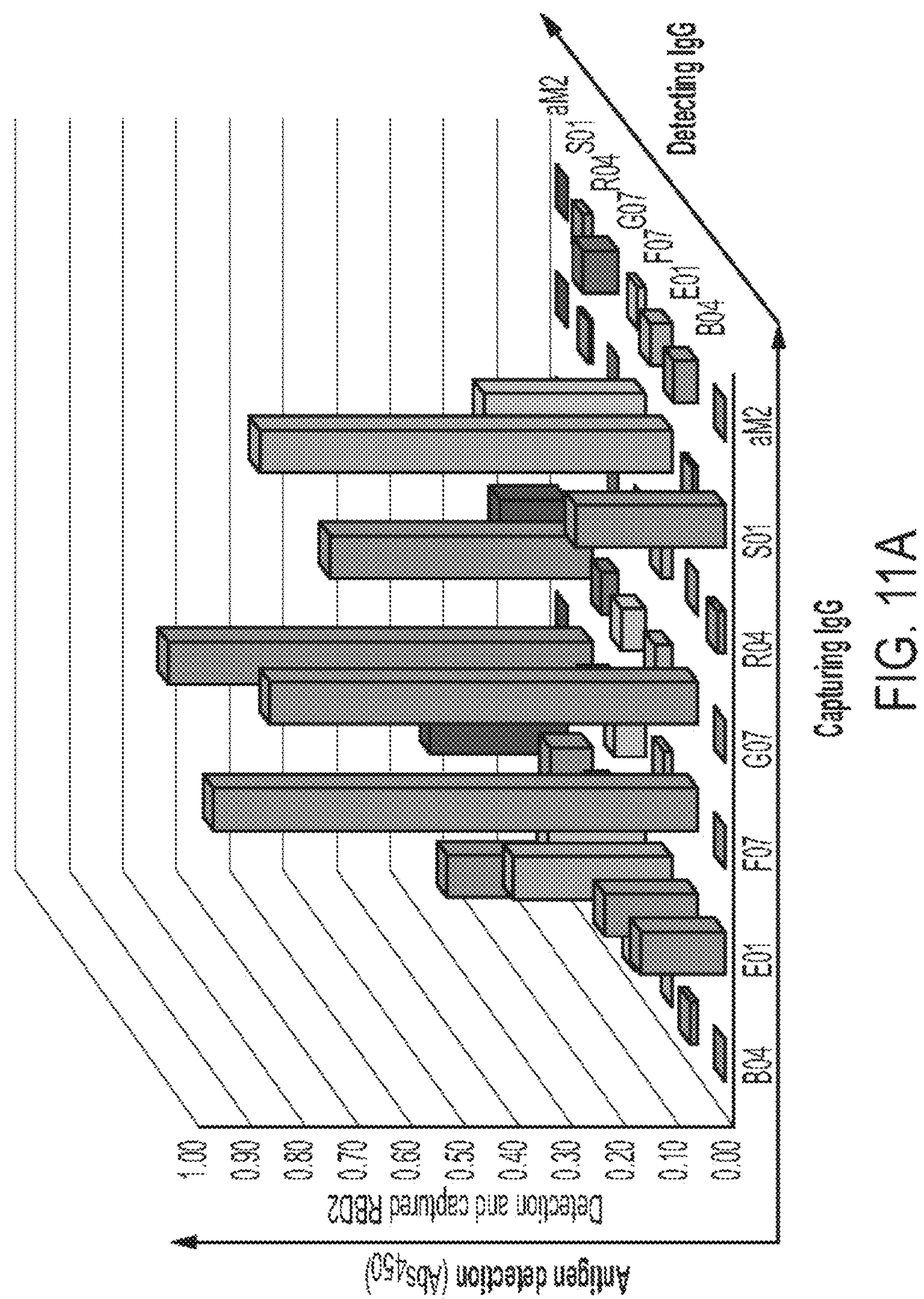
Figures 11C, 11D:
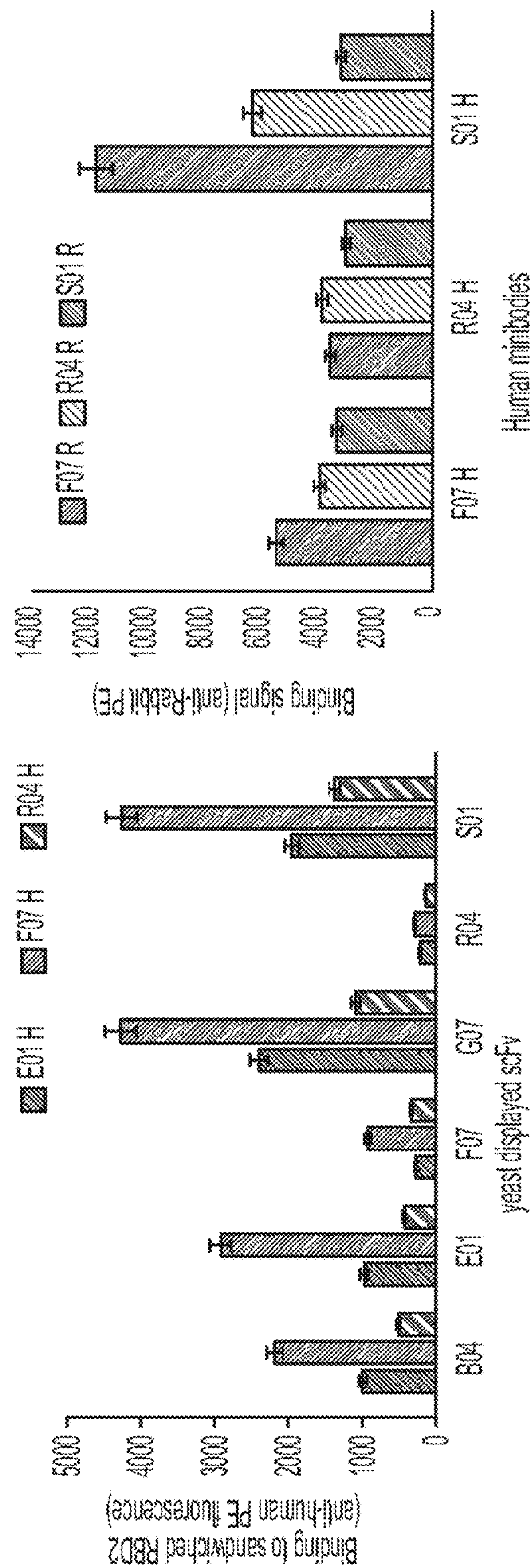

FIGS. 9A and 9B illustrate specificity of IgG interactions in accordance with certain embodiments of the invention;

FIG. 10 illustrates affinity variations depending on antibody format in accordance with certain embodiments of the invention;

Figure 11B:
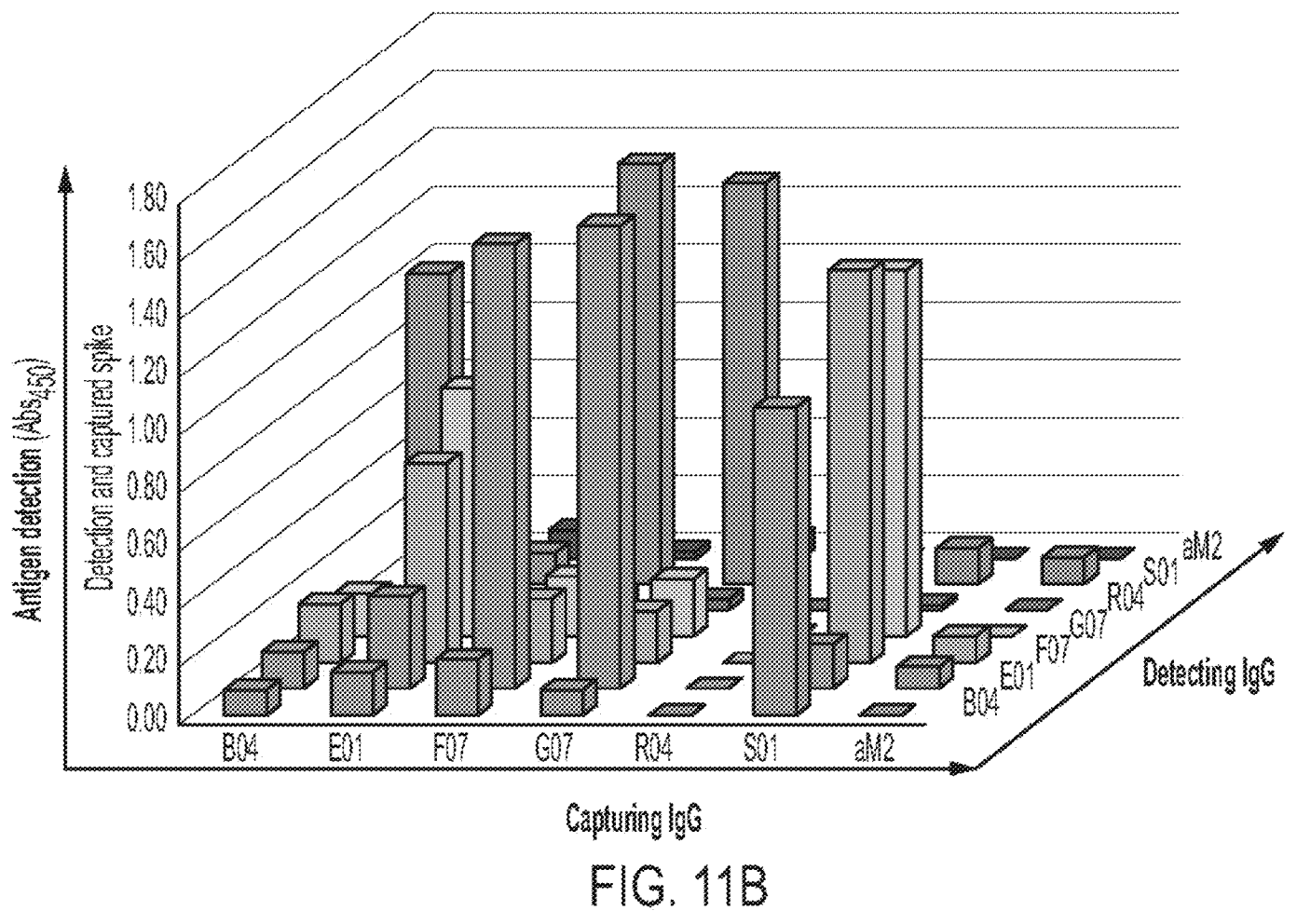

FIGS. 11A, 11B, 11C, and 11D illustrate epitope binning by sandwich ELISA experiments. FIGS. 11A and 11B illustrate identification of antibody pairs (capturing and detecting IgG) capable of binding to distinct regions (epitopes) of SARS-CoV 2 spike protein receptor binding domain (RBD2, FIG. 11A) and SARS-CoV 2 whole spike protein (FIG. 11B). FIGS. 11C and 11D illustrate testing for orthogonal binding pairs.

Figures 12A, 12B:
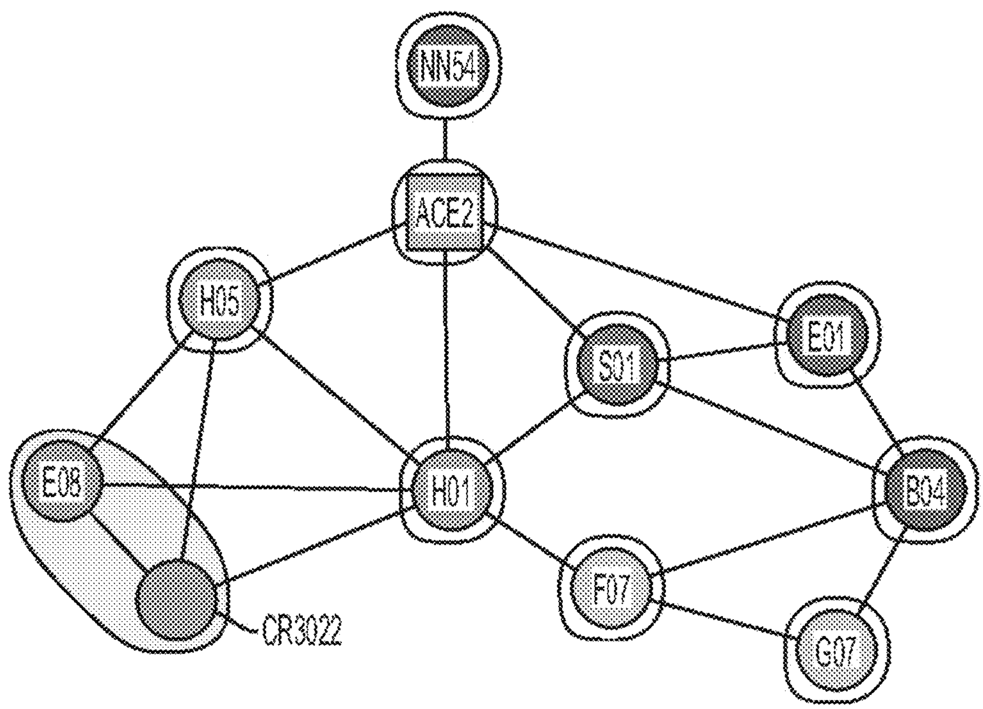

FIGS. 12A and 12B illustrate antibody epitope binning by surface plasmon resonance (SPR). FIGS. 12A and 12B used commercial anti-RBD2 antibody CR3022 in the analysis. FIG. 12A is a heat map rendition of the SPR data. FIG. 12B is a network plot rendition of the SPR data.

Figures 13A, 13B:
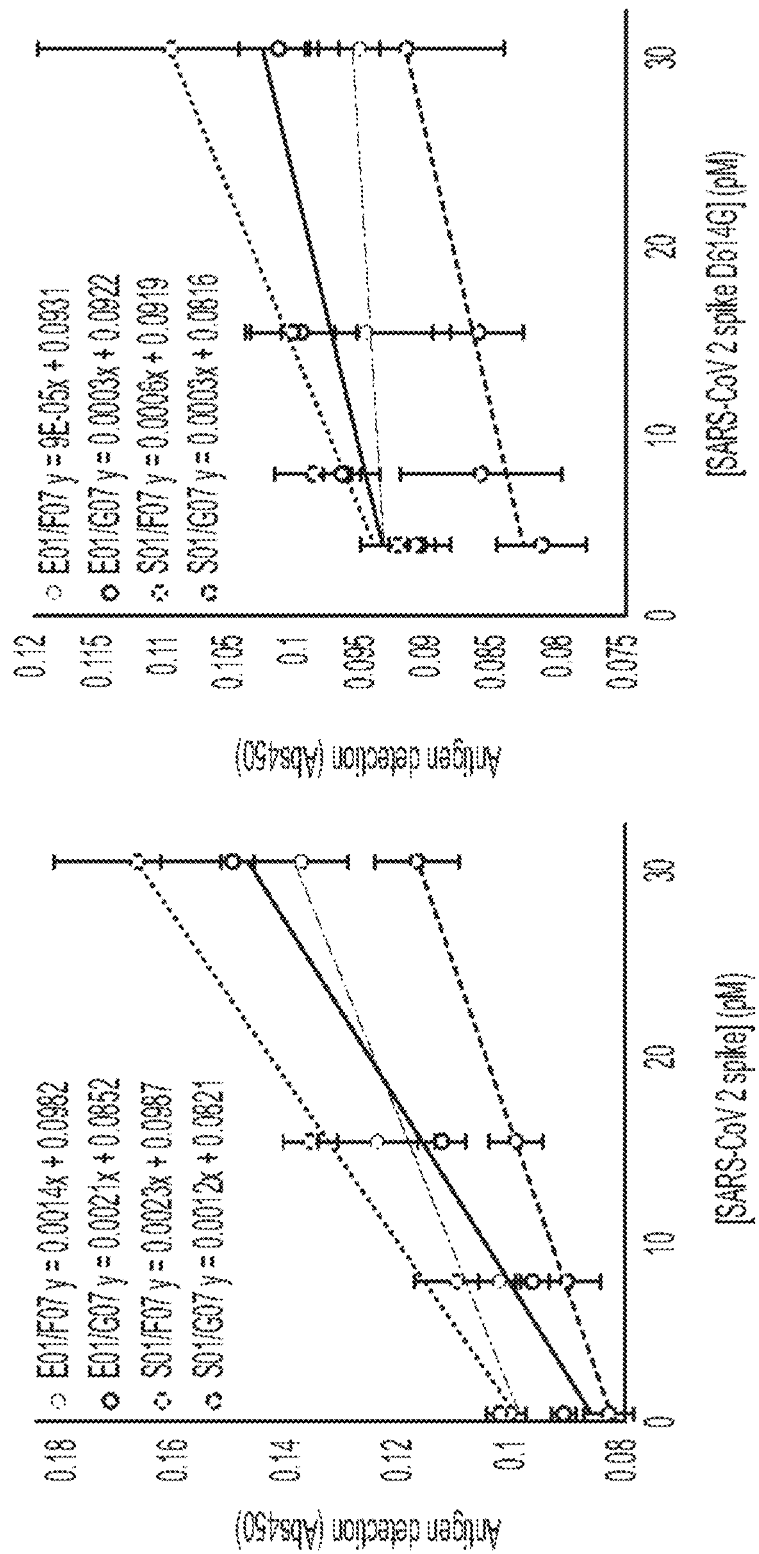
Figures 13C, 13D:
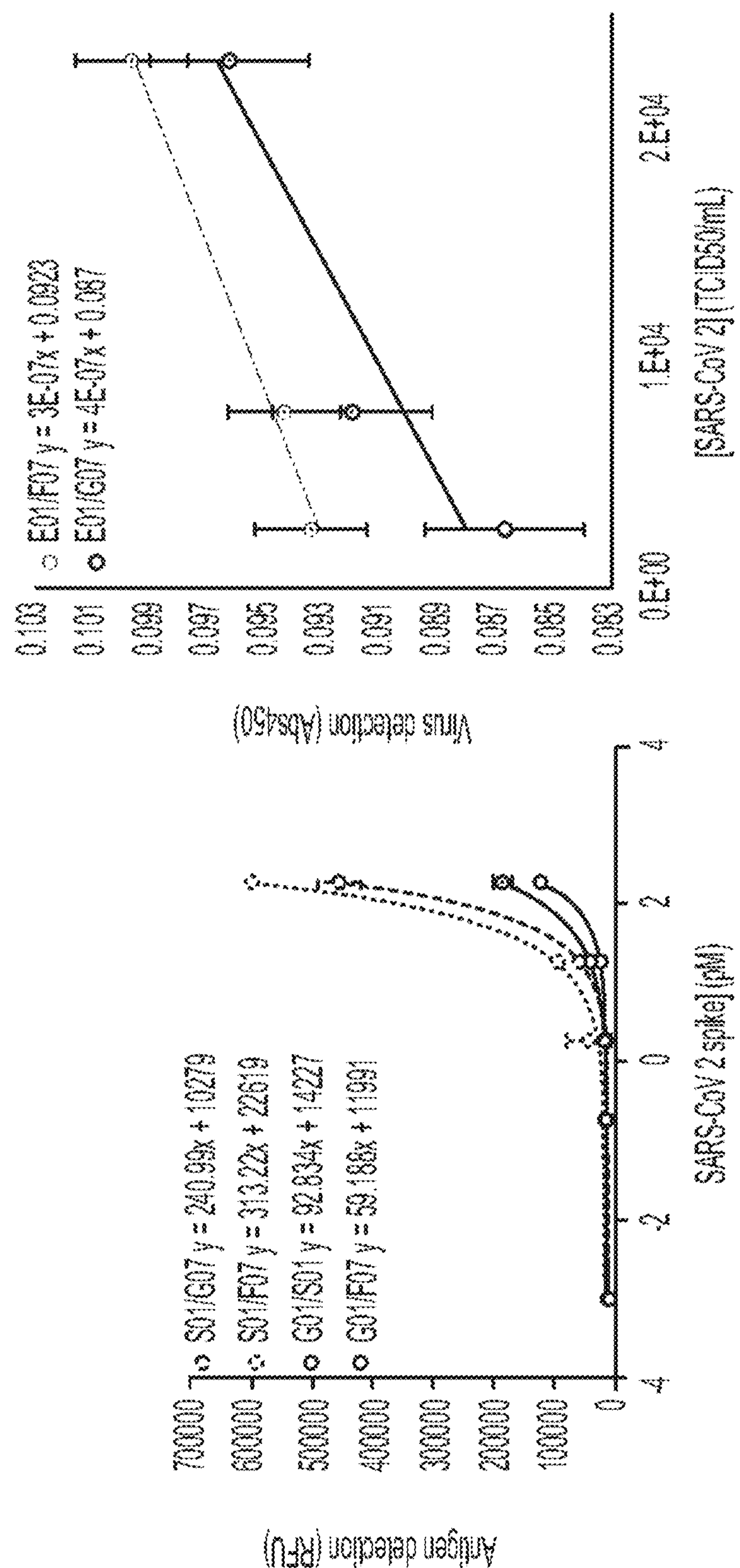

FIGS. 13A-D illustrate detection of trimeric spike or whole SARS-CoV 2 virus by sandwich immunoassays. FIG. 13A illustrates detection of wild type spike by sandwich ELISA. FIG. 13B illustrates detection of D614G mutant spike by sandwich ELISA. FIG. 13C illustrates detection of wild type spike by SpinDx. FIG. 13D illustrates detection of heat inactivated whole SARS-CoV 2 virus by sandwich ELISA.

Figure 14A:
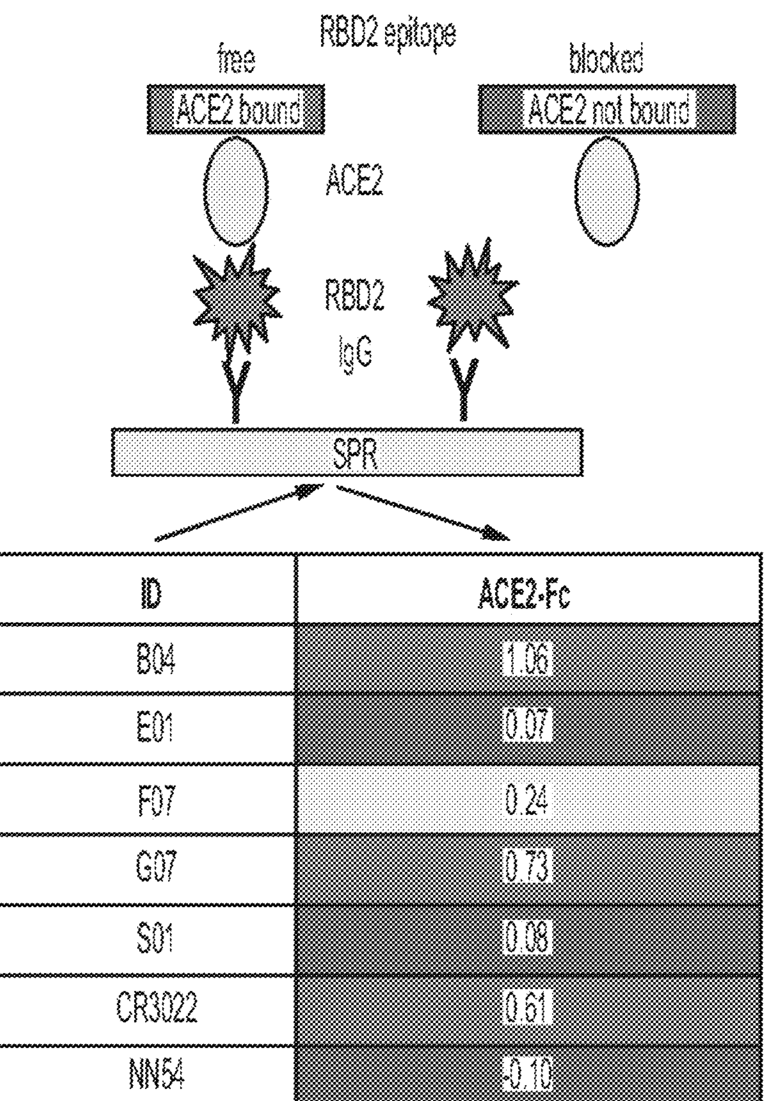
Figure 14B:
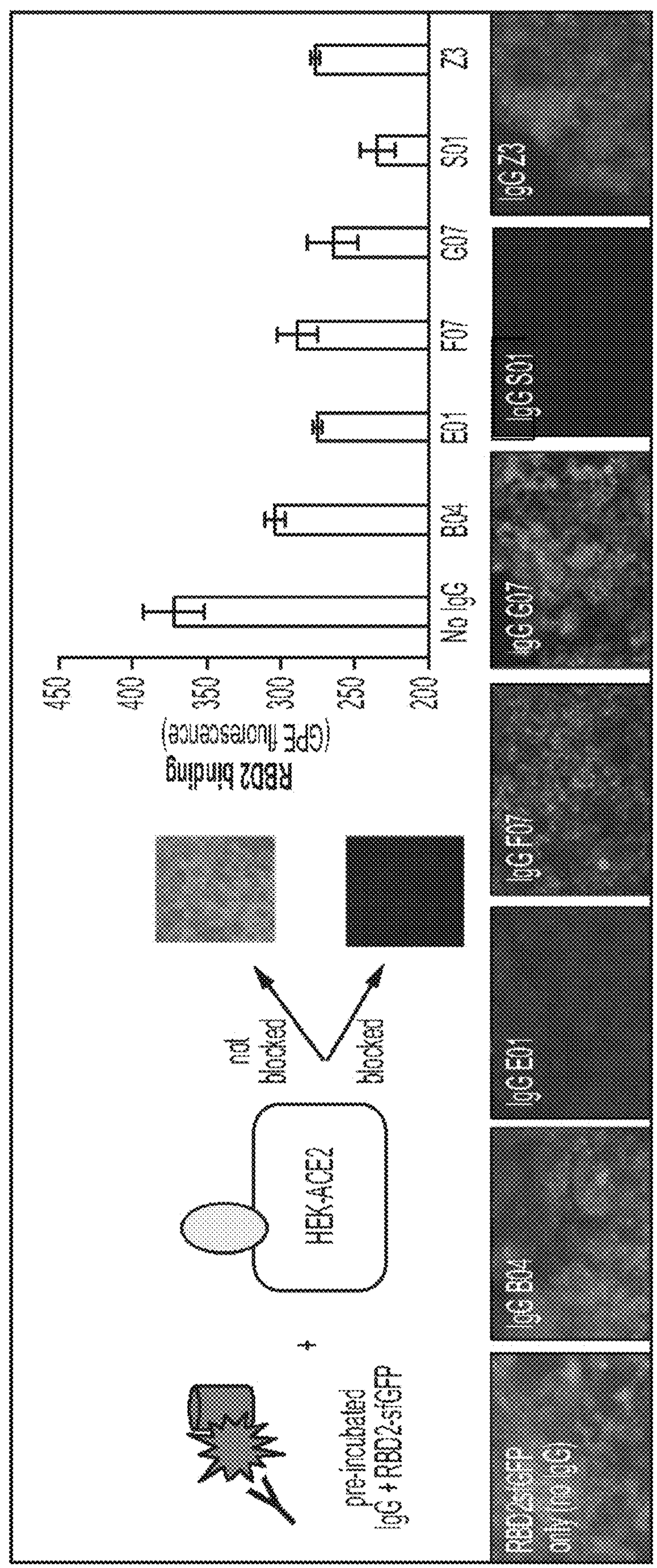
Figure 14C:
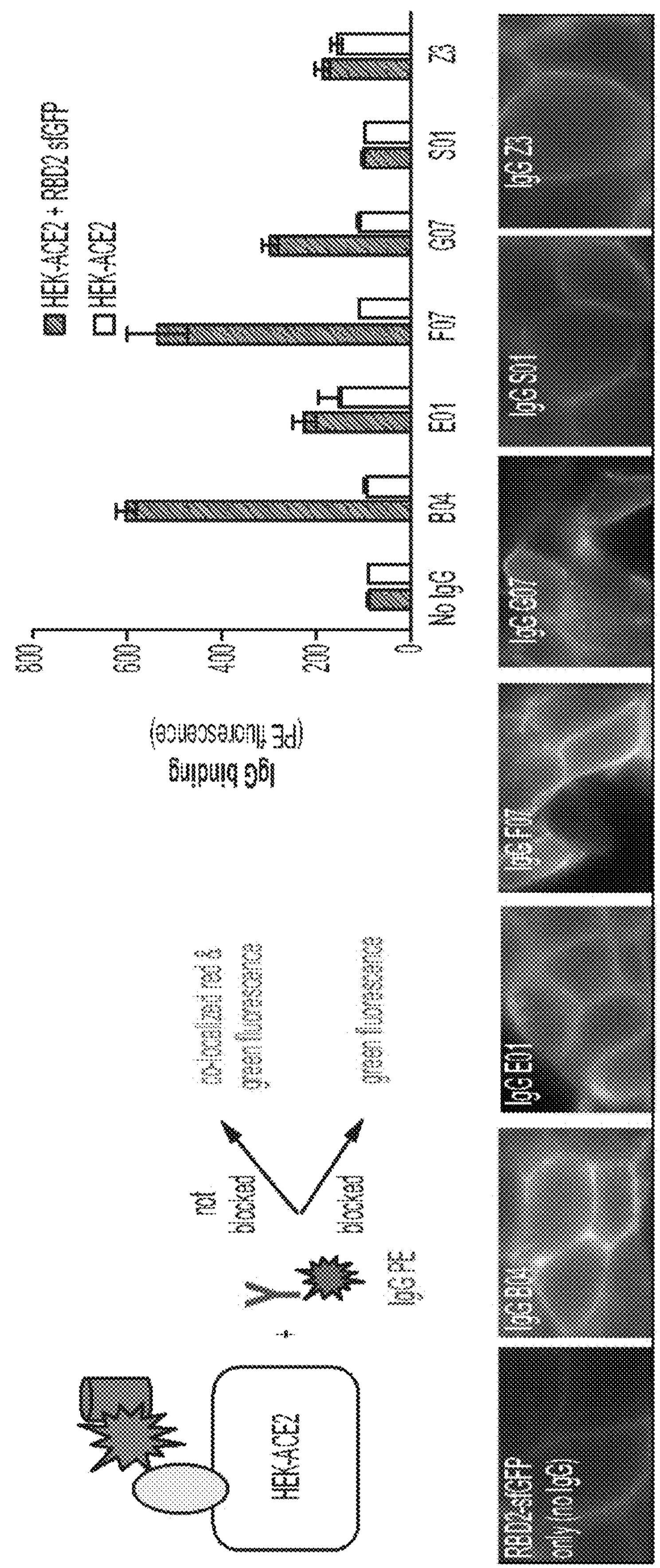

FIGS. 14A, 14B, and 14C illustrate antibody interference with binding of SARS-CoV 2 spike protein's receptor-binding domain (RBD2) to ACE2. FIG. 14A is a heat map plot of surface plasmon resonance SPR data, depicting normalized ACE2-Fc binding to RBD2 captured by immobilized antibodies. FIGS. 14B and 14C illustrate immunocytochemistry studies using human embryonic kidney (HEK) cells expressing ACE2 and microscopy analysis, using either unlabeled (FIG. 14B) or phycoerythrin (PE)-labelled anti RBD2 antibodies (FIG. 14C).

Figure 15:
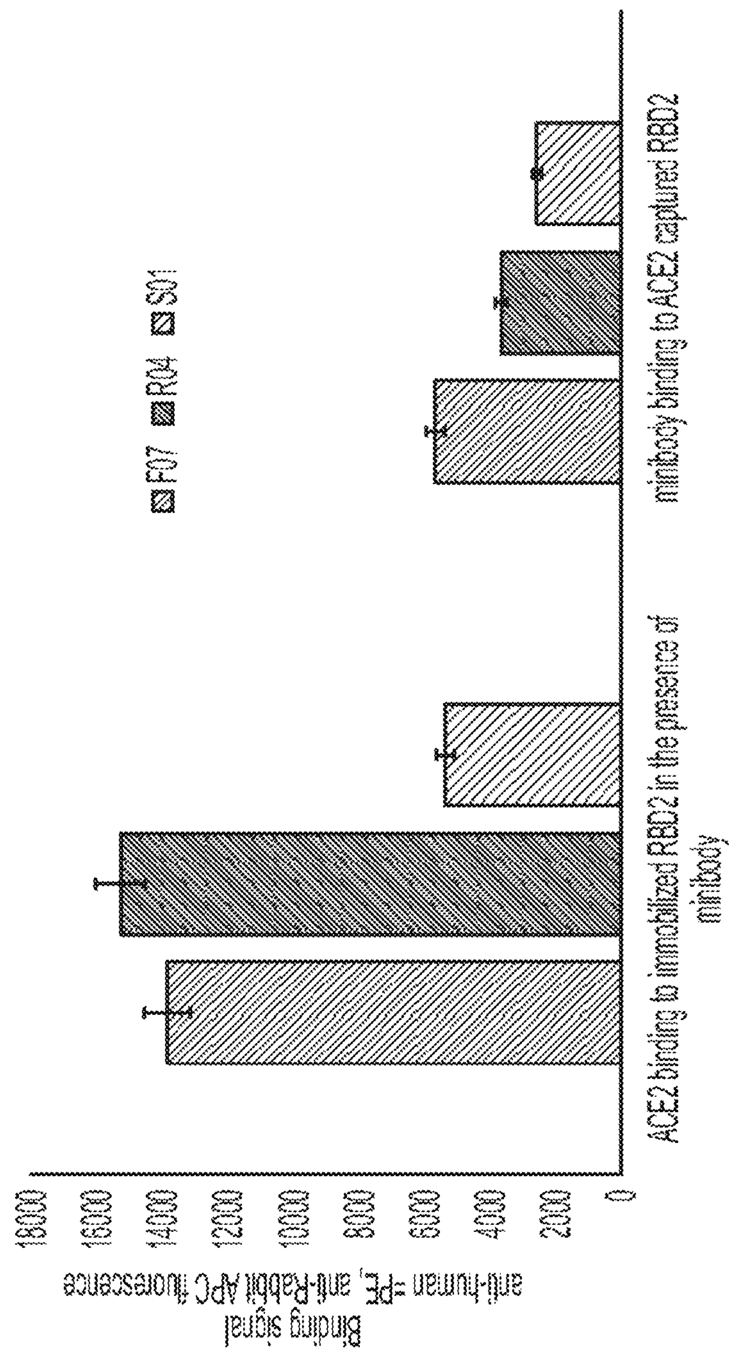
Figure 16A:
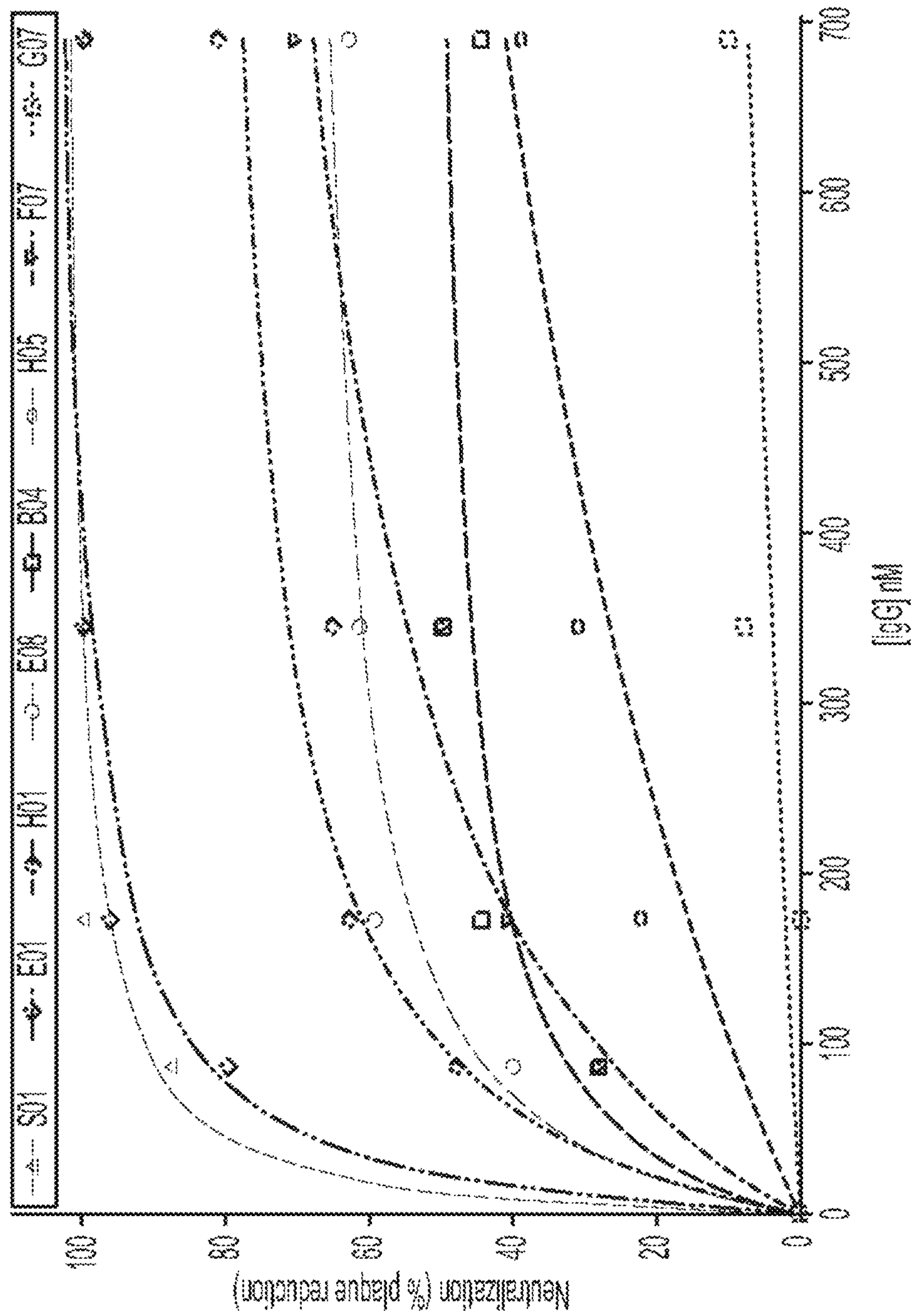
Figure 16B:
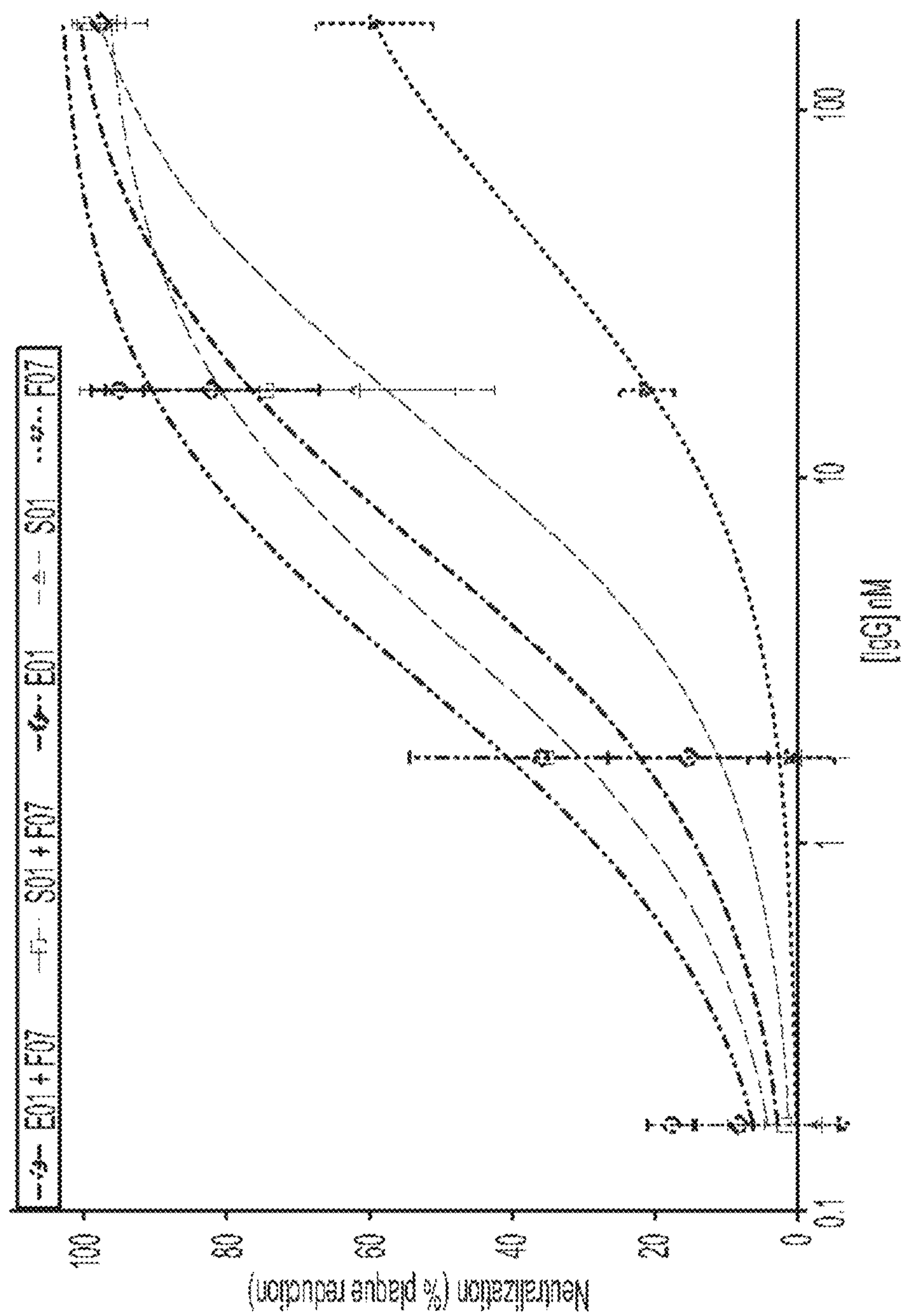

FIG. 15 illustrates testing for competition with of ACE2 in binding to RBD2 in accordance with certain embodiments of the invention;

FIG. 16A and FIG. 16B illustrate in vitro neutralization of authentic SARS-CoV-2. FIG. 16A illustrates results from a preliminary screen of 8 antibodies. FIG. 16B illustrates results of retesting the three IgGs with the lowest half neutralizing titers (NT50) in triplicate alone or in combination.

BRIEF DESCRIPTION OF THE SEQUENCES

SEQ ID NO:1 sets forth the amino acid sequence of B04 light chain.

SEQ ID NO:2 sets forth the amino acid sequence of B10 light chain.

SEQ ID NO:3 sets forth the amino acid sequence of D07 light chain.

SEQ ID NO:4 sets forth the amino acid sequence of D10 light chain.

SEQ ID NO:5 sets forth the amino acid sequence of D11 light chain.

SEQ ID NO:7 sets forth the amino acid sequence of E01 light chain.

SEQ ID NO:9 sets forth the amino acid sequence of E08 light chain.

SEQ ID NO:10 sets forth the amino acid sequence of F07 light chain.

SEQ ID NO:11 sets forth the amino acid sequence of G07 light chain.

SEQ ID NO:12 sets forth the amino acid sequence of H01 light chain.

SEQ ID NO:13 sets forth the amino acid sequence of H02 light chain.

SEQ ID NO:14 sets forth the amino acid sequence of H03 light chain.

SEQ ID NO:15 sets forth the amino acid sequence of H05 light chain.

SEQ ID NO:16 sets forth the amino acid sequence of R04 light chain.

SEQ ID NO:17 sets forth the amino acid sequence of R09 light chain.

SEQ ID NO:18 sets forth the amino acid sequence of R26 light chain.

SEQ ID NO:19 sets forth the amino acid sequence of S01 light chain.

SEQ ID NO:20 sets forth the amino acid sequence of B04 heavy chain.

SEQ ID NO:21 sets forth the amino acid sequence of B10 heavy chain.

SEQ ID NO:22 sets forth the amino acid sequence of D07 heavy chain.

SEQ ID NO:23 sets forth the amino acid sequence of D10 heavy chain.

SEQ ID NO:24 sets forth the amino acid sequence of D11 heavy chain.

SEQ ID NO:26 sets forth the amino acid sequence of E01 heavy chain.

SEQ ID NO:28 sets forth the amino acid sequence of E08 heavy chain.

SEQ ID NO:29 sets forth the amino acid sequence of F07 heavy chain.

SEQ ID NO:30 sets forth the amino acid sequence of G07 heavy chain.

SEQ ID NO:31 sets forth the amino acid sequence of H01 heavy chain.

SEQ ID NO:32 sets forth the amino acid sequence of H02 heavy chain.

SEQ ID NO:33 sets forth the amino acid sequence of H03 heavy chain.

SEQ ID NO:34 sets forth the amino acid sequence of H05 heavy chain.

SEQ ID NO: 35: sets forth the amino acid sequence of R04 heavy chain.

SEQ ID NO:36 sets forth the amino acid sequence of R09 heavy chain.

SEQ ID NO:37 sets forth the amino acid sequence of R26 heavy chain.

SEQ ID NO:38 sets forth the amino acid sequence of S01 heavy chain.

SEQ ID NO:39 sets forth the amino acid sequence of a linker.

SEQ ID NO:40 sets forth the amino acid sequence of a linker.

SEQ ID NO:41 sets forth the amino acid sequence of B04 scFv.

SEQ ID NO:42 sets forth the amino acid sequence of B10 scFv.

SEQ ID NO:43 sets forth the amino acid sequence of D04 scFv.

SEQ ID NO:4 sets forth the amino acid sequence of D07 scFv.

SEQ ID NO:45 sets forth the amino acid sequence of D10 scFv.

SEQ ID NO:46 sets forth the amino acid sequence of D11 scFv.

SEQ ID NO:47 sets forth the amino acid sequence of E01 scFv.

SEQ ID NO:48 sets forth the amino acid sequence of E08 scFv.

SEQ ID NO:49 sets forth the amino acid sequence of F07 scFv.

SEQ ID NO:50 sets forth the amino acid sequence of G07 scFv.

SEQ ID NO:51 sets forth the amino acid sequence of H01 scFv.

SEQ ID NO:52 sets forth the amino acid sequence of H02 scFv.

SEQ ID NO:53 sets forth the amino acid sequence of H03 scFv.

SEQ ID NO:54 sets forth the amino acid sequence of H05 scFv.

SEQ ID NO:55 sets forth the amino acid sequence of R04 scFv.

SEQ ID NO: 56 sets forth the amino acid sequence of R09 scFv.

SEQ ID NO:57 sets forth the amino acid sequence of R26 scFv.

SEQ ID NO:58 sets forth the amino acid sequence of S01 scFv.

SEQ ID NO:59 sets forth the amino acid sequence of a linker.

SEQ ID NO:60 sets forth the amino acid sequence of a linker.

SEQ ID NO:61 sets forth the amino acid sequence of a linker.

SEQ ID NO:62 sets forth the amino acid sequence of a linker.

SEQ ID NO:63 sets forth the amino acid sequence of a linker.

SEQ ID NO:64 sets forth the amino acid sequence of D04 heavy chain.

SEQ ID NO:65 sets forth the amino acid sequence of D04 light chain.

SEQ ID NO:66 sets forth the amino acid sequence of D12 scFv.

SEQ ID NO:67 sets forth the amino acid sequence of E07 scFv.

SEQ ID NO:68 sets forth the amino acid sequence of a consensus scFv sequence of FIGS. 2A, 2B, 2C, and 2D.

SEQ ID NO:69 sets forth the nucleotide sequence of a primer.

SEQ ID NO:70: sets forth the nucleotide sequence of a primer.

SEQ ID NO:71 sets forth the nucleotide sequence of a primer.

SEQ ID NO:72 sets forth the nucleotide sequence of a primer.

SEQ ID NO:73 sets forth the amino acid sequence of B04 Kabat-Chothia Composite CDR-L1.

SEQ ID NO:74 sets forth the amino acid sequence of B04 Kabat-Chothia Composite CDR-L2.

SEQ ID NO: 75 sets forth the amino acid sequence of B04 Kabat-Chothia Composite CDR-L3.

SEQ ID NO:76 sets forth the amino acid sequence of B04 Kabat-Chothia Composite CDR-Ht.

SEQ ID NO:77 sets forth the amino acid sequence of B04 Kabat-Chothia Composite CDR-H2.

SEQ ID NO:78 sets forth the amino acid sequence of B04 Kabat-Chothia Composite CDR-H3.

SEQ ID NO:79 sets forth the amino acid sequence of B10 Kabat-Chothia Composite CDR-L1.

SEQ ID NO:80 sets forth the amino acid sequence of B10 Kabat-Chothia Composite CDR-L2.

SEQ ID NO:81 sets forth the amino acid sequence of B10 Kabat-Chothia Composite CDR-L3.

SEQ ID NO:82 sets forth the amino acid sequence of B10 Kabat-Chothia Composite CDR-H1.

SEQ ID NO:83 sets forth the amino acid sequence of B10 Kabat-Chothia Composite CDR-H2.

SEQ ID NO:84 sets forth the amino acid sequence of B10 Kabat-Chothia Composite CDR-H3.

SEQ ID NO:85 sets forth the amino acid sequence of D04 Kabat-Chothia Composite CDR-L1.

SEQ ID NO:86 sets forth the amino acid sequence of D04 Kabat-Chothia Composite CDR-L2.

SEQ ID NO:87 sets forth the amino acid sequence of D04 Kabat-Chothia Composite CDR-L3.

SEQ ID NO:88 sets forth the amino acid sequence of D04 Kabat-Chothia Composite CDR-H1.

SEQ ID NO:89 sets forth the amino acid sequence of D04 Kabat-Chothia Composite CDR-H2.

SEQ ID NO:90 sets forth the amino acid sequence of D04 Kabat-Chothia Composite CDR-H3.

SEQ ID NO:91 sets forth the amino acid sequence of D07 Kabat-Chothia Composite CDR-L1.

SEQ ID NO:92 sets forth the amino acid sequence of D07 Kabat-Chothia Composite CDR-L2.

SEQ ID NO:93 sets forth the amino acid sequence of D07 Kabat-Chothia Composite CDR-L3.

SEQ ID NO:94 sets forth the amino acid sequence of D07 Kabat-Chothia Composite CDR-H1.

SEQ ID NO:95 sets forth the amino acid sequence of D07 Kabat-Chothia Composite CDR-H2.

SEQ ID NO:96 sets forth the amino acid sequence of D07 Kabat-Chothia Composite CDR-H3.

SEQ ID NO:97 sets forth the amino acid sequence of D10 Kabat-Chothia Composite CDR-L1.

SEQ ID NO:98 sets forth the amino acid sequence of D10 Kabat-Chothia Composite CDR-L2.

SEQ ID NO:99 sets forth the amino acid sequence of D10 Kabat-Chothia Composite CDR-L3.

SEQ ID NO:100 sets forth the amino acid sequence of D10 Kabat-Chothia Composite CDR-H1.

SEQ ID NO:101 sets forth the amino acid sequence of D10 Kabat-Chothia Composite CDR-H2.

SEQ ID NO:102 sets forth the amino acid sequence of D10 Kabat-Chothia Composite CDR-H3.

SEQ ID NO:103 sets forth the amino acid sequence of D11 Kabat-Chothia Composite CDR-L1.

SEQ ID NO:104 sets forth the amino acid sequence of D11 Kabat-Chothia Composite CDR-L2.

SEQ ID NO:105 sets forth the amino acid sequence of D11 Kabat-Chothia Composite CDR-L3.

SEQ ID NO:106 sets forth the amino acid sequence of D11 Kabat-Chothia Composite CDR-H1.

SEQ ID NO:107 sets forth the amino acid sequence of D11 Kabat-Chothia Composite CDR-H2.

SEQ ID NO:108 sets forth the amino acid sequence of D11 Kabat-Chothia Composite CDR-H3.

SEQ ID NO:109 sets forth the amino acid sequence of D12 Kabat-Chothia Composite CDR-L1.

SEQ ID NO:110 sets forth the amino acid sequence of D12 Kabat-Chothia Composite CDR-L2.

SEQ ID NO:111 sets forth the amino acid sequence of D12 Kabat-Chothia Composite CDR-L3.

SEQ ID NO:112 sets forth the amino acid sequence of D12 Kabat-Chothia Composite CDR-H1.

SEQ ID NO:113 sets forth the amino acid sequence of D12 Kabat-Chothia Composite CDR-H2.

SEQ ID NO:114 sets forth the amino acid sequence of D12 Kabat-Chothia Composite CDR-H3.

SEQ ID NO:115 sets forth the amino acid sequence of E01 Kabat-Chothia Composite CDR-L1.

SEQ ID NO:116 sets forth the amino acid sequence of E01 Kabat-Chothia Composite CDR-L2.

SEQ ID NO:117 sets forth the amino acid sequence of E01 Kabat-Chothia Composite CDR-L3.

SEQ ID NO:118 sets forth the amino acid sequence of E01 Kabat-Chothia Composite CDR-H1.

SEQ ID NO:119 sets forth the amino acid sequence of E01 Kabat-Chothia Composite CDR-H2.

SEQ ID NO:120 sets forth the amino acid sequence of E01 Kabat-Chothia Composite CDR-H3.

SEQ ID NO:121 sets forth the amino acid sequence of E07 Kabat-Chothia Composite CDR-L1.

SEQ ID NO:122 sets forth the amino acid sequence of E07 Kabat-Chothia Composite CDR-L2.

SEQ ID NO:123 sets forth the amino acid sequence of E07 Kabat-Chothia Composite CDR-L3.

SEQ ID NO:124 sets forth the amino acid sequence of E07 Kabat-Chothia Composite CDR-H1.

SEQ ID NO:125 sets forth the amino acid sequence of E07 Kabat-Chothia Composite CDR-H2.

SEQ ID NO:126 sets forth the amino acid sequence of E07 Kabat-Chothia Composite CDR-H3.

SEQ ID NO:127 sets forth the amino acid sequence of E08 Kabat-Chothia Composite CDR-L1.

SEQ ID NO:128 sets forth the amino acid sequence of E08 Kabat-Chothia Composite CDR-L2.

SEQ ID NO:129 sets forth the amino acid sequence of E08 Kabat-Chothia Composite CDR-L3.

SEQ ID NO:130 sets forth the amino acid sequence of E08 Kabat-Chothia Composite CDR-H1.

SEQ ID NO:131 sets forth the amino acid sequence of E08 Kabat-Chothia Composite CDR-H2.

SEQ ID NO:132 sets forth the amino acid sequence of E08 Kabat-Chothia Composite CDR-H3.

SEQ ID NO:133 sets forth the amino acid sequence of F07 Kabat-Chothia Composite CDR-L1.

SEQ ID NO:134 sets forth the amino acid sequence of F07 Kabat-Chothia Composite CDR-L2.

SEQ ID NO:135 sets forth the amino acid sequence of F07 Kabat-Chothia Composite CDR-L3.

SEQ ID NO:136 sets forth the amino acid sequence of F07 Kabat-Chothia Composite CDR-H1.

SEQ ID NO:137 sets forth the amino acid sequence of F07 Kabat-Chothia Composite CDR-H2.

SEQ ID NO:138 sets forth the amino acid sequence of F07 Kabat-Chothia Composite CDR-H3.

SEQ ID NO:139 sets forth the amino acid sequence of G07 Kabat-Chothia Composite CDR-L1.

SEQ ID NO:140 sets forth the amino acid sequence of G07 Kabat-Chothia Composite CDR-L2.

SEQ ID NO:141 sets forth the amino acid sequence of G07 Kabat-Chothia Composite CDR-L3.

SEQ ID NO:142 sets forth the amino acid sequence of G07 Kabat-Chothia Composite CDR-H1.

SEQ ID NO:143 sets forth the amino acid sequence of G07 Kabat-Chothia Composite CDR-H2.

SEQ ID NO:144 sets forth the amino acid sequence of G07 Kabat-Chothia Composite CDR-H3.

SEQ ID NO:145 sets forth the amino acid sequence of H01 Kabat-Chothia Composite CDR-L1.

SEQ ID NO:146 sets forth the amino acid sequence of H01 Kabat-Chothia Composite CDR-L2.

SEQ ID NO:147 sets forth the amino acid sequence of H01 Kabat-Chothia Composite CDR-L3.

SEQ ID NO:148 sets forth the amino acid sequence of H01 Kabat-Chothia Composite CDR-H1.

SEQ ID NO:149 sets forth the amino acid sequence of H01 Kabat-Chothia Composite CDR-H2.

SEQ ID NO:150 sets forth the amino acid sequence of H01 Kabat-Chothia Composite CDR-H3.

SEQ ID NO:151 sets forth the amino acid sequence of H02 Kabat-Chothia Composite CDR-L1.

SEQ ID NO:152 sets forth the amino acid sequence of H02 Kabat-Chothia Composite CDR-L2.

SEQ ID NO:153 sets forth the amino acid sequence of H02 Kabat-Chothia Composite CDR-L3.

SEQ ID NO:154 sets forth the amino acid sequence of H02 Kabat-Chothia Composite CDR-H1.

SEQ ID NO:155 sets forth the amino acid sequence of H02 Kabat-Chothia Composite CDR-H2.

SEQ ID NO:156 sets forth the amino acid sequence of H02 Kabat-Chothia Composite CDR-H3.

SEQ ID NO:157 sets forth the amino acid sequence of H03 Kabat-Chothia Composite CDR-L1.

SEQ ID NO:158 sets forth the amino acid sequence of H03 Kabat-Chothia Composite CDR-L2.

SEQ ID NO:159 sets forth the amino acid sequence of H03 Kabat-Chothia Composite CDR-L3.

SEQ ID NO:160 sets forth the amino acid sequence of H03 Kabat-Chothia Composite CDR-H1.

SEQ ID NO:161 sets forth the amino acid sequence of H03 Kabat-Chothia Composite CDR-H2.

SEQ ID NO:162 sets forth the amino acid sequence of H03 Kabat-Chothia Composite CDR-H3.

SEQ ID NO:163 sets forth the amino acid sequence of H05 Kabat-Chothia Composite CDR-L1.

SEQ ID NO:164 sets forth the amino acid sequence of H05 Kabat-Chothia Composite CDR-L2.

SEQ ID NO:165 sets forth the amino acid sequence of H05 Kabat-Chothia Composite CDR-L3.

SEQ ID NO:166 sets forth the amino acid sequence of H05 Kabat-Chothia Composite CDR-H1.

SEQ ID NO:167 sets forth the amino acid sequence of H05 Kabat-Chothia Composite CDR-H2.

SEQ ID NO:168 sets forth the amino acid sequence of H05 Kabat-Chothia Composite CDR-H3.

SEQ ID NO:169 sets forth the amino acid sequence of R04 Kabat-Chothia Composite CDR-L1.

SEQ ID NO:170 sets forth the amino acid sequence of R04 Kabat-Chothia Composite CDR-L2.

SEQ ID NO:171 sets forth the amino acid sequence of R04 Kabat-Chothia Composite CDR-L3.

SEQ ID NO:172 sets forth the amino acid sequence of R04 Kabat-Chothia Composite CDR-H1.

SEQ ID NO:173 sets forth the amino acid sequence of R04 Kabat-Chothia Composite CDR-H2.

SEQ ID NO:174 sets forth the amino acid sequence of R04 Kabat-Chothia Composite CDR-H3.

SEQ ID NO:175 sets forth the amino acid sequence of R09 Kabat-Chothia Composite CDR-L1.

SEQ ID NO:176 sets forth the amino acid sequence of R09 Kabat-Chothia Composite CDR-L2.

SEQ ID NO:177 sets forth the amino acid sequence of R09 Kabat-Chothia Composite CDR-L3.

SEQ ID NO:178 sets forth the amino acid sequence of R09 Kabat-Chothia Composite CDR-H1.

SEQ ID NO:179 sets forth the amino acid sequence of R09 Kabat-Chothia Composite CDR-H2.

SEQ ID NO:180 sets forth the amino acid sequence of R09 Kabat-Chothia Composite CDR-H3.

SEQ ID NO:181 sets forth the amino acid sequence of R26 Kabat-Chothia Composite CDR-L1.

SEQ ID NO:182 sets forth the amino acid sequence of R26 Kabat-Chothia Composite CDR-L2.

SEQ ID NO:183 sets forth the amino acid sequence of R26 Kabat-Chothia Composite CDR-L3.

SEQ ID NO:184 sets forth the amino acid sequence of R26 Kabat-Chothia Composite CDR-H1.

SEQ ID NO:185 sets forth the amino acid sequence of R26 Kabat-Chothia Composite CDR-H2.

SEQ ID NO:186 sets forth the amino acid sequence of R26 Kabat-Chothia Composite CDR-H3.

SEQ ID NO:187 sets forth the amino acid sequence of S01 Kabat-Chothia Composite CDR-L1.

SEQ ID NO:188 sets forth the amino acid sequence of S01 Kabat-Chothia Composite CDR-L2.

SEQ ID NO:189 sets forth the amino acid sequence of S01 Kabat-Chothia Composite CDR-L3.

SEQ ID NO:190 sets forth the amino acid sequence of S01 Kabat-Chothia Composite CDR-H1.

SEQ ID NO:191 sets forth the amino acid sequence of S01 Kabat-Chothia Composite CDR-H2.

SEQ ID NO:192 sets forth the amino acid sequence of S01 Kabat-Chothia Composite CDR-H3.

DETAILED DESCRIPTION

Various embodiments of the inventions now will be described more fully hereinafter, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The term "exemplary" is used to be examples with no indication of quality level.

I. General

The invention provides antibodies and scFvs that bind to SARS-CoV-2 Spike protein receptor binding domain. Antibodies and scFvs recognizing SARS-CoV-2 Spike protein RBD with no cross reactivity with the SARS-CoV counterpart are presented herewith. In certain embodiments, scFvs comprising a light chain variable region, a linker, and a heavy chain variable region are described herein. Also described herein are nucleic acid molecules encoding the scFv and antibody molecules, methods and uses thereof for treating SARS-CoV-2 virus infection, and diagnostic methods, agents, and kits thereof.

II. Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, M D, 1987 and 1991), the Chothia definition (Chothia & Lesk, J. Mol. Biol. 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24-L34 | L24-L34 | L24-L34 | L24-L34 | L30-L36 |
| L2 | L50-L56 | L50-L56 | L50-L56 | L50-L56 | L46-L55 |
| L3 | L89-L97 | L89-L97 | L89-L97 | L89-L97 | L89-L96 |
| H1 | H31-H35B | H26-H32 . . . H34* | H26-H35B* | H26-H35B | H30-H35B |
| H2 | H50-H65 | H52-H56 | H50-H65 | H50-H58 | H47-H58 |
| H3 | H95-H102 | H95-H102 | H95-H102 | H95-H102 | H93-H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', F(ab')2., F(ab)c, Dabs, nanobodies, and Fv. The term "antibody" also includes scFvs and minibodies. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols, in Methods in Molecular Biology*, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The terms "protein," "polypeptide," and "peptide," used interchangeably herein, refer to polymeric forms of amino acids of any length, including coded and non-coded amino acids and chemically or biochemically modified or derivatized amino acids. The terms include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, refer to polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

"Codon optimization" refers to a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a fusion polypeptide can be modified to substitute codons having a higher frequency of usage in a given host cell as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" refers to the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |

-continued

| | | | | | |
|---|---|---|---|---|---|
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) refers to a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence.

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment. A fragment can also be, for example, a functional fragment or an immunogenic fragment.

The term "variant" as used herein includes modifications, derivatives, or chemical equivalents of the amino acid and nucleic acid sequences disclosed herein that perform substantially the same function as the polypeptides or nucleic acid molecules disclosed herein in substantially the same way. For instance, the variants have the same function of being able to bind to RBD2 of SARS-CoV-2 virus. In one embodiment, variants of polypeptides disclosed herein include, without limitation, conservative amino acid substitutions. Variants of polypeptides also include additions and deletions to the polypeptide sequences disclosed herein. In addition, variant nucleotide sequences and polypeptide sequences include analogs and derivatives thereof. In another embodiment, the variants include polypeptides that can bind to the same epitope or antigen recognized by the isolated light chain variable regions and isolated heavy chain variable regions disclosed herein. In embodiments, the variations of the variant consists of conservative amino acid modifications in the linker region.

The term "in vitro" refers to artificial environments and to processes or reactions that occur within an artificial environment (e.g., a test tube).

The term "in vivo" refers to natural environments (e.g., a cell or organism or body) and to processes or reactions that occur within a natural environment.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value or variations±0.5%, 1%, 5%, or 10% from a specified value.

The singular forms of the articles "a," "an," and "the" include plural references unless the context clearly dictates otherwise. For example, the term "an antigen" or "at least one antigen" can include a plurality of antigens, including mixtures thereof.

Statistically significant means p≤50.05.

II. Target Molecules

The receptor binding domain (RBD) of SARS-CoV virus interacts with the ACE2 receptor of the host cells prior to cell invasion. The RBD of the SARS-CoV-2 (causative agent of the current SARS pandemic) is significantly different than SARS-CoV (causative agent of 2003 SARS epidemic) RBD. From now on, the RBD of SARS-CoV-2 virus will be referred to as RBD2, and the RBD of SARS-CoV virus will be referred to as RBD1 The region where these proteins differ the most is called RBM (receptor binding motif). The majority of anti-RBD antibodies currently available recognize both RBD1 and RBD2. The currently available antibodies are therefore unlikely to specifically recognize SARS-CoV-2 (when used for diagnostic applications) or efficiently inhibit SARS-CoV-2 cell invasion (when used for therapeutic applications).

IV. Antibodies

A. Binding Specificity and Functional Properties

The invention provides antibodies and scFvs that bind to the SARS-CoV-2 receptor binding domain (RBD2). The examples describe isolation of antibodies against the SARS-CoV-2 receptor binding domain.

The receptor-binding domain of SARS CoV 2 spike protein (RBD2) was used as the target antigen of phage and yeast display selection. SARS CoV receptor-binding domain (RBD1) was used as a counter selection target to focus the selection on the receptor binding motif (RBM) of RBD2 and to verify the specificity of the selected antibodies. Antibodies were identified by sequencing and characterized by flow cytometry and ELISA for affinity, specificity, and uniqueness of interaction with RBD2. Selected performers were converted to IgGs and further characterized. Surface plasmon resonance (SPR) was used for affinity measurements and epitope binning. SPR, competitive ELISA, and fluorescent microscopy were used to study the influence of the antibodies on ACE2-RBD2 interaction. The diagnostic potential of selected antibody pairs (where each pair member binds RBD2 non-competitively) was tested by measuring limit of detection of trimeric SARS-CoV 2 spike protein by sandwich ELISA and SpinDx and of whole virus by sandwich ELISA. The diagnostic potential of the entire IgG suite was tested by in vitro studies, measuring the level of neutralization of HEK cells' infection by active SARS-CoV 2.

FIG. 1 provides a graphical summary of the antibody selection and characterization workflow. Phage and yeast display technologies were used in tandem for selection of anti-SARS-CoV 2 spike protein RBD (RBD2). Display organisms (either phage or yeast) are represented schematically to indicate the displayed antibody (colored circles) and the gene coding for it (colored square inside the organism's body). Selection steps a through f are described in the figure. Actions color-coded in green and red pertain to phage and yeast selections, respectively. Subtractive selection strategies used non-biotinylated SARS-CoV RBD (RBD1, orange half-moon) during the incubation step (a). Selection of RBD2-specific antibodies was encouraged by adding excess non-biotinylated RBD2 (blue half-moon) during the phage display elution step and non-biotinylated RBD1 during sorting (c).

Most of the scFvs, (i.e. excluding only R04 and R09) bind RBD2 selectively. FIGS. 2A, 2B, 2C, and 2D depict an alignment of light variable region sequences (FIGS. 2A and 2B) and heavy chain variable region sequences (FIGS. 2C and 2D). The various amino acids in FIGS. 2A, 2B, 2C, and 2D are identified by their one letter code. The color-highlighted letters in FIGS. 2A, 2B, 2C, and 2D indicate amino acids conserved throughout the sequence series. These same amino acids are the only colored ones in the consensus line (top of FIGS. 2A, 2B, 2C, and 2D). The grey portions of the consensus correspond to positions of high diversity, which are mainly found in the complementarity determining regions (CDRs) and are particularly prevalent in the heavy (H) regions of the antibodies (second half of the sequences). The CDRs, and in particular the CDRs of the heavy region (CDRH 1, 2, and 3), usually are the heaviest contributors to specific interaction with the antigen. CDRL stands for CDR in the light (L) region. Kabat-Chothia Composite CDR sequences are indicated in red in FIGS. 2A, 2B, 2C, and 2D. FIGS. 4A, 4B, and 4C illustrate the scFv sequences described herein and in FIGS. 2A, 2B, 2C, and 2D in accordance with certain embodiments of the invention; Bolded=CDRLs (1, 2, and 3 respectively; Kabat-Chothia Composite definition); Italicized and Double Underlined=Linker; Bolded Underlined=CDRHs (1, 2 and 3 respectively; Kabat-Chothia Composite definition). VL is left of linker and VH is right of linker. Single chain antibodies (scFvs) B04 through H05 were obtained by competitive selections using chemically biotinylated RBD2 as a target. scFvs R04 through 501 were obtained by non-competitive selections using avitagged-biotinylated RBD2 as a target.

Based on the alignment shown in FIGS. 2A, 2B, 2C, and 2D, percentages of identity (FIGS. 3A-1, 3A-2, and 3A-3) and similarity (FIGS. 3B-1, 3B-2, and 3B-3) were calculated. The antibody names are indicated at the top and the left side of FIGS. 3A-1, 3A-2, and 3A-3 and FIGS. 3B-1, 3B-2, and 3B-3, each cell indicating the % of identity (FIGS. 3A-1, 3A-2, and 3A-3) and similarity (FIGS. 3B-1, 3B-2, and 3B-3) of the intersecting scFvs. The lighter the cell color, the lower the identity/similarity of the intersecting scFvs. The lightest intersecting pairs might be the orthogonal antigen binders (they might bind different regions of the same antigen). Each member of these paired binders might be used as capturer and detector in highly specific diagnostic devices like sandwich lateral flow assay (LFA). Pairs E01:G07 and E01:S01 stand out because not only do they have some of the lowest identity/similarity scores, but they are also the antibodies with the highest affinity for RBD2 (indicated by the asterisk). These pairs might be good candidates for high accuracy and sensitivity LFAs.

Some antibodies disclosed herein only bind RBD2 and do not cross react with RBD1. Some antibodies disclosed herein bind different regions of RBD2. Antibodies of the invention have affinity for RBD2 of 14-290 nM, of 4-900 nM, or of 50-2000 nM. Antibodies disclosed herein are useful to detect trimeric SARS-CoV-2 spike. In some embodiments, the antibodies detect wild-type trimeric SARS-CoV-2 spike and/or D614G mutant trimeric SARS-CoV-2 spike. Some antibodies detect wild-type trimeric SARS-CoV-2 spike at a lowest limit of detection of ~200 fM. Antibodies disclosed herein are useful to detect whole SARS-CoV-2 virus, with some antibodies detecting whole SARS-CoV-2 virus at a lowest limit of detection of 3E +4 TCID50/mL. Antibodies disclosed herein interfere with binding of RBD2 to ACE2 in in vitro assays and/or in cell-based assays. Some antibodies neutralize SARS-CoV-2 infection of HEK cells in vitro, with some antibodies neutralizing SARS-CoV-2 infection of HEK cells in vitro with a lowest half neutralizing titer of 6.2 nM, 14.1 nM, 2.7 nM, or 3.7 nM.

In an effort to obtain antibodies that only recognize SARS-CoV-2 and/or efficiently inhibit cell invasion, in vitro selection of phage and yeast-displayed libraries of human single chain variable fragments (scFvs), including RBD1 as a competitive target, was used. This strategy was meant to eliminate antibodies binding to conserved regions of the two RBDs, so that only antibodies binding RBD2-unique regions would survive selection. ScFvs were tested to determine those which only bind RBD2 and do not cross react with RBD1. Antibodies according to certain embodiments of the invention are useful as diagnostics for detection of SARS-CoV-2 virus and therapeutics for treatment of patients infected with SARS-CoV-2 virus. Some antibodies appear to target different epitopes of the RBD2 antigen and, therefore, when used as a cocktail, may retain activity against mutated virus (i.e. future pandemics).

Current diagnostics for detection of SARS-CoV-2 virus (e.g. RT-PCR) require multiple steps, sophisticated instrumentation, a highly specialized laboratory environment, and expert personnel. These requirements lead to long processing time, high costs, and ultimately sub-optimal testing frequency. Containment of this pandemic requires more frequent (faster, cheaper, and deployable), sensitive, and accurate testing. Sera obtained from recovered infected patients (immune sera) have shown some promises in treating SARS-CoV-2 patients. However, this treatment option has several drawbacks, including: 1) not all immune sera are effective; 2) there is not on-demand supply of effective immune sera; 3) sera need to be tested for pathogens; etc. The overarching goal of the presented work was to obtain antibodies and scFvs that could be used as reagents in immunodiagnostics and as immunotherapeutic cocktails. Antibodies binding RBD2 were obtained by in vitro selection of human single chain variable fragments (scFv) libraries displayed on phage and yeast. In vitro selections (more than the most common animal-based selections) can be designed to obtain high specificity and affinity antibodies needed for sensitive and accurate diagnostics. Additionally, when using human libraries as the source of antibodies, there is no need to humanize the selected molecules (a process that might result in loss of desired activity) for therapeutic application. The use of two very different display organisms allowed selection for well-expressed antibodies that could be produced in easy-to-manipulate and economic bacteria/yeast-based systems. The selective pressure of the in vitro selection strategy used was the exclusive binding to RBD2. By using RBD1 as a negative selection target, only antibodies targeting unique regions of RBD2 region were allowed to reproduce and become prevalent during selection (enrichment of desired binders). Furthermore, progressive reduction of the target concentration during the selection process allowed only the highest affinity antibodies to survive evolution. Finally, toggling between phage and yeast allowed selection of binders unbiased by the display platform context and well-expressed in prokaryotic and eukaryotic organisms.

There remains an immediate need for more effective diagnostics and therapeutics for the SARS-CoV-2 virus. Disclosed herein are antibodies and scFvs that can serve as new reagents needed for better SARS-CoV-2 virus infection diagnosis and treatment. Furthermore, there remains an immediate need for specific recognition of SARS-CoV-2. Some antibodies according to certain embodiments of the invention recognize only RBD2 and do not cross react with RBD1 (see FIGS. 6, 7A-C, and 9A-B and Examples 5-6). Moreover, there remains an immediate need for accurate diagnostics and resistance-abating therapeutics. Based on percentage of identity and homology (see FIGS. 3A-1, 3A-2, and 3A-3 and 3B1, 3B-2, and 3B-3), and epitope binning experiments (see FIGS. 11A-D and 12A-B, and Example 7), some of the antibodies and scFvs disclosed herein are likely to bind different regions of RBD2, making them excellent candidates for sandwich immunoassay, where orthogonal binders act as non-competing, capturing, and detecting reagents, for accurate detection of SARS-CoV-2 virus. Additionally, since antibodies and scFvs disclosed herein are of human origin (i.e. they are recognized as "self" by the immune system), they could also be developed into therapeutics. The RBM-specific antibodies could inhibit virus infection by out-competing ACE2 binding and consequently inhibit viral penetration in human cells (i.e. viral infection). Antibodies binding to other regions of RBD could be derivatized with virus-killing agents (e.g. radionuclides), neutralizing the virus and stopping/reducing infection. Finally, a cocktail of therapeutic antibodies (which considering the diversity of the scFvs disclosed herein may be obtained) might retain activity against mutant strains of SARS-CoV-2. There remains an immediate need for highly sensitive diagnostics and low dose (affordable) therapeutics. Some antibodies disclosed herein have affinity for RBD2 in the nanomolar range (Table 9). High affinity antibodies are needed for high sensitivity immunodiagnostics and immunotherapeutics effective at low concentrations.

Some antibodies of the invention recognize different RBD2 regions (epitopes) as shown, for example in epitope binning studies as described in FIGS. 11A-D and 12A-B, and Example 7. Such antibodies recognizing different RBD2 regions (epitopes) are useful in therapeutic cocktails of antibodies and in diagnostics. Although antibodies are well known for their specificity, the use of multiple antibodies binding multiple epitopes of the target antigen instead of one, allows for a more precise recognition of the antigen. When only one epitope is recognized, a mutation of the target antigen may result in immunoescape and consequent failure of the immunodiagnostics and immunotherpeutic strategy. See, e.g., di Marzo Veronese F, Reitz M, Gupta G, et al. Loss of a neutralizing epitope by a spontaneous point mutation in the V3 loop of HIV-1 isolated from an infected laboratory worker. *Journal of Biological Chemistry.* 1993; 268(34):25894-25901 and Zhang S, Vogt MR, Oliphant T, et al. Development of resistance to passive therapy with a potently neutralizing humanized monoclonal antibody against West Nile virus. *The Journal of infectious diseases.* 2009; 200(2):202-205). Mutations spanning different regions of a functional antigen (e.g. RBD) are less likely to happen, since they might result in major structural changes and loss of function (e.g. inhibition of interaction with ACE2 receptor and host cell invasion). Therefore, a suite (or cocktail) of antibodies targeting multiple epitopes of an antigen indispensable to a microorganism's pathogenicity is useful to counter immunoescape.

The antibodies and scFvs disclosed herein can be used as reagents in rapid and portable diagnostics such as lateral flow assays (e.g., similar to a pregnancy test). The specificity of these antibodies and scFvs for SARS-CoV-2 are useful in selective recognition of the virus responsible for the current pandemic and possibly future pandemics caused by mutated virus. The high affinity of these antibodies and scFvs for the target virus are useful in high sensitivity assays. A test with these features will be highly competitive (cheaper, easier, faster, deployable, etc.) with currently used PCR-based tests. In general, the lateral flow assay market is expected to reach USD 8.7 billion by 2023 (from an estimated USD 6.0 billion in 2018), with the sandwich lateral flow assay (LFA) format expected to hold the largest market share, owing to its affordability, accuracy, and ease of use.

Since the antibodies and scFvs disclosed herein are of human origin and highly specific for their target antigen, they could also be used as therapeutics with minimal side effects. Antibodies or scFvs recognizing RBM with high affinity and competing off the RBM-ACE2 binding could be candidates for passive immunity-based treatment of SARS-CoV-2 infections. This passive immunity approach would overcome most of the issues associated with immune sera treatment (unknown composition, need for pathogen testing, inefficient response to demand, etc.). Antibodies or scFvs binding to regions other than RBM could still be developed into therapeutics if coupled with virus-killing agents (e.g. radionuclides). Considering the selection strategy that was employed, these antibodies or scFvs are likely to be "well-behaved proteins" whose production could be sustainably scaled up and adequate to demand.

In some embodiments, a scFv where VH and VL domains are connected via flexible polypeptide is provided. Accordingly, the present disclosure provides a scFv that binds SARS-CoV-2 virus comprising (a) a light chain variable region; (b) a linker; and (c) a heavy chain variable region. In one embodiment, the linker is a polypeptide linker. In another embodiment, the linker comprises one or more glycine and/or serine amino acid residues. In an embodiment, the linker comprises 2-20 amino acids.

In certain embodiments, the linker comprises the sequence SGGSTITSNNVYYTKLSSSGT (SEQ ID NO: 39). In one embodiment, the linker comprises the sequence SGGSAITSYNVYYTKLSSSGT (SEQ ID NO: 40). In one embodiment, the linker comprises the sequence SGGSTITSYNVYYTKLSSSGA (SEQ ID NO: 59). In one embodiment, the linker comprises the sequence SGGSTITSYNVNYTKLSSSGA (SEQ ID NO: 60). In one embodiment, the linker comprises the sequence SGGSTITSYNVYDTKLSSSGT (SEQ ID NO: 61). In one embodiment, the linker comprises the sequence SGGSTITSYNVYYTKLSSSGT (SEQ ID NO: 62). In one embodiment, the linker comprises the sequence SGGSTITSYNVYYTKLSSSDT (SEQ ID NO: 63).

An scFv antibody designated B04, characterized by a sequence of SEQ ID NO:41, is an exemplary antibody binding to RBD2. B04 has variable heavy and light regions characterized by SEQ ID NO:20 and SEQ ID NO:1 respectively. B04 is characterized by Kabat-Chothia Composite heavy chain CDRs CDR-H1 of SEQ ID NO:76, CDR-H2 of SEQ ID NO:77, and CDR-H3 of SEQ ID NO:78, and by Kabat-Chothia Composite light chain CDRs CDR-L1 of SEQ ID NO:73, CDR-L2 of SEQ ID NO:74, and CDR-L3 of SEQ ID NO:75. The antibody has been deposited as [DEPOSIT NUMBER].

An scFv antibody designated B10, characterized by a sequence of SEQ ID NO:42, is an exemplary antibody binding to RBD2. B10 has variable heavy and light regions characterized by SEQ ID NO:21 and SEQ ID NO:2 respectively. B10 is characterized by Kabat-Chothia Composite heavy chain CDRs CDR-H1 of SEQ ID NO:82, CDR-H2 of SEQ ID NO:83, and CDR-H3 of SEQ ID NO:84, and by Kabat-Chothia Composite light chain CDRs CDR-L1 of SEQ ID NO:79, CDR-L2 of SEQ ID NO:80, and CDR-L3 of SEQ ID NO:81. The antibody has been deposited as [DEPOSIT NUMBER].

An scFv antibody designated D04, characterized by a sequence of SEQ ID NO:43, is an exemplary antibody binding to RBD2. D04 has variable heavy and light regions characterized by SEQ ID NO:65 and SEQ ID NO:64 respectively. D04 is characterized by Kabat-Chothia Composite heavy chain CDRs CDR-H1 of SEQ ID NO:88, CDR-H2 of SEQ ID NO:89, and CDR-H3 of SEQ ID NO:90, and by Kabat-Chothia Composite light chain CDRs CDR-L1 of SEQ ID NO:85, CDR-L2 of SEQ ID NO:86, and CDR-L3 of SEQ ID NO:87. The antibody has been deposited as [DEPOSIT NUMBER].

An scFv antibody designated D07, characterized by a sequence of SEQ ID NO:44, is an exemplary antibody binding to RBD2. D07 has variable heavy and light regions characterized by SEQ ID NO:22 and SEQ ID NO:3 respectively. D07 is characterized by Kabat-Chothia Composite heavy chain CDRs CDR-H1 of SEQ ID NO:94, CDR-H2 of SEQ ID NO:95, and CDR-H3 of SEQ ID NO:96, and by Kabat-Chothia Composite light chain CDRs CDR-L1 of SEQ ID NO:91, CDR-L2 of SEQ ID NO:92, and CDR-L3 of SEQ ID NO:93. The antibody has been deposited as [DEPOSIT NUMBER].

An scFv antibody designated D10, characterized by a sequence of SEQ ID NO:45, is an exemplary antibody binding to RBD2. D10 has variable heavy and light regions characterized by SEQ ID NO:23 and SEQ ID NO:4 respectively. D10 is characterized by Kabat-Chothia Composite heavy chain CDRs CDR-H1 of SEQ ID NO:100, CDR-H2 of SEQ ID NO:101, and CDR-H3 of SEQ ID NO:102, and by Kabat-Chothia Composite light chain CDRs CDR-L1 of SEQ ID NO:97, CDR-L2 of SEQ ID NO:98, and CDR-L3 of SEQ ID NO:99. The antibody has been deposited as [DEPOSIT NUMBER].

An scFv antibody designated D11, characterized by a sequence of SEQ ID NO:46, is an exemplary antibody binding to RBD2. D11 has variable heavy and light regions characterized by SEQ ID NO:24 and SEQ ID NO:5 respectively. D11 is characterized by Kabat-Chothia Composite heavy chain CDRs CDR-H1 of SEQ ID NO:106, CDR-H2 of SEQ ID NO:107, and CDR-H3 of SEQ ID NO:108, and by Kabat-Chothia Composite light chain CDRs CDR-L1 of SEQ ID NO:103, CDR-L2 of SEQ ID NO:104, and CDR-L3 of SEQ ID NO:105. The antibody has been deposited as [DEPOSIT NUMBER].

An scFv antibody designated D12, characterized by a sequence of SEQ ID NO:66 is an exemplary antibody binding to RBD2. D12 has variable heavy and light regions characterized by SEQ ID NO:25 and SEQ ID NO:6 respectively. D12 is characterized by Kabat-Chothia Composite heavy chain CDRs CDR-H1 of SEQ ID NO: 112, CDR-H2 of SEQ ID NO: 113, and CDR-H3 of SEQ ID NO:114, and by Kabat-Chothia Composite light chain CDRs CDR-L1 of SEQ ID NO:109, CDR-L2 of SEQ ID NO:110, and CDR-L3 of SEQ ID NO:111. The antibody has been deposited as [DEPOSIT NUMBER].

An scFv antibody designated E01, characterized by a sequence of SEQ ID NO:47, is an exemplary antibody binding to RBD2. E01 has variable heavy and light regions characterized by SEQ ID NO:26 and SEQ ID NO:7 respectively. E01 is characterized by Kabat-Chothia Composite heavy chain CDRs CDR-H1 of SEQ ID NO: 118, CDR-H2 of SEQ ID NO: 119, and CDR-H3 of SEQ ID NO:120, and by Kabat-Chothia Composite light chain CDRs CDR-L1 of SEQ ID NO:115, CDR-L2 of SEQ ID NO:116, and CDR-L3 of SEQ ID NO: 117. The antibody has been deposited as [DEPOSIT NUMBER].

An scFv antibody designated E07, characterized by a sequence of SEQ ID NO:67, is an exemplary antibody binding to RBD2. E07 has variable heavy and light regions characterized by SEQ ID NO:27 and SEQ ID NO:8 respectively. E07 is characterized by Kabat-Chothia Composite heavy chain CDRs CDR-H1 of SEQ ID NO:124, CDR-H2 of SEQ ID NO:125, and CDR-H3 of SEQ ID NO:126, and by Kabat-Chothia Composite light chain CDRs CDR-L1 of SEQ ID NO:121, CDR-L2 of SEQ ID NO:122, and CDR-L3 of SEQ ID NO:123. The antibody has been deposited as [DEPOSIT NUMBER].

An scFv antibody designated E08, characterized by a sequence of SEQ ID NO:48, is an exemplary antibody binding to RBD2. E08 has variable heavy and light regions characterized by SEQ ID NO:28 and SEQ ID NO:9 respectively. E08 is characterized by Kabat-Chothia Composite heavy chain CDRs CDR-H1 of SEQ ID NO:130, CDR-H2 of SEQ ID NO:131, and CDR-H3 of SEQ ID NO:132, and by Kabat-Chothia Composite light chain CDRs CDR-L1 of SEQ ID NO:127, CDR-L2 of SEQ ID NO:128, and CDR-L3 of SEQ ID NO:129. The antibody has been deposited as [DEPOSIT NUMBER].

An scFv antibody designated F07, characterized by a sequence of SEQ ID NO:49, is an exemplary antibody binding to RBD2. F07 has variable heavy and light regions characterized by SEQ ID NO:29 and SEQ ID NO:10 respectively. F07 is characterized by Kabat-Chothia Composite heavy chain CDRs CDR-H1 of SEQ ID NO:136, CDR-H2 of SEQ ID NO:137, and CDR-H3 of SEQ ID NO:138, and by Kabat-Chothia Composite light chain CDRs CDR-L1 of SEQ ID NO:133, CDR-L2 of SEQ ID NO:134, and CDR-L3 of SEQ ID NO:135. The antibody has been deposited as [DEPOSIT NUMBER].

An scFv antibody designated G07, characterized by a sequence of SEQ ID NO:50, is an exemplary antibody binding to RBD2. G07 has variable heavy and light regions characterized by SEQ ID NO:30 and SEQ ID NO:11 respectively. G07 is characterized by Kabat-Chothia Composite heavy chain CDRs CDR-H1 of SEQ ID NO:142, CDR-H2 of SEQ ID NO:143, and CDR-H3 of SEQ ID NO:144, and by Kabat-Chothia Composite light chain CDRs CDR-L1 of SEQ ID NO:139, CDR-L2 of SEQ ID NO:140, and CDR-L3 of SEQ ID NO:141. The antibody has been deposited as [DEPOSIT NUMBER].

An scFv antibody designated H01, characterized by a sequence of SEQ ID NO:51, is an exemplary antibody binding to RBD2. H01 has variable heavy and light regions characterized by SEQ ID NO:31 and SEQ ID NO:12 respectively. H01 antibody is characterized by Kabat-Chothia Composite heavy chain CDRs CDR-H1 of SEQ ID NO:148, CDR-H2 of SEQ ID NO:149, and CDR-H3 of SEQ ID NO:150, and by Kabat-Chothia Composite light chain CDRs CDR-L1 of SEQ ID NO:145, CDR-L2 of SEQ ID NO:146, and CDR-L3 of SEQ ID NO:147. The antibody has been deposited as [DEPOSIT NUMBER].

An scFv antibody designated H02, characterized by a sequence of SEQ ID NO:52, is an exemplary antibody binding to RBD2. H02 has variable heavy and light regions characterized by SEQ ID NO:32 and SEQ ID NO:13 respectively. H02 is characterized by Kabat-Chothia Composite heavy chain CDRs CDR-H1 of SEQ ID NO:154, CDR-H2 of SEQ ID NO:155, and CDR-H3 of SEQ ID NO:156, and by Kabat-Chothia Composite light chain CDRs CDR-L1 of SEQ ID NO:151, CDR-L2 of SEQ ID NO:152, and CDR-L3 of SEQ ID NO:153. The antibody has been deposited as [DEPOSIT NUMBER].

An scFv antibody designated H03, characterized by a sequence of SEQ ID NO:53, is an exemplary antibody binding to RBD2. H03 has variable heavy and light regions characterized by SEQ ID NO:33 and SEQ ID NO:14 respectively. H03 is characterized by Kabat-Chothia Composite heavy chain CDRs CDR-H1 of SEQ ID NO:160, CDR-H2 of SEQ ID NO:161, and CDR-H3 of SEQ ID NO:162, and by Kabat-Chothia Composite light chain CDRs CDR-L1 of SEQ ID NO:157, CDR-L2 of SEQ ID NO:158, and CDR-L3 of SEQ ID NO:159. The antibody has been deposited as [DEPOSIT NUMBER].

An scFv antibody designated H05, characterized by a sequence of SEQ ID NO:54, is an exemplary antibody binding to RBD2. H05 has variable heavy and light regions characterized by SEQ ID NO:34 and SEQ ID NO:15 respectively. H05 is characterized by Kabat-Chothia Composite heavy chain CDRs CDR-H1 of SEQ ID NO:166, CDR-H2 of SEQ ID NO:167, and CDR-H3 of SEQ ID NO:168, and by Kabat-Chothia Composite light chain CDRs CDR-L1 of SEQ ID NO:163, CDR-L2 of SEQ ID NO:164, and CDR-L3 of SEQ ID NO:165. The antibody has been deposited as [DEPOSIT NUMBER].

An scFv antibody designated R04, characterized by a sequence of SEQ ID NO:55, is an exemplary antibody binding to RBD2. R04 has variable heavy and light regions characterized by SEQ ID NO:35 and SEQ ID NO:16 respectively. R04 is characterized by Kabat-Chothia Composite heavy chain CDRs CDR-H1 of SEQ ID NO:172, CDR-H2 of SEQ ID NO:173, and CDR-H3 of SEQ ID NO:174, and by Kabat-Chothia Composite light chain CDRs CDR-L1 of SEQ ID NO:169, CDR-L2 of SEQ ID NO:170, and CDR-L3 of SEQ ID NO:171. The antibody has been deposited as [DEPOSIT NUMBER].

An scFv antibody designated R09, characterized by a sequence of SEQ ID NO:56, is an exemplary antibody binding to RBD2. R09 has variable heavy and light regions characterized by SEQ ID NO:36 and SEQ ID NO:17 respectively. R09 is characterized by Kabat-Chothia Composite heavy chain CDRs CDR-H1 of SEQ ID NO:178, CDR-H2 of SEQ ID NO:179, and CDR-H3 of SEQ ID NO:180, and by Kabat-Chothia Composite light chain CDRs CDR-L1 of SEQ ID NO:175, CDR-L2 of SEQ ID NO:176, and CDR-L3 of SEQ ID NO:177. The antibody has been deposited as [DEPOSIT NUMBER].

An scFv antibody designated R26, characterized by a sequence of SEQ ID NO:57, is an exemplary antibody binding to RBD2. R26 has variable heavy and light regions characterized by SEQ ID NO:37 and SEQ ID NO:18 respectively. R26 is characterized by Kabat-Chothia Composite heavy chain CDRs CDR-H1 of SEQ ID NO:184, CDR-H2 of SEQ ID NO:185, and CDR-H3 of SEQ ID NO:186, and by Kabat-Chothia Composite light chain CDRs CDR-L1 of SEQ ID NO:181, CDR-L2 of SEQ ID NO:182, and CDR-L3 of SEQ ID NO:183. The antibody has been deposited as [DEPOSIT NUMBER].

An scFv antibody designated S01, characterized by a sequence of SEQ ID NO:58, is an exemplary antibody binding to RBD2. S01 has variable heavy and light regions characterized by SEQ ID NO:38 and SEQ ID NO:19 respectively. S01 is characterized by Kabat-Chothia Composite heavy chain CDRs CDR-H1 of SEQ ID NO:190, CDR-H2 of SEQ ID NO:191, and CDR-H3 of SEQ ID NO:192, and by Kabat-Chothia Composite light chain CDRs CDR-L1 of SEQ ID NO:187, CDR-L2 of SEQ ID NO:188, and CDR-L3 of SEQ ID NO:189. The antibody has been deposited as [DEPOSIT NUMBER].

An scFv antibody designated D04, characterized by a sequence of SEQ ID NO:43, is an exemplary antibody binding to RBD2. D04 has variable heavy and light regions characterized by SEQ ID NO:65 and SEQ ID NO:64 respectively. D04 is characterized by Kabat-Chothia Composite heavy chain CDRs CDR-H1 of SEQ ID NO:88, CDR-H2 of SEQ ID NO:89, and CDR-H3 of SEQ ID NO:90, and by Kabat-Chothia Composite light chain CDRs CDR-L1 of SEQ ID NO:85, CDR-L2 of SEQ ID NO:86, and CDR-L3 of SEQ ID NO:87. The antibody has been deposited as [DEPOSIT NUMBER].

In one embodiment, an antibody has a variable light chain region with at least 95% identity with a sequence selected from the group consisting of SEQ ID NOs: 1-19 and 64. In another embodiment, an antibody has a variable light chain region with at least 90%, at least 91%, at least 92%, at least 93%, at least 94%, at least 95%, at least 96%, at least 97%, at least 98%, at least 99%, or 100% identity with a sequence selected from the group consisting of SEQ ID NOs: 1-19 and 64. In one embodiment, an antibody has a variable heavy chain region with at least 95% identity with a sequence selected from the group consisting of SEQ ID NOs: 20-38 and 65. In another embodiment, an antibody has a variable heavy chain region with at least 90%, at least 91%, at least 92%, at least 93%, at least 94%, at least 95%, at least 96%, at least 97%, at least 98%, at least 99%, or 100% identity with a sequence selected from the group consisting of SEQ ID NOs: 20-38 and 65.

In one embodiment, an antibody has a variable light chain region with at least 95% identity with a sequence selected from the group consisting of SEQ ID NOs: 1-19 and 64 and a variable heavy chain region with at least 95% identity with a sequence selected from the group consisting of SEQ ID NOs: 20-38 and 65.

In one embodiment, an antibody has a variable light chain region with at least 95% identity with a sequence selected from the group consisting of SEQ ID NOs: 1, 7, 9, 10, 11, 12, 15, 16, and 19. In another embodiment, an antibody has a variable light chain region with at least 90%, at least 91%, at least 92%, at least 93%, at least 94%, at least 95%, at least 96%, at least 97%, at least 98%, at least 99%, or 100% identity with a sequence selected from the group consisting of SEQ ID NOs: 1, 7, 9, 10, 11, 12, 15, 16, and 19. In one embodiment, an antibody has a variable heavy chain region with at least 95% identity with a sequence selected from the group consisting of SEQ ID NOs: 20, 26, 28, 29, 30, 31, 34, 35, and 38. In another embodiment, an antibody has a variable heavy chain region with at least 90%, at least 91%, at least 92%, at least 93%, at least 94%, at least 95%, at least 96%, at least 97%, at least 98%, at least 99%, or 100% identity with a sequence selected from the group consisting of SEQ ID NOs: 20, 26, 28, 29, 30, 31, 34, 35, and 38.

In one embodiment, an antibody has a variable light chain region with at least 95% identity with a sequence selected from the group consisting of SEQ ID NOs: 1, 7, 9, 10, 11, 12, 15, 16, and 19 and a variable heavy chain region with at least 95% identity with a sequence selected from the group consisting of SEQ ID NOs: 20, 26, 28, 29, 30, 31, 34, 35, and 38.

In one embodiment, an antibody has a variable light chain region with at least 95% identity with SEQ ID NO: 1 and a variable heavy chain region with at least 95% identity with SEQ ID NO: 20. In one embodiment, an antibody has a variable light chain region comprising SEQ ID NO: 1 and a variable heavy chain region comprising SEQ ID NO: 20.

In one embodiment, an antibody has a variable light chain region with at least 95% identity with SEQ ID NO: 7 and a variable heavy chain region with at least 95% identity with SEQ ID NO: 26. In one embodiment, an antibody has a variable light chain region comprising SEQ ID NO: 7 and a variable heavy chain region comprising SEQ ID NO: 26.

In one embodiment, an antibody has a variable light chain region with at least 95% identity with SEQ ID NO: 9 and a variable heavy chain region with at least 95% identity with SEQ ID NO: 28. In one embodiment, an antibody has a variable light chain region comprising SEQ ID NO: 9 and a variable heavy chain region comprising SEQ ID NO: 28.

In one embodiment, an antibody has a variable light chain region with at least 95% identity with SEQ ID NO: 10 and a variable heavy chain region with at least 95% identity with SEQ ID NO: 29. In one embodiment, an antibody has a variable light chain region comprising SEQ ID NO: 10 and a variable heavy chain region comprising SEQ ID NO: 29.

In one embodiment, an antibody has a variable light chain region with at least 95% identity with SEQ ID NO: 11 and a variable heavy chain region with at least 95% identity with SEQ ID NO: 30. In one embodiment, an antibody has a variable light chain region comprising SEQ ID NO: 11 and a variable heavy chain region comprising SEQ ID NO: 30.

In one embodiment, an antibody has a variable light chain region with at least 95% identity with SEQ ID NO: 12 and a variable heavy chain region with at least 95% identity with SEQ ID NO: 31. In one embodiment, an antibody has a variable light chain region comprising SEQ ID NO: 12 and a variable heavy chain region comprising SEQ ID NO: 31.

In one embodiment, an antibody has a variable light chain region with at least 95% identity with SEQ ID NO:15 and a variable heavy chain region with at least 95% identity with SEQ ID NO: 34. In one embodiment, an antibody has a variable light chain region comprising SEQ ID NO: 15 and a variable heavy chain region comprising SEQ ID NO: 34.

In one embodiment, an antibody has a variable light chain region with at least 95% identity with SEQ ID NO: 16 and a variable heavy chain region with at least 95% identity with SEQ ID NO: 35. In one embodiment, an antibody has a variable light chain region comprising SEQ ID NO: 16 and a variable heavy chain region comprising SEQ ID NO: 35.

In one embodiment, an antibody has a variable light chain region with at least 95% identity with SEQ ID NO: 19 and a variable heavy chain region with at least 95% identity with SEQ ID NO: 38. In one embodiment, an antibody has a variable light chain region comprising SEQ ID NO: 19 and a variable heavy chain region comprising SEQ ID NO: 38.

In another embodiment, an antibody comprises a variable light chain region with at least one CDR from SEQ ID Nos: 1-19 and 64. In another embodiment, an antibody comprises a variable light chain region with at least 2 or at least 3 CDRs from SEQ ID Nos: 1-19 and 64.

In another embodiment, an antibody comprises a variable heavy chain region with at least one CDR from SEQ ID Nos: 20-38 and 65. In another embodiment, an antibody comprises a variable heavy chain region with at least 2 or at least 3 CDRs from SEQ ID Nos: 20-38 and 65.

In one embodiment, an antibody comprises a variable light chain region with at least one CDR from SEQ ID NO: 7 and a variable heavy chain region with at least one CDR from SEQ ID NO: 26. In one embodiment, an antibody comprises a variable light chain region with at least one CDR from SEQ ID NO: 10 and a variable heavy chain region with at least one CDR from SEQ ID NO: 29. In one embodiment, an antibody comprises a variable light chain region with at least one CDR from SEQ ID NO: 11 and a variable heavy chain region with at least one CDR from SEQ ID NO: 30. In one embodiment, an antibody comprises a variable light chain region with at least one CDR from SEQ ID NO: 12 and a variable heavy chain region with at least one CDR from SEQ ID NO: 31. In one embodiment, an antibody comprises a variable light chain region with at least one CDR from SEQ ID NO:15 and a variable heavy chain region with at least one CDR from SEQ ID NO: 34. In one embodiment, an antibody comprises a variable light chain region with at least one CDR from SEQ ID NO: 19 and a variable heavy chain region with at least one CDR from SEQ ID NO: 38.

In one embodiment, an antibody comprises a variable light chain region with the CDRs from SEQ ID NO: 7 and a variable heavy chain region with the CDRs from SEQ ID NO: 26. In one embodiment, an antibody comprises a variable light chain region with the CDRs from SEQ ID NO: 10 and a variable heavy chain region with the CDRs from SEQ ID NO: 29. In one embodiment, an antibody comprises a variable light chain region with the CDRs from SEQ ID NO: 11 and a variable heavy chain region with the CDRs from SEQ ID NO: 30. In one embodiment, an antibody comprises a variable light chain region with the CDRs from SEQ ID NO: 12 and a variable heavy chain region with the CDRs from SEQ ID NO: 31. In one embodiment, an antibody comprises a variable light chain region with the CDRs from SEQ ID NO: 15 and a variable heavy chain region with the CDRs from SEQ ID NO: 34. In one embodiment, an antibody comprises a variable light chain region with the CDRs from SEQ ID NO: 19 and a variable heavy chain region with the CDRs from SEQ ID NO: 38.

In one embodiment, an antibody has an amino acid sequence with at least 95% identity with a sequence selected from the group consisting of SEQ ID NOs: 41-58 and 66-67. In another embodiment, an antibody has an amino acid sequence at least 90%, at least 91%, at least 92%, at least 93%, at least 94%, at least 95%, at least 96%, at least 97%, at least 98%, at least 99%, or 100% identity with a sequence selected from the group consisting of SEQ ID NOs: 41-58 and 66-67.

G. Expression of Recombinant Antibodies

A number of methods are known for recombinant expression of antibodies. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells or induced pluripotent stem cells (iPSCs), and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; W020041050884; W02008/012142; W02008/012142; W02005/019442; W02008/107388; W02009/027471; and U.S. Pat. No. 5,888,809).

Antibodies can be expressed as tetramers containing two light and two heavy chains, as separate heavy chains, light chains, as Fab, Fab', F(ab)2, and Fv, or as single chain antibodies in which heavy and light chain mature variable domains are linked through a spacer, for example as a scFv. Some antibodies can be expressed as a scFv-Fc (minibody). Some minibodies comprise a rabbit fragment crystallizable (Fc) region. Some minibodies comprise a human fragment crystallizable (Fc) region. Some antibodies are expressed in IgG isotype 1 (IgG1) format.

V. Nucleic Acids

The invention further provides nucleic acids encoding any of the heavy and light chains described above (e.g., SEQ ID NOS:1-19, 20-38, 41-58, 64-67). Optionally, such nucleic acids further encode a signal peptide and can be expressed with the signal peptide linked to the variable region. Coding sequences of nucleic acids can be operably linked with regulatory sequences to ensure expression of the coding sequences, such as a promoter, enhancer, ribosome binding site, transcription termination signal, and the like. The regulatory sequences can include a promoter, for example, a prokaryotic promoter or a eukaryotic promoter. The nucleic acids encoding heavy or light chains can be codon-optimized for expression in a host cell. The nucleic acids encoding heavy and light chains can encode a selectable gene. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

VI. Pharmaceutical Compositions and Methods of Use

Patients amenable to treatment include individuals at risk of SARS-CoV-2 infection but not showing symptoms, as well as patients presently showing symptoms. Optionally, presence or absence of symptoms, signs, or risk factors of a disease is determined before beginning treatment.

In prophylactic applications, an antibody or a pharmaceutical composition comprising the same is administered to a patient susceptible to, or otherwise at risk of, a disease (e.g., COVID-19) in regime (dose, frequency, and route of administration) effective to reduce the risk, lessen the severity, or delay the onset of at least one sign or symptom of the disease. In therapeutic applications, an antibody or agent to induce an antibody is administered to a patient suspected of, or already suffering from, a disease (e.g., COVID-19) in a regime (dose, frequency, and route of administration) effective to ameliorate or at least inhibit further deterioration of at least one sign or symptom of the disease. Exemplary pharmaceutical compositions comprise at least one of: an antibody comprising three light chain CDRs and three heavy chain CDRs of B04, an antibody comprising three light chain CDRs and three heavy chain CDRs of B10, an antibody comprising three light chain CDRs and three heavy chain CDRs of D04, an antibody comprising three light chain CDRs and three heavy chain CDRs of D07, an antibody comprising three light chain CDRs and three heavy chain CDRs of D10, an antibody comprising three light chain CDRs and three heavy chain CDRs of D11, an antibody comprising three light chain CDRs and three heavy chain CDRs of D12, an antibody comprising three light chain CDRs and three heavy chain CDRs of E01, an antibody comprising three light chain CDRs and three heavy chain CDRs of E07, an antibody comprising three light chain CDRs and three heavy chain CDRs of E08, an antibody comprising three light chain CDRs and three heavy chain CDRs of F07, an antibody comprising three light chain CDRs and three heavy chain CDRs of G07, an antibody comprising three light chain CDRs and three heavy chain CDRs of H01, an antibody comprising three light chain CDRs and three heavy chain CDRs of H02, an antibody comprising three light chain CDRs and three heavy chain CDRs of H03, an antibody comprising three light chain CDRs and three heavy chain CDRs of H05, an antibody comprising three light chain CDRs and three heavy chain CDRs of R04, an antibody comprising three light chain CDRs and three heavy chain CDRs of R09, an antibody comprising three light chain CDRs and three heavy chain CDRs of R26, and an antibody comprising three light chain CDRs and three heavy chain CDRs of S01.

In some embodiments, a pharmaceutical composition comprises at least 1, 2, 3, 4, 5, 6, 7, 8, 9, 10, 11, 12, 13, 14, 15, 16, 17, 18, 19, or all 20 of: an antibody comprising three light chain CDRs and three heavy chain CDRs of B04, an antibody comprising three light chain CDRs and three heavy chain CDRs of B10, an antibody comprising three light chain CDRs and three heavy chain CDRs of D04, an antibody comprising three light chain CDRs and three heavy chain CDRs of D07, an antibody comprising three light chain CDRs and three heavy chain CDRs of D10, an antibody comprising three light chain CDRs and three heavy chain CDRs of D11, an antibody comprising three light chain CDRs and three heavy chain CDRs of D12, an antibody comprising three light chain CDRs and three heavy chain CDRs of E01, an antibody comprising three light chain CDRs and three heavy chain CDRs of E07, an antibody comprising three light chain CDRs and three heavy chain CDRs of E08, an antibody comprising three light chain CDRs and three heavy chain CDRs of F07, an antibody comprising three light chain CDRs and three heavy chain CDRs of G07, an antibody comprising three light chain CDRs and three heavy chain CDRs of H01, an antibody comprising three light chain CDRs and three heavy chain CDRs of H02, an antibody comprising three light chain CDRs and three heavy chain CDRs of H03, an antibody comprising three light chain CDRs and three heavy chain CDRs of H05, an antibody comprising three light chain CDRs and three heavy chain CDRs of R04, an antibody comprising three light chain CDRs and three heavy chain CDRs of R09, an antibody comprising three light chain CDRs and three heavy chain CDRs of R26, and an antibody comprising three light chain CDRs and three heavy chain CDRs of S01.

Some pharmaceutical compositions comprise at least one of antibodies B04, B10, D04, D07, D10, D11, D12, E01, E07, E08, F07, G07, H01, H02, H03, H05, R04, R09, R26, and S01. Some pharmaceutical compositions comprise at least 1, 2, 3, 4, 5, 6, 7, 8, 9, 10, 11, 12, 13, 14, 15, 16, 17, 18, 19, or all 20 of antibodies B04, B10, D04, D07, D10, D11, D12, E01, E07, E08, F07, G07, H01, H02, H03, H05, R04, R09, R26, and S01. In some embodiments, a pharmaceutical composition comprises at least one of antibodies B04, E01, E08, F07, G07, H01, H05, and S01. In some embodiments, a pharmaceutical composition comprises at least 1, 2, 3, 4, 5, 6, 7, or all 8 of antibodies B04, E01, E08, F07, G07, H01, H05, and S01. In some embodiments, a pharmaceutical composition comprises antibodies E01 and F07 or comprises antibodies S01 and F07.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses vary depending on many different factors, such as means of administration, target site, physiological state of the patient, whether the patient is human or an animal, other medications administered, and whether treatment is prophylactic or therapeutic.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients, or auxiliaries. The formulation depends on the route of administration chosen.

An effective amount of an antibody or a pharmaceutical composition comprising the same is an amount that is sufficient to generate a desired response, such as to reduce or eliminate a sign or symptom of a condition or disease. For instance, this can be the amount necessary to inhibit viral replication or to measurably alter outward symptoms of the viral infection. In general, this amount will be sufficient to measurably inhibit virus (for example, SARS-CoV-2) replication or infectivity. When administered to a subject, a dosage will generally be used that will achieve target tissue concentrations that has been shown to achieve in vitro inhibition of viral replication. In some embodiments, an "effective amount" is one that treats (including prophylaxis) one or more symptoms and/or underlying causes of any of a disorder or disease, for example to treat a coronavirus infection. In some embodiments, an effective amount is a therapeutically effective amount. In some embodiments, an effective amount is an amount that prevents one or more signs or symptoms of a particular disease or condition from developing, such as one or more signs or symptoms associated with coronaviral infections.

The pharmaceutical compositions of the invention can be readily employed in a variety of therapeutic or prophylactic applications, e.g., for treating SARS-CoV-2 infection. In various embodiments, the pharmaceutical compositions can be used for treating or preventing SARS-CoV-2 infection. Depending on the specific subject and conditions, pharmaceutical compositions of the invention can be administered to subjects by a variety of administration modes known to the person of ordinary skill in the art, for example, topical, intravenous, oral, subcutaneous, intraarterial, intra-articular, intracranial, intrathecal, intraperitoneal, intranasal, intraocular, parenteral, or intramuscular routes. A subcutaneous or intramuscular injection is most typically performed in the arm or leg muscles.

For prophylactic applications, the pharmaceutical composition is provided in advance of any symptom, for example in advance of infection. The prophylactic administration of the pharmaceutical compositions serves to prevent or ameliorate any subsequent infection. Thus, in some embodiments, a subject to be treated is one who has, or is at risk for developing, an infection (e.g., SARS-CoV-2 infection), for example because of exposure or the possibility of exposure to the virus (e.g., SARS-CoV-2). Following administration of a therapeutically effective amount of the disclosed therapeutic compositions, the subject can be monitored for an infection (e.g., SARS-CoV-2 infection), symptoms associated with an infection (e.g., SARS-CoV-2 infection), or both.

For therapeutic applications, the pharmaceutical composition is provided at or after the onset of a symptom of disease or infection, for example after development of a symptom of infection (e.g., SARS-CoV-2 infection), or after diagnosis of the infection. The pharmaceutical composition can thus be provided prior to the anticipated exposure to the virus so as to attenuate the anticipated severity, duration or extent of an infection and/or associated disease symptoms, after exposure or suspected exposure to the virus, or after the actual initiation of an infection. The pharmaceutical composition of the invention can be combined with other agents known in the art for treating or preventing infections by a relevant pathogen (e.g., SARS-CoV-2 infection).

VII. Diagnostic Assays

The antibodies of the invention can also be used in diagnostic assays to detect SARS-CoV-2 in samples from subjects, such as saliva, nasal or throat swabs or blood, plasma, or serum. The assays detect specific binding of an antibody of the invention to RBD2. Some diagnostic assays use at least one of: an antibody comprising three light chain CDRs and three heavy chain CDRs of B04, an antibody comprising three light chain CDRs and three heavy chain CDRs of B10, an antibody comprising three light chain CDRs and three heavy chain CDRs of D04, an antibody comprising three light chain CDRs and three heavy chain CDRs of D07, an antibody comprising three light chain CDRs and three heavy chain CDRs of D10, an antibody comprising three light chain CDRs and three heavy chain CDRs of D11, an antibody comprising three light chain CDRs and three heavy chain CDRs of D12, an antibody comprising three light chain CDRs and three heavy chain CDRs of E01, an antibody comprising three light chain CDRs and three heavy chain CDRs of E07, an antibody comprising three light chain CDRs and three heavy chain CDRs of E08, an antibody comprising three light chain CDRs and three heavy chain CDRs of F07, an antibody comprising three light chain CDRs and three heavy chain CDRs of G07, an antibody comprising three light chain CDRs and three heavy chain CDRs of H01, an antibody comprising three light chain CDRs and three heavy chain CDRs of H02, an antibody comprising three light chain CDRs and three heavy chain CDRs of H03, an antibody comprising three light chain CDRs and three heavy chain CDRs of H05, an antibody comprising three light chain CDRs and three heavy chain CDRs of R04, an antibody comprising three light chain CDRs and three heavy chain CDRs of R09, an antibody comprising three light chain CDRs and three heavy chain CDRs of R26, and an antibody comprising three light chain CDRs and three heavy chain CDRs of S01.

Some diagnostic assays use at least 1, 2, 3, 4, 5, 6, 7, 8, 9, 10, 11, 12, 13, 14, 15, 16, 17, 18, 19, or all 20 of: an antibody comprising three light chain CDRs and three heavy chain CDRs of B04, an antibody comprising three light chain CDRs and three heavy chain CDRs of B10, an antibody comprising three light chain CDRs and three heavy chain CDRs of D04, an antibody comprising three light chain CDRs and three heavy chain CDRs of D07, an antibody comprising three light chain CDRs and three heavy chain CDRs of D10, an antibody comprising three light chain CDRs and three heavy chain CDRs of D11, an antibody comprising three light chain CDRs and three heavy chain CDRs of D12, an antibody comprising three light chain CDRs and three heavy chain CDRs of E01, an antibody comprising three light chain CDRs and three heavy chain CDRs of E07, an antibody comprising three light chain CDRs and three heavy chain CDRs of E08, an antibody comprising three light chain CDRs and three heavy chain CDRs of F07, an antibody comprising three light chain CDRs and three heavy chain CDRs of G07, an antibody comprising three light chain CDRs and three heavy chain CDRs of H01, an antibody comprising three light chain CDRs and three heavy chain CDRs of H02, an antibody comprising three light chain CDRs and three heavy chain CDRs of H03, an antibody comprising three light chain CDRs and three heavy chain CDRs of H05, an antibody comprising three light chain CDRs and three heavy chain CDRs of R04, an antibody comprising three light chain CDRs and three heavy chain CDRs of R09, an antibody comprising three light chain CDRs and three heavy chain CDRs of R26, and an antibody comprising three light chain CDRs and three heavy chain CDRs of S01.

Some diagnostic assays use at least one of antibodies B04, B10, D04, D07, D10, D11, D12, E01, E07, E08, F07, G07, H01, H02, H03, H05, R04, R09, R26, and S01. Some diagnostic assays use at least 1, 2, 3, 4, 5, 6, 7, 8, 9, 10, 11, 12, 13, 14, 15, 16, 17, 18, 19, or all 20 of antibodies B04, B10, D04, D07, D10, D11, D12, E01, E07, E08, F07, G07, H01, H02, H03, H05, R04, R09, R26, and S01. Some diagnostic assays use E01, S01, and/or G07 as capturing antibody. Exemplary pairs of antibodies for use in diagnostic assays are S01 (capture)/F07 (detection); S01 (captureyG07 (detection); G07 (captureyS01 (detection); G07 (capture/F07 (detection); E01 (capture/F07 (detection); and E01 (capture)/G07 (detection). An exemplary capturing antibody to detect D614G SAR-CoV-2 spike is E01. Exemplary pairs of antibodies for use in detecting D614G SAR-CoV-2 spike are E01 (capture)/G07 (detection) and E01 (capture/F07 (detection). An exemplary capturing antibody to detect wild-type SARS-CoV-2 spike is S01. Exemplary pairs of antibodies for use in detecting wild-type SARS-CoV-2 spike are S01 (capture)/F07 (detection) and S01 (captureyG07 (detection), and G07 (capture)/S01 (detection).

Immunometric or sandwich assays are a suitable format. Such assays use a first anti-RBD2 antibody immobilized to a solid phase as capture agent, and a second RBD2 antibody in solution as detection agent. Typically, the detection agent is labeled. The first anti-RBD2 antibody and second anti-RBD2 antibody typically bind different epitope specificities within the target antigen, and the sensitivity relies on both affinity of the capturing antibody for the target, and on the ability of capturing and detecting antibodies to bind the target not competitively.

Competitive assays can also be used. In some methods, target antigen in a sample competes with exogenously supplied labeled target antigen for binding to anti-RBD2 detection antibody. The amount of labeled target antigen bound to the detection reagent is inversely proportional to the amount of target antigen in the sample.

Lateral flow devices are a preferred format (see, e.g., U.S. Pat. Nos. 5,569,608; 6,297,020; and 6,403,383). Lateral flow devices work by applying fluid to a test strip that has been treated with specific biologicals. Carried by the liquid sample, phosphors labeled with corresponding biologicals flow through the strip and can be captured as they pass into specific zones. The amount of phosphor signal found on the strip is proportional to the amount of the target analyte. A sample suspected of containing SARS-CoV-2 is added to a lateral flow device, the sample is allowed to move by diffusion, and a line or colored zone indicates the presence of the virus. The lateral flow typically contains a solid support (for example nitrocellulose membrane) that contains three specific areas: a sample addition area, a capture area containing one or more anti-RBD2 antibodies, and a read-out area that contains one or more zones, each zone containing one or more labels.

Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

EXAMPLES

Example 1: Antigen Preparation

Avitagged-biotinylated SARS CoV-2 RBD (RBD2, SPD C82E9) and S1 protein (SIN C82E8), and unlabeled RBD2 (SPD C52H3), SARS CoV1 RBD (RBD1, SPD S52H6), trimeric SARS CoV 2 spike protein (SPN C52H9), and SARS CoV2 spike protein variant D614G (SPNC52H3) were purchased from AcrosBiosystems. Unlabeled RBD2 and RBD1 were chemically biotinylated using the ThermoFisher EZ link NHS-LC-LC biotinylation kit (21343), (the resultant biotinylated RBD2/1 were called CB RBD2/1) or the Novus Biologicals Lightning link kit (370-0010), according to manufacturer's recommendations. The CB RBD2/1 biotinylation level was measured using Fluorescence Biotin Quantitation Kit (Thermofisher 46610) according to the manufacturer's recommendations and was 2.5:1 (RBD1) and 3.1:1 (RBD2).

RBD2 and RBD1-super folder GFP (sfGFP) chimeras were produced at Los Alamos National Laboratory. Human codon-optimized DNA construct encoding for the RBD domain (residue #333-529) of SARS-CoV-2 spike protein (GenBank YP_009724390.1) was obtained as a gift from Erik Procko. The construct was N-terminally fused to an influenza HA signal peptide and C-terminally fused to superfolder GFP (sfGFP). A 6-Histidine tag was added to the C-terminus of sfGFP for protein purification purpose. A similar human codon-optimized construct was synthesized for the RBD domain (residue #320-515) of SARS-CoV 1 spike protein (GenBank QKY12178.1). The protein fragment length was obtained by analyzing the sequence alignment of the Spike proteins from the two virus strains and optimizing sequence length for best comparison with RBD2. These constructs were cloned into pcDNA3.1(+) (Invitrogen) via NheI-XhoI sites. Both RBD1-sfGFP-6His and RBD2-sfGFP-6His recombinant proteins were expressed using Expi293F expression system kit cells (ThermoFisher) following the manufacturer's protocol. Briefly: 1) Expi293F cell cultures were grown in Expi293 Expression Medium at 37° C., 125 rpm, 8% $CO_2$ to $2\times10^{6}$ cells/ml; 2) DNA plasmid was added at 500 ng/mL cell culture; 3) transfection enhancers were added after 20 hours of transfection; and 4) cells were cultured for an additional ~ 5 days. Cell cultures were centrifuged at 3,000 rpm for 15 minutes, and cell culture medium was collected and filtered for subsequent protein purification.

RBD1-sfGFP-6His and RBD2-sfGFP-6His proteins secreted in culture medium were incubated with Talon resin pre-equilibrated in binding buffer—50 mM Tris-HCl pH 7.4, 300 mM NaCl, 10% glycerol using 30:1 volume ratio for 2 hours with gentle shaking at room temperature. Resin was then loaded onto the column and the column was washed three times with 10× column volumes of binding buffer. 40 mL elution buffer (same as binding buffer plus 150 mM imidazole) was added to the column and the flow through was collected in 8 fractions. Fractions containing the protein (as revealed by fluorescence measurements) were pooled together (~40 ml) and dialyzed against 2 L 1× with phosphate-buffered saline (PBS) overnight at 4° C. to dilute the imidazole. Dialysis buffer was changed 2 times and proteins were collected, concentrated to 500 μg/ml and 360 μg/ml for RBD1-sfGFP-6His and RBD2-sfGFP-6His, respectively, in final buffer containing 1×PBS, 10% Trehalose. Protein concentration was determined using BCA Protein Assay Kit (Pierce). Protein solutions were split into 500 μL aliquots and stored at −80° C.

Example 2: Phage Display Selection, and Identification of Unique Monoclonal Antibodies 20 anti-RBD2 antibodies were obtained by in vitro selection of a human single chain (scFv) library [Sblattero D, Bradbury A. Exploiting recombination in single bacteria to make large phage antibody libraries. *Nature biotechnology.* 2000; 18(1):75-80], synergizing phage and yeast (Example 3) display technologies. A variety of selection strategies (FIG. 1) were adopted, including competition strategies meant to focus the selection to the RBM domain, and non-competition strategies meant to target any immunogenic component of RBD2 and to augment the epitope diversity of the selected antibodies.

As shown in the FIG. 1 schematic, a phage display library of human scFvs was enriched for RBD2 binders by multiple iterations of the following steps: 1) incubation with biotinylated antigen; 2) capturing the RBD2-bound phage-displayed scFvs onto streptavidin beads; 3) eluting phage; and 4) amplifying eluted phage. The naïve antibody library was derived from 40 healthy donors and subjected to VL and VH shuffling. Different selection strategies were employed to increase the chances of obtaining antibodies binding orthogonal epitopes of RBD2. Non-competitive selections were aimed to target the most antigenic RBD2 epitopes, whereas selections including competitor RBD1 were aimed to obtain antibodies to the RBM region of RBD2, where RBD1 and RBD2 differ the most. Various formats of RBD2 and RBD1 were used as selection/counter-selection antigens: 1) avitagged and biotinylated (Beckett D, Kovaleva E, Schatz P J. A minimal peptide substrate in biotin holoenzyme synthetase-catalyzed biotinylation. *Protein Science.* 1999; 8(4):921-929) RBD2 (AB RBD2); 2) chemically biotinylated RBD2 or RBD1 (CB RBD2/1); and 3) unlabeled RBD2 or RBD1 (RBD2/1). At the elution step of the phage selection cycle, either HCl (non-selective elution) or excess non-biotinylated antigen was employed to favor elution of more specific phage-displayed scFvs. Various combination of antigen formats and elution strategies resulted in seven different selection strategies (Tables 2 and 3). Phage selections were monitored by calculating increments in output phage with respect to the first selection cycle. After the 3rd round of non-competitive selections 1, 2 and 3, these increments were 6, 80 and 600-fold respectively. For competitive selections 4, 5, 6 and 7, increments were 3.4, 45.0, 12.7 and 113.0-fold respectively. The lower increments in competitive selections are expected considering the higher stringency of these selections due to addition of a competitor. The final phage outputs of the phage selections were subcloned in yeast.

Methods: scFv Antibody Selections by Phage Display 7 different selection strategies were adopted, where the selection antigen was always biotinylated RBD2. Selections 1, 2, and 3 were non-competitive (Table 2) and used avitagged-biotinylated RBD2 (AB RBD2).

TABLE 2

| Non-competitive phage selection strategies | | | | |
|---|---|---|---|---|
| | Antigen AB | Elution | Stringency increment | |
| Strategy | RBD2[a] | method | 2nd round | 3rd round |
| 1 | 30 nM | 0.1N HCl | Wash times increased | 10-fold [AB RBD2] reduction |
| 2 | 30 nM | 10× RBD2 | from 30 s | 10-fold [RBD2] reduction |
| 3 | 150 nM | 0.1N HCl | to 5 m | for competitive elution |

[a]Receptor-binding domain of SARS-CoV 2 (RBD2) avitagged and biotinylated (AB)

Selection 4, 5, 6, and 7 were competitive (Table 3) and used chemically biotinylated (EZ link) RBD2 (CB RBD2).

TABLE 3

| Competitive phage selection strategies | | | | | |
|---|---|---|---|---|---|
| | Antigen CB | Competing antigen RBD1[b] or CB | Elution | Stringency increment | |
| Strategy | RBD2[a] | RBD1[a] | method | 2nd round | 3rd round |
| 4 | 100 nM | 200 nM RBD1 | 0.1N HCl | Wash times | 4-fold |
| 5 | 100 nM | 200 nM RBD1 | 4× RBD2 | increased from 30 s to 5 m; 2-fold [RBD1] increment | [RBD1] increment |
| 6 | 100 nM | Preincubation | 0.1N HCl | Wash times | Pre- |
| 7 | 100 nM | with CB RBD1 and RBD1 binders subtraction by bead capturing | 4× RBD2 | increased from 30 s to 5 m | subtraction with 2-fold higher [CB RBD1] |

[a]Receptor-binding domain of SARS-CoV 2 or 1 (RBD2 or 1) chemically biotinylated with NHS-LC-LC biotin (CB)
[b]Receptor-binding domain of SARS-CoV 1

For any given selection 180 μL of phage-displayed scFv library [Diagnostics C. Mouse Anti-SARS-CoV-2 Spike Neutralizing Monoclonal antibody, clone NN54 (CABT-CS064). 2020. World Wide Web at creative-diagnostics-.com/pdf/CABT-CS064.pdf](pfu $10^{13}$/mL) was pre-treated by blocking with 0.5-1% bovine serum albumin (BSA) in 1×PBS for 0.5-1 h with rotation. For selections 6 and 7 library pre-treatment included one more step, i.e. CB RBD1 was incubated with the blocked library for 1 h with rotation, and RBD1-bound phage was removed by incubation with washed and blocked streptavidin beads (Dynabeads M-80, 11205D, ThermoFisher) and magnetic separation. The pre-treated library was incubated with either AB RBD2 (selections 1, 2, and 3), CB RBD2 plus RBD1 (selections 4 and 5) or CB RBD2 (selections 6 and 7) and incubated for 1 h at RT for 1 h. The antigen/counter antigen concentrations are indicated in Tables 2 and 3. 10 μL of blocked streptavidin beads were added to 200 μL of antigen-incubated library, and KingFisher magnetic particle purification system (5400000, ThermoFisher) was used to incubate and wash the beads and to elute bead-captured phage. Three PBST (1×PBS 0.1-0.05% Tween 20) and three PBSLT (1×PBS 0.005% Tween 20) or PBS washes were performed for each selection cycle. The wash times are indicated in Tables 2 and 3. Non-specific elution was conducted by dispersing the washed beads in 150 μL 0.1N HCl for four minutes and neutralizing the pH with 50 μL of 1.5 M Tris pH 8.8. Specific elution was performed by incubation with excess non-biotinylated RBD2 for 30 minutes. 10 mL of Omnimax T1 (C854003, ThermoFisher) grown at mid log phase ($Abs_{600}$ or OD600=0.5) at 37° C. were infected with eluted phage for 1 h, at 37° C. static incubation, collected by centrifugation, and plated on 2XYT agar plates containing carbenicillin (50 μg/mL) and glucose (3%). Standard phage amplification using M13 helper phage and PEG precipitation protocols were used to prepare the input phage subsequent rounds of selection (Vanhercke, T. et al., J. Biomolecular Screening 10(2):$10^8$-117, 2005; Velappan N, Mahajan A, Naranjo L, et al. Selection and characterization of FcεRI phospho-ITAM specific antibodies. Paper presented at: MAbs2019). Cells infected with the output phage from the 3rd selection cycle were used for plasmid preparation (Qiagen Inc. #27106). scFv-encoding genes were PCR amplified using primers (GTTCTGGTGGTGGTGGTTCTGCTAGAGGCGCGC (SEQ ID NO:69) and GCAGTGGGTTTGGGATTGGTTTGCC (SEQ ID NO:70)). These primers added flanking sequences to the scFv gene that allow homologous recombination with the yeast display vector upon yeast transformation (see Example 4 below). The PCR products were purified using Qiagen PCR purification kit (Qiagen Inc. cat #28104).

Example 3: Yeast Display Selection, and Identification of Unique Monoclonal Antibodies As shown in the FIG. 1 schematic, yeast display libraries were enriched for RBD2 binders by incubation with biotinylated RBD2, staining of RBD2-bound yeast with fluorescently labelled streptavidin and anti-SV5 tag (SV5 is expressed with the scFv and this staining ascertains yeast expression), isolating doubly stained yeast (i.e., yeast displaying RBD2-binding scFvs) by flow cytometry sorting, and amplifying sorted yeast. As for phage selections, different strategies were employed to increase the chances of obtaining antibodies recognizing orthogonal epitopes of RBD2 with high specificity. The various antigen formats as described above were used plus an additional one. The spike protein of both SARS-CoV 1 and 2 is a trimer of a protein composed of two domains, S1 and S2. RBD is part of S1 domain (Xia S, Zhu Y, Liu M, et al. Fusion mechanism of 2019-nCoV and fusion inhibitors targeting HR1 domain in spike protein. *Cellular & molecular immunology.* 2020; 17(7):765-767). Therefore, avitagged S1 from SARS CoV 2 was introduced to sort antibodies that recognize RBD2 in a more native context. Before the first sort, yeast display libraries from competitive phage selection (except for selection 4, the least enriched library), bound RBD2 between 2 and 5-fold better than RBD1, they also showed comparable binding to RBD2 and S1. -The details of the various selections are described in Table 4.

TABLE 4

| Yeast sorting strategies | | | | | |
|---|---|---|---|---|---|
| | Antigen CB-RBD2[a] | Competition | Stringency increment | | |
| Strategy | and AB-S1[b] | RBD1[c] | 2nd round | 3rd round | 4th round |
| 1 | 100 nM CB-RBD2 | None in 1st round | 40 nM AB-S1 | 20 nM AB-S1 + 120 nM RBD1 | none |
| 2 | 100 nM AB-RBD2 | None in 1st round | 50 nM AB-RBD2 | 10 nM AB-RBD2 | 10 nM AB-RBD2 |
| 3 | 100 nM AB-S1 | None in 1st round | 50 nM AB-S1 | 10 nM AB-S1 | 10 nM AB-S1 |
| 4 | 100 nM AB-RBD2 | None in 1st round | 50 nM AB-RBD2 | 50 nM CB-RBD1 | 10 nM CB-RBD1 |

[a]Receptor-binding domain of SARS-CoV 2 (RBD2) chemically biotinylated with NHS-LC-LC biotin (CB)

[b]S1 domain of SARS-CoV 2 spike protein monomer (contains RBD2) avitagged and biotinylated (AB)

[c]Receptor-binding domain of SARS-CoV 1

[d]RBD1 chemically biotinylated with NHS-LC-LC biotin (CB)

Selection progress was monitored by calculating increments in percentage of doubly labelled yeast with respect to the first selection round. At the 3rd round of non-competitive selections, these increments ranged from 28 to 40-fold respectively. For competitive selections increments ranged from 8 to 21-fold.

Methods: scFv Antibody Selections by Yeast Display

The yeast display vector pDNL6 (Velappan N, et al. Selection and characterization of FcεRI phospho-ITAM specific antibodies. Paper presented at: MAbs2019) plasmid was digested with restriction enzymes BssH II, Nhe I and Nco I and purified using Qiagen PCR purification columns (Qiagen Inc. cat #28104). Vector and scFv fragments prepared as described above were co-transformed into EBY100 yeast cells using Yeast 1Kit (Sigma Aldrich Inc. cat #YEAST1) to allow cloning by gap repair (Velappan N, Mahajan A, Naranjo L, et al. Selection and characterization of FcεRI phospho-ITAM specific antibodies. Paper presented at: MAbs2019). The transformed yeast were grown in selective media (SD/CAA) and induced using SG/RCAA media as previously described (Velappan N. et al. Paper presented at: MAbs2019). The yeast cultures were grown in SD/CAA medium at 30° C., allowed to reach an OD600 >2.0, and mixed 1:10 with SG/R CAA induction medium. Yeast expression induction proceeded at 20° C. overnight with shaking (250 rpm). Induced yeast were washed with yeast washing buffer (1× PBS, 0.5% BSA, 20 mM EDTA) and incubated for 1 h at RT with shaking in the presence of different biotinylated antigens, with or without non biotinylated RBD1 (as indicated in Table 4). Phycoerythrin labelled anti-SV5 antibody (anti-SV5 PE) was also included at 1 μg/mL to label the SV5 expression tag appended to the displayed scFv. After more washing, Streptavidin Alexa 633 (S21375, ThermoFisher) was added to the yeast at 5 μg/mL to label the biotinylated antigen, following incubation and washing as described before. Yeast sorting was performed on FACS Aria (Becton Dickinson). Sorted yeast were amplified and induced for subsequent selection rounds.

Example 4: Yeast Plasmid Preparation and scFv Gene Sequencing

Plasmids encoding yeast-displayed scFvs were purified from the sorted yeast and were subcloned in *E. coli*. Four hundred single plasmids were sequenced to identify selected monoclonal scFvs. Competitive selections yielded 14 unique clones (B04-H05) while non-competitive selections yielded 4 unique clones; S01, R04, R09, and R26 (FIGS. 4A, 4B, 4C). A comparison of Kabat-Chothia Composite CDRs of 18 scFvs B04, B10, D04, D07, D10, D11, E01, E08, F07, G07, H01, H02, H03, H05, R04, R09, R26, and S01 with those published in the CoV-AbDab database (World Wide Web at opig.stats.ox.ac.uk/webapps/covabdab Oct. 16, 2020), revealed the uniqueness of the 18 scFvs (FIG. 5). In particular: 1) only a few single CDRs or CDR pairs were shared between the 18 scFvs and the CoV-AbDab database antibodies; 2) none of these shared CDRs were CRDH3 (the biggest contributor to specificity of antigen recognition (Xu J L, Davis M M. Diversity in the CDR3 region of VH is sufficient for most antibody specificities. *Immunity.* 2000; 13(1):37-45); 3) none of the 18 scFvs shared the entire set of CDRs with any antibody in the CoV-AbDab database; 4) only three of the 18 scFvs (B04, B10 and R04) share CDRL3 with antibodies in the CoV-AbDab database; and 5) antibody E01 did not share any of its CDRs with any antibody in the CoV-AbDab database (FIG. 5).

Methods: Yeast Plasmid Preparation and scFv Gene Sequencing

Plasmids from enriched yeast display libraries obtained from 3rd and 4th round selections were isolated from 2 mL o/n yeast cultures using a modified Qiagen miniprep procedure (Qiagen 27106) where: 1) the buffer volumes were doubled; 2) after addition of buffer PE, 100 μL of glass beads (MilliporeSigma #G8772) were added and the mixture was incubated at RT on a vortex (maximum rpm) for 10 min; 3) the final DNA solution was added to the same column in two 800 μL aliquots. Plasmids were transformed in One Shot *E. coli* Omnimax T1 (C854003, ThermoFisher). Due to the low concentration/purity of yeast plasmid solutions, the entire transformation suspension was plated to obtain a few tens of colonies. Single *E. coli* transformants were used to inoculate 2XTY-Carb-Glu (50 μg/ml carbenicillin, 3% glucose) in the wells of a 96-well sterile plate, and the plate was incubated o/n at 37° C. with rotation (900 rpm). 2 μL of the o/n culture in each well were deposited on a 2XYT-Carb-glu agar plate. After o/n incubation at 37° C., the plate was submitted for Sanger sequencing service to GeneWiz together with PNL6 Forward and Reverse primers (CACTGTACTTT-TAGCTCGTAC SEQ ID NO:71, TAGATACCCAT-ACGACGTTC, SEQ ID NO:72). ~400 single colonies were sequenced from various sort libraries and the scFv sequence was analyzed to identify unique clones. Plasmid encoding unique scFvs were miniprepped from the bacterial colonies and transformed back to EBY100 yeast cells for specificity and affinity measurements.

Example 5: Specificity of Binding and Kinetic Study of Yeast-Dissolved scFvs and Soluble scFvs Binding of yeast-displayed scFvs and soluble scFvs to RBD2 vs RBD1 was analyzed. A flow cytometry-based assay, which used yeast displayed antibodies and sub-saturating antigen concentration, was used to determine relative affinities of yeast-displayed scFvs for RBD2 vs. RBD1 (FIG. 7A). Soluble scFvs were also expressed in tandem with either human (FIG. 7B and FIG. 6) or rabbit (FIG. 7C and FIG. 6) fragment crystallizable Fc (scFv, called minibodies) and analyzed by ELISA.

Selected antibodies have been tested for binding to RBD2 from RBD1 as yeast-displayed scFvs. In this form most of the antibodies selectively recognize RBD2 except for R04 and R09. Some of the yeast-expressed antibodies have also been tested for binding to RBD from various sources and to the full spike protein (D04, E01 and E07). Some of the yeast-expressed antibodies have been converted to minibodies (human, H, or rabbit, R, soluble antibodies). FIG. 6 shows that soluble antibodies E01, F07, and 501 selectively recognize RBD2, whereas soluble antibody R04 recognizes both RBD2 and RBD1. ACE2 has been added as a positive binding control. ACE2 bind both RBDs with a slight preference for RBD2.

All antibodies tested in FIGS. 7A, 7B, and 7C recognized RBD2. Data include binding to a negative control antigen (ubiquitin, UBI), and a negative control human anti-influenza M2 antigen scFv (Figure A)/rabbit minibody (FIG. 7C) called Z3. The height of each bar is an average of three measurements and the error bars correspond to the standard deviations of each set of three measurements. Competitive selections yielded a lower percentage of antibodies cross-reacting with RBD1 than non-competitive selections (7% and 25% respectively). Notable antibodies are B04 and E01, which exhibited the highest specificity for RBD2, and antibodies E08 and R04, which recognized both RBDs, with the former preferring RBD2 and the latter preferring RBD1.

Kinetic Analysis of Yeast-Displayed scFvs and Soluble scFvs

Minibody $K_D$ values were determined by surface plasmon resonance (SPR) only and ranged from ~4 to 900 nM, with E08, H02 and, E1 having the highest affinity for RBD2 of those antibodies tested (see Table 9 in Example 10, and in Table 6).

Of the two assays described above (ELISA—based and flow cytometry-based), the flow cytometry-based assay, which used yeast displayed antibodies and sub-saturating antigen concentration, was the most reliable for determination of relative affinities. Therefore, based on data in FIG. 7A, nine highest affinity antibodies were chosen from competitive and 2 highest affinity antibodies from non-competitive selections, together with the only antibody preferring RBD1 over RBD2 (R04), for further studies. Kinetic study of yeast displayed scFvs binding to RBD2 or RBD1 included: 1) measuring antigen binding of yeast displayed antibodies at various concentrations of biotinylated antigen; 2) plotting binding vs antigen concentration; and 3) fitting the data to the Michaelis and Menten equation (also called one-site binding equation, FIGS. 8A-D). FIG. 8A contains D07 kinetics at lower yeast density (1/10 of all the other experiments including the second D07 experiment). The fact that D07 $K_D$ did not change significantly at the two yeast densities suggests there is no antigen depletion in these experiments and therefore the $K_D$ measurement should be accurate. FIG. 8D contains kinetics of R01 binding to both RBD1 and RBD2. Negative control antibody Z3 is also included in this graph. The resulting affinity constant ($K_D$) values are reported in Table 9, below in Example 10. $K_D$ ranged from ~14 to 290 nM, with scFvs B04, E01 and E08 having the highest affinity for RBD2. Data for antibodies are also presented in Table 5 and Table 6.

TABLE 5

Affinity of yeast expressed antibodies for cognate antigen

| | scFvs | | |
|---|---|---|---|
| | B04, E01[a], F07 [a], G07, R26, S01[a] | B10, D12, D07[a], , H01, R04[a], R26[a] | D04, D10, D11, E07[a] H02, R09[a] |
| RBD2 affinity range ($K_D$, nM) | $16 < K_D < 280$ | $280 < K_D < 421$ | $K_D > 421$ |
| RBD1 affinity ($K_D$, nM) | — | 203.1 +/− 43.6 (R04) | N/D (R09) |

[a]The $K_{DS}$ of each of these antibodies for RBD2 was determined to be: E01 = 16.1 ± 3.0; F07 = 279.7 ± 15.2; S01 = 52.3 ± 9.6; D07 =268.2 ± 23.2 ; R04 = 422.8 ± 121.0; R04 = 182.1 ± 53.1; E07 = 436.5 ± 17.5; R09 = 4820.8 ± 5612.8.

TABLE 6

Affinity of antibodies for RBD2 or RBD1 antigen

| | Antibody | Affinity for RBD2 ($k_D$, nM)a | | |
|---|---|---|---|---|
| | name | scFv | Minibody | IgG |
| Competitive selections | B04 | 13.9 ± 1.5 | 56.8 ± 3.5 | 210.0 ± 42.0 |
| | B10 | N/D[f] | 343.5 ± 99.7 | N/A[c] |
| | D04 | 33.0 ± 3.0 | 123.5 ± 139.3 | N/A[c] |
| | D07 | 112.8 ± 18.9 | 134.5 ± 68.6 | N/A[c] |
| | D10 | N/D[b] | N/D[b] | N/A[c] |
| | D11 | N/D[b] | 798.5 ± 567.8 | N/A[c] |
| | E01 | 13.9 ± 1.3 | 21.5 ± 2.12 | 90.0 ± 22.0 |
| | E08 | 13.9 ± 1.8 | 3.6 ± 2.0 | 27.0 ± 3.2 |
| | F07 | 67.5 ± 6.8 | 61.5 ± 3.5 | 300 ± 65.0 |
| | G07 | 60.3 ± 5.5 | ND | 320.0 ± 76.0 |
| | H01 | 66.4 ± 5.1 | 281.0 ± 162.6 | 800 ± 440.0 |
| | H02 | N/D[b] | 15.5 ± 7.8 | N/A[c] |
| | H03 | N/D[b] | 117.0 ± 52.3 | N/A[c] |
| | H05 | 16.7 ± 4.0 | N/D[b] | 51.0 ± 8.6 |
| Non-competitive selections | R04 (RBD2) | 293.3 ± 24.0 | 127.5 ± 70.0 | 190E+3 |
| | R04 (RBD1) | 175.1 ± 20.3 | N/D[b] | N/A[c] |
| | R09 | N/D[b] | 539.0 ± 223.4 | N/A[c] |
| | R26 | 65.3 ± 2.6 | 887.5 ± 724.78 | N/A[c] |
| | S01 | 44.1 ± 2.5 | N/D[b] | 170.0 ± 40.0 |
| Ref. IgG | CR3022 | N/D | N/D | 110.0 ± 15.0 |

[a]Determined either by flow cytometry (scFvs) or by surface plasmon resonance, SPR (minibodies or IgGs)

[b]Not Determined

[c]Not available in IgG format

Methods: Specificity of Binding and Kinetic Study of Yeast-Displayed scFvs

Yeast colonies transformed with unique scFvs were picked from SD/CAA agar plates and grown in SD/CAA liquid culture. Yeast induction and antigen staining were performed as previously described. A 96-well filter plate (MSGVN22, EMD Millipore) was used for high throughput washes. The analysis was performed either on FACS Aria or FACS ACURI 600 plus flow cytometers (Becton Dickinson). The specificity and affinity measurements were performed using on RBD2, RBDt1 or ubiquitin (control antigen) biotinylated with the lightning link kit. The anti-influenza A M2 protein scFv Z3 [Velappan N, et al., Selection and verification of antibodies against the cytoplasmic domain of M2 of influenza, a transmembrane protein. MABS 2020, Vol. 12, No. 1] was used as the negative control antibody. Specificity assays were performed at non-saturating 20 nM antigen concentration. Each measurement was obtained in triplicate and averaged. Dissociation constants for the highest affinity antibodies identified by this preliminary screening were obtained by: 1) measuring antibody binding (y) at various concentrations of CB RBD2 (x, serial 2-fold dilutions from 500 to 0.8 nM); 2) plotting the data in Kaleidagraph (Version 4.5); and 3) fitting the data to the Michaelis Menten equation adapted to antibody binding: $y=AB_{max}/(K_D+x)$, where $AB_{max}$=maximum antibody binding and; $K_D$=antibody affinity constant.

Methods: Conversion of scFvs to scFv-Fc (Minibody)

The scFv genes from the clones were excised from PDNL6 plasmids by restriction digestion with enzymes BssHII (New England Biolabs, R0199S) and NheI (New England Biolabs, R3131S) and gel purified. These genes were inserted into a yeast scFv-Fc expression vector pDNL9 sacB plasmids digested with the same restriction enzymes by ligation (T4 DNA ligase, M0202, NEB). Ligation reactions were transformed in One Shot Omnimax T1 *E. coli* cells and 4 clones/ligation reaction were analyzed by colony PCR for the right size insert by using pNL6 FW and REV primers and DNA sequencing. Plasmids were prepared from selected clones and transformed in YVH10 yeast cells (in-house stocks, gift from Wittrup lab at MIT) using yeast transformation kit protocol. Transformed yeast were plated on SD/CAA plates supplemented with tryptophan (final concentration 80 μg/mL). Single YVH10 colonies were further grown in SD/CAA liquid culture medium and induced following the yeast secretion protocols described by Wentz A E and Shusta E V (*Applied and environmental microbiology*. 2007; 73(4):1189-1198). Culture supernatants were used in the ELISA-based binding assays described in Example 14.

Example 6: Conversion of Antibodies to IgG Format

Based on scFvs and minibodies kinetics (Table 9 in Example 10 below) and epitope binning studies (Example 7), antibodies E01, 501, F07, G07, B04, E08, H01, and H05 were selected for conversion to IgG isotype 1 (IgG1) format for further characterization. Antibody R04 was also selected for conversion, due to its preference for RBD1 (unique among the antibodies described here). IgGs were produced at 100 mL scale, in yields ranging from 0.42 to 0.27 mg/mL (Table 7).

TABLE 7

Yield of IgG production

| Antibody | Yield mg/mL culture)[a] | Yield quality (folds above minimum)[b] |
|---|---|---|
| B04 | 0.33 | 3.3 |
| E01 | 0.42 | 4.2 |
| E08 | 0.29 | 2.9 |
| F07 | 0.41 | 4.1 |
| G07 | 0.41 | 4.1 |
| H01 | 0.35 | 3.5 |
| H05 | 0.41 | 4.1 |
| R04 | 0.27 | 2.7 |
| S01 | 0.38 | 3.8 |

[a]from 100 mL culture
[b]yield/minimum yield (0.1 mg/mL)

Some of the IgGs' specificity for RBD2 was analyzed via ELISA (FIG. 9A) and FLISA (FIG. 9B). The antigens used were biotinylated-RBD2, RBD2 fused with super folder green fluorescent protein (sfGFP), and RBD2 within the S1 unit of spike protein avitagged and biotinylated. As expected, every IgG analyzed bound specifically to RBD2 in any of the formats used, except R04. IgGs were immobilized on plastic and tested for recognition of either (FIG. 9A) chemically biotinylated SARS-CoV 2 RBD (RBD2) and SARS-CoV RBD (RBD1) and avitag-biotinylated SARS-CoV 2 spike subunit 1 (S1), subsequently stained with streptavidin-Alexa 633), or (FIG. 9B) super folded GFP-RBD2 (RBD2)) and super folded GFP-RBD1 (RBD1) chimeras. Chemically biotinylated lysozyme (Lys) and anti-*Y. pestis* F1 antigen antibody AM2 (AM2) were used as negative controls antigen and antibody respectively. Average or three measurements plus standard deviations (error bars) are reported.

Next, IgGs were analyzed by SPR to measure $K_{DS}$ of interaction with RBD2 (Table 9, below, and FIGS. 8E, 8F, and 8G). The range of $K_D$ values was 50-2000 nM, with E01 having the highest affinity ($K_D$ 48 nM); S01, F07, and B04 having mid-range affinities at 100-300 nM; and G07 having the lowest affinity (2000 nM). For the majority of the antibodies tested a progressive drop of affinity (higher $K_{DS}$) was observed going from scFv to minibody to IgG format (Table 6, Table 9 in Example 10, below and FIG. 10). Based on SPR affinity constant ($K_D$) measurement (Table 9), selected antibodies fall in or below the 43-percentile within a set of 180 anti-RBD2 antibodies characterized by the La Jolla Institute of Immunology (World Wide Web at covic.lji.org/database/). In FIG. 10, antibody affinities for SARS-CoV 2 spike protein's receptor-binding domain (RBD2) are reported as dissociation constants ($K_D$, lower $K_D$→higher affinity) for the following formats: 1) single chain (scFv) yeast-expressed; 2) scFv-Fc (minibody); 3) immunoglobulin G (IgG). For affinity measurements repeated in triplicate, $K_D$ averages and corresponding standard deviations (error bars) are reported.

Methods: Conversion of scFvs to IgG Formats

Selected scFvs were also converted to IgGs by inserting the amino acid sequences corresponding to the variable heavy (VH) and variable light (VL) antibody regions into a standard IgG1 scaffold. The resulting protein sequences were submitted to ATUM Inc. (Newark, CA, USA) for codon-optimized back-translation, gene synthesis, and expression as full-length IgG1 antibodies in HEK293 cells. IgGs were received as PBS solutions from ATUM, and stored in small aliquots at −80° C. before use in various assays.

Example 7 Antibody Epitope Binning by Sandwich ELISA and by Surface Plasmon Resonance Epitopes bound by the antibodies were analyzed non-competitively by sandwich ELISA (FIGS. 11A-D, methods as in Example 14) and by surface plasmon resonance (SPR) (FIGS. 12A-B, methods as in Example 14). The eight highest affinity IgGs appear to recognize different RBD2 regions (epitopes) based on SPR analysis (FIGS. 12A-B) and sandwich ELISA (FIGS. 11A-D) epitope binning.

Sandwich ELISA Experiments. Results and Conclusions

FIGS. 11A and 11B illustrate identification of antibody pairs (capturing and detecting IgG) capable of binding to distinct regions (epitopes) of SARS-CoV 2 spike protein receptor binding domain (RBD2, FIG. 11A) and SARS-CoV 2 whole spike protein (FIG. 11B). Antibodies analyzed were B04, E01, F07, G07, R04, and 501. Plastic bound capturing IgG (xaxis) immobilize the antigen, and HRP-conjugated detecting IgG (z axis) reports the captured antigen. Anti-influenza M2 antigen (αM2) antibody was used as a negative control IgG. Signals above αM2-mediated antigen detection (noise) reveal antibody pairs non competitively binding to the antigen.

FIGS. 11C and 11D illustrate testing for orthogonal binding pairs. (FIG. 11C) yeast displayed antibodies and soluble human minibodies were tested for their ability to bind RBD2 noncompetitively (or to "sandwich RBD2"). Yeast initially bound to RBD2, were incubated with human minibodies and subsequently stained with anti-human phycoerythrin (PE). The yeast-associated fluorescence was used as a measure of ability of the tested antibodies to bind as pairs. When subtracting "self binding" (e.g. yeast expressed E01 binding to minibody E01, this control is available for some antibodies), it appears that following might be good pairs: B04:F07; E01:F07; G07:E01/F07; S01:E01/F07/R04. (FIG. 11D) Some antibodies were tested as pairs in soluble form by measuring binding of rabbit minibody to RBD2 captured on plate by human minibody. Rabbit minibody binding (as detected by anti-rabbit-allophycocyanin, APC, staining) was used as a measure of pair formation. When subtracting self-binding (e.g. human F07 minibody binding to rabbit F07 minibody) the following were confirmed as pairs: S01:F07/R04.

SPR Analysis, Results and Conclusions

From now on, a set of two antibodies binding non-competitively to RBD2 will be referred to as a "pair". The 8 antibodies analyzed by SPR (B04, E01, E08, F07, G07, H01, H05, and S01) combined in a total of 25 pairs. Some of the 8 antibodies analyzed by SPR formed pairs with previously described anti-RBD2 antibody CDR3022 (FIG. 12A-B) [Yuan M, et al., *Science.* 2020; 368(6491):630-633; Ter Meulen J, et al., *PLoS Med.* 2006; 3(7):e237] and (FIG. 12A) with described anti-RBD2 antibody NN54 (commercially available from Creative Diagnostics [Mouse Anti-SARS-CoV-2 Spike Neutralizing Monoclonal antibody, clone NN54 (CABT-CS064). 2020. World Wide Web at creative-diagnostics.com/pdf/CABT-CS064.pdf)]. SPR was also used to determine whether the IgGs were able to compete with ACE2 in binding to RBD2, revealing that IgGs E01, H01, H05 and S01 (and possibly F07) are competitors. Antibody+antibody and antibody+ACE2 RBD2 interactions with RBD2 suggest that each of the 8 IgGs behave uniquely and therefore is in its own "bin" (i.e. interacts with a RBD2 epitope not overlapping with any other)

In FIGS. 12A and 12B, IgGs were tested pairwise for their ability to bind SARS-CoV-2 spike protein's receptor binding domain (RBD2-His tag) by SPR. An anti-His tag antibody was used as a positive control non-competitive antibody. Commercial anti-RBD2 antibodies CR3022 and NN54, and recombinant human receptor angiotensin-converting enzyme 2-fragment crystallizable chimera (ACE2-Fc) were included in the analysis. SPR competition data is represented as a heat map (FIG. 12A) and displays intersections of two proteins (IgG or ACE2) with the immobilized antibody shown as rows and the injected analyte antibody shown as columns. Non-competing interactions (sandwiching) are shown as green, competing as red, and mildly competitive as yellow cells. Antibody pairs that were not analyzed (N/D) are indicated by grey cells. Notice that the global cutoffs shown for most ligands are 0.2 for the red to yellow transition and 0.25 for the yellow to green transition. However, cutoffs were adjusted individually for ligands H01, S01, B04, and G07 as their binding kinetics were quite different. Therefore, sometime different color cells bear similar values (e.g. S01/G07=0.11=yellow, while F07/H01=0.10=red). The network plot rendition of the SPR data (FIG. 12B) indicates competing IgG or ACE2/IgG pairs connected by a line, whereas all the non-competing IgGs are isolated. The different colors indicate antibodies targeting different epitopes (epitope bin) based on their interaction with RBD2 in the presence of either other antibodies or ACE2-Fc. An epitope bin is also represented by the gray shading covering E08 and CR3022 which share an identical competition profile.

IgGs E08, H05, H01, S01, E01, B04, G07, and F07 appear to recognize different RBD2 regions (epitopes) as shown by SPR (FIGS. 12A and 12B) and sandwich ELISA (FIGS. 11A and 11B) epitope binning.

Example 8: Diagnostic Application Using Pairs of Antibodies: Detection of Spike and Heat Inactivated SARS-CoV-2 Virus by ELISA Antibodies were analyzed for recognition of full-length trimeric spike protein, both in purified form or as part of the whole virus. Antibodies were tested for recognition of wild-type spike and D614G spike (aspartic acid (D) to glycine (G) mutation at amino acid position 614 of spike protein, D614G variant), [Lorenzo-Redondo R, et al., *MedRxiv.* 2020; Korber B, et al., *Cell.* 2020; 182(4):812-827. e819].

Based on their performance in previously described experiments, antibodies E1, F07, G07, and S01 (in various pairwise combinations) were selected for both sandwich ELISA and SpinDX experiments (FIGS. 13A-D and Table 8). The antibody pairs used for detection are indicated in FIGS. 13A-D as (antigen-capturing IgG)/(antigen-detecting IgG) (e.g. S01/G07). Only antibody pairs E0l/F07 and E01/G07 could detect whole virus at the concentration of virus tested with limited amount of virus available for use. RFU=relative fluorescence unit; TCID50=half tissue culture infection dose.

For the sandwich ELISA (FIGS. 13A, 13B, and 13D) the capturing antibody was immobilized on plate and the detecting antibody was chemically labelled with HRP. The detection of the captured antigen was monitored by absorbance ($Abs_{450}$) of the HRP substrate conversion product. ELISA epitope binning experiments (FIGS. 11A-11B) revealed that S01 and E01 acting as capturing antibodies, form optimal pairs with G07 and F07 as detection counterparts. Therefore, S01/G07 or F07 and E01/G07 or F07 antibody combinations were used for the ELISA-based detection experiments (FIGS. 13A, 13B, and 13D).

Limit of detection (LoD) and limit of quantification (LoQ) for spike (ELISA and SpinDX) and whole heat-inactivated virus (ELISA only) were determined using noise signals for negative control analytes (myoglobin and rhino coronavirus for spike and whole virus detection, respectively, in ELISAs) and or for no analyte (SpinDx). These signals plus 3 or 8 standard deviations were inputted in the equations defining the "signal to analyte-concentration" relationship for each antibody pair analyzed (FIGS. 13A-D) to obtain LoD and LoQ, respectively (Table 8).

TABLE 8

Sensitivity of two sandwich immunoassays

| Assay | Antibody pair[a] | Wild-type Spike LoD[b] (pM) | Wild-type Spike LoQ[c] (pM) | Spike D614G LoD (pM) | Spike D614G LoQ (pM) | Whole virus LoD (TCID50[d]/mL) | Whole virus LoQ (TCID50[d]/mL) |
|---|---|---|---|---|---|---|---|
| ELISA[e] | S01/F07 | 1.22 | 18.2 | 664.2 | 1786.1 | >2.5E+4 | >53.7E+4 |
| | S01/G07 | 4.1 | 24.1 | 125.4 | 425.6 | >2.5E+4 | >53.7E+4 |
| | E01/G07 | 21.2 | 64.1 | 15.6 | 75.0 | 1.8E+4 | 12.0E+4 |
| | E01/F07 | 39.1 | 111.2 | 85.6 | 225.8 | 2.5E+4 | 53.7E+4 |

TABLE 8-continued

Sensitivity of two sandwich immunoassays

| Assay | Antibody pair[a] | Wild-type Spike LoD[b] (pM) | Wild-type Spike LoQ[c] (pM) | Spike D614G LoD (pM) | Spike D614G LoQ (pM) | Whole virus LoD (TCID50[d]/mL) | Whole virus LoQ (TCID50[d]/mL) |
|---|---|---|---|---|---|---|---|
| SpinDx[f] | S01/F07 | 0.16 | 26.5 | N/D[g] | | | |
| | G07/S01 | 1.9 | 43.1 | | | | |
| | S01/G07 | 10.3 | 26.5 | | | | |

[a](antigen-capturing IgG)/(antigen-detecting IgG)
[b]Limit of Detection
[c]Limit of Quantification
[d]Tissue culture infectious dose 50 (i.e. the dilution of virus required to infect 50% of the cell monolayers)
[e]Enzyme-linked immunosorbent assay
[f]Portable Multiplexed bead-based Immunoassay platform
[g]Not determined S01 was the more sensitive capturing antibody for detection of wild type spike protein (FIG. 13A), whereas E01 was the more sensitive capturing antibody for detection of the D614G spike variant (FIG. 13B). Antibody pairs S01/F07 and S01/G07 detected wild type spike at LoDs 1.22 pM and 4.1 pM respectively, whereas pairs E01/G07 and E01/F07 detected D614G spike variant at LoDs 15.6 and 85.6 pM, respectively. Overall, antibody S01 seems to be more sensitive to changes in the spike amino acid sequence (31-fold minimum reduction of wild-type vs D614G spike detection sensitivity) than antibody E01 (2-fold maximum reduction of wild-type vs D614G spike detection sensitivity). Sandwich ELISA was also used to determine the limit of detection for heat inactivated virus (FIG. 13D) and revealed that pair E01/G07 affords the lowest LoD (1.8E+4 half tissue culture infectious dose, TCI50).

Example 9: Diagnostic Application Using Pairs of Antibodies: Detection of Spike and Heat Inactivated SARS-CoV-2 Virus by SpinDx SpinDx technology is a portable centrifugal microfluidic device that utilizes microsphere (beads) sedimentation for rapid detection of antigens, as previously reported by investigators at Sandia National Laboratories, Livermore, CA USA. See for example, Walsh III D I, Sommer G J, Schaff U Y, Hahn P S, Jaffe G J, Murthy S K. A centrifugal fluidic immunoassay for ocular diagnostics with an enzymatically hydrolyzed fluorogenic substrate. *Lab on a Chip.* 2014; 14(15):2673-2680; Koh C-Y, Schaff U Y, Piccini M E, et al. Centrifugal microfluidic platform for ultrasensitive detection of botulinum toxin. *Analytical chemistry.* 2015; 87(2): 922-928; Litvinov J, Moen S T, Koh C-Y, Singh A K. Centrifugal sedimentation immunoassays for multiplexed detection of enteric bacteria in ground water. *Biomicrofluidics.* 2016; 10(1):014103; Phaneuf C R, Mangadu B, Piccini M E, Singh A K, Koh C-Y. Rapid, portable, multiplexed detection of bacterial pathogens directly from clinical sample matrices. *Biosensors.* 2016; 6(4):49; and Phaneuf C R, Mangadu B, Tran H M, et al. Integrated LAMP and immunoassay platform for diarrheal disease detection. *Biosensors and Bioelectronics.* 2018; 120:93-101.

The SpinDx assay is a bead-based sandwich immunoassay where antigen-specific antibodies are covalently bound to silica microspheres and used to capture antigen in a complex sample matrix. Captured antigen is than detected with a second antibody labeled with fluorescent dye. The sandwich immunoassay complex is loaded into a microfluidic disc preloaded with density media and processed in the SpinDx device to allow sedimentation of the complexes via centrifugation. As the bead complexes pass through the density media gradient, any unbound antigen or detector antibodies are excluded from sedimentation, thus allowing a homogeneous, no-wash assay for rapid and sensitive antigen detection. Limit of detection (LoD) and limit of quantification (LoQ) for spike (ELISA and SpinDX) and whole heat-inactivated virus (ELISA only) were determined using noise signals for negative control analytes (myoglobin and rhino coronavirus for spike and whole virus detection, respectively, in ELISAs) and or for no analyte (SpinDx). These signals plus 3 or 8 standard deviations were inputted in the equations defining the "signal to analyte-concentration" relationship for each antibody pair analyzed (FIGS. 13A-D) to obtain LoD and LoQ, respectively (Table 8).

Antibodies were tested for recognition of full-length trimeric spike protein, both in purified form or as part of the whole virus. Antibodies were tested for recognition of wild-type spike and D614G spike. Based on their performance in previously described experiments, antibodies E1, F07, G07 and S01 (in various pairwise combinations) were selected for SpinDX experiments (FIG. 13C and Table 8). The antibody pairs used for detection are indicated in FIGS. 13A-D as (antigen-capturing IgG)/(antigen-detecting IgG) (e.g. S01/G07). RFU=relative fluorescence unit; TCID50=half tissue culture infection dose.

Among four of the antibodies tested as diagnostic reagents S01/F07 had the lowest limit of detection of spike and whole virus (~200 fM and ~3E+4 Tissue Culture Infectious Dose 50 (TCID50)/mL, respectively).

Due to limited availability of whole virus, SpinDx was only used for detection of spike protein (FIG. 13C). Prior to performing LoD experiments, a preliminary single-point antigen concentration screening allowed to identify the pairs/pair configuration affording the highest signal/noise ratio (data not shown). Pairs S01/F01 (with S01 used as capturing antibody) and S01/G07 and G07/S01 (with S01 used as capturing or detecting antibody), were selected. As for sandwich ELISA, pair S01/F07 was the most sensitive pair for detection of wild type spike protein (spike protein LoD=0.16 pM) and allowed ~8-fold more sensitive detection of wild-type spike than in ELISA. Interestingly when S01 paired up with antibody G07 it performed better (five-fold higher sensitivity) as detecting rather than capturing antibody (spike protein LoD=1.9 vs. 10.3 pM).

Methods: Spin Dx Based Assays

SpinDx Immunoassay Reagent Preparation: Anti-RBD2 IgGs E01, 501, F07, G07 were used to generate reagents for the SpinDx sandwich immunoassays. To generate capture beads, 1 μm carboxylic acid-functionalized silica microspheres (Bangs Laboratories, Fishers, IN, USA), were activated with N-ethyl-N0-(3-dimethylaminopropyl)carbodiimide and n-hydroxy succinimide (0.5 mmoles of each) in 0.5 mL of 500 mM MES at pH 6.0 for 20 minutes at room temperature. Microspheres were washed twice with 100 mM phosphate buffered saline (PBS; 138 mM NaCl, 2.7 mM KCl, 10 mM $Na_2HPO_4$, pH 7.4). Each capture antibody was added to a final concentration of 1 μg of antibody per 1 mg of microspheres per reaction in 0.5 mL PBS raised to pH 8.15 with 1 M $NaHCO_3$ and allowed to conjugate overnight at room temperature. The particles were then washed twice with PBS and blocked with Superblock (Thermo Fisher, Waltham, MA, USA) for 60 min at room temperature. After blocking, the particles were washed in wash buffer (0.1% (w/v) Tween-20 in PBS) and resuspended in assay buffer (1% (w/v) bovine serum albumin, 0.1% (w/v) Tween-20 in PBS) to a concentration of 12% beads. To generate detection antibodies, each antibody was labeled with Alexa Fluor 647 (Life Technologies, Carlsbad, CA, USA). 10 μg of antibody was brought up to a volume of 40 μL with PBS. For each antibody, one vial of activated Alexa Fluor 647 was reconstituted in 5 μL of dimethyl sulfoxide and then added to the diluted antibody. The mixture was brought up to pH 8.15 with 5 μL of 1 M sodium bicarbonate, and allowed to react at room temperature for 15 min in the dark. After the reaction was complete, unreacted dye was separated from labelled antibody using desalting spin columns with 7 kDa molecular weight cut-off(Thermo Fisher, Waltham, MA, USA). Concentrations, and dye-to-antibody ratios were determined spectrophotometrically by UV absorbance.

SpinDx Immunoassay Protocol: Serial dilutions of the antigen, SARS-CoV-2 trimeric spike protein (Acro Biosystems, SPN-C52H8) were prepared to five times of the final concentrations of 0 ng/mL, 1 ng/mL, 10 ng/mL 100 ng/mL and 1000 ng/mL in assay buffer. (1% (w/v) bovine serum albumin, 0.1% (w/v) Tween-20 in PBS) To start the sandwich immunoassay, 1 μL of antigen (various concentrations) and 1 μL of detection antibody (2 nM) were added to 3 μL of a 12% (w/v) suspension of capture microspheres. Capture beads, antigen, and detector antibody were incubated at room temperature for 20 m to allow bead complexes to form. Each antigen concentration was tested with the following capturing/detecting antibody combinations: S01/G07, S01/F07, G07/S01 and G07/F07, which were selected following a preliminary screening assay using all the antibody combinations (not reported) determining which antibody combinations produced the highest dynamic range. After incubation, the suspensions were mixed to resuspend beads that had settled and the entire volume (5 μL) of each suspension was added to the channel of a SpinDx microfluidic disc preloaded with 3 μL of density medium (Percoll, 0.1% Tween20). Discs were then placed into the SpinDx device, secured with a thumbscrew, and the analysis protocol was started via the computer-controlled graphical user interface. The device automatically spins the disc at 5000 RPM, indexes the channels, analyses each channel via laser-induced fluorescence, and reports relative fluorescence values to the connected computer. The fluorescence values are then exported to Prism (GraphPad Software, San Diego, CA, USA) for data analysis and reduction. Replicate data points were averaged, standard deviations were graphed as the error bars, and the data were fit to a four-parameter sigmoidal curve. Limits of detection (LoD) and limits of quantification (LoQ) were interpolated from the curve fit using the IUPAC definition of three and eight standard deviations above the noise, respectively. [Allegrini F, et al., *Analytical chemistry.* 2014; 86(15):7858-7866].

Example 10: Summary of Data Obtained for Antibodies in Various Formats

TABLE 9

Summary of data obtained for antibodies in various formats

| Selection strategy | Antibody name (antigen) | Affinity for RBD ($k_D$, nM)[a] | | Non-competitive RBD2 binders | Competitive RBD2 binders | Recognize D614G mutant? |
|---|---|---|---|---|---|---|
| +C, CB[b] | E01 (RBD2) | 13.9 ± 1.3<br>21.5 ± 2.12<br>90.0 ± 22.0 | scFv<br>Minibody<br>IgG | E08, F07, G07, H01, HO5, CR3022, and NN54 | B04, S01 and ACE2 | Yes |
| −C, AB[c] | S01 (RBD2) | 44.1 ± 2.5<br>22.7E+3<br>170.0 ± 40.0 | scFv<br>Minibody<br>IgG | E08, F07, G07 H05, CR3022, and NN54 | B04, E01, H01, and ACE2 | Yes |
| +C, CB[b] | F07 (RBD2) | 67.5 ± 6.8<br>61.5 ± 3.5<br>300.0 ± 65.0 | scFv<br>Minibody<br>IgG | E01, E08, H05, S01, CR3022, and NN54 | B04, G07, H01, and ACE2 | Yes |
| +C, CB[b] | G07 (RBD2) | 60.3 ± 5.5<br>63.9E+3<br>320.0 ± 76.0 | scFv<br>Minibody<br>IgG | E01, E08, H01, H05, S01, CR3022, NN54, and ACE2 | B04, and F07 | Yes |
| +C, CB[b] | B04 (RBD2) | 13.9 ± 1.5<br>56.8 ± 3.5<br>210 ± 42.4 | scFv<br>Minibody<br>IgG | E08, H1, H05, CRR3022, NN54, and ACE2 | E01, F07, G07, and S01 | NT |
| +C, CB[b] | E08 (RBD2) | 13.9 ± 1.8<br>3.6 ± 2.0<br>27.0 ± 3.2 | scFv<br>Minibody<br>IgG | B04, E01, F07, G07, S01, and ACE2 | H1, H5, and CR3022 | NT |
| +C, CB[b] | H01 (RBD2) | 66.4 ± 5.1<br>281.0 ± 162.6<br>800.0 ± 440.0 | scFv<br>Minibody<br>IgG | B04, E01, and G07 | E08, F07, H1, H05, S01, CR3022, and ACE2 | NT |
| +C, CB[b] | H05 (RBD2) | 16.7 ± 4.0<br>51 ± 8.6 | scFv<br>IgG | B04, E01, F07, G07, and S01 | E08, H01, CR3022, and ACE2 | NT |

TABLE 9-continued

Summary of data obtained for antibodies in various formats

| Selection strategy | Antibody name (antigen) | Affinity for RBD ($k_D$, nM)[a] | | Non-competitive RBD2 binders | Competitive RBD2 binders | Recognize D614G mutant? |
|---|---|---|---|---|---|---|
| −C, AB[c] | R04 (RBD2) | 293.3 ± 24.0<br>127.5 ± 70.0<br>190.0E+3 | scFv<br>Minibody<br>IgG | ND | ND | NT |
| | R04 (RBD1) | 175.1 ± 20.3 | scFv | NT | NT | NT |

[a]Determined either by flow cytometry (scFvs) or by surface plasmon resonance, SPR (minibodies or IgGs)

[b]+C = with competition; CB = chemically biotinylated target antigen

[c]−C = no competition; AB = target antigen biotinylated through the avitag

Example 11: Identification of Antibodies Competing with ACE2 for RBD2 Binding, SPR Analysis It has been established that ACE2 acts as the cellular doorway that allows SARS-CoV 2 entry into many types of cells, resulting in COVID 19 disease (Yang J, Petitjean S J, Koehler M, et al. Molecular interaction and inhibition of SARS-CoV-2 binding to the ACE2 receptor. *Nature communications*. 2020; 11(1):1-10). Therefore, in an effort to explore the therapeutic potential of the antibodies, antibody ability to block ACE2-RBD2 interaction was tested in three different assays.

The first assay was part of the surface plasmon resonance (SPR) assay described in Example 7 and depicted in FIGS. 12A-B that involved antibody+ACE2-Fc interactions with RBD2. FIG. 14A captures the relevant part of the data in FIG. 12A. Five out of eight tested antibodies, E01, H01, H05, S01, and possibly F07 competed with ACE2-Fc binding to RBD2. E01, H01, and S01-were identified as the strongest competitors. H01 competition was even superior to that of NN54, which in this experiment served as a positive competitor control. A heat map plot of surface plasmon resonance SPR data (FIG. 14A) depicts normalized ACE2-Fc binding to RBD2 captured by immobilized antibodies. The green, red and yellow cells indicate non-competing, competing and mildly competing binding relationships, respectively. Antibodies CR3022 and NN54, known to not compete and compete with ACE2, respectively, were included as controls.

Competition with of ACE2 in binding to RBD2 is shown in FIG. 15. The results of two different experiments are presented. In the first experiment (set of bars on left side of graph), ACE2 binding to plate-immobilized RBD2 was measured in the presence of rabbit minibodies F07, R04 and S01. ACE2 binding was detected with anti-human allophycocyanin (APC). In the second experiment (set of bars on the right side of graph) rabbit minibodies F07, R04 and S01 were tested for binding to RBD2 captured by plate-immobilized ACE2. In both cases the APC signal was used as an inverse measure of competition. ScFvs F07 and R04 seem to not compete with ACE2 for binding but S01 does.

Example 12: Identification of Antibodies Competing with ACE2 for RBD2 Binding, Immunocytochemistry Analysis The second assay included immunocytochemistry analysis (FIGS. 14B and 14C) of RBD2 binding to human embryonic kidney (HEK) cells with stable expression of ACE2 receptor. RBD2-superfolder GFP (sfGFP) chimera, and either unlabeled (FIG. 14B) or phycoerythrin (PE)-labelled anti RBD2 antibodies (FIG. 14C), were applied. E01, F07, G07, and S01 were tested in IgG format. A fluorescent anti-influenza M2 antibody, Z3, was used as a negative RBD2 competitor control.

FIGS. 14B and 14C evaluate the effect of the antibodies on interaction between HEK cells constitutively expressing ACE2 (HEK-ACE2) and RBD2-sfGFP chimera (green fluorescence). Both panels provide three pieces of information: a graphical representation of the experimental design, quantitative fluorescence data in bar graph format (error bars show standard deviation of triplicate experiment) and representative microscopy images for each of the antibodies. Data obtained without IgGs (only RBD2sfGFP) and anti-influenza M2 IgG Z3 were used as a control for absence of inhibition (FIG. 14B) or binding (FIG. 14C).

In the first set of experiments (FIG. 14B), unlabeled antibodies were tested for their ability to block RBD2-sfGFP binding to ACE2 expressed on the cell surface. By measuring cell-associated green fluorescence, it was found that E01 and S01 were the strongest inhibitors of RBD2-ACE2 interaction (lower florescence=more efficient blocking). The remaining antibodies-B04, F07, G07, including the negative control Z3 did not significantly inhibit RBD2 binding to the native ACE2 receptor.

In a second set of experiments (FIG. 14C) the epitope targeted by the anti-RBD2 antibodies was characterized. First, RBD2-sfGFP was pre-incubated with ACE2 receptor-expressing HEK cells. This step was followed by removal of the unbound RBD2-sfGFP peptide and second incubation with PE-labelled anti-RBD2 antibodies. Thus, results with singly labeled with GFP cells indicate that the PE-labelled anti-RBD2 antibody is specific to the epitope occupied by the ACE2 receptor, while double labelled cells signify that the anti-RBD2 antibody recognized an epitope outside of the ACE2 binding site. The results from this assay indicated that E01 and S01 specifically bind to the RBD epitope occupied by ACE2, whereas antibodies B04, F07 and G07 could bind outside of the ACE2-occupied epitope since both red and green fluorescence were detected. Collectively, the immunocytochemistry experiments confirmed the results from the SPR assay demonstrating that antibodies E1 and S01 were competitive inhibitors of ACE2-RBD2 interaction. (FIG. 14A). The mild inhibition of ACE2-RBD2 interaction by F07 revealed by the SPR experiment (FIG. 14A) was not observed in the immunocytochemistry studies of FIGS. 14B and 14C. This might be due to the different format of ACE2 presentation (i.e., receptor expressed on the cell surface versus soluble protein in the SPR assays). The specificity of antibody binding to RBD2 versus ACE2 receptor was further validated by comparison of fluorescence intensity generated by PE-labeled antibodies incubated with ACE2 293 HEK cells and the parental 293 HEK strain not expressing ACE2 receptors. All tested antibodies demonstrated specific labelling of the ACE2-expressing cells in the presence of RBD2 peptide.

Methods: Fluorescent Microscopy with HEK-ACE2 Cell and RBD2-sfGFP

Human ACE2 293 cell line (Takara Bio USA, Mountain View, CA) was cultured in DMEM media supplemented with 10% fetal bovine serum. To activate the expression of the ACE2 receptors from a transgene integrated into the cellular genome, 1p g/mL puromycin was added in the cell growth media. For the microscopy experiments, cells were plated onto 8-chambered borosilicate glass slides (Nunc LabTek, cat #155411) coated with poly-L-Lysine (EMD Millipore/Sigma). The cells were fixed using 4% paraformaldehyde (PFA) in 1×PBS for 15 minutes, washed twice with 1×PBS and blocked using 2% BSA in 1×PBS for at least 30 minutes (up to 24 h). Two types of binding assays were performed using ACE2 293 cells, (1) in vitro RBD2 sfGFP reagent, and (2) unlabelled or PE-labelled IgGs.

In the first binding assay, antibody binding to the RBD2 in solution was investigated. RBD2-sfGFP (2 μg/mL, 36 pM) was incubated with unlabeled IgG (200 μg/mL, 1.33 pM) for 1 hr prior to addition of the antibody to the ACE2 293 cells-coated chamber slides. Unbound proteins were washed and fluorescent microscopy images were obtained with Zeiss Axio Observer Z.1.

In the second binding assay, antibody ability to recognize ACE2; bound RBD2 sfGFP was evaluated. Here 100 μL of ~2 μg/mL (36 nM) of RBD2-sfGFP was added to each of the wells containing the HEK ACE2 cells and allowed to bind for 1 hr at RT. Excess protein was washed 3×PBST and 3×PBS. PE conjugated IgGs (1 μg/mL) was added to the wells and incubated for another hour, followed by washing steps as described for the primary antibody. Fluorescent images were analyzed with the ZenPro software.

Example 13: Identification of Antibodies Competing with ACE2 for RBD2 Binding, In Vitro Neutralization of SARS-CoV2 Infection of HEK Cells The third assay was based on in vitro neutralization of SARS-CoV-2 infection of ACE2-expressing HEK cells (FIGS. 16A and 16B). A preliminary screen of anti-RBD2 antibodies B04, E01, E08, F07, G07, H01, H05, and S01 was performed at four dilutions, to assess the relative neutralizing potency (FIG. 16A).

E01, F07; H01; H05, S01, E08, B04 and G07 inhibit viral infection in vivo (Table 10 and FIG. 16A). The three IgGs with the lowest half neutralizing titers (NT50) (E01, S01, and F07) were retested in triplicate alone or in combination (FIG. 16B). The highest potency antibodies E01, S01, and F07 were selected for further studies, also based on orthogonality of their RBD2 binding sites (see epitope binning in FIG. 12A-B) and their performance in immunocytochemistry assays described above in Example 12 and FIGS. 14B and 14C. Individual antibodies as well as pairs E01+F07 and S01+F07 were tested (Table 10). Antibody E01 was the most potent antibody to block SARS-CoV2 entry in these studies (NT50, 6.2 nM), followed by antibody S01 (NT50, 14.6 nM). NT50s were further reduced when E01 and S01 were each used in combination with F07 (E01/F07 NT50 2.7 nM, an ~2-fold increase in neutralization efficiency; S01/F07 NT50 3.7 nM, an ~4-fold increase in neutralization efficiency). These NT50 values are in the 32-percentile within a set of 224 anti-RBD2 IgG subjected to a similar in vitro study at the La Jolla Institute of Immunology (World Wide Web at covic.lji.org/database/).

TABLE 10

In vitro neutralization assay results

| Antibody | $N_{max}$ (%_)[a] | NT50 (nM)[b] |
|---|---|---|
| B04 | 53.3 ± 6.2 | 56.7 ± 31.1 |
| E01 | 104 ± 8.5 | 6.4 ± 2.4 |
| E01 + F07 | 104 ± 8.5 | 2.7 ± 1.1 |
| E08 | 70.4 ± 4.8 | 52.9 ± 17.7 |
| F07 | 74.7 ± 11.3 | 45.2 ± 21.9 |
| G07 | ND[c] | ND[c] |
| H01 | 87.7 ± 5.4 | 69.6 ± 18.7 |
| H05 | ND[c] | ND[c] |
| S01 | 106.0 ± 11.8 | 14.6 ± 6.3 |
| S01 + F07 | 98.1 ± 6.0 | 3.8 ± 1.2 |

[a]Neutralization maximum
[b]Half neutralization titer
[c]Not determined

Methods: Viral Neutralization Assay

The neutralizing activity of the 8 IgGs was conducted using plaque assays with active virus as described in Bradfute S B, et al., [2019. *The Journal of infectious diseases.* 2020; 222(10):1620-1628]. SARS-CoV-2 (isolate USA-WA1/2020, obtained from BEI Resources) was diluted to 50-100 PFU/200 μL in viral growth medium (VGM, minimal essential medium with 2.5% heat inactivated fetal calf serum) and incubated 1:1 with IgGs at concentrations ranging from 700 to 0 nM (preliminary assay) or 172 to 0.172 nM (assay using selected antibodies/antibody combinations) in VGM and incubated at 37° C. for 1 1.5 hours. Virus-IgG mixtures were added to 80% confluent Vero-E6 cells (ADCC, CRL-1586) and incubated for 2 hours at 37° C. Supernatants were then removed and cells were washed once with PBS and then overlaid with 1 mL virus overlay medium (equal volumes of 2% agarose/2× minimal essential medium with 5% fetal calf serum and 2× penicillin/streptomycin). Cells were then incubated at 37° C. for 2 days and fixed at 4° C. overnight with 4% formaldehyde. Fixative and viral overlay was removed and cells were stained with 0.5% crystal violet for 1 2 minutes, washed, and dried.

Example 14: Methods for Soluble Antibody Characterization Assays

Common Steps in ELISA/FLISA/Sandwich ELISA

For all these assays a 96-well NUNC Maxisorp plate (transparent, 442404 or black, 43711) was coated with soluble antibody (minibody or IgG) in PBS (70 μL/well) either directly or through interaction with goat anti-human antibody (Southern Biotech Inc. Fc-UNLB #2048-01) Blocking was done using 5% BSA solution in PBS (200 μL/well). Antigens and detecting IgGs (for sandwich assays) were added as 0.5% BSA in PBS solutions (70 μL); for one-concentration assays, antigen concentration was always 100 nM. Incubation steps were at 28° C. for 1 hr, unless otherwise stated. Washing included 3 consecutive PBST (PBS+0.05% Tween20) and 3 consecutive PBSLT (PBS+0.005% Tween20) addition (300 μL/well) and removal. Upon adding 100 μL/well PBS the plate's UV/vis absorbance or fluorescence was measured. Data were obtained in triplicate (except for epitope binning in FIG. 11A-B, which was a qualitative test), and measurements' average/standard deviation were calculated and plotted against antigen concentration using Microsoft Excel/Kaleidagraph.

Minibody ELISA: Maxisorp plates (ThermoFisher, #442404) was coated with neutravidin (ThermoFisher, cat #31050) at 10 μg/mL (100 μL/well) overnight at 4° C. or for 1 h at 37° C. The wells were washed twice with 1×PBS and blocked with 2% milk PBS for 1 h. 0.5-1 μg of lightning link-biotinylated antigens (RBD2, RBD1, or ubiquitin) were added and incubated for 30 minutes. Unbound proteins were washed with 2×PBS. Upon addition of primary antibodies (either human or rabbit minibody crudes, 100 μL/well), the plate was incubated for 1 h. Primary antibody solutions were removed and the plate was washed. Upon addition of secondary antibodies (Abcam Inc., #ab97165(anti-human), ThermoFisher G21234 (anti-rabbit)) labelled with HRP (1:2000 dilution, final concentration 0.5 μg/mL) incubation was carried out for 1 h, and secondary antibody solution removed. Upon washing (4×PBST and 4×PBS), HRP activity was detected by adding its substrate 3,3', 5, 5' tetramethylbenzidine dihydrochloride (TMB, T0440, Sigma, 100 μL/well). Once blue color started to develop the reaction was quenched by adding 1M $H_2SO_4$ (50 μL/well). Absorbance at 450 nm was measured using spectrophotometer.

IgG FLISA (Velappan N, Clements J, Kiss C, Valero-Aracama R, Pavlik P, Bradbury A. Fluorescence linked immunosorbant assays using microtiter plates. *Journal of immunological methods*. 2008; 336(2):135-141). A black maxisorp plate was coated with goat anti-human antibody by: 1) adding a PBS solution of antibody (25 μg/mL, 70 μL/well); 2) incubating the plate at 4° C. overnight; and 3) upon removal of antibody solution, blocking with 5% BSA in PBS (250 mL/well, 1 h, 25° C.). Anti-RBD2 IgGs were added to the plate (10 nM solutions in 0.5% BSA PBS, 70 μL/well), incubated for 1 h at 25° C., and removed. After washing, biotinylated antigens (11B RBD1, 11B RBD2, AB fraction S1 of spike, and negative control 11B lysozyme), or RBD1/RBD2-sfGFP chimeras (produced at Los Alamos National Laboratory) were added (100 nM solutions in 0.5% BSA PBS, 70 μL/well), followed by incubation and washes. When biotinylated antigens were used, a 200-fold diluted streptavidin-Alexa Fluor 633 solution (ThermoFisher, #S21375) was added (1:200 dilution in 0.5% BSA PBS, 100 μL/well), followed by washing, addition of PBS (100 μL/well) and plate reading at Ex/Em 595/660 nm. When sfGFP antigen chimeras were used, after washing and addition of PBS, the plate was read at Ex/Em 480/520 nm.

Sandwich ELISA. Each capturing IgGs were immobilized on a 96-well Nunc Maxisorp plate (ThermoFisher #12-565-136) by depositing 70 μL of a 340 nM IgG PBS solution in each well, incubating, and blocking. The analyte (either RBD2, trimeric spike protein (BEI NR-53257), whole heat-inactivated SARS-CoV 2 virus (BEI NR-52287 (2.8E+5 $TCID_{50}$/mL, diluted to 2.52 E+5 $TCID_{50}$/mL*0.69=1.7E+5 $TCID_{50}$/mL, total virus particle in 70 μL=1.2E+4), or negative controls myoglobin/human coronavirus OC43 (ATCC, VR-1558) were added at various concentrations (for binning: [RBD2]=10 nM and [Spike]=20 nM; for LoD/LoQ determination see concentration ranges in FIG. 13A-D). After incubation and washing the detecting IgG-HRP conjugates were added at concentrations either 50 nM (binning) or 50 nM (LoD/LoQ), followed by incubation and washing. 90 μL HRP substrate TMB was added until a blue color started to develop, followed by acidification (i.e. addition of 90 μL 1 M $H_2SO_4$ to interrupt the enzymatic reaction) and reading of $Abs_{450}$. For binning, each $Abs_{450}$ value was plotted in MS Excel (3D bar graph) as a bar at the intersection of the corresponding capturing (x axis)/detecting (z axis) antibody. For LoQ/LoD calculations, averages of three experiments and corresponding standard deviations (error bars) were calculated in MS Excel, plotted vs the antigen concentration and fitted to linear equations. Averages of three $Abs_{450}$ measurements obtained for negative antigens myoglobin and rhino coronavirus (at max value of the antigen concentration range) plus 3 or 8 standard deviations were used as y values in the linear equations defining the signal vs antigens concentration obtained for each antibody combination, to find the antigen concentrations (x values) corresponding to the LoDs and LoQs, respectively.

Epitope binning by SPR. Epitope binning was performed with a classical sandwich assay format on a Carterra LSA SPR instrument equipped with a HC200M sensor chip (200 nm linear polycarboxylate surface) at 25° C. and in a HBSTE-BSA running buffer (10 mM HEPES pH 7.4, 150 mM NaCl, 3 mM EDTA, 0.05% Tween-20, supplemented with 0.5 mg/ml BSA). Two microfluidic modules, a 96-channel print-head (96PH) and a single flow cell (SFC), were used to deliver samples onto the sensor chip. Surface preparation was performed with 25 mM MES pH 5.5 with 0.05% Tween-20 as a running buffer. The chip was activated with a freshly prepared solution of 130 mM 1-ethyl-3-(3-dimethylaminopropyl)carbodiimide (EDC)+33 mM N-hydroxysulfosuccinimide (Sulfo-NHS) in 0.1 M MES pH 5.5 using the SFC. Antibodies were immobilized using the 96PH for 10 minutes at 15 μg/mL diluted into 10 mM sodium acetate (pH 4.25). Unreactive esters were quenched with a 7-minute injection of 1 M ethanolamine-HCl (pH 8.5) using the SFC. The binning analysis was performed over this array with the HBSTE-BSA buffer as the running buffer and sample diluent. The RBD antigen was injected in each cycle for 4 minutes at 100 nM (3.6 μg/mL) and followed immediately by a 4 minute injection of the analyte antibody at 30 μg/mL (200 nM for IgG constructs). The surface was regenerated each cycle with two 30 second pulses of Pierce IgG Elution Buffer (pH 2.8) with 1 M NaCl. Data was processed and analyzed with Epitope Tool tool (Carterra). Briefly, data was referenced using unprinted locations on the array and each binding cycle was normalized to the RBD capture level. The binding level of the analyte antibody just after the end of the injection was compared to that of a buffer alone injection. Signals that increased relative to the buffer controls are described as sandwiching and represent non-blocking behavior. Competition results were visualized as a heat map in which red, yellow, and green cells represent blocked, intermediate, and not blocked analyte/ligand pairs, respectively. Clones having identical patterns of competition are classified as being within the same bin cluster.

Kinetics by SPR. Binding kinetics was also performed on the same array surface as described for epitope binning. Kinetics were analyzed at 25° C. in HBSTE-BSA running buffer. The RBD antigen was injected with 5 minutes of association at six concentrations in a three-fold dilution series starting at 500 nM to 1.49 nM with a 10 minute dissociation. Data was analyzed in the Carterra Kinetics tool. Data was processed by double referencing with the subtraction of an interspot reference and buffer blank cycle, then fit to a 1:1 Langmuir model to determine the $k_a$, $k_d$, $K_D$, and $R_{max}$.

LISTING OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus. In light chain, heavy chain, and scFv sequences, light chain CDRs are bolded, heavy chain CDRs are underlined, and linker sequences are italicized.

TABLE 11

| Antibody sequences | | | | | |
|---|---|---|---|---|---|
| Antibody Name | SEQ ID NO of light chain variable region | SEQ ID NOs of Light Chain CDRs | SEQ ID NO of heavy chain variable region | SEQ ID NOs of Heavy Chain CDRs | SEQ ID NO of scFv |
| B04 | 1 | 73-75 | 20 | 76-78 | 41 |
| B10 | 2 | 79-81 | 21 | 82-84 | 42 |
| D04 | 64 | 85-87 | 65 | 88-90 | 43 |
| D07 | 3 | 91-93 | 22 | 94-96 | 44 |
| D10 | 4 | 97-99 | 23 | 100-102 | 45 |
| D11 | 5 | 103-105 | 24 | 106-108 | 46 |
| D12 | 6 | 109-111 | 25 | 112-114 | 66 |
| E01 | 7 | 115-117 | 26 | 118-120 | 47 |
| E07 | 8 | 121-123 | 27 | 124-126 | 67 |
| E08 | 9 | 127-129 | 28 | 130-132 | 48 |
| F07 | 10 | 133-135 | 29 | 136-138 | 49 |
| G07 | 11 | 139-141 | 30 | 142-144 | 50 |
| H01 | 12 | 145-147 | 31 | 148-150 | 51 |
| H02 | 13 | 151-153 | 32 | 154-156 | 52 |
| H03 | 14 | 157-159 | 33 | 160-162 | 53 |
| H05 | 15 | 163-165 | 34 | 166-168 | 54 |
| R04 | 16 | 169-171 | 35 | 172-174 | 55 |
| R09 | 17 | 175-177 | 36 | 178-180 | 56 |
| R26 | 18 | 181-183 | 37 | 184-186 | 57 |
| S01 | 19 | 187-189 | 38 | 190-192 | 58 |

amino acid sequence of B04 light chain SEQ ID NO: 1
SYVLTQPPSVSVAPGKTARITCGGNNIGIRSVHWYQQKPGQAPVLVIYYDSDRPSGIPE RFSGSKSGNTATLTISRVEAGDEADYYCQVWDSSSDHPVFGGGTKLTVL amino acid sequence of B10 light chain SEQ ID NO: 2
QSVVTQPPSVSGAPGQRVTISCTGSSSNIGSRTVN WYQQLPGTAPKLLIYANNQRPSGV PDRFSGSKSGTSASLAISGLQSEDEADYYCAAWDDSLNGYVFGTGTKLTVL amino acid sequence of D07 light chain SEQ ID NO: 3
SYELTQPPSVSVAPGETARMTCGGNNIGTKGVHWYQQKPGQAPVLVVYDDSDRPSGI PERFSGSNAGNTATLTISRVEAGDEADYYCQVWDSRSDQYVFGTRTKLTVL amino acid sequence of D10 light chain SEQ ID NO: 4
QSVVTQPPSASGSPGQTVTISCSGNSANIGGNPVNWYQQLPGTAPKLLIYSNNQRPSGV PDRFSGSKSGISASLAISGLQSEDEADYYCAAWDDSLNGVIFGGGTKLTVL amino acid sequence of D11 light chain SEQ ID NO: 5
SYELTQPPSVSVAPGQTARITCGGNNIGSKSVHWYQQKPGQAPVLVVYDDSDRPSGIPE RFSGSNSGNTATLTISGTQAMDEADYYCQAWDSSTAYVFGSGTKLTVL amino acid sequence of D12 light chain SEQ ID NO:6
SYELTQPPSVSVAPGQTARITCGGNNIGSKPVHWYQQMPGQAPVLVVYDNNNRPSGIP ERFSGSNSGNTATLTISRVEAGDEADYFCQVWDSSSDLWVFGGRTKLTVL amino acid sequence of E01 light chain SEQ ID NO: 7
SYELTQPPSVSVAPGETARITCGGDNIGRRHVHWYQQKPGQAPVLVIYDDSDRPSGIPD RFSGSNSGNTATLTIGRVEAGDEADYYCQVWGSSNDPHVFGTGTKLTVL amino acid sequence of E07 light chain SEQ ID NO:8
SYVLTQPPSVSVAPGQTARITCGGNNIGSKSVHWYQQKPGQAPVLVVYDDSDRPSGIPE RFSGSNSGNTATLIISRVEAGDEADYYCQVWDSSSVHYVFGTGTKLTVL amino acid sequence of E08 light chain SEQ ID NO: 9
SYVLTQPPSVSVAPGKTARITCGGNNIGWKSVHWYQQKPGQAPVLVVYDDSDRPSGIP ERFSGSNSGNTATLTISRVEAGDEADYYCQVWDSSSDLVVFGGGTKLTVL amino acid sequence of F07 light chain SEQ ID NO: 10
SYVLTQPPSVSVAPGQTARITCGGNNIGSKSVHWYQQKPGQAPVLVVYDDSDRPSGIPE RFSGSNSGNTATLIISRVEAGDEADYYCQVWDSSSVHYVFGTGTKLTVL amino acid sequence of G07 light chain SEQ ID NO: 11
QSVLIQPPSASGTPGQRVTISCSGSNSNFGSNSVSWYQQRPGTAPKLLIEGNNQRPSGVP ERFSGSKSGTSASLAISGLQSEDEAEYSCASWDDSLNAFVFGPGTKLTVL amino acid sequence of H01 light chain SEQ ID NO: 12
QPGLTQPPSVSLAPGQTARITCGGNNIGSKSVHWYQQKPGQAPVLVVYDDSDRPSGIPE RFSGSNAGNTATLTISRVEAGDEADYYCQVWDSRSDQYVFGTRTKLTVL amino acid sequence of H02 light chain SEQ ID NO: 13
QSVVTQPPSVSAAPGQKVTISCSGSSSNIGNNYVSWYQQLPGTAPKLLIYRDTQRPSGV PDRFSGSKSGTSASLAISGLRSEDEADYYCATWDKSLSGPVFGGGTKVTVL amino acid sequence of H03 light chain SEQ ID NO: 14
SYELTQPPSVSVAPGQTARITCGGNNIGSKSVHWYQQKPGQAPVLVIYYDSDRPSGIPE RFSGSNSGNTATLTISRVEAGDEADYYCQVWDSSSALYVFGTRTKVTVL amino acid sequence of H05 light chain SEQ ID NO: 15
SYVLTQPPSVSVAPGQTARITCGANNIGRISVHWYQQKPGQAPVLVVYDDSDRPSGIPE RFSGSNFGNTATLTISRVEAGDEADYYCQVWDSYSDHVIFGGGTKLTVL amino acid sequence of R04 light chain SEQ ID NO: 16
EIVMTQSPSSLSASVGDRVTITCQASQDISNYLNWCQQKPGKAPKLLIYDASNLETGVP SRFSGSGSGTGFTFTISSLQPEDFATYYCQQSYSTPYTFGQGTKVEIK amino acid sequence of R09 light chain SEQ ID NO: 17
QPGLTQPPSVSVSPGQTASITCSGDKLGYKYVSWYQQKPGQSPVLVIYEDTKRPSGIPK RFSGSNSGNTATLTICGTQAVDEADYYCQAWDSSVVFGGGTKLTVL amino acid sequence of R26 light chain SEQ ID NO: 18
SYELTQPPSVSVAPGQTATITCGGKNIESKSVHW YQQKPGQAPVLVVSDDTDRASGIPE RFSGSNSGGAATLTISRVEAGDEADYYCQVWDSPSDHYVFGPGTKLTVL amino acid sequence of S01 light chain SEQ ID NO: 19
EIVMTQSPSSLSASVGDSVTITCQASQDISNYLNWYQQKPGKAPKLLIYDASNLETGVPS RFSGGGSGTDFTLTITSLQPEDIATYYCQQYDNFPPTFGPGTKVDIK amino acid sequence of B04 heavy chain SEQ ID NO: 20
QVQLVESGAEVKKPGASVKVSCKASGYTFTRYYMHWVRQAPGQGLEWMGI-

INPSGGT TSYAQKFOGRVTMTRDTST-STVYMELSSLRSEDTAVYYCARSFGELTSFDYW GQGTLV TVSS amino acid sequence of B10 heavy chain SEQ ID NO: 21 QVQLQQSGPGLVKPSQTLSLTCAISGDSVSSN-SATWNWIRQSPSRGLEWLGRTYYGSKW HSDYAVSVKSRITINPDTSKNQISLHLNPVTPED-TAVYYCARGRSYAFDIWDQGTMVTV SS amino acid sequence of D07 heavy chain SEQ ID NO: 22 QVTLKESGPVLVKPTETLTLTCTVSGFSL-SNARMGVSWIRQPPGKALEWLAHIFSNGEKS YSTSLKSRLTISKDTSKSQVVLTMTNMDPVD-TATYYCARTLDYYDSSGYLVGGAFDIW GQGTMVTVSS amino acid sequence of D10 heavy chain SEQ ID NO: 23 QVQLVQSGAEVKKPGESLKISCKGSGYSFTSY-WIGWVRQMPGKGLEWMGIIYPGDSDT RYSPSFQGQVTISADKSISTAYLQWSSLKASD-TAMYYCARRHSGSYSGAFDIWGQGTM VTVSS amino acid sequence of D11 heavy chain SEQ ID NO: 24 QVQLEESGGGLVQPGGSLRLS-CAASGFTFSNYAMSWVRQAPGKGLEWVSAIS-GSGGAT FHADSVKGRFTISRDNSKNT-LYLQMNSLRAEDTAVYYCARRVGYDSSGYYWS DAFDIW GQGTMVTVSS amino acid sequence of D12 heavy chain SEQ ID NO:25 QVQLVESGGGLVQPGRSLRLSCAASGFTFDDY-AMHWVRQAPGKGLEWVSGTSWNSGS IGYADSVKGRFTISRDNAKNSLYLQMNSLRAED-TALYYCAKDKGYYDSSAGFDIWGQG TMVTVSS amino acid sequence of E01 heavy chain SEQ ID NO: 26 QVQLQQWGAGLLKPSETLSLKCA-VYGGSFSGYYWGWIRQSTGKGLEWIGEINRSG-STN YNPSLKSRVTISVDTSKNQFSLKLSSVTAAD-TAVYYCARGGARYYYGSGSYRSTPRPYY EDYWGQGTLVTVSS amino acid sequence of E07 heavy chain SEQ ID NO:27 QVQLVQSGAEVKKPGSSVRVSCKVSGYTFT GYYMHWVRQAPGQGLEWMGIINPSGGS TSYAQKFOGRVTMTRDTSTSTVYMELSSLRSED-TAVYYCARVRVGASDAFDIWGQGT MVTVSS amino acid sequence of E08 heavy chain SEQ ID NO: 28 QVQLVQSGAEVKKPGSSVKVSCK-ASGGTFSSYAISWVRQAPGQGLEWMGGIIP-IFGTAN YAQKFOGRVTITADEST-STAYMELSSLRSEDTAVYYCARASGRWLQFWH-YYGMDVWG QGTTVTVSS amino acid sequence of F07 heavy chain SEQ ID NO: 29 QVQLVQSGAEVKKPGSSVRVSCKVSGYTGY-YMHWVRQAPGQGLEWMGIINPSGGS TSYAQKFOGIRVTMTRDTST-STVYMELSSLRSEDTAVYYCARVRVGAS-DAFDIWGQGT MVTVSS amino acid sequence of G07 heavy chain SEQ ID NO: 30 QVQLVQSGAEVKKPGESLKISCKGSGYSFTSY-WIGWVRQMPGKGLEWMGIIYPGDSDIR YSPSFOGQVTISADKSFSSAYLQWSSLKASD-TAMYYCARLGATGAFDIWGQGTTVTVSS amino acid sequence of H01 heavy chain SEQ ID NO: 31 QVTLKESGPVLVKPTETLTLTCTVSGFSL-SNARMGVSWIRQPPGKALEWLAHIFSNGEKS YSTSLKSRLTISKDTSKSQVVLTMTNMDPVD-TATYYCARTLDYYDSSGYLVGGAFDIW GQGTMVTVSS amino acid sequence of H02 heavy chain SEQ ID NO: 32 QVQLQQSGPGLVKPSQTLSLTCAISGDSVSSN-SAAWNWIRQSPSRGLEWLGRTYYRSK WYN-DYAVSVKSRIIINPDTSKNQFSLQLNSVTPED-TAVYYCARQDNNPYYGLDVWGQG TTVTVSS amino acid sequence of H03 heavy chain SEQ ID NO: 33 QVQLVESGGGLVQPGRSLRLSCAASGFTFDDY-AMHWVRQAPGKGLEWVSGISWNSGSI GYADSVKGRFTISRDNAKNSLYLQVNSLRAED-TAVYYCARELIVGTTSPQTDAFDIWGQ GTMVTVSS amino acid sequence of H05 heavy chain SEQ ID NO: 34 QVQLVQSGAEVKKPGSSVKVSCK-ASGGTFSSYAISWVRQAPGQGLEWMGGIIP-IFGTAN YAOKFQGRVTITADEST-STAYMELSSLRSEDTAVYYCARSIFGWVHSHAD-GYYYGMDV WGQGTTVTVSS amino acid sequence of R04 heavy chain SEQ ID NO: 35 QVQLQQSGPGLVKSSQTLSLTCAISGDSVSSN-GAAWHWIRQSPSRGLEWLGRTYYRSG WYN-DYAVSVKSRITINQDTSKNQFSLQLNSVTPED-TAVYFCARFGGGGRMDVWSQGTT VTVSS amino acid sequence of R09 heavy chain SEQ ID NO: 36 QVQLVQSGAEVKKPGASVKVSCKASGYTFTSY-GISWVRQAPGQGLEWMGWISAYNGN TNYAQKFOGRVTMTTDTST-STAYMELRSLRSDDTAVYYCARD-MELRPPFDYWGQGTL VTVSS amino acid sequence of R26 heavy chain SEQ ID NO: 37 QVQLVESGGGVVQPGRSLRLSCAASGFTFSSY-AMHWVRQAPGKGLEWVAVISYDGSN KYY-ADSVKGRFTISRDKAKNTLYLQMNSLRGED-TAVYYCARELSYYDSSGYLRGDWY FDLWGRGTLVTVSS amino acid sequence of S01 heavy chain SEQ ID NO: 38 QVQLVESGGGLVKPGGSLRLSCAASGFTVG-SNYMSWVRQAPGKGLEWVSVIYSGGSTY YADSVKGRFTISRDNSKNTLYLQMNSLRAED-TAVYYCARGSSGAWYFDLWGRGTLVT VSS amino acid sequence of linker SGGSTITSNN-VYYTKLSSSGT (SEQ ID NO: 39). SGGSTITSNN-VYYTKLSSSGT amino acid sequence of linker SGGSAITSYN-VYYTKLSSSGT (SEQ ID NO: 40). SGGSAITSYN-VYYTKLSSSGT amino acid sequence of B04 scFv (SEQ ID NO: 41) SYVLTQPPSVSVAPGKTARITCGGNNI-GIRSVHWYQQKPGQAPVLVIYYDSDRPSGIPE RFSGSKSGNTATLTISRVEAGDEAD-YYCQVWDSSSDHPVFGGGTKLTVLSGGSTIT-SYNV YYTKLSSSGTQVQLVESGAEVKKP-GASVKVSCKASGYTFTRYYMHWVRQAPGQGL-EW MGIINPSGGTTSYAQKFOGRVTMTRDTST-STVYMELSSLRSEDTAVYYCARSFGELTSFD YWGQGTLVTVSS amino acid sequence of B10 scFv (SEQ ID NO: 42) QSVVTQPPSVSGAPGQRVTISCTGSSSNIGSRTV-NWYQQLPGTAPKLLIYANNQRPSGV PDRFSG-SKSGTSASLAISGLQSEDEADYYCAAWDD-SLNGYVFGTGTKLTVLSGGSTITSY NVYYTKLSSSGTQVQLQQSGPGLVKPSQTLSLT-CAISGDSVSSNSATWNWIRQSPSRGLEW LGRTYYGSKWHSDYAVSVKSRITINPDTSKNQIS-LHLNPVTPEDTAVYYCARGRSYAFDI WDQGTMVTVSS amino acid sequence of D04 scFv (SEQ ID NO: 43) SYVLTQPPSVSVAPGKTARITCGGN-NIGWKSVHWYQQKPGQAPVLVVYNDN-DRPSGV PERFSGSNSGNTATLTISRVVAGDEAD- YYCQVWDSSSDHVLFGGGTKLTVLSGGSTITSY NVYYTKLSSSGTQVQLVQS-GAEVKKPGSSVKVSCK-ASGGTFSSYAISWVRQAPGQGLEW MGGIIP-IFGTANYAQKFOGRVTITADESTSTAYMELSSLR-SEDTAVYYCARASGRWLQF WHYYGMDVWGQGTTVTVS amino acid sequence of D07 scFv (SEQ ID NO: 44) SYELTQPPSVSVAPGETARMTCGGN-NIGTKGVHWYQQKPGQAPVLVVYDDSDRPSGI PERFSGSNAGNTATLTISRVEAGDEAD-YYCQVWDSRSDQYVFGTRTKLTVLSGGSTITSY NVYYTKLSSSGAQVTL-KESGPVLVKPTETLTLTCTVSGFSL-SNARMGVSWIRQPPGKALE WLAHIFSNGEK-SYSTSLKSRLTISKDTSKSQVVLTMTNMDPVDT-ATYYCARTLDYYDSS GYLVG-GAFDIWGQGTMVTVSS amino acid sequence of D10 scFv (SEQ ID NO: 45) QSVVTQPPSASGSPGQTVTISCSGNSANIGG-NPVNWYQQLPGTAPKLLIYSNNQRPSGV PDRFSGSKSGISASLAISGLQSEDEADYY-CAAWDDSLNGVIFGGGTKLTVLSGGSTITSYN VYYTKLSSSGTQVQLVQSGAEVKKPGESLKIS-CKGSGYSFTSYWIGWVRQMPGKGLEWM GIIYPGDSDTRYSPSFOGQVTISADKSISTAY-LQWSSLKASDTAMYYCARRHSGSYSGAF DIWGQGTMVTVSS amino acid sequence of D11 scFv (SEQ ID NO: 46) SYELTQPPSVSVAPGQTARITCGGNNIG-SKSVHWYQQKPGQAPVLVVYDDSDRPSGIPE RFSGSNSGNTATLTISGTQAMDEAD-YYCQAWDSSTAYVFGSGTKLTVLSGGSTIT-SYNVY YTKLSSSGTQVQLEESGG-GLVQPGGSLRLSCAASGFTFSNYAMSWVRQAP-GKGLEWVS AISGSGGATFHADSVKGRFTIS-RDNSKNTLYLQMNSLRAEDTAVYY-CARRVGYDSSG YYWSDAFDIWGQGTMVTVSS amino acid sequence of E01 scFv (SEQ ID NO: 47) SYELTQPPSVSVAPGETARITCGGDNIGR-RHVHWYQQKPGQAPVLVIYDDSDRPSGIPD RFSGSNSGNTATLTIGRVEAGDEAD-YYCQVWGSSNDPHVFGTGTKLTVLSGG-STITSNN VYYTKLSSSGTQVQLQQWGAGLLKP-SETLSLKCAVYGGSFSGYYWGWIRQSTGKGLE-WI GEINRSG-STNYNPSLKSRVTISVDTSKNQFSLKLSSVTAAD-TAVYYCARGGARYYYGSG SYRST-PRPYYFDYWGQGTLVTVSS amino acid sequence of E08 scFv (SEQ ID NO: 48) SYVLTQPPSVSVAPGKTARITCGGN-NIGWKSVHWYQQKPGQAPVLVVYDDSDRPS-GIP ERFSGSNSGNTATLTISRVEAGDEAD-YYCQVWDSSSDLVVFGGGTKLTVLSGGSTITSYN VYYTKLSSSGTQVQLVQS-GAEVKKPGSSVKVSCK-ASGGTFSSYAISWVRQAPGQGLEWM GGIIP-IFGTANYAQKFOGRVTITADESTSTAYMELSSLR-SEDTAVYYCARASGRWLQFW HYYGMDVWGQGTTVTVSS amino acid sequence of F07 scFv (SEQ ID NO: 49) SYVLTQPPSVSVAPGQTARITCGGNNIG-SKSVHWYQQKPGQAPVLVVYDDSDRPSGIPE RFSGSNSGNTATLIISRVEAGDEAD-YYCQVWDSSSVHYVFGTGTKLTVLSGGSTIT-SYNV YYTKLSSSGTQVQLVQS-GAEVKKPGSSVRVSCKVSGYTFTGYYMHWVR-QAPGQGLEWM GIINPSGGST-SYAQKFOGRVTMTRDTSTSTVYMELSSLRSED-TAVYYCARVRVGASDAF DIWGQGTMVTVSS amino acid sequence of G07 scFv (SEQ ID NO: 50) QSVLIQPPSASGTPGQRVTISCSGSNSNFGSNS-VSWYQQRPGTAPKLLIEGNNQRPSGVP ERFSG-SKSGTSASLAISGLQSEDEAEYSCASWDD-SLNAFVFGPGTKLTVLSGGSAITSYNV YYTKLSSSGTQVQLVQSGAEVKKPGESLKIS-CKGSGYSFTSYWIGWVRQMPGKGLEWMG IIYPGDSDIRYSPSFOGQVTISADKSFSSAY-LQWSSLKASDTAMYYCARLGATGAFDIWG QGTTVTVSS amino acid sequence of H01 scFv (SEQ ID NO: 51) QPGLTQPPSVSLAPGQTARITCGGNNIG-SKSVHWYQQKPGQAPVLVVYDDSDRPSGIPE RFSGSNAGNTATLTISRVEAGDEAD-YYCQVWDSRSDQYVFGTRTKLTVLSGGSTIT-SYN VYYTKLSSSGAQVTL-KESGPVLVKPTETLTLTCTVSGFSLSNARMGVS-WIRQPPGKALEW LAHIFSNGEKSYST-SLKSRLTISKDTSKSQVVLTMTNMDPVDTATYY-CARTLDYYDSSG YLVGGAFDIWGQGTMVTVSS amino acid sequence of H02 scFv (SEQ ID NO: 52) QSVVTQPPSVSAAPGQKVTISCSGSSS-NIGNNYVSWYQQLPGTAPKLLIYRDTQRPSGV PDRFSGSKSGTSASLAISGLRSEDEADYY-CATWDKSLSGPVFGGGTKVTVLSGGSTITSY NVYYTKLSSSGTQVQLQQSGPGLVKPSQTLSLT-CAISGDSVSSNSAAWNWIRQSPSRGLE WLGRTYYRSKWYNDYAVSVKSRII-INPDTSKNQFSLQLNSVTPEDTAVYY-CARODNNP YYGLDVWGQGTTVTVSS amino acid sequence of H03 scFv (SEQ ID NO: 53) SYELTQPPSVSVAPGQTARITCGGNNIG-SKSVHWYQQKPGQAPVLVIYYDSDRPSGIPE RFSGSNSGNTATLTISRVEAGDEAD-YYCQVWDSSSALYVFGTRTKVTVLSGGSTIT-SYNV YYTKLSSSGTQVQLVESGG-GLVQPGRSLRLSCAASGFTFDDYAMHWVRQAP-GKGLEWV SGISWNSGSIGYADSVKGRFTISRD-NAKNSLYLQVNSLRAEDTAVYYCARELIVGTT-SPQ TDAFDIWGQGTMVTVSS amino acid sequence of H05 scFv (SEQ ID NO: 54) SYVLTQPPSVSVAPGQTARITCGANNI-GRISVHWYQQKPGQAPVLVVYDDSDRPSGIPE RFSGSNFGNTATLTISRVEAGDEADYYCQVWD-SYSDHVIFGGGTKLTVLSGGSTITSYNV YYTKLSSSGTQVQLVQS-GAEVKKPGSSVKVSCK-ASGGTFSSYAISWVRQAPGQGLEWMG GIIP-IFGTANYAQKFQGRVTITADESTSTAYMELSSLR-SEDTAVYYCARSIFGVVIISHADG YYYGMDVWGQGTTVTVSS amino acid sequence of R04 scFv (SEQ ID NO: 55) EIVMTQSPSSLSASVGDRVTITCQASQDIS-NYLNWCQQKPGKAPKLLIYDASNLETGVP SRFSGSGSGTGFTFTISSLQPEDFATYYCQQSYS-TPYTFGQGTKVEIKSGGSTITSYNVNYT KLSSSGAQVQLQQSGPGLVKSSQTLSLTCAIS-GDSVSSNGAAWHWIRQSPSRGLEWLGRT YYRSGWYNDYAVSVKSRIT-INQDTSKNQFSLQLNSVTPEDTAVYFCAREGGG-GRMDV WSQGTTVTVSS amino acid sequence of R09 scFv (SEQ ID NO: 56) QPGLTQPPSVSVSPGQTA-SITCSGDKLGYKYVSWYQQKPGQSPVLVI-YEDTKRPSGIPK RFSGSNSGNTATL-TICGTQAVDEADYYCQAWDSSVVFGGGTKLTV-LSGGSTITSYNVYDT KLSSSGTQVQLVQS-GAEVKKPGASVKVSCKASGYTFTSY-GISWVRQAPGQGLEWMGWI SAYN-GNTNYAQKFQGRVTMTTDTSTSTAYMELRSLR-SDDTAVYYCARDMELRPPFDY WGQGTLVTVSS amino acid sequence of R26 scFv (SEQ ID NO: 57) SYELTQPPSVSVAPGQTATITCGGKNIESKSVHW-YQQKPGQAPVLVVSDDTDRASGIPE RFSGSNSG-GAATLTISRVEAGDEADYYCQVWD-SPSDHYVFGPGTKLTVLSGGSTITSYNV YYTKLSSSGTQVQLVESGGGVVQPGRSLRLS-CAASGFTFSSYAMHWVRQAPGKGLEWV AVI-SYDGSNKYYADSVKGRFTISRDKAKNT-LYLQMNSLRGEDTAVYYCARELSYYDSS GYLRGDWYFDLWGRGTLVTVSS amino acid sequence of S01 scFv (SEQ ID NO: 58) EIVMTQSPSSLSASVGDSVTITCQASQDIS-NYLNWYQQKPGKAPKLLIYDASNLETGVPS RFSGGGSGTDFTLTITSLQPEDI-ATYYCQQYDNFPPTFGPGTKVDIKSGGSTIT-SYNVYYTK LSSSDTQVQLVESGG-GLVKPGGSLRLSCAASGFTVGSNYMSWVRQAP GKGLEWVSVIYS GGSTYYADSVKGRFTIS-RDNSKNTLYLQMNSLRAEDTAVYY-CARGSSGAWYFDLWGR GTLVTVSS amino acid sequence of linker (SEQ ID NO: 59). SGG-STITSYNVYYTKLSSSGA amino acid sequence of linker (SEQ ID NO: 60). SGG-STITSYNVNYTKLSSSGA ( amino acid sequence of linker (SEQ ID NO: 61). SGG-STITSYNVYDTKLSSSGT amino acid sequence of linker (SEQ ID NO: 62). SGG-STITSYNVYYTKLSSSGT amino acid sequence of linker (SEQ ID NO: 63). SGG-STITSYNVYYTKLSSSDT amino acid sequence of D04 light chain (SEQ ID NO:64) SYVLTQPPSVSVAPGKTARITCGGN-NIGWKSVHWYQQKPGQAPVLVVYNDN-DRPSGV PERFSGSNSGNTATLTISRVVAGDEAD-YYCQVWDSSSDHVLFGGGTKLTVL amino acid sequence of D04 heavy chain. (SEQ ID NO:65) QVQLVQSGAEVKKPGSSVKVSCK-ASGGTFSSYAISWVRQAPGQGLEWMGGIIP-IFGTAN YAQKFOGRVTITADEST-STAYMELSSLRSEDTAVYYCARASGRWLQFWH-YYGMDVWG QGTTVTVS amino acid sequence of D12 scFv (SEQ ID NO:66) SYELTQPPSVSVAPGQTARITCGGNNIG-SKPVHWYQQMPGQAPVLVVYDNNNRPSGIP ERFSGSNSGNTATLTISRVEAGDEAD-YFCQVWDSSSDLWVFGGRTKLTVLSGGSTIT-SYN VYYTKLSSSGTQVQLVESGG-GLVQPGRSLRLSCAASGETEDDYAMHWVRQAP GKGLEW VSGTSWNSGSIYADSVKGRFTISRD-NAKNSLYLQMNSLRAEDTALYYCAKDKGYYDS SAGFDIWGQGTMVTVSS amino acid sequence of E07 scFv (SEQ ID NO:67). SYVLTQPPSVSVAPGQTARITCGGNNIG-SKSVHWYQQKPGQAPVLVVYDDSDRPSGIPE RFSGSNSGNTATLIISRVEAGDEAD-YYCQVWDSSSVHYVFGTGTKLTVLSGGSTIT-SYNV YYTKLSSSGTQVQLVQS-GAEVKKPGSSVRVSCKVSGYTFTGYYMHWVR-QAPGQGLEWM GIINPSGGST-SYAQKFOGRVTMTRDTSTSTVYMELSSLRSED-TAVYYCARVRVGASDAF DIWGQGTMVTVSS amino acid sequence of consensus scFv sequence of FIGS. 2A, 2B, 2C, and 2D (SEQ ID NO:68) ZSYVLTQPPSVSVAPGQTARITCGGNNIG-SKSVHWYQQKPGQAPVLVIYDDSDRPSGIPE RFSGSNSGNTATLTISRVEAGDEAD-YYCQVWDSSSDHYVFGGGTKLTVLSGGSTIT-SYN VYYTKLSSSGTQVQLVQSGAGLVKPGESLKLS-CAASGFTFSSYAMSWVRQAPGKGLEW MGGIYPGSGXTNYAQSXKGRVTISRDTSKSTAY-LQLXSLRAEDTAVYYCARXLGGXXY AFDIWGQGTMVTVSS SEQ ID NO:69: nucleotide sequence of a primer. GTTCTGGTGGTGGTGGTTCTGCTAGAGGCGC-GC SEQ ID NO:70: nucleotide sequence of a primer. GCAGTGGGTTTGGGATTGGTTTGCC SEQ ID NO:71: nucleotide sequence of a primer. CACTGTACTTTTAGCTCGTAC SEQ ID NO:72: nucleotide sequence of a primer. TAGA-TACCCATACGACGTTC SEQ ID NO:73: amino acid sequence of B04 Kabat-Chothia Composite CDR-L1. GGNNIGIRSVH SEQ ID NO:74: amino acid sequence of B04 Kabat-Chothia Composite CDR-L2. YYDSDRPS SEQ ID NO: 75: amino acid sequence of B04 Kabat-Chothia Composite CDR-L3. QVWDSSSDHPV SEQ ID NO:76: amino acid sequence of B04 Kabat-Chothia Composite CDR-H1. GYTFTRYYMH SEQ ID NO:77: amino acid sequence of B04 Kabat-Chothia Composite CDR-H2. IINPSGGTT-SYAQKFQG SEQ ID NO:78: amino acid sequence of B04 Kabat-Chothia Composite CDR-H3. SFGELTSFDY SEQ ID NO:79: amino acid sequence of B10 Kabat-Chothia Composite CDR-L1. TGSSSNIGSRTVN SEQ ID NO:80: amino acid sequence of B10 Kabat-Chothia Composite CDR-L2. YANNQRPS SEQ ID NO:81: amino acid sequence of B10 Kabat-Chothia Composite CDR-L3. AAWDDSLNGYV SEQ ID NO:82: amino acid sequence of B10 Kabat-Chothia Composite CDR-H1. GDSVSSNSAT SEQ ID NO:83: amino acid sequence of B10 Kabat-Chothia Composite CDR-H2. RTYYG-SKWHSDYAVSVKS SEQ ID NO:84: amino acid sequence of B10 Kabat-Chothia Composite CDR-H3. GRSYAFDI SEQ ID NO:85: amino acid sequence of D04 Kabat-Chothia Composite CDR-L1. GGNNIGWKSVH SEQ ID NO:86: amino acid sequence of D04 Kabat-Chothia Composite CDR-L2. YNDNDRPS SEQ ID NO:87: amino acid sequence of D04 Kabat-Chothia Composite CDR-L3. QVWDSSSDHVL SEQ ID NO:88: amino acid sequence of D04 Kabat-Chothia Composite CDR-H1. GGTFSSYAIS SEQ ID NO:89: amino acid sequence of D04 Kabat-Chothia Composite CDR-H2. GIIPIFGTAN-YAQKFQG SEQ ID NO:90: amino acid sequence of D04 Kabat-Chothia Composite CDR-H3. ASGRWLQF SEQ ID NO:91: amino acid sequence of D07 Kabat-Chothia Composite CDR-L1. GGNNIGTKGVH SEQ ID NO:92: amino acid sequence of D07 Kabat-Chothia Composite CDR-L2. YDDSDRPS SEQ ID NO:93: amino acid sequence of D07 Kabat-Chothia Composite CDR-L3. QVWDSRSDQYV SEQ ID NO:94: amino acid sequence of D07 Kabat-Chothia Composite CDR-H1. GFSLSNARMGVS SEQ ID NO:95: amino acid sequence of D07 Kabat-Chothia Composite CDR-H2. HIFSNGEKSYSTSLKS SEQ ID NO:96: amino acid sequence of D07 Kabat-Chothia Composite CDR-H3. TLDYYDSSGYLVGGAFDI SEQ ID NO:97: amino acid sequence of D10 Kabat-Chothia Composite CDR-L1. SGNSANIGGNPVN SEQ ID NO:98: amino acid sequence of D10 Kabat-Chothia Composite CDR-L2. YSNNQRPS SEQ ID NO:99: amino acid sequence of D10 Kabat-Chothia Composite CDR-L3. AAWDDSLNGVI SEQ ID NO:100: amino acid sequence of D10 Kabat-Chothia Composite CDR-H1. GYSFTSYWIG SEQ ID NO:101: amino acid sequence of D10 Kabat-Chothia Composite CDR-H2. IIYPGDSDTRYSPSFQG SEQ ID NO:102: amino acid sequence of D10 Kabat-Chothia Composite CDR-H3. RHSGSYSGAFDI SEQ ID NO:103: amino acid sequence of D11 Kabat-Chothia Composite CDR-L1. GGNNIGSKSVH SEQ ID NO:104: amino acid sequence of D11 Kabat-Chothia Composite CDR-L2. YDDSDRPS SEQ ID NO:105: amino acid sequence of D11 Kabat-Chothia Composite CDR-L3. QAWDSSTAYV SEQ ID NO:106: amino acid sequence of D11 Kabat-Chothia Composite CDR-H1. GFTFSNYAMS SEQ ID NO:107: amino acid sequence of D11 Kabat-Chothia Composite CDR-H2. AISGSGGATFHADSVKG SEQ ID NO:108: amino acid sequence of D11 Kabat-Chothia Composite CDR-H3. RVGYDSSGYYWSDAFDI SEQ ID NO:109: amino acid sequence of D12 Kabat-Chothia Composite CDR-L1. GGNNIGSKPVH SEQ ID NO:110: amino acid sequence of D12 Kabat-Chothia Composite CDR-L2. YDNNNRPS SEQ ID NO:111: amino acid sequence of D12 Kabat-Chothia Composite CDR-L3. QVWDSSSDLWV SEQ ID NO: 112: amino acid sequence of D12 Kabat-Chothia Composite CDR-H1. GFTFDDYAMH SEQ ID NO: 113: amino acid sequence of D12 Kabat-Chothia Composite CDR-H2. GTSWNSGSIGYADSVKG SEQ ID NO:114: amino acid sequence of D12 Kabat-Chothia Composite CDR-H3. DKGYYDSSAGFDI SEQ ID NO:115: amino acid sequence of E01 Kabat-Chothia Composite CDR-L1. GGDNIGRRHVH SEQ ID NO:116: amino acid sequence of E01 Kabat-Chothia Composite CDR-L2. DDSDRPS SEQ ID NO:117: amino acid sequence of E01 Kabat-Chothia Composite CDR-L3. QVWGSSNDPHV SEQ ID NO: 118: amino acid sequence of E01 Kabat-Chothia Composite CDR-H1. GGSFSGYYWG SEQ ID NO: 119: amino acid sequence of E01 Kabat-Chothia Composite CDR-H2. EINRSGSTNYNPSLKS SEQ ID NO:120: amino acid sequence of E01 Kabat-Chothia Composite CDR-H3. GGARYYYGSGSYRSTPRPYYFD SEQ ID NO:121: amino acid sequence of E07 Kabat-Chothia Composite CDR-L1. GGNNIGSKSVH SEQ ID NO:122: amino acid sequence of E07 Kabat-Chothia Composite CDR-L2. DDSDRPS SEQ ID NO:123: amino acid sequence of E07 Kabat-Chothia Composite CDR-L3. QVWDSSSVHYV SEQ ID NO:124: amino acid sequence of E07 Kabat-Chothia Composite CDR-H1. GYTFTGYYMH SEQ ID NO:125: amino acid sequence of E07 Kabat-Chothia Composite CDR-H2. IINPSGGSTSYAQKFQG SEQ ID NO:126: amino acid sequence of E07 Kabat-Chothia Composite CDR-H3. VRVGASDAFDI SEQ ID NO:127: amino acid sequence of E08 Kabat-Chothia Composite CDR-L1. GGNNIGWKSVH SEQ ID NO:128: amino acid sequence of E08 Kabat-Chothia Composite CDR-L2. DDSDRPS SEQ ID NO:129: amino acid sequence of E08 Kabat-Chothia Composite CDR-L3. QVWDSSSDLVV SEQ ID NO:130: amino acid sequence of E08 Kabat-Chothia Composite CDR-H1. GGTFSSYAIS SEQ ID NO:131: amino acid sequence of E08 Kabat-Chothia Composite CDR-H2. GIIPIFGTANYAQKFQG SEQ ID NO:132: amino acid sequence of E08 Kabat-Chothia Composite CDR-H3. ASGRWLQFWHYYGMDV SEQ ID NO:133: amino acid sequence of F07 Kabat-Chothia Composite CDR-L1. GGNNIGSKSVH SEQ ID NO:134: amino acid sequence of F07 Kabat-Chothia Composite CDR-L2. DDSDRPS SEQ ID NO:135: amino acid sequence of F07 Kabat-Chothia Composite CDR-L3. QVWDSSSVHYV SEQ ID NO:136: amino acid sequence of F07 Kabat-Chothia Composite CDR-H1. GYTFTGYYMH SEQ ID NO:137: amino acid sequence of F07 Kabat-Chothia Composite CDR-H2. IINPSGGSTSYAQKFQG SEQ ID NO:138: amino acid sequence of F07 Kabat-Chothia Composite CDR-H3. VRVGASDAFDI SEQ ID NO:139: amino acid sequence of G07 Kabat-Chothia Composite CDR-L1. SGSNSNFGSNSVS SEQ ID NO:140: amino acid sequence of G07 Kabat-Chothia Composite CDR-L2. GNNQRPS SEQ ID NO:141: amino acid sequence of G07 Kabat-Chothia Composite CDR-L3. ASWDDSLNAFV SEQ ID NO:142: amino acid sequence of G07 Kabat-Chothia Composite CDR-H1. GYSFTSYWIG SEQ ID NO:143: amino acid sequence of G07 Kabat-Chothia Composite CDR-H2. IIYPGDSDIRYSPSFQG SEQ ID NO:144: amino acid sequence of G07 Kabat-Chothia Composite CDR-H3. LGATGAFDI SEQ ID NO:145: amino acid sequence of H01 Kabat-Chothia Composite CDR-L1. GGNNIGSKSVH SEQ ID NO:146: amino acid sequence of H01 Kabat-Chothia Composite CDR-L2. DDSDRPS SEQ ID NO:147: amino acid sequence of H01 Kabat-Chothia Composite CDR-L3. QVWDSRSDQYV SEQ ID NO:148: amino acid sequence of H01 Kabat-Chothia Composite CDR-H1. GFSLSNARMGVS SEQ ID NO:149: amino acid sequence of H01 Kabat-Chothia Composite CDR-H2. HIFSNGEKSYSTSLKS SEQ ID NO:150: amino acid sequence of H01 Kabat-Chothia Composite CDR-H3. TLDYYDSSGYLVGGAFDI SEQ ID NO:151: amino acid sequence of H02 Kabat-Chothia Composite CDR-L1. SGSSSNIGNNYVS SEQ ID NO:152: amino acid sequence of H02 Kabat-Chothia Composite CDR-L2. RDTQRPS SEQ ID NO:153: amino acid sequence of H02 Kabat-Chothia Composite CDR-L3. ATWDKSLSGPV SEQ ID NO:154: amino acid sequence of H02 Kabat-Chothia Composite CDR-H1. GDSVSSNSAA SEQ ID NO:155: amino acid sequence of H02 Kabat-Chothia Composite CDR-H2. RTYYRSKWYN-DYAVSVKS SEQ ID NO:156: amino acid sequence of H02 Kabat-Chothia Composite CDR-H3. QDNNPYYGLDV SEQ ID NO:157: amino acid sequence of H03 Kabat-Chothia Composite CDR-L1. GGNNIGSKSVH SEQ ID NO:158: amino acid sequence of H03 Kabat-Chothia Composite CDR-L2. YDSDRPS SEQ ID NO:159: amino acid sequence of H03 Kabat-Chothia Composite CDR-L3. QVWDSSSALYV SEQ ID NO:160: amino acid sequence of H03 Kabat-Chothia Composite CDR-H1. GFTFDDYAMH SEQ ID NO:161: amino acid sequence of H03 Kabat-Chothia Composite CDR-H2. GISWNSGSIG-YADSVKG SEQ ID NO:162: amino acid sequence of H03 Kabat-Chothia Composite CDR-H3. ELIVGTTSPQTDAFDI SEQ ID NO:163: amino acid sequence of H05 Kabat-Chothia Composite CDR-L1. GANNIGRISVH SEQ ID NO:164: amino acid sequence of H05 Kabat-Chothia Composite CDR-L2. DDSDRPS SEQ ID NO:165: amino acid sequence of H05 Kabat-Chothia Composite CDR-L3. QVWDSYSDHVI SEQ ID NO:166: amino acid sequence of H05 Kabat-Chothia Composite CDR-H1. GGTFSSYAIS SEQ ID NO:167: amino acid sequence of H05 Kabat-Chothia Composite CDR-H2. GIIPIFGTAN-YAQKFQG SEQ ID NO:168: amino acid sequence of H05 Kabat-Chothia Composite CDR-H3. SIFGVVII-SHADGYYYGMDV SEQ ID NO:169: amino acid sequence of R04 Kabat-Chothia Composite CDR-L1. QASQDISNYLN SEQ ID NO:170: amino acid sequence of R04 Kabat-Chothia Composite CDR-L2. DASNLET SEQ ID NO:171: amino acid sequence of R04 Kabat-Chothia Composite CDR-L3. QQSYSTPYT SEQ ID NO:172: amino acid sequence of R04 Kabat-Chothia Composite CDR-H1. GDSVSSNGAA SEQ ID NO:173: amino acid sequence of R04 Kabat-Chothia Composite CDR-H2. RTYYRSGWYN-DYAVSVKS SEQ ID NO:174: amino acid sequence of R04 Kabat-Chothia Composite CDR-H3. EGGGGRMDV SEQ ID NO:175: amino acid sequence of R09 Kabat-Chothia Composite CDR-L1. SGDKLGYKYVS SEQ ID NO:176: amino acid sequence of R09 Kabat-Chothia Composite CDR-L2. EDTKRPS SEQ ID NO:177: amino acid sequence of R09 Kabat-Chothia Composite CDR-L3. QAWDSSVV SEQ ID NO:178: amino acid sequence of R09 Kabat-Chothia Composite CDR-H1. GYTFTSYGIS SEQ ID NO:179: amino acid sequence of R09 Kabat-Chothia Composite CDR-H2. WISAYN-GNTNYAQKFQG SEQ ID NO:180: amino acid sequence of R09 Kabat-Chothia Composite CDR-H3. MELRPPFDY SEQ ID NO:181: amino acid sequence of R26 Kabat-Chothia Composite CDR-L1. GGKNIESKSVH SEQ ID NO:182: amino acid sequence of R26 Kabat-Chothia Composite CDR-L2. DDTDRAS SEQ ID NO:183: amino acid sequence of R26 Kabat-Chothia Composite CDR-L3. QVWDSPSDHYV SEQ ID NO:184: amino acid sequence of R26 Kabat-Chothia Composite CDR-H1. GFTFSSYAMH SEQ ID NO:185: amino acid sequence of R26 Kabat-Chothia Composite CDR-H2. VISYDGSNKYY-ADSVKG SEQ ID NO:186: amino acid sequence of R26 Kabat-Chothia Composite CDR-H3. ELSYYDSSGYLRGDWYFDL SEQ ID NO:187: amino acid sequence of S01 Kabat-Chothia Composite CDR-L1. QASQDISNYLN SEQ ID NO:188: amino acid sequence of S01 Kabat-Chothia Composite CDR-L2. DASNLET SEQ ID NO:189: amino acid sequence of S01 Kabat-Chothia Composite CDR-L3. QQYDNFPPT SEQ ID NO:190: amino acid sequence of S01 Kabat-Chothia Composite CDR-H1. GFTVGSNYMS SEQ ID NO:191: amino acid sequence of S01 Kabat-Chothia Composite CDR-H2. VIYSGGSTYY-ADSVKG SEQ ID NO:192: amino acid sequence of S01 Kabat-Chothia Composite CDR-H3. GSSGAWYFDL Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An antibody that binds to the receptor binding domain of SARS-CoV-2 virus comprising a light chain variable region comprising three light chain CDRs of SEO ID NO:9 and a heavy chain variable region comprising three heavy chain CDRs of SEO ID NO: 28.

2. The antibody of claim 1, wherein the antibody comprises a light chain variable region comprising three Kabat-Chothia Composite light chain CDRs SEQ ID NO:127, SEQ ID NO:128, and SEQ ID NO:129 and a heavy chain variable region comprising three Kabat-Chothia Composite heavy chain CDRs SEQ ID NO:130, SEQ ID NO:131, and SEQ ID NO:132.

3. The antibody of claim 2, wherein the light chain variable region comprises the amino acid sequence of SEQ ID NO: 9 and the heavy chain variable region comprises the amino acid sequence of SEQ ID NO: 28.

4. The antibody of claim 3, wherein the antibody comprises the amino acid sequence of SEQ ID NO:48.

5. The antibody of claim 1, wherein the antibody is an intact antibody.

6. The antibody of claim 1, wherein the antibody is an antigen-binding fragment.

7. The antibody of claim 6, wherein the antigen-binding fragment is a single-chain antibody, Fab fragment, F(ab')2 fragment, or minibody.

8. A composition comprising the antibody of claim 1 and a pharmaceutically acceptable excipient.

* * * * *

UNITED STATES PATENT AND TRADEMARK OFFICE

CERTIFICATE OF CORRECTION

PATENT NO. : 12,018,066 B1
APPLICATION NO. : 17/514903
DATED : June 25, 2024
INVENTOR(S) : Antonietta Maria Lillo et al.

It is certified that error appears in the above-identified patent and that said Letters Patent is hereby corrected as shown below:

In the Claims

In Column 179, Line 44, Claim 1, delete “SEO ID” and insert -- SEQ ID --, therefor.
In Column 179, Line 46, Claim 1, delete “SEO ID” and insert -- SEQ ID --, therefor.
In Column 180, Line 51, Claim 7, delete “F(ab’)2” and insert -- F(ab’)$_2$ --, therefor.

Signed and Sealed this
Twenty-ninth Day of October, 2024

Katherine Kelly Vidal

Katherine Kelly Vidal
*Director of the United States Patent and Trademark Office*